US011201296B2

(12) United States Patent
Parham et al.

(10) Patent No.: US 11,201,296 B2
(45) Date of Patent: Dec. 14, 2021

(54) COMPOUNDS HAVING FLUORENE STRUCTURES

(71) Applicant: Merck Patent GmbH, Darmstadt (DE)

(72) Inventors: Amir Hossain Parham, Frankfurt am Main (DE); Thomas Eberle, Landau (DE); Anja Jatsch, Frankfurt am Main (DE); Tobias Grossmann, Darmstadt (DE); Jonas Valentin Kroeber, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 346 days.

(21) Appl. No.: 15/747,398

(22) PCT Filed: Jul. 28, 2016

(86) PCT No.: PCT/EP2016/001308
§ 371 (c)(1),
(2) Date: Jan. 24, 2018

(87) PCT Pub. No.: WO2017/016667
PCT Pub. Date: Feb. 2, 2017

(65) Prior Publication Data
US 2018/0226587 A1    Aug. 9, 2018

(30) Foreign Application Priority Data

Jul. 29, 2015 (EP) .................... 15178816

(51) Int. Cl.
| | | |
|---|---|---|
| *H01L 51/50* | (2006.01) | |
| *H01L 51/00* | (2006.01) | |
| *C07D 405/10* | (2006.01) | |
| *C07D 401/14* | (2006.01) | |
| *C07D 239/82* | (2006.01) | |
| *C07D 401/04* | (2006.01) | |
| *C07D 239/74* | (2006.01) | |
| *C07D 403/10* | (2006.01) | |
| *C07D 409/04* | (2006.01) | |
| *C07D 405/04* | (2006.01) | |
| *C07D 471/04* | (2006.01) | |
| *C07D 471/14* | (2006.01) | |

(52) U.S. Cl.
CPC ........ *H01L 51/0072* (2013.01); *C07D 239/74* (2013.01); *C07D 239/82* (2013.01); *C07D 401/04* (2013.01); *C07D 401/14* (2013.01); *C07D 403/10* (2013.01); *C07D 405/04* (2013.01); *C07D 405/10* (2013.01); *C07D 409/04* (2013.01); *C07D 471/04* (2013.01); *C07D 471/14* (2013.01); *H01L 51/0052* (2013.01); *H01L 51/0058* (2013.01); *H01L 51/0067* (2013.01); *H01L 51/0073* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 2007/0007882 A1* | 1/2007 | Fukuoka | ............ H01L 51/0051 313/503 |
| 2010/0045150 A1* | 2/2010 | Lee et al. | ................ H01L 51/50 428/690 |
| 2014/0061609 A1 | 3/2014 | Kim et al. | |
| 2014/0284580 A1 | 9/2014 | Balaganesan et al. | |
| 2015/0065730 A1 | 3/2015 | Montenegro et al. | |
| 2016/0197289 A1* | 7/2016 | Sado | .................... C07D 405/14 257/40 |
| 2018/0170902 A1 | 6/2018 | Han et al. | |

FOREIGN PATENT DOCUMENTS

| | | | | |
|---|---|---|---|---|
| EP | 2108689 A2 | 10/2009 | | |
| EP | 3395799 A1 | 10/2018 | | |
| JP | 2009-249378 A | 10/2009 | | |
| JP | 2014-501699 A | 1/2014 | | |
| JP | 2014-513083 A | 5/2014 | | |
| JP | 2014-518900 A | 8/2014 | | |
| JP | 2014-522400 A | 9/2014 | | |
| JP | 2014-531747 A | 11/2014 | | |
| JP | 2015-513530 A | 5/2015 | | |
| JP | 2018-520097 A | 7/2018 | | |
| KR | 2012116272 | * | 10/2012 | ............. C09K 11/06 |
| KR | 20120116272 | | 10/2012 | |
| KR | 20140020208 A | | 2/2014 | |
| KR | 20140030786 A | | 3/2014 | |
| KR | 10-2015-0044658 A | | 4/2015 | |
| KR | 10-2015-0044668 A | | 4/2015 | |

(Continued)

OTHER PUBLICATIONS

International Preliminary Report on Patentability received for PCT Patent Application No. PCT/EP2016/001308, dated Feb. 8, 2018, 17 pages (11 pages of English Translation and 6 pages of Original Document).
International Search Report and Written Opinion received for PCT Patent Application No. PCT/EP2016/001308, dated Oct. 6, 2016, 21 pages (11 pages of English Translation and 10 pages of Original Document).

* cited by examiner

*Primary Examiner* — Gregory D Clark
(74) *Attorney, Agent, or Firm* — Faegre Drinker Biddle & Reath LLP

(57) ABSTRACT

The present invention describes fluorene derivatives substituted by electron-transporting groups, especially for use as triplet matrix materials in electronic devices. The invention further relates to a process for preparing the compounds of the invention and to electronic devices comprising these.

74 Claims, No Drawings

(56) References Cited

FOREIGN PATENT DOCUMENTS

| KR | 10-2016-0004513 | A  |   | 1/2016  |             |
|----|-----------------|----|---|---------|-------------|
| KR | 10-2016-0027940 | A  |   | 3/2016  |             |
| TW | 201302974       | A  |   | 1/2013  |             |
| WO | 2012/050371     | A1 |   | 4/2012  |             |
| WO | 2012141499      | A1 |   | 10/2012 |             |
| WO | 2012/169821     | A1 |   | 12/2012 |             |
| WO | 2012165832      | A1 |   | 12/2012 |             |
| WO | 2013/032284     | A1 |   | 3/2013  |             |
| WO | 2014/097711     | A1 |   | 6/2014  |             |
| WO | 2015/090405     | A1 |   | 6/2015  |             |
| WO | 2015/090504     | A2 |   | 6/2015  |             |
| WO | 2016003225      | A2 |   | 1/2016  |             |
| WO | 2016/068633     | A2 |   | 5/2016  |             |
| WO | 2017/111420     | A1 |   | 6/2017  |             |
| WO | WO 2012/141499  |    | * | 10/2021 | ... H01L 51/54 |

COMPOUNDS HAVING FLUORENE STRUCTURES

RELATED APPLICATIONS

This application is a national stage entry, filed pursuant to 35 U.S.C. § 371, of PCT/EP2016/001308, filed Jul. 28, 2016, which claims the benefit of European Patent Application No. 15178816.3, filed Jul. 29, 2015, which is incorporated herein by reference in its entirety.

The present invention describes fluorene derivatives substituted by electron-transporting groups, especially for use in electronic devices. The invention further relates to a process for preparing the compounds of the invention and to electronic devices comprising these compounds.

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime.

The properties of phosphorescent OLEDs are not just determined by the triplet emitters used. More particularly, the other materials used, for example matrix materials, are also of particular significance here. Improvements to these materials can thus also lead to distinct improvements in the OLED properties.

Frequently used according to the prior art as matrix materials for phosphorescent compounds and as electron transport materials are heteroaromatic compounds, for example triazine derivatives or benzimidazole derivatives. Suitable matrix materials for phosphorescent compounds are also carbazole derivatives. Known derivatives for this function are, for example, spirobifluorene derivatives substituted in the 2 position by triazine groups, as disclosed in WO 2010/015306 and WO 2010/072300. In the case of these compounds, there is still need for improvement both in the case of fluorescent and in the case of phosphorescent OLEDs, especially with regard to efficiency, lifetime and operating voltage on use in an organic electroluminescent device. Moreover, JP 2014183315A discloses heterocyclic compounds having fluorene structures. Similar compounds are additionally known from EP 2842954 A1.

In general terms, in the case of these materials for use as matrix materials, there is still need for improvement, particularly in relation to lifetime, but also in relation to the efficiency and operating voltage of the device.

It is an object of the present invention to provide compounds suitable for use in a phosphorescent or fluorescent OLED, especially as matrix material. More particularly, it is an object of the present invention to provide matrix materials which are suitable for red-, yellow- and green-phosphorescing OLEDs and possibly also for blue-phosphorescing OLEDs, and which lead to long lifetime, good efficiency and low operating voltage. Particularly the properties of the matrix materials too have an essential influence on the lifetime and efficiency of the organic electroluminescent device.

Moreover, the compounds should be processible in a very simple manner, and especially exhibit good solubility and film formation. For example, the compounds should exhibit elevated oxidation stability and an improved glass transition temperature.

Moreover, the matrix materials should especially be suitable for phosphorescent emitters containing ketoketonate ligands.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, devices containing compounds comprising structures of the following formula (I) and/or formula (II) have improvements over the prior art, especially when used as matrix material for phosphorescent dopants.

The present invention therefore provides a compound comprising structures of the following formula (I) and/or formula (II), or compounds of the formulae (I) and/or (II)

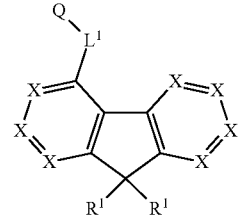

Formula (I)

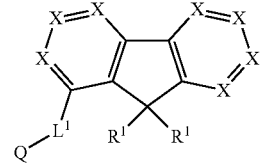

Formula (II)

where the symbols used are as follows:

X is the same or different at each instance and is N or $CR^1$, preferably $CR^1$, with the proviso that not more than two of the X groups in one cycle are N;

Q is an electron transport group;

$L^1$ is a bond or an aromatic ring system which has 5 to 24 aromatic ring atoms and may be substituted by one or more $R^1$ radicals;

$R^1$ is the same or different at each instance and is H, D, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, $SO$ or $SO_2$ and where one or more hydrogen atoms may be replaced by D, F, Cl, Br, I, CN or $NO_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or a combination of these systems; at the same time, two or more adjacent $R^1$ substituents may also form a mono- or polycyclic aliphatic or aromatic ring system with one another;

R² is the same or different at each instance and is H, D, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R³ radicals, where one or more nonadjacent CH₂ groups may be replaced by —R³C=CR³—, —C≡C—, Si(R³)₂, C=O, C=S, C=NR³, —C(=O)O—, —C(=O)NR³—, NR³, P(=O)(R³), —O—, —S—, SO or SO₂ and where one or more hydrogen atoms may be replaced by D, F, Cl, Br, I, CN or NO₂, or an aromatic or heteroaromatic ring system which has 5 to 40 aromatic ring atoms, each of which may be substituted by one or more R³ radicals, or an aryloxy or heteroaryloxy group which has 5 to 40 aromatic ring atoms and may be substituted by one or more R³ radicals, or a combination of these systems; at the same time, two or more adjacent R² substituents may also form a mono- or polycyclic aliphatic or aromatic ring system with one another;

R³ is the same or different at each instance and is H, D, F or an aliphatic hydrocarbyl radical having 1 to 20 carbon atoms, in which one or more hydrogen atoms may be replaced by D or F, or an aromatic and/or heteroaromatic ring system having 5 to 30 carbon atoms, in which one or more hydrogen atoms may be replaced by D or F; at the same time, two or more adjacent R³ substituents together may also form a mono- or polycyclic, aliphatic or aromatic ring system.

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

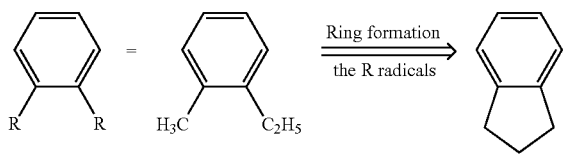

In addition, however, the abovementioned wording shall also be understood to mean that, if one of the two radicals is hydrogen, the second radical binds to the position to which the hydrogen atom was bonded, forming a ring. This shall be illustrated by the following scheme:

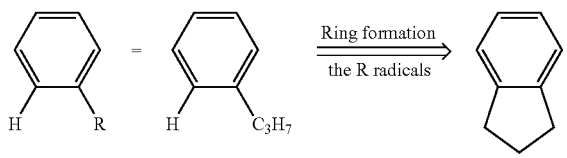

A fused aryl group in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a C₁- to C₂₀-alkyl group in which individual hydrogen atoms or CH₂ groups may also be substituted by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl) cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred configuration, the compounds of the invention may form a structure of formula (III) and/or (IV)

Formula (III)

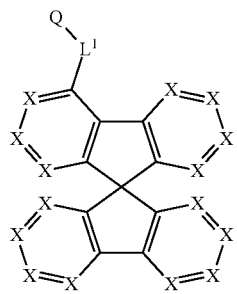

Formula (IV)

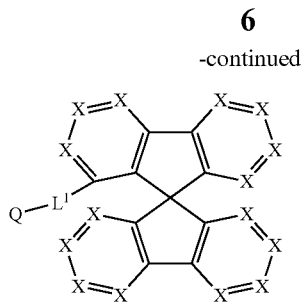

in which
the symbols X, $L^1$ and Q have the definition given above, especially for formula (I) and/or (II).

Furthermore, preference is given to compounds which are characterized in that, in formulae (I), (II), (III) and/or (IV), not more than two X groups are N and preferably not more than one X group is N, and preferably all X are $CR^1$, where preferably at most 4, more preferably at most 3 and especially preferably at most 2 of the $CR^1$ groups that X represents are not the CH group.

It may further be the case that the $R^1$ radicals of the X groups in the formulae (I), (II), (III) and/or (IV) do not form a fused ring system with the ring atoms of the fluorene structure. This includes the formation of a fused ring system with possible $R^2$, $R^3$ substituents which may be bonded to the $R^1$ radicals. It may preferably be the case that the $R^1$ radicals of the X groups in the formulae (I), (II), (III) and/or (IV) do not form a ring system with the ring atoms of the fluorene structure. This includes the formation of a ring system with possible $R^2$, $R^3$ substituents which may be bonded to the $R^1$ radicals.

Preferably, the compounds of the invention may comprise structures of formulae (Ia), (IIa), (IIIa) and/or (IVa)

Formula (Ia)

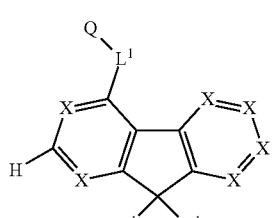

Formula (IIa)

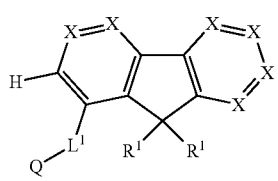

Formula (IIIa)

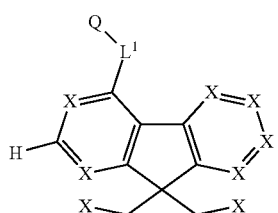

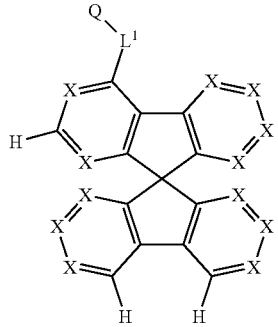

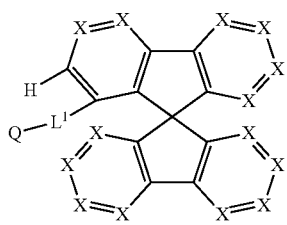

Formula (IVa)

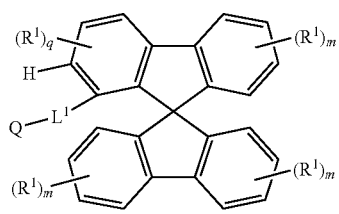

Formula (IVb)

in which the symbols X, $R^1$, $L^1$ and Q have the definition set out above, especially for formula (I) and/or (II).

It may additionally be the case that the $R^1$ substituents of the fluorene structure in the formulae (Ia), (IIa), (IIIa) and/or (IVa) do not form a fused ring system with the ring atoms of the fluorene structure. This includes the formation of a fused ring system with possible $R^2$, $R^3$ substituents which may be bonded to the $R^1$ radicals. It may preferably be the case that the $R^1$ substituents of the fluorene structure in the formulae (Ia), (IIa), (IIIa) and/or (IVa) do not form a ring system with the ring atoms of the fluorene structure. This includes the formation of a ring system with possible $R^2$, $R^3$ substituents which may be bonded to the $R^1$ radicals.

It may further be the case that, in formulae (Ia), (IIa), (IIIa) and (IVa), not more than two X groups are N and preferably not more than one X group is N, and preferably all X are $CR^1$, where preferably at most 4, more preferably at most 3 and especially preferably at most 2 of the $CR^1$ groups that X represents are not the CH group.

In a further-preferred embodiment, the compounds of the invention may comprise structures of formulae (Ib), (IIb), (IIIb) and/or (IVb)

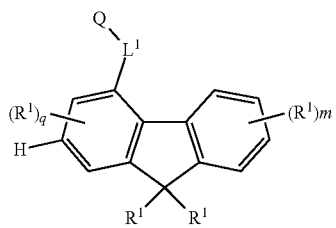

Formula (Ib)

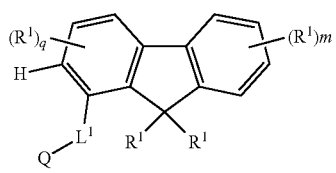

Formula (IIb)

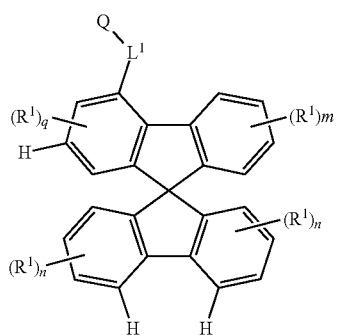

Formula (IIIb)

in which the symbols Q, $L^1$ and $R^1$ have the definition set out above, especially for formula (I) and/or (II), m is 0, 1, 2, 3 or 4, preferably 0, 1 or 2, n is 0, 1, 2 or 3, preferably 0, 1 or 2, and q is 0, 1 or 2, preferably 0 or 1.

Furthermore, preference is given to compounds which are characterized in that the two $R^1$ radicals bonded to the carbon atom in position 9 in the fluorene structure of the formulae (I), (II), (Ia), (IIa), (Ib), (IIb) are each an aromatic or heteroaromatic ring system which has 5 to 30 aromatic ring atoms and may be substituted by one or more $R^1$ radicals, where the two ring systems bonded to the carbon atom in position 9 in the fluorene structure of the formulae (I), (II), (Ia), (IIa), (Ib), (IIb) are not bonded to one another; or in that the two $R^1$ radicals bonded to the carbon atom in position 9 in the fluorene structure of the formulae (I), (II), (Ia), (IIa), (Ib), (IIb) are each independently H, D, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by —$R^2C$=$CR^2$—, —C≡C—, $Si(R^2)_2$, C=O, C=S, C=$NR^2$, —C(=O)O—, —C(=O)$NR^2$—, $NR^2$, P(=O)($R^2$), —O—, —S—, SO or $SO_2$ and where one or more hydrogen atoms may be replaced by D, F, Cl, Br, I, CN or $NO_2$; or in that one of the two $R^1$ radicals bonded to the carbon atom in position 9 in the fluorene structure of the formulae (I), (II), (Ia), (IIa), (Ib), (IIb) are each an aromatic or heteroaromatic ring system which has 5 to 30 aromatic ring atoms and may be substituted by one or more $R^1$ radicals, and one of the two $R^1$ radicals bonded to the carbon atom in position 9 in the fluorene structure of the formulae (I), (II), (Ia), (IIa), (Ib), (IIb) is H, D, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by —$R^2C$=$CR^2$—, —C≡C—, $Si(R^2)_2$, C=O, C=S, C=$NR^2$, —C(=O)O—, —C(=O)$NR^2$—, $NR^2$, P(=O)($R^2$), —O—, —S—, SO or $SO_2$ and where one or more hydrogen atoms may be replaced by D, F, Cl, Br, I, CN or $NO_2$.

In a preferred configuration, compounds comprising structures of formula (I), (Ia), (Ib), (II), (IIa), (IIb), (IIa), (III), (IIIa), (IIIb), (IV), (IVa) and (IVb) can be represented by structures of formula (I), (Ia), (Ib), (II), (IIa), (IIb), (IIa), (III), (IIIa), (IIIb), (IV), (IVa) and (IVb). Preferably, compounds comprising structures of formula (I), (Ia), (Ib), (II), (IIa), (IIb), (IIa), (III), (IIIa), (IIIb), (IV), (IVa) and (IVb) have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

The Q group is an electron-transporting group. Electron-transporting groups are widely known in the technical field and promote the ability of compounds to transport and/or conduct electrons.

Moreover, compounds of formula (I) and/or (II) show surprising advantages where, in formulae (I), (Ia), (Ib), (II), (IIa), (IIb), (IIa), (III), (IIIa), (IIIb), (IV), (IVa) and (IVb), the Q group comprises at least one structure selected from the group of pyridines, pyrimidines, pyrazines, pyridazines, triazines, quinazolines, quinoxalines, quinolines, isoquinolines, imidazoles and/or benzimidazoles.

Furthermore, preference is given to compounds which are characterized in that the Q group in formula (I), (Ia), (Ib), (II), (IIa), (IIb), (IIa), (III), (IIIa), (IIIb), (IV), (IVa) and (IVb) is a heteroaromatic ring system having at least two fused rings which may be substituted by one or more $R^1$ radicals, but is preferably unsubstituted, where the ring atoms of the at least two fused rings comprise at least one nitrogen atom, where $R^1$ has the definition set out above, especially for formula (I) and/or (II).

In a further configuration, it may be the case that the Q group shown, inter alia, in the formulae (I), (Ia), (Ib), (II), (IIa), (IIb), (IIa), (III), (IIIa), (IIIb), (IV), (IVa) and (IVb) is a heteroaromatic ring system, where the ring atoms comprise 1 to 4 nitrogen atoms and the ring system may be substituted by one or more $R^1$ radicals, but is preferably unsubstituted, where $R^1$ has the definition set out above, especially for formula (I) and/or formula (II).

Moreover, it may be the case that the Q group shown, inter alia, in the formulae (I), (Ia), (Ib), (II), (IIa), (IIb), (IIa), (III), (IIIa), (IIIb), (IV), (IVa) and (IVb) is a heteroaromatic ring system which has 9 to 14 and preferably 10 ring atoms and may be substituted by one or more $R^1$ radicals, where $R^1$ has the definition set out above, especially for formula (I) and/or formula (II), but is preferably unsubstituted.

Preferably, the Q group shown, inter alia, in the formulae (I), (Ia), (Ib), (II), (IIa), (IIb), (IIa), (III), (IIIa), (IIIb), (IV), (IVa) and (IVb) may be selected from structures of the formulae (Q-1), (Q-2) and/or (Q-3)

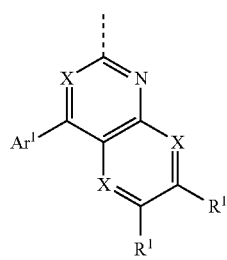

Formula (Q-1)

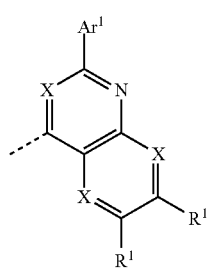

Formula (Q-2)

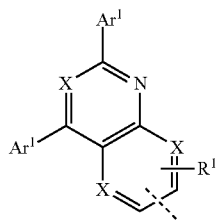

Formula (Q-3)

where the symbols X and $R^1$ have the definition given above for formula (I) and/or (II) inter alia, the dotted bond marks the attachment position and $Ar^1$ is an aromatic or heteroaromatic ring system which has 6 to 40 carbon atoms and may be substituted in each case by one or more $R^2$ radicals, an aryloxy group which has 5 to 60 aromatic ring atoms and may be substituted by one or more $R^2$ radicals, or an aralkyl group which has 5 to 60 aromatic ring atoms and may be substituted in each case by one or more $R^2$ radicals, where two or more adjacent $R^1$ or $R^2$ substituents may optionally form a mono- or polycyclic aliphatic ring system which may be substituted by one or more $R^3$ radicals, where the symbols $R^1$ and $R^2$ have the definition given above, especially for formula (I) and/or (II).

In a further embodiment, the Q group shown, inter alia, in the formulae (I), (Ia), (Ib), (II), (IIa), (IIb), (IIa), (III), (IIIa), (IIIb), (IV), (IVa) and (IVb) may be selected from structures of the formulae (Q-4), (Q-5), (Q-6), (Q-7), (Q-8) (Q-9), (Q-10), (Q-11), (Q-12), (Q-13), (Q-14) and/or (Q-15)

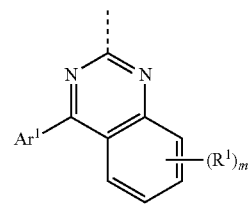

Formula (Q-4)

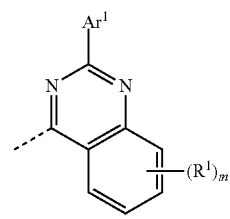

Formula (Q-5)

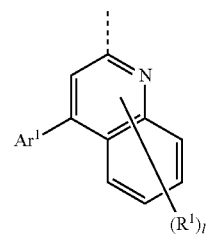

Formula (Q-6)

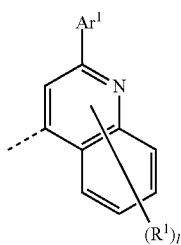
(Formula (Q-7))

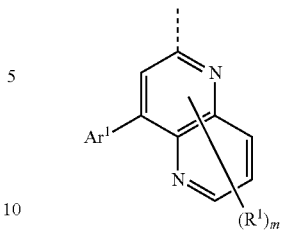
Formula (Q-13)

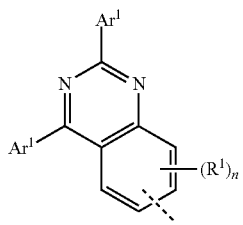
Formula (Q-8)

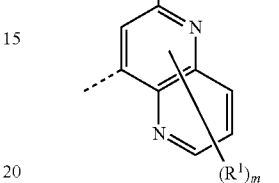
Formula (Q-14)

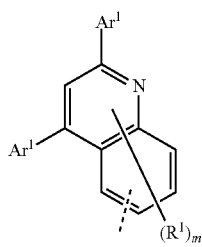
Formula (Q-9)

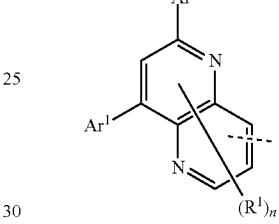
Formula (Q-15)

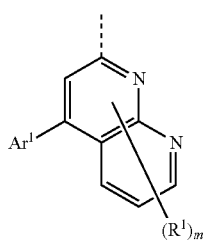
Formula (Q-10)

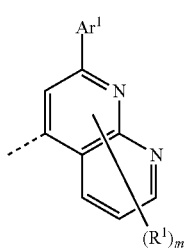
Formula (Q-11)

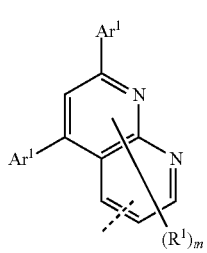
Formula (Q-12)

in which the symbols $Ar^1$ and $R^1$ have the definition set out above, inter alia, for formula (I) and (Q-1), the dotted bond represents the attachment position and m is 0, 1, 2, 3 or 4, preferably 0, 1 or 2, n is 0, 1, 2 or 3, preferably 0 or 1, and l is 1, 2, 3, 4 or 5, preferably 0, 1 or 2.

Preferably, the symbol $Ar^1$ represents an aryl or heteroaryl radical, such that an aromatic or heteroaromatic group of an aromatic or heteroaromatic ring system is bonded directly, i.e. via an atom of the aromatic or heteroaromatic group, to the respective atom of the further group, for example the carbon or nitrogen atom of the (Q-1) to (Q-15) groups shown above.

In a further preferred embodiment of the invention, $Ar^1$ is the same or different at each instance and is an aromatic or heteroaromatic ring system having 6 to 24 aromatic ring atoms, preferably 6 to 18 aromatic ring atoms, and is more preferably an aromatic ring system having 6 to 12 aromatic ring atoms or a heteroaromatic ring system having 6 to 13 aromatic ring atoms, each of which may be substituted by one or more $R^2$ radicals, but is preferably unsubstituted, where $R^2$ may have the definition given above, especially in formula (I) and/or formula (II). Examples of suitable $Ar^1$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted. In a preferred embodiment, the $Ar^1$ radical and/or a substituent $R^2$ bonded to $Ar^1$ according to the formulae (Q-1) to (Q-15) may comprise a structural element selected from structures of formulae (Q-1) to (Q-15) and/or from structures according to formula (Q-16) or (Q-17)

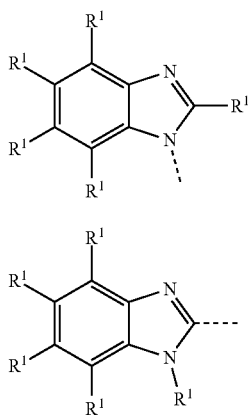

Formula (Q-16)

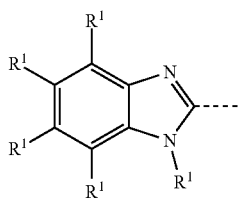

Formula (Q-17)

where the symbol R¹ has the definition given above, especially for formula (I) and/or (II), and the dotted bonds in each case mark the attachment positions at which the structural element of formula (Q-16) or (Q-17) binds to other structural elements of the Ar¹ radical or to the substituent R² or to a structure of formulae (Q-1) to (Q-15).

Advantageously, Ar¹ in the formulae (Q-1) to (Q-15) is an aromatic ring system which has 6 to 12 aromatic ring atoms and may be substituted by one or more R² radicals, but is preferably unsubstituted, where R² may have the definition given above, especially for formula (I) and/or (II).

Preferably, the R¹ radicals in the formulae (Q-1) to (Q-17) do not form a fused ring system with the ring atoms of the heteroaryl group to which the R¹ radicals are bonded. This includes the formation of a fused ring system with possible R², R³ substituents which may be bonded to the R¹ radicals.

Preferably, the R² radicals in the formulae (Q-1) to (Q-15) do not form a fused ring system with the ring atoms of the aryl group or heteroaryl group Ar¹ to which the R² radicals are bonded. This includes the formation of a fused ring system with possible R³ substituents which may be bonded to the R² radicals.

When X is CR¹ or when the aromatic and/or heteroaromatic groups are substituted by R¹ substituents, these R¹ substituents are preferably selected from the group consisting of H, D, F, CN, N(Ar¹)₂, C(=O)Ar¹, P(=O)(Ar¹)₂, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more R² radicals, where one or more nonadjacent CH₂ groups may be replaced by O and where one or more hydrogen atoms may be replaced by D or F, an aromatic or heteroaromatic ring system which has 5 to 24 aromatic ring atoms, each of which may be substituted by one or more R² radicals, but is preferably unsubstituted, or an aralkyl or heteroaralkyl group which has 5 to 25 aromatic ring atoms and may be substituted by one or more R² radicals; at the same time, it is optionally possible for two R¹ substituents bonded to the same carbon atom or adjacent carbon atoms to form a monocyclic or polycyclic, aliphatic, aromatic or heteroaromatic ring system which may be substituted by one or more R¹ radicals. The Ar¹ group may have the definition given above, especially for structure (Q-1). Preferably, the symbol Ar¹ represents an aryl or heteroaryl radical, such that an aromatic or heteroaromatic group of an aromatic or heteroaromatic ring system is bonded directly, i.e. via an atom of the aromatic or heteroaromatic group, to the respective atom of the further group, for example the carbon, nitrogen or phosphorus atom of the N(Ar¹)₂, C(=O)Ar¹, P(=O)(Ar¹)₂ groups.

More preferably, these R¹ substituents are selected from the group consisting of H, D, F, CN, N(Ar¹)₂, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more R² radicals, but is preferably unsubstituted, or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more nonaromatic R¹ radicals, but is preferably unsubstituted; at the same time, it is optionally possible for two R¹ substituents bonded to the same carbon atom or two adjacent carbon atoms to form a monocyclic or polycyclic aliphatic ring system which may be substituted by one or more R² radicals, but is preferably unsubstituted. The Ar¹ group may have the definition given above, especially for structure (Q-1). Preferably, the symbol Ar¹ represents an aryl or heteroaryl radical, such that an aromatic or heteroaromatic group of an aromatic or heteroaromatic ring system is bonded directly, i.e. via an atom of the aromatic or heteroaromatic group, to the respective atom of the further group, for example the nitrogen atom of the N(Ar¹)₂ group.

Most preferably, the R¹ substituents are selected from the group consisting of H and an aromatic or heteroaromatic ring system having 6 to 18 aromatic ring atoms, preferably having 6 to 13 aromatic ring atoms, each of which may be substituted by one or more nonaromatic R² radicals, but is preferably unsubstituted. Examples of suitable R¹ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R² radicals, but are preferably unsubstituted.

It may additionally be the case that, in a structure of formula (I), (II), (III), (IV), (Ia), (IIa), (IIIa), (IVa), (Ib), (IIb), (IIIb) and/or (IVb), at least one R¹ and/or Ar¹ radical is a group selected from the formulae (R¹-1) to (R¹-79)

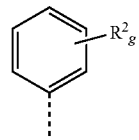

Formula (R¹-1)

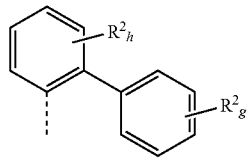

Formula (R¹-2)

-continued

Formula (R¹-3)

Formula (R¹-4)

Formula (R¹-5)

Formula (R¹-6)

Formula (R¹-7)

Formula (R¹-8)

Formula (R¹-9)

-continued

Formula (R¹-10)

Formula (R¹-11)

Formula (R¹-12)

Formula (R¹-13)

Formula (R¹-14)

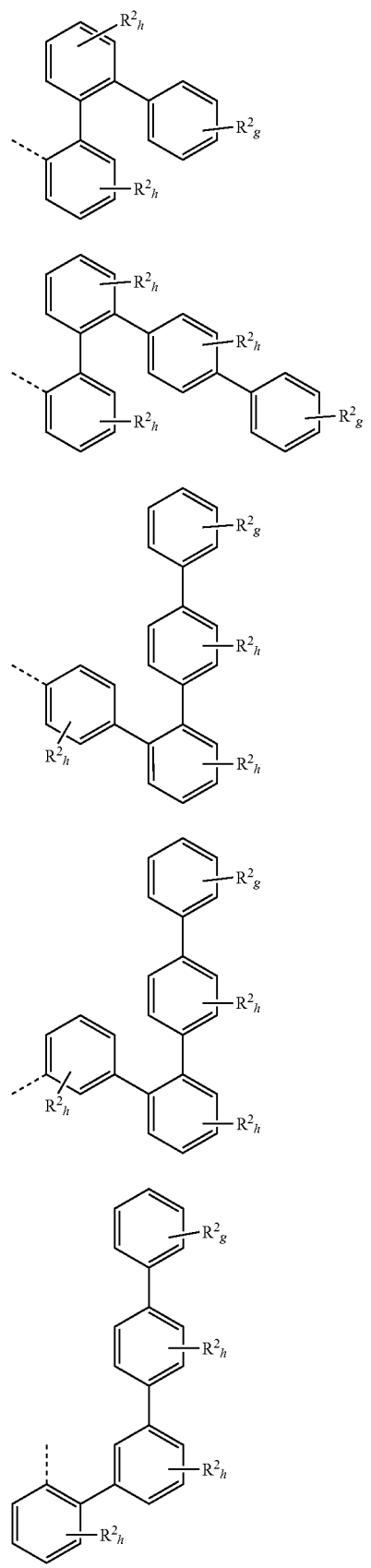
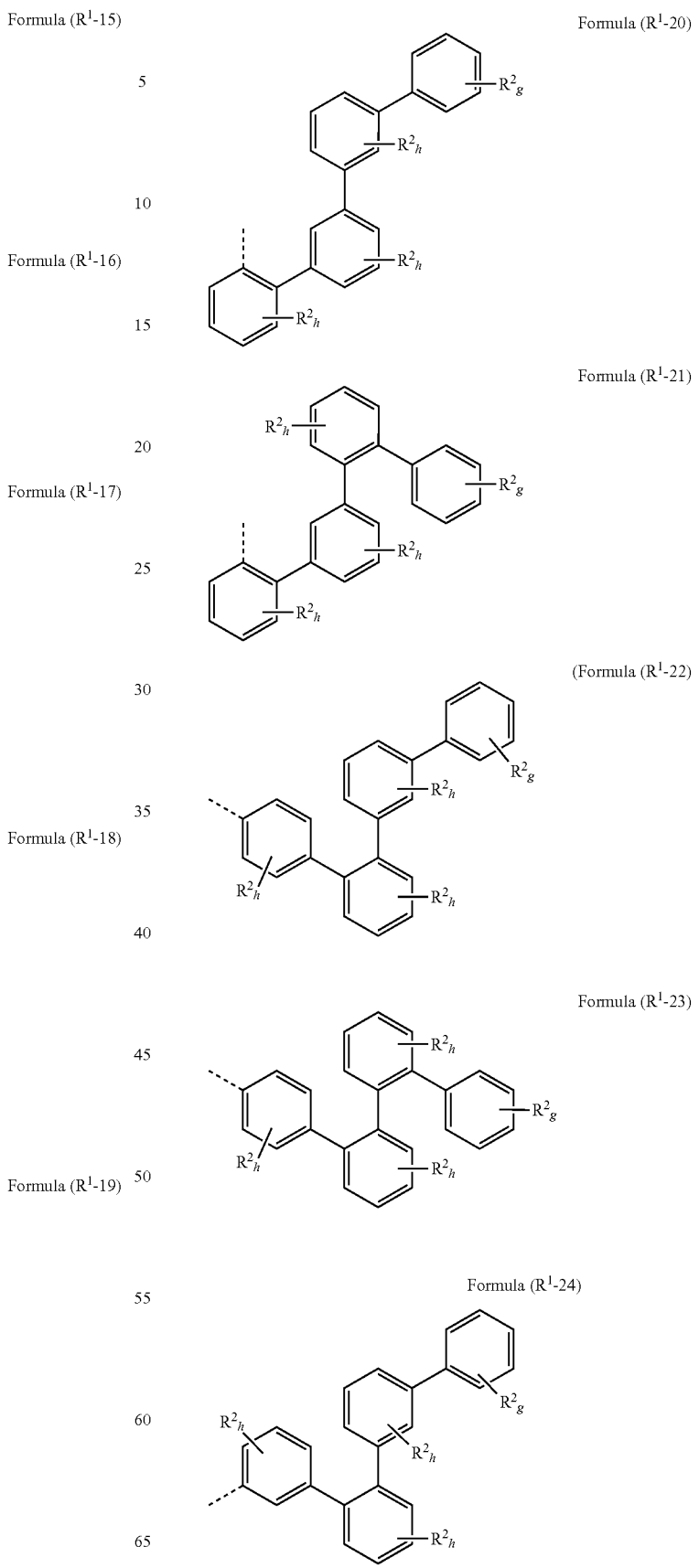

-continued
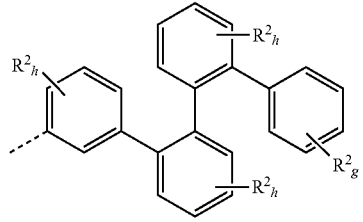
Formula (R¹-25)
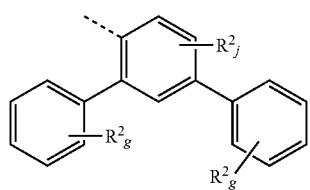
Formula (R¹-26)
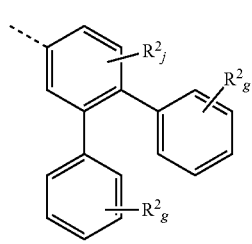
Formula (R¹-27)
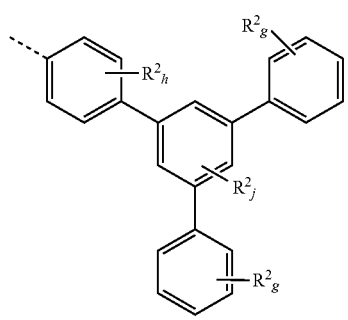
Formula (R¹-28)
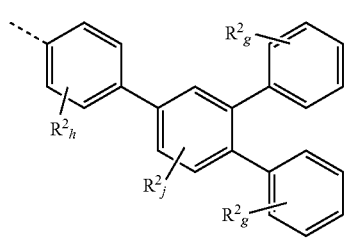
Formula (R¹-29)
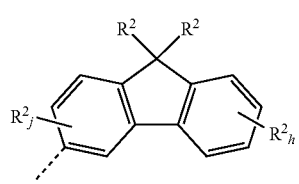
Formula (R¹-30)
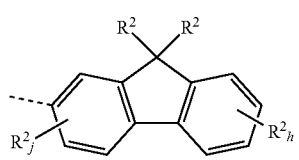
Formula (R¹-31)
-continued
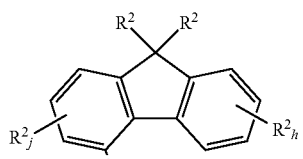
Formula (R¹-32)
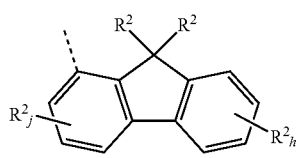
Formula (R¹-33)
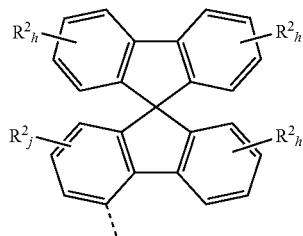
Formula (R¹-34)
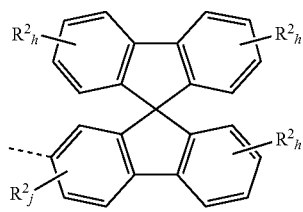
Formula (R¹-35)
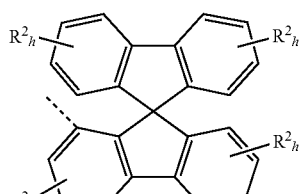
Formula (R¹-36)
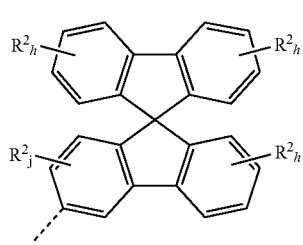
Formula (R¹-37)
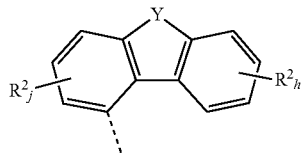
Formula (R¹-38)
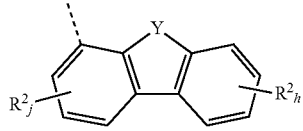
Formula (R¹-39)

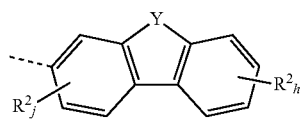 Formula (R¹-40)
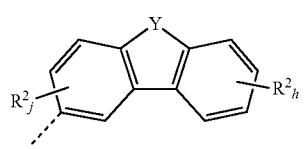 Formula (R¹-41)
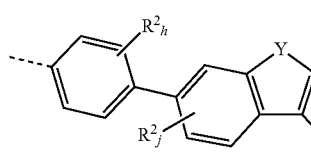 Formula (R¹-42)
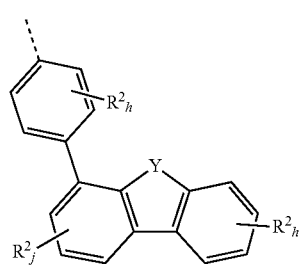 Formula (R¹-43)
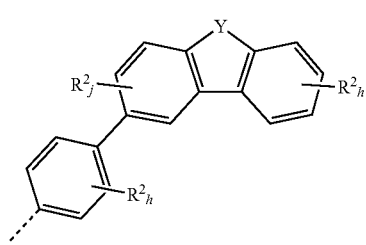 Formula (R¹-44)
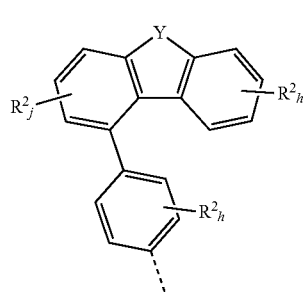 Formula (R¹-45)
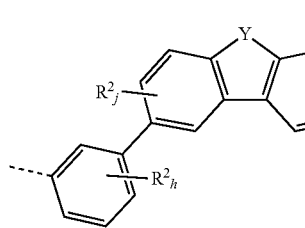 Formula (R¹-46)
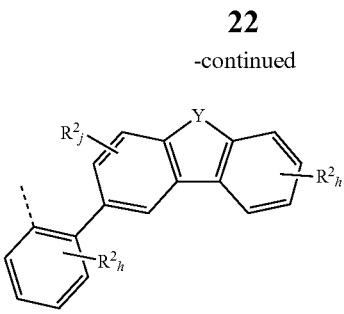 Formula (R¹-47)
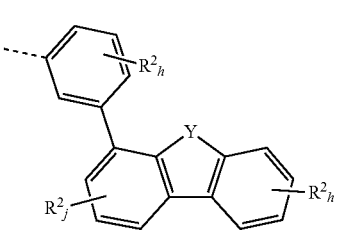 Formula (R¹-48)
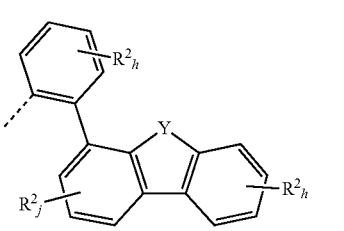 Formula (R¹-49)
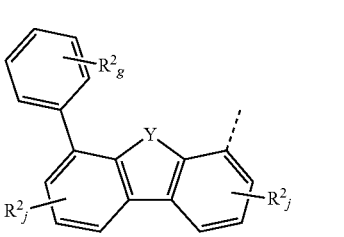 Formula (R¹-50)
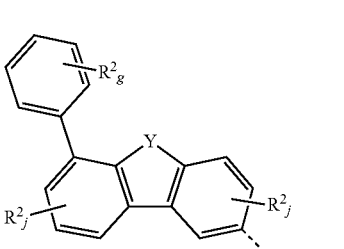 Formula (R¹-51)
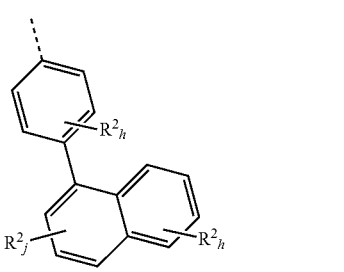 Formula (R¹-52)

Formula (R¹-53)
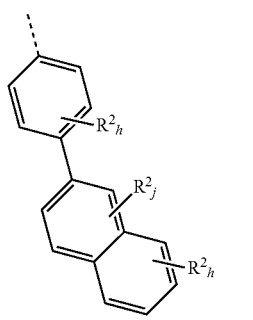
Formula (R¹-54)
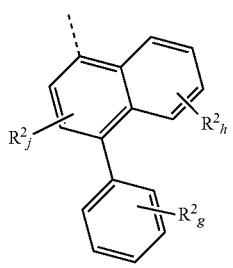
Formula (R¹-55)
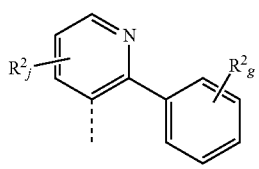
Formula (R1-56)
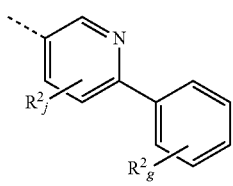
Formula (R1-57)
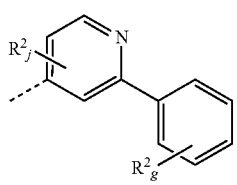
Formula (R1-58)
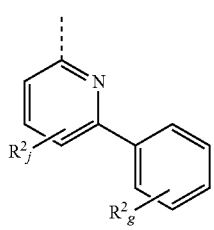
Formula (R1-59)
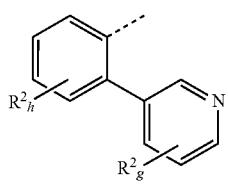
Formula (R1-60)
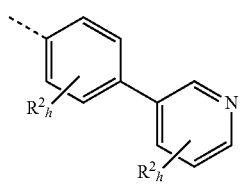
Formula (R¹-61)
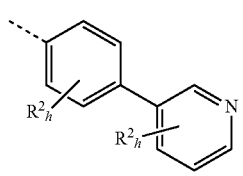
Formula (R¹-62)
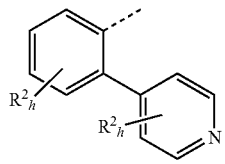
Formula (R¹-63)
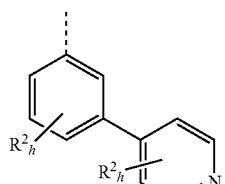
Formula (R¹-64)
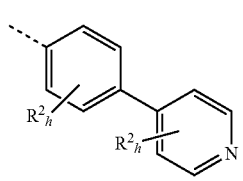
Formula (R¹-65)
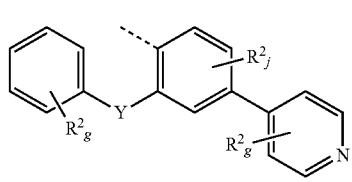
(Formula R¹-66)
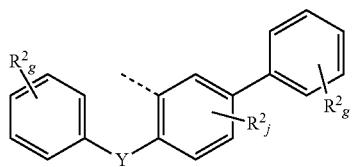
Formula (R¹-67)
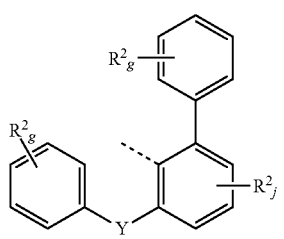

Formula (R¹-68)

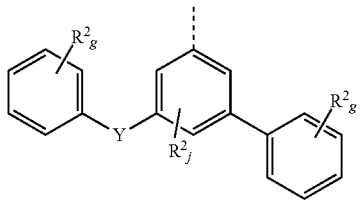

Formula (R¹-69)

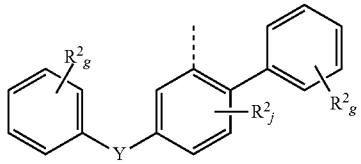

Formula (R¹-70)

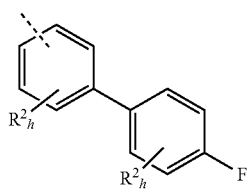

Formula (R¹-71)

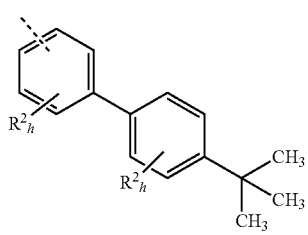

Formula (R¹-72)

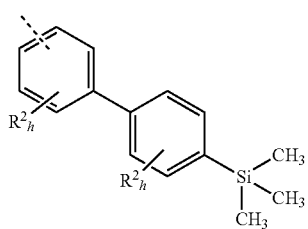

Formula (R¹-73)

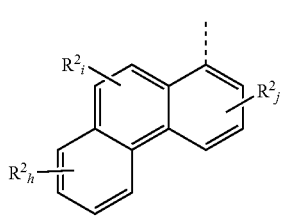

Formula (R¹-74)

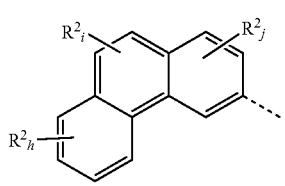

Formula (R¹-75)

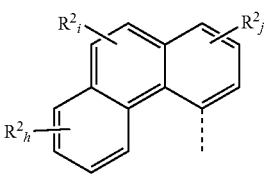

Formula (R¹-76)

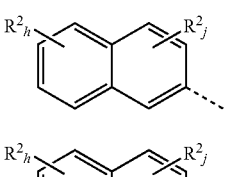

Formula (R¹-77)

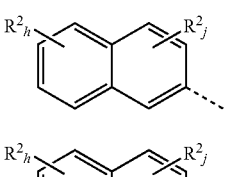

Formula (R¹-78)

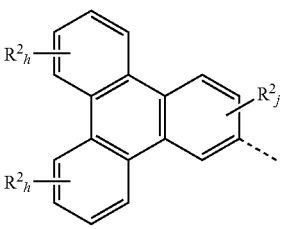

Formula (R¹-79)

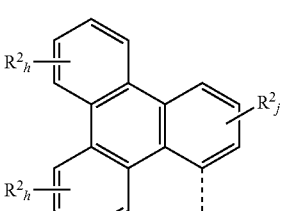

where the symbols used are as follows:
Y is O, S or NR², preferably O or S;
i at each instance is independently 0, 1 or 2;
j independently at each instance is 0, 1, 2 or 3;
h independently at each instance is 0, 1, 2, 3 or 4;
g independently at each instance is 0, 1, 2, 3, 4 or 5;
$R^2$ may have the definition given above, especially for formula (I) and/or (II), and
the dotted bond marks the attachment position.

It may preferably be the case that the sum total of the indices i, j, h and g in the structures of the formula (R¹-1) to (R¹-79) is not more than 3 in each case, preferably not more than 2 and more preferably not more than 1.

Preferably, the $L^1$ group may form through-conjugation with the electron-transporting Q group and the fluorene structure of the formula (I), (II), (III), (IV), (Ia), (IIa), (IIIa), (IVa), (Ib), (IIb), (IIIb) and/or (IVb). Through-conjugation of the aromatic or heteroaromatic systems is formed as soon as direct bonds are formed between adjacent aromatic or heteroaromatic rings. A further bond between the aforementioned conjugated groups, for example via a sulphur, nitrogen or oxygen atom or a carbonyl group, is not detrimental to conjugation. In the case of a fluorene system, the two aromatic rings are bonded directly, where the sp³-hybridized carbon atom in position 9 does prevent fusion of these rings, but conjugation is possible, since this sp³-hybridized carbon atom in position 9 does not necessarily lie between the electron-transporting Q group and the fluorene structure. In contrast, in the case of a spirobifluorene structure, through-conjugation can be formed if the bond between the electron-transporting Q group and the fluorene structure of the formula (I), (II), (III), (IV), (Ia), (IIa), (IIIa), (IVa), (Ib), (IIb), (IIIb) and/or (IVb) is via the same phenyl group in the spirobifluorene structure or via phenyl groups in the spirobifluorene structure that are bonded directly to one another and are in one plane. If the bond between the electron-transporting Q group and the fluorene structure of the formula (I), (II), (III), (IV), (Ia), (IIa), (IIIa), (IVa), (Ib), (IIb), (IIIb) and/or (IVb) is via different phenyl groups of the spirobifluorene structure which are bonded via the sp$^3$-hybridized carbon atom in position 9, the conjugation is interrupted.

In a further preferred embodiment of the invention, $L^1$ is the same or different at each instance and is a single bond or an aromatic or heteroaromatic ring system which has 5 to 24 aromatic ring atoms and may be substituted by one or more $R^2$ radicals. More preferably, $L^1$ is the same or different at each instance and is a single bond or an aromatic ring system having 6 to 12 aromatic ring atoms or a heteroaromatic ring system having 6 to 13 aromatic ring atoms, each of which may be substituted by one or more $R^2$ radicals, but is preferably unsubstituted, where $R^2$ may have the definition given above, especially for formula (I) and/or (II). Further preferably, the symbol $L^1$ is the same or different at each instance and is a single bond or an aryl or heteroaryl radical, such that an aromatic or heteroaromatic group of an aromatic or heteroaromatic ring system is bonded directly, i.e. via an atom in the aromatic or heteroaromatic group, to the respective atom in the other group. More preferably, $L^1$ is a single bond. Examples of suitable aromatic or heteroaromatic ring systems $L^1$ are selected from the group consisting of ortho-, meta- or para-phenylene, biphenyl, fluorene, pyridine, pyrimidine, triazine, dibenzofuran and dibenzothiophene, each of which may be substituted by one or more $R^2$ radicals, but are preferably unsubstituted.

Preference is given to compounds comprising structures of the formulae (I), (II), (III), (IV), (Ia), (IIa), (IIIa), (IVa), (Ib), (IIb), (IIIb) and/or (IVb) in which the $L^1$ group of formula (I), (II), (III), (IV), (Ia), (IIa), (IIIa), (IVa), (Ib), (IIb), (IIIb) and/or (IVb) is a bond or a group selected from the formulae (L-1) to (L-70)

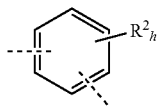

Formula (L-1)

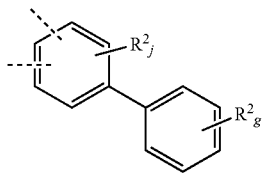

Formula (L-2)

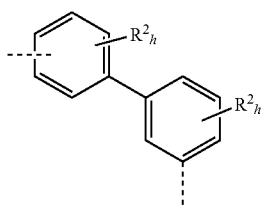

Formula (L-3)

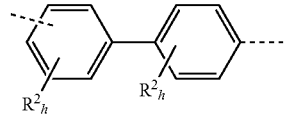

Formula (L-4)

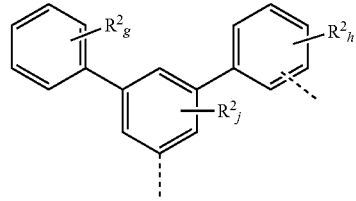

Formula (L-5)

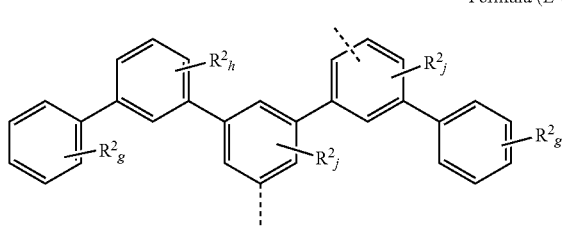

Formula (L-6)

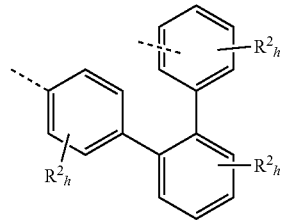

Formula (L-7)

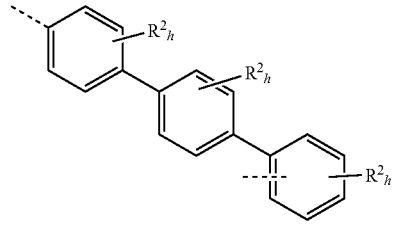

Formula (L-8)

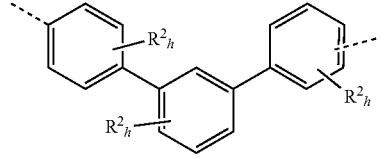

Formula (L-9)

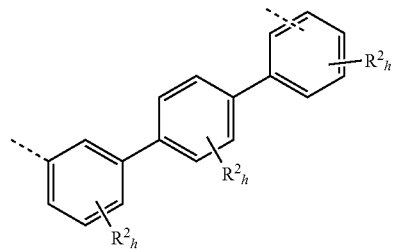

Formula (L-10)

Formula (L-11)
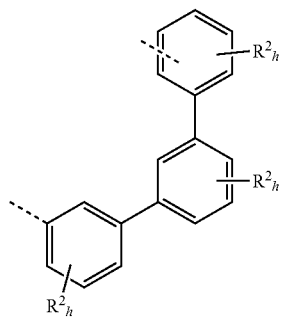
Formula (L-12)
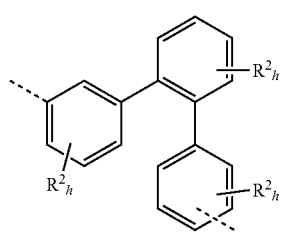
Formula (L-13)
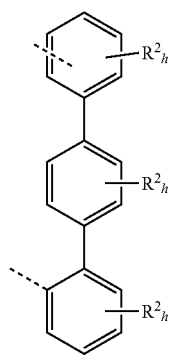
Formula (L-14)
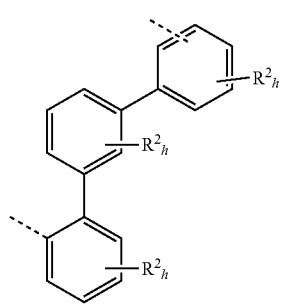
Formula (L-15)
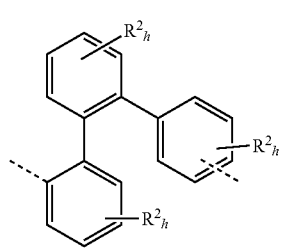
Formula (L-16)
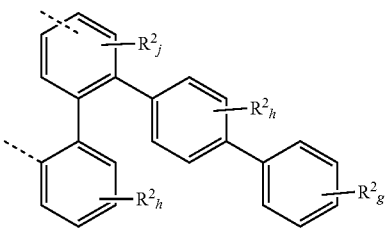
Formula (L-17)
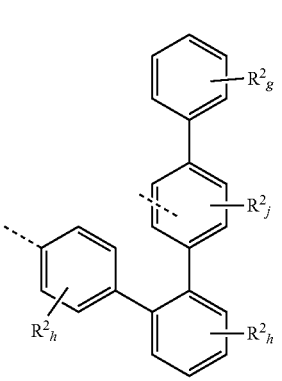
Formula (L-18)
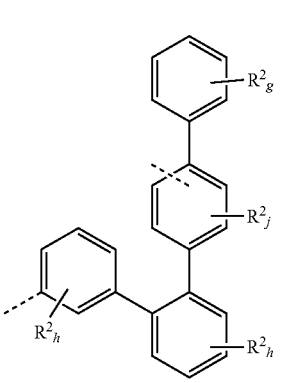
Formula (L-19)
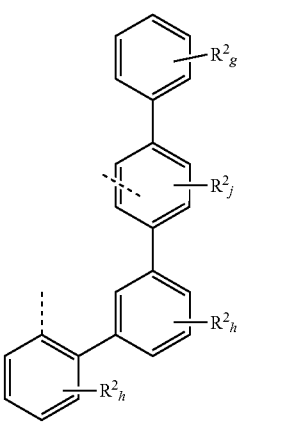

Formula (L-20)
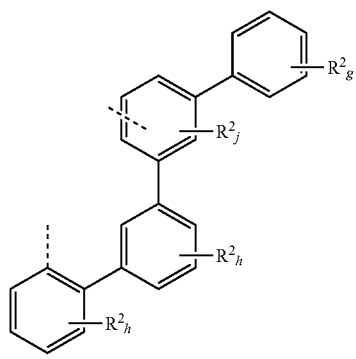
Formula (L-21)
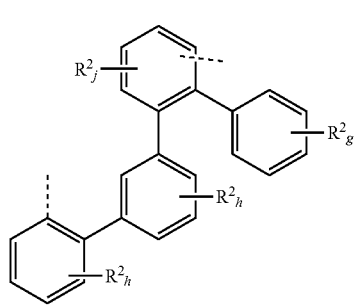
Formula (L-22)
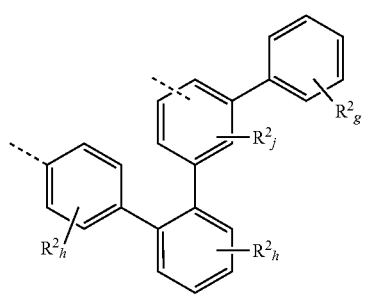
Formula (L-23)
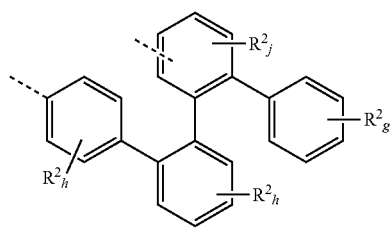
Formula (L-24)
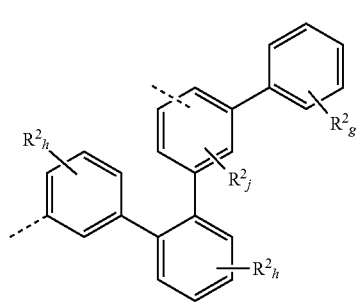
Formula (L-25)
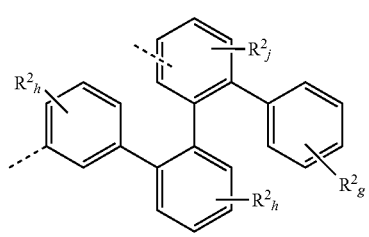
Formula (L-26)
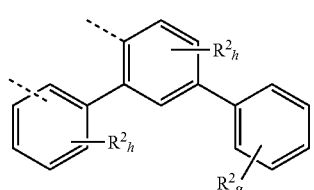
Formula (L-27)
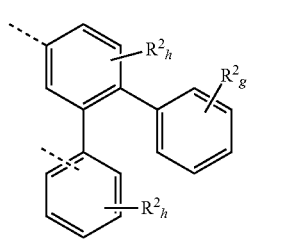
Formula (L-28)
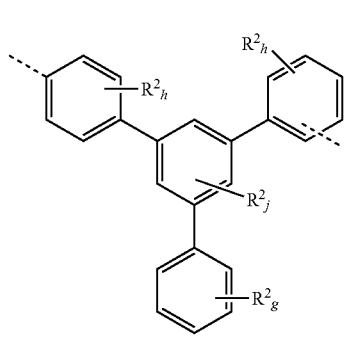
Formula (L-29)
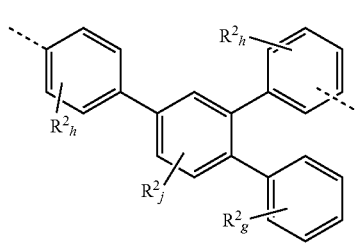
Formula (L-30)
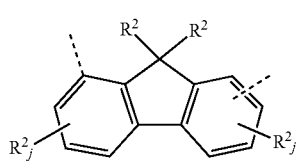
Formula (L-31)
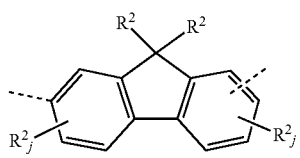

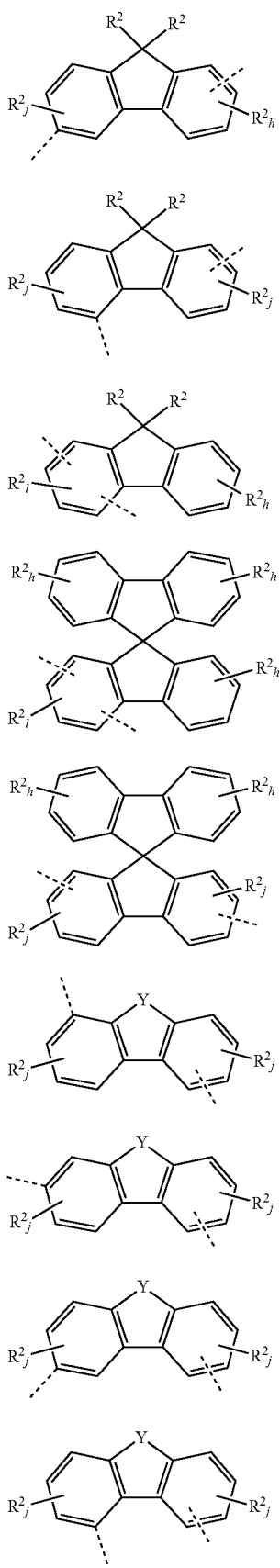
Formula (L-32)
Formula (L-33)
Formula (L-34)
Formula (L-35)
Formula (L-36)
Formula (L-37)
Formula (L-38)
Formula (L-39)
Formula (L-40)
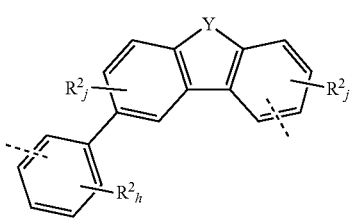
Formula (L-41)
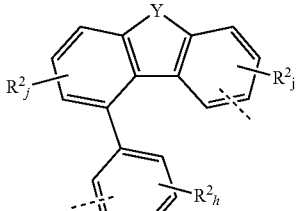
Formula (L-42)
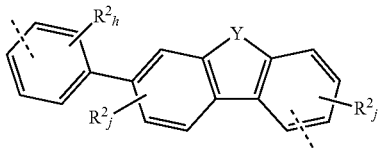
Formula (L-43)
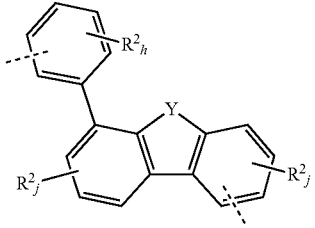
Formula (L-44)
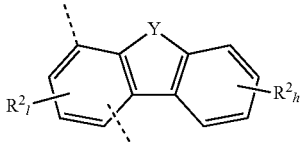
Formula (L-45)
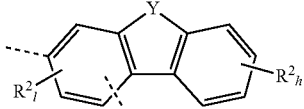
Formula (L-46)
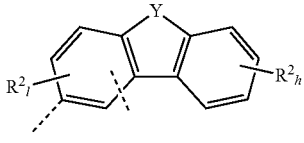
Formula (L-47)
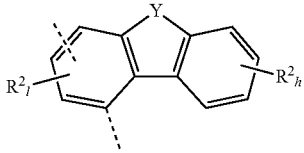
Formula (L-48)

Formula (L-49)
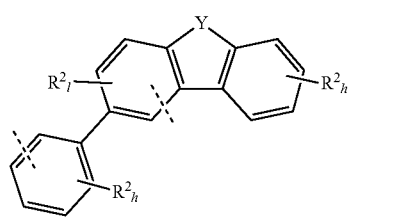
Formula (L-50)
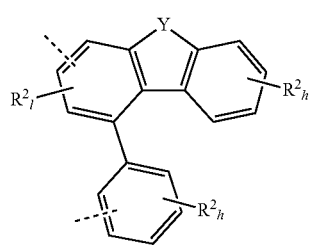
Formula (L-51)
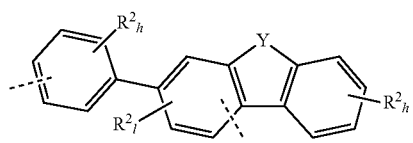
Formula (L-52)
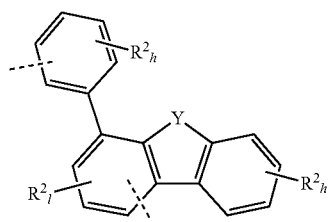
Formula (L-53)
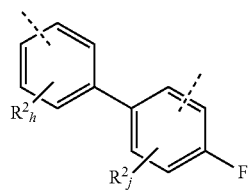
Formula (L-54)
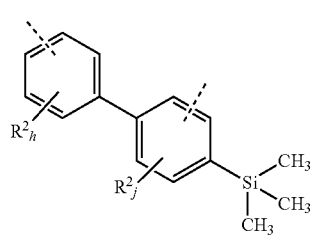
Formula (L-55)
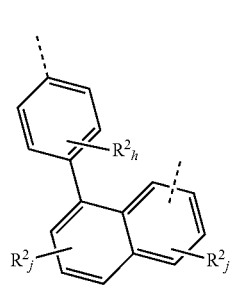
Formula (L-56)
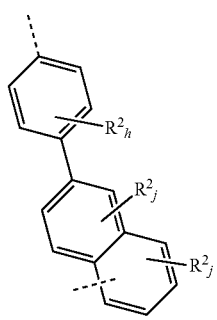
Formula (L-57)
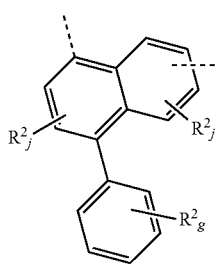
Formula (L-58)
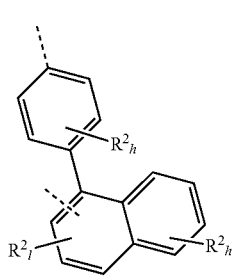
Formula (L-59)
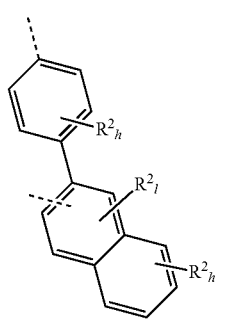
Formula (L-60)
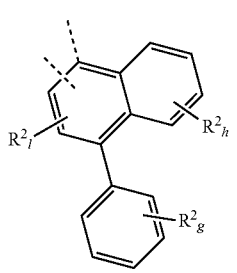
Formula (L-61)
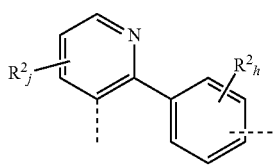

Formula (L-62)
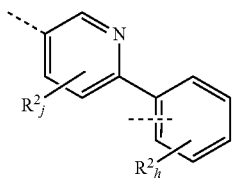

Formula (L-63)
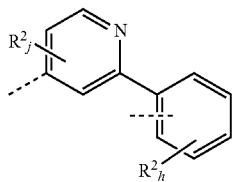

Formula (L-64)
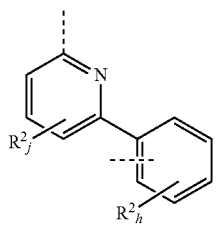

Formula (L-65)
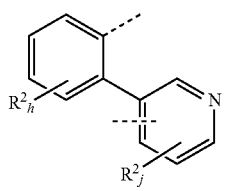

Formula (L-66)
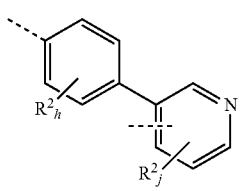

Formula (L-67)
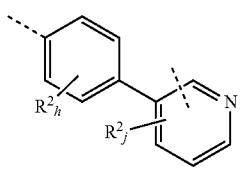

Formula (L-68)
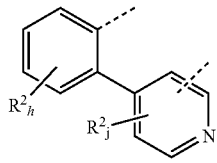

Formula (L-69)
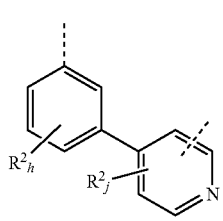

Formula (L-70)
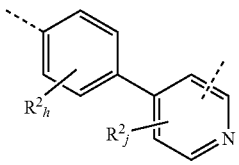

where the dotted bonds in each case mark the attachment positions, the index l is 0, 1 or 2, the index g is 0, 1, 2, 3, 4 or 5, j independently at each instance is 0, 1, 2 or 3; h independently at each instance is 0, 1, 2, 3 or 4; Y is O, S or $NR^2$, preferably O or S; and $R^2$ has the definition given above, especially for formula (I) and/or (II).

It may preferably be the case that the sum total of the indices l, g, h and j in the structures of the formula (L-1) to (L-70) is at most 3 in each case, preferably at most 2 and more preferably at most 1.

In a further embodiment, it may be the case that a compound of the invention comprising at least one structure of formula (I), (II), (III), (IV), (Ia), (IIa), (IIIa), (IVa), (Ib), (IIb), (IIIb) and/or (IVb) comprises two or more electron transport groups.

In a particular configuration, a compound of the invention may comprise structures of the following formula (V) and/or formula (VI):

Formula (V)

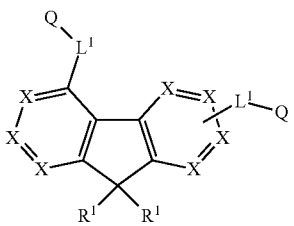

Formula (VI)

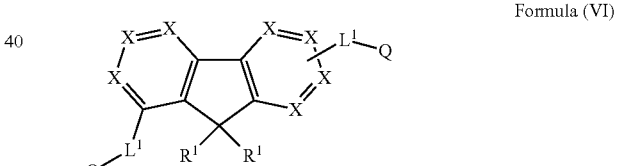

where the symbols X, $L^1$ and Q are the same or different at each instance and have the definition given above, especially for formula (I), and X is the attachment site of the $(-L^1-Q)$ C group.

In a preferred configuration, the compounds of the invention may form a structure of formula (VII) and/or (VIII)

Formula (VII)

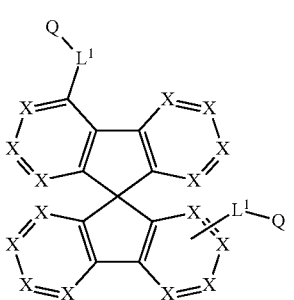

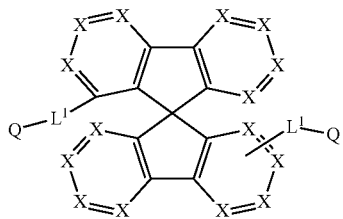

Formula (VIII)

where the symbols X, L¹ and Q are the same or different at each instance and have the definition given above, especially for formula (I), and X is the attachment site of the (-L¹-Q) C group.

Preference is further given to compounds comprising structures of the formulae (Va), (Vb), (VIIa) and (VIIb)

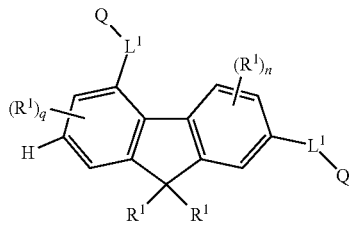

Formula (Va)

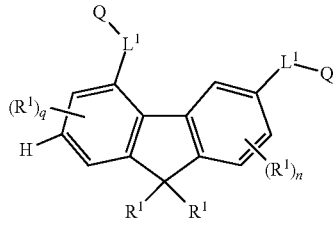

Formula (Vb)

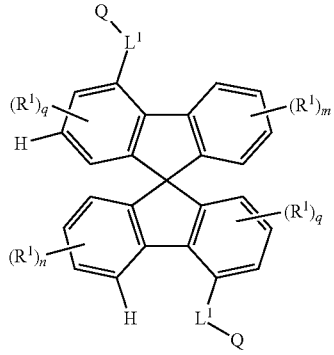

Formula (VIIa)

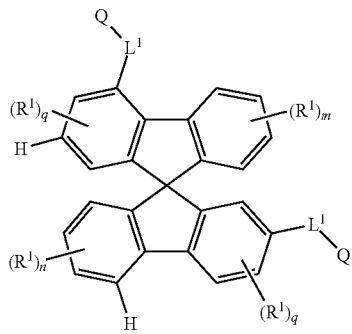

Formula (VIIb)

in which the symbols Q, L¹ and R¹ have the definition set out above, especially for formula (I) and/or (II), m is 0, 1, 2, 3 or 4, preferably 0, 1 or 2, n is 0, 1, 2 or 3, preferably 0, 1 or 2, and q is 0, 1 or 2, preferably 0 or 1.

Advantageously, it may be the case that a compound of the invention comprising at least one structure of formula (I), (II), (III), (IV), (Ia), (IIa), (IIIa), (IVa), (Ib), (IIb), (IIIb) and/or (IVb) does not comprise any carbazole and/or triarylamine group. More preferably, a compound of the invention does not comprise any hole-transporting group. Hole-transporting groups are known in the specialist field, these groups in many cases being carbazole, indenocarbazole, indolocarbazole, arylamine or diarylamine structures.

In a further configuration, it may be the case that a compound of the invention comprising at least one structure of formula (I), (II), (III), (IV), (Ia), (IIa), (IIIa), (IVa), (Ib), (IIb), (IIIb) and/or (IVb) comprises at least one hole-transporting group, preferably a carbazole and/or triarylamine group. In addition, hole-transporting groups provided may also be indenocarbazole, indenocarbazole, arylamine or diarylamine group.

In a further preferred embodiment of the invention, $R^2$, for example in a structure of formula (I) and/or (II) and preferred embodiments of these structures or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system having 5 to 30 aromatic ring atoms, preferably having 5 to 24 aromatic ring atoms, more preferably having 5 to 13 aromatic ring atoms, which may be substituted by one or more alkyl groups each having 1 to 4 carbon atoms, but is preferably unsubstituted.

In a further preferred embodiment of the invention, $R^3$, for example in a structure of formula (I) and/or (II) and preferred embodiments of these structures or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system having 5 to 30 aromatic ring atoms, preferably having 5 to 24 aromatic ring atoms, more preferably having 5 to 13 aromatic ring atoms, which may be substituted by one or more alkyl groups each having 1 to 4 carbon atoms, but is preferably unsubstituted.

When the compound of the invention is substituted by aromatic or heteroaromatic $R^1$ or $R^2$ or $Ar^1$ groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

Examples of suitable compounds of the invention are the structures shown below of the following formulae 1 to 216:
Formula 1
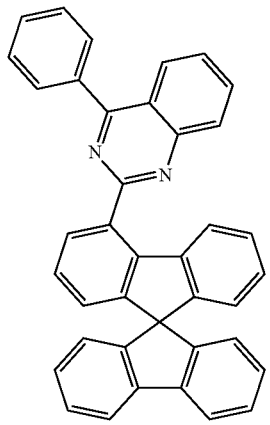
Formula 2
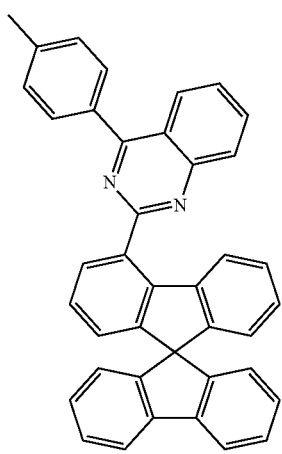
Formula 3
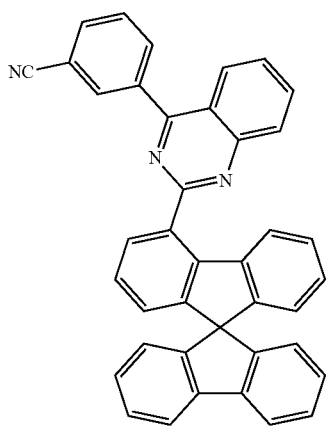
Formula 4
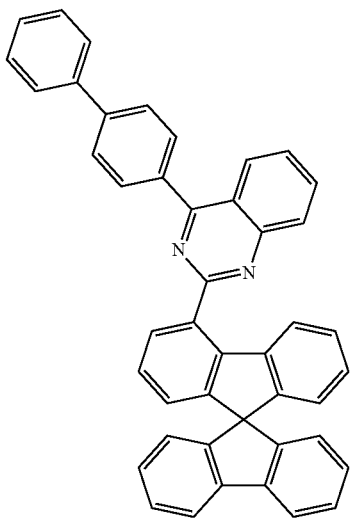
Formula 5
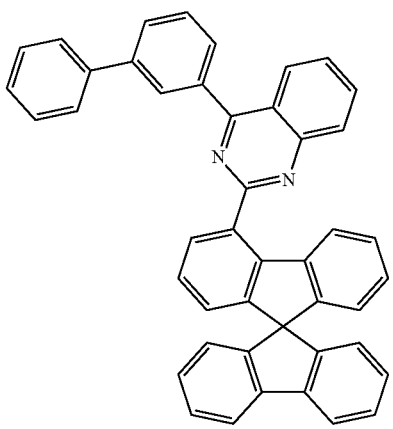
Formula 6
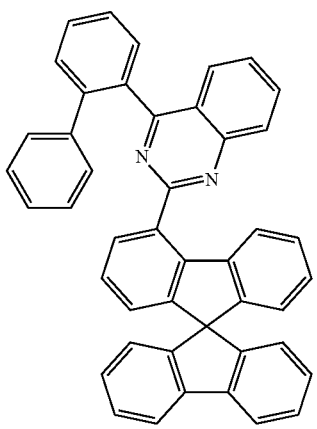

Formula 7
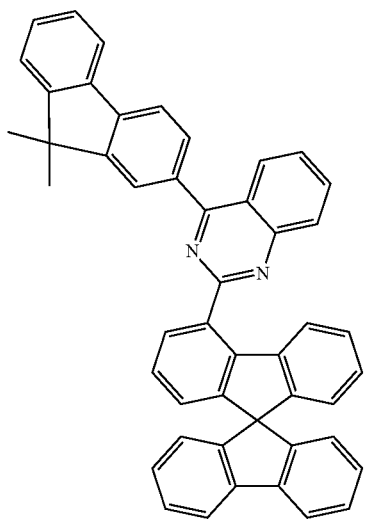
Formula 8
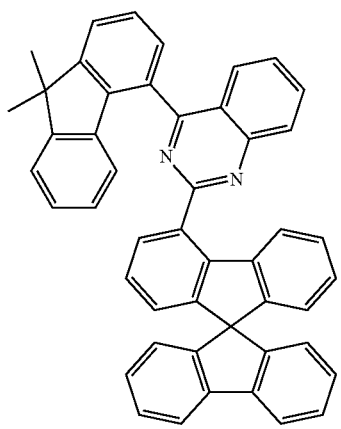
Formula 9
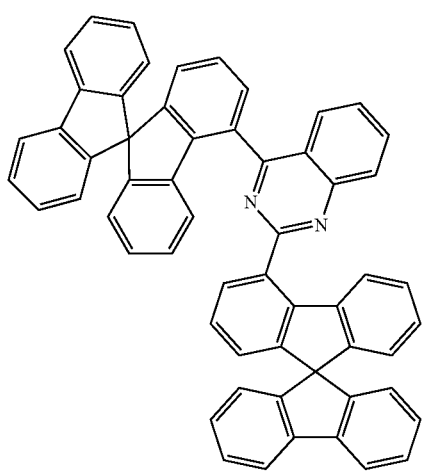
Formula 10
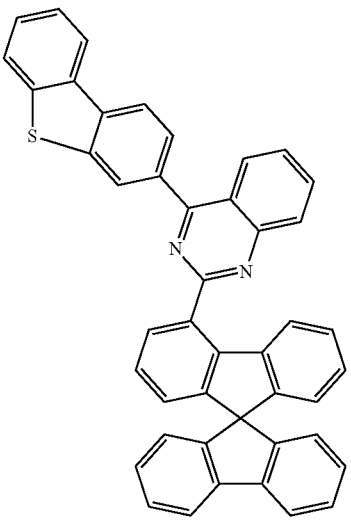
Formula 11
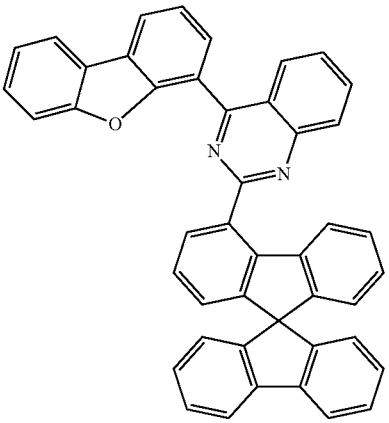
Formula 12
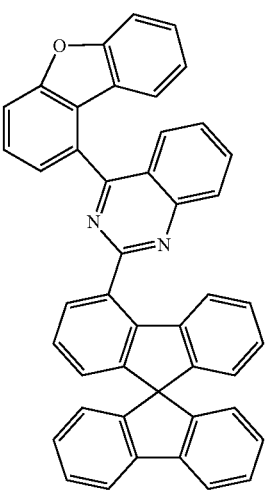

Formula 13
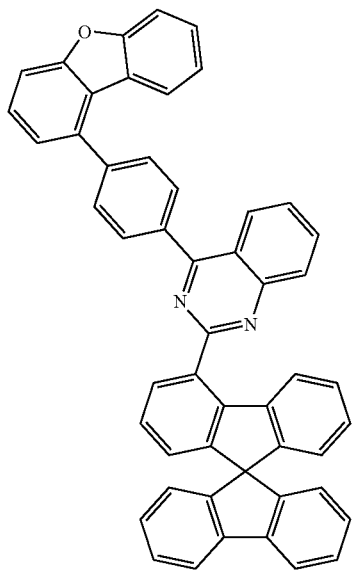
Formula 14
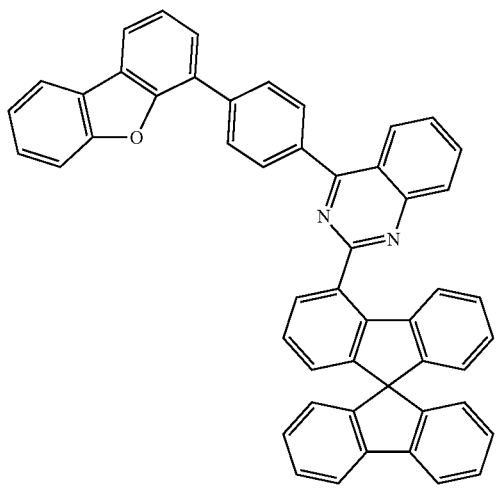
Formula 15
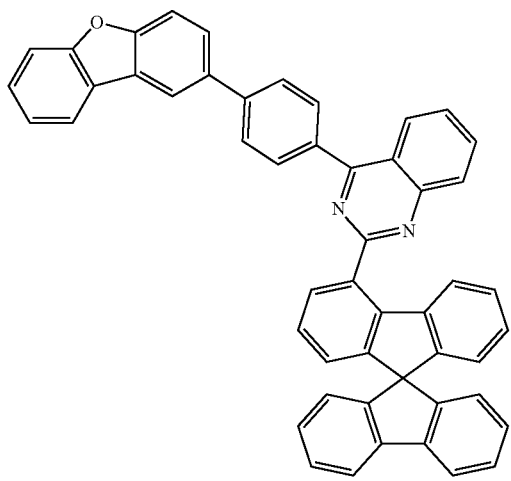
Formula 16
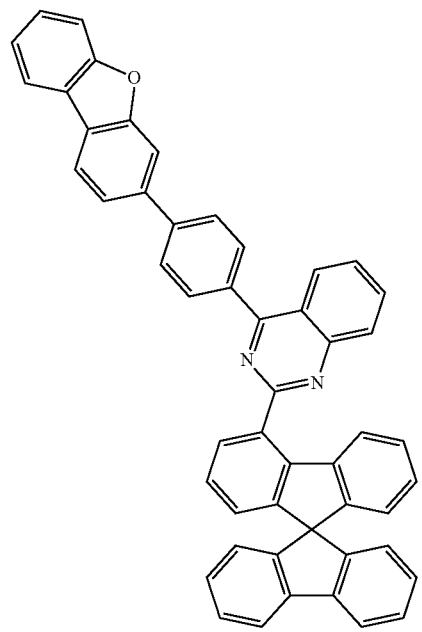
Formula 17
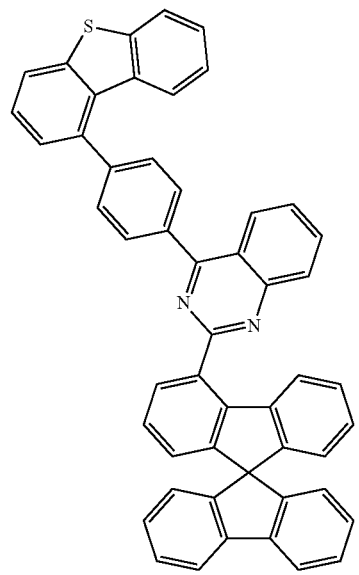

-continued
Formula 18
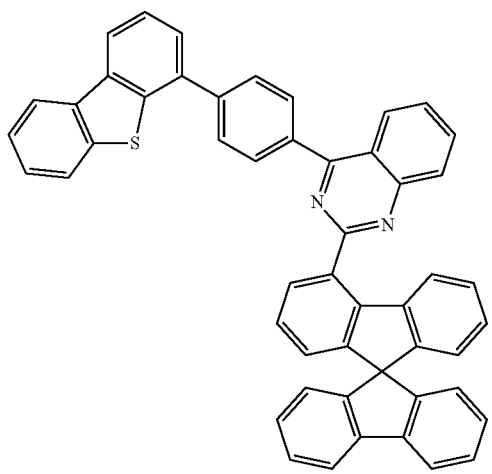
Formula 19
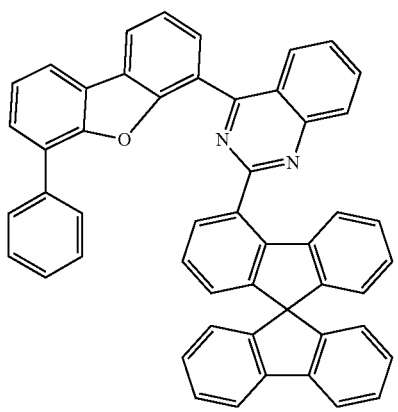
Formula 20
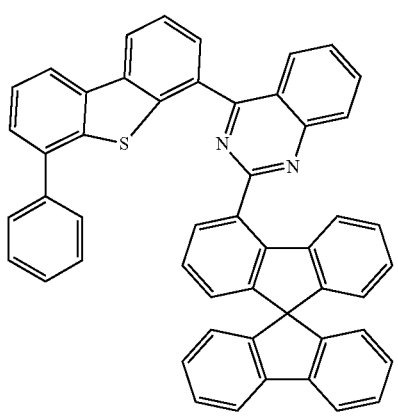
-continued
Formula 21
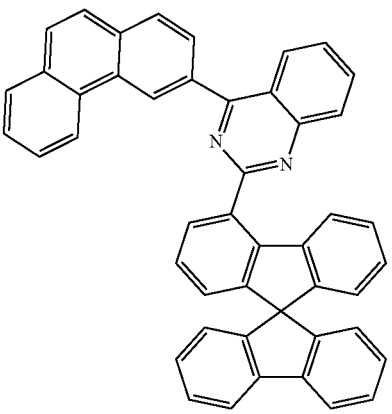
Formula 22
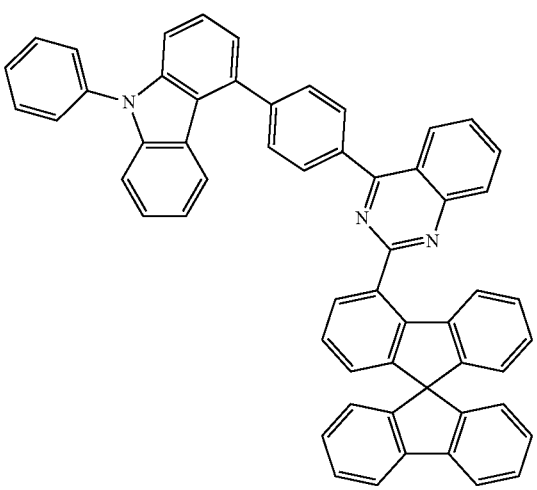
Formula 23
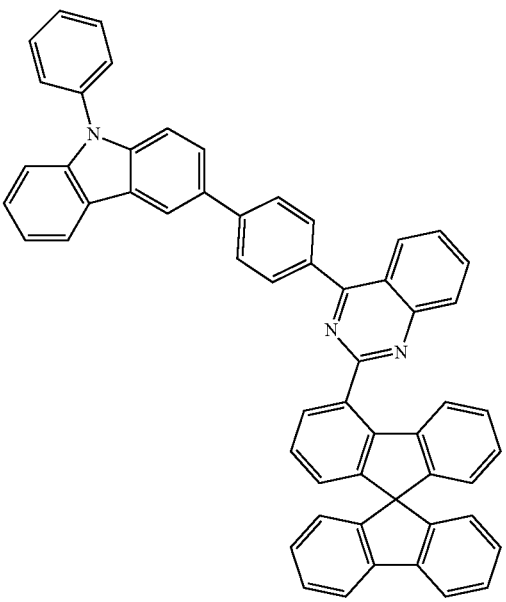

Formula 24
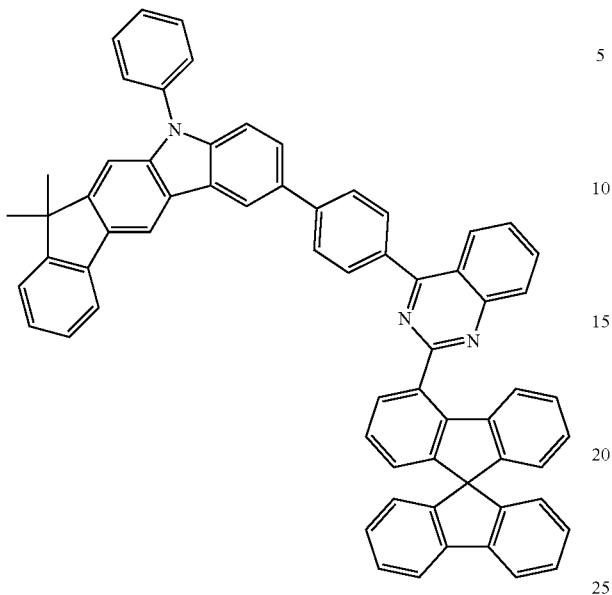
Formula 25
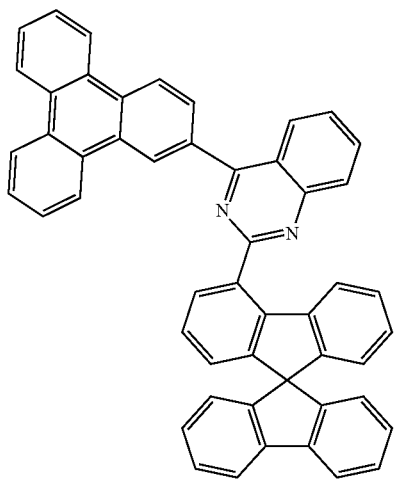
Formula 26
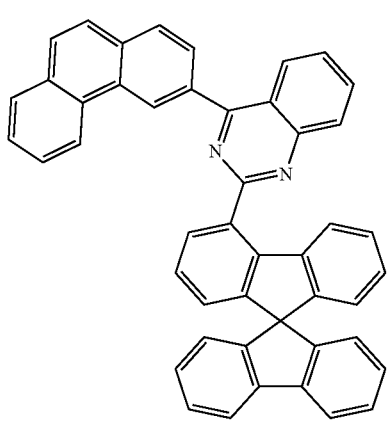
Formula 27
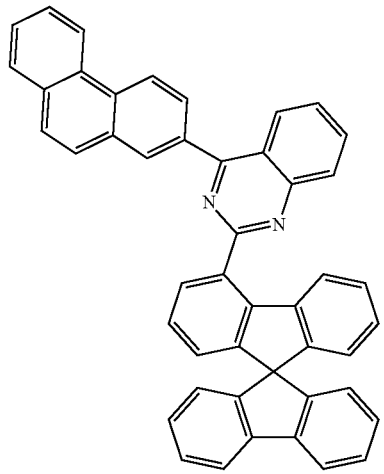
Formula 28
Formula 29

Formula 30
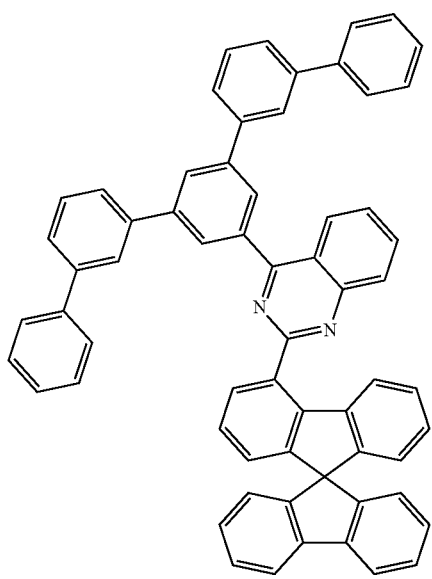
Formula 31
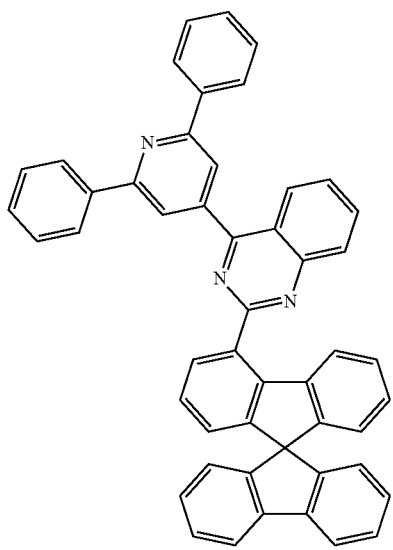
Formula 32
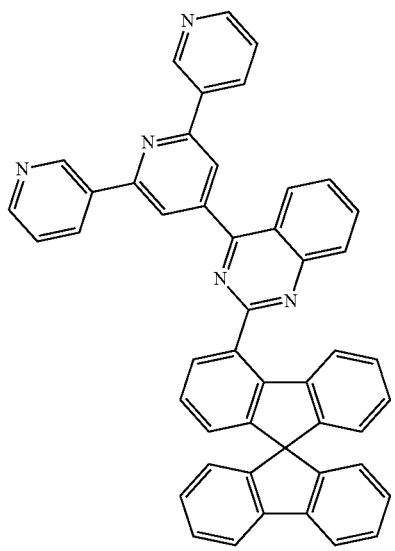
Formula 33
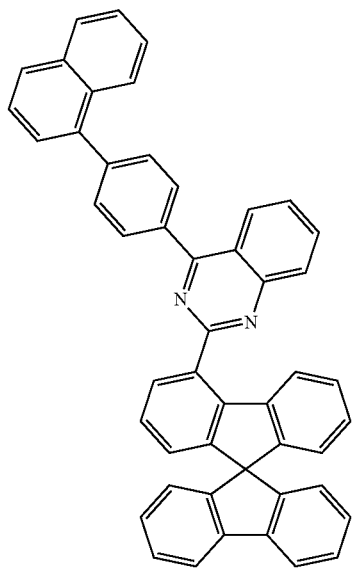

Formula 34
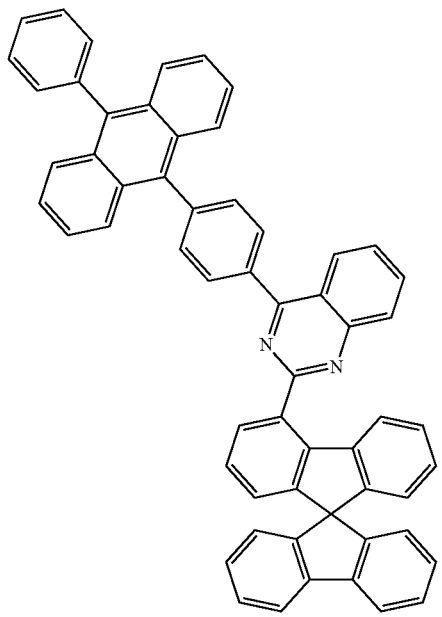
Formula 35
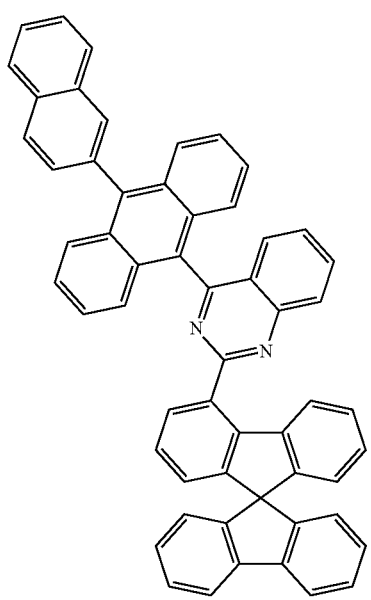
Formula 36
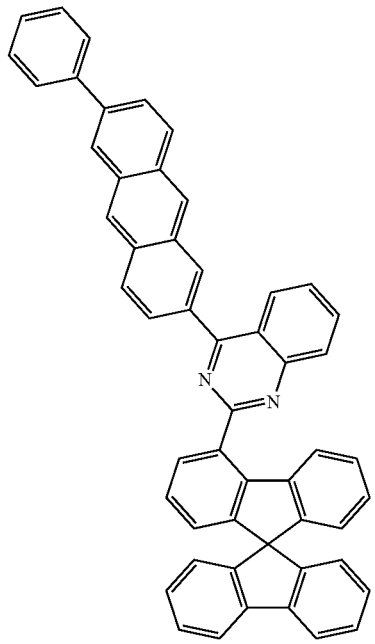
Formula 37
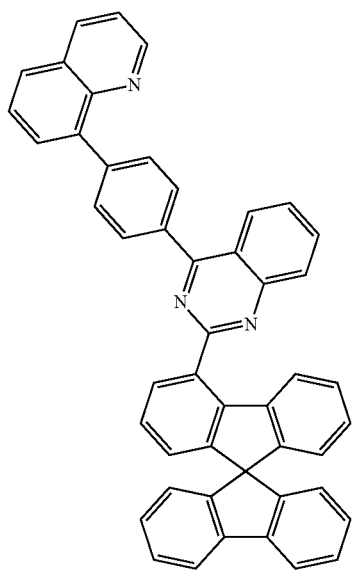

Formula 38
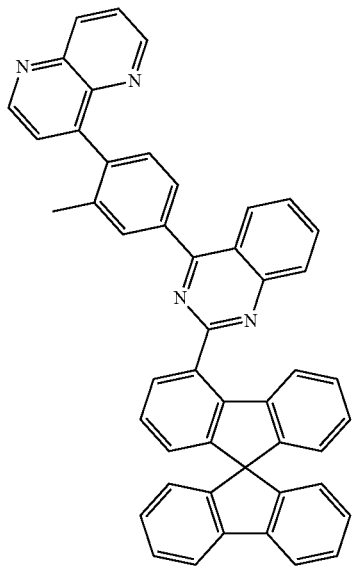
Formula 39
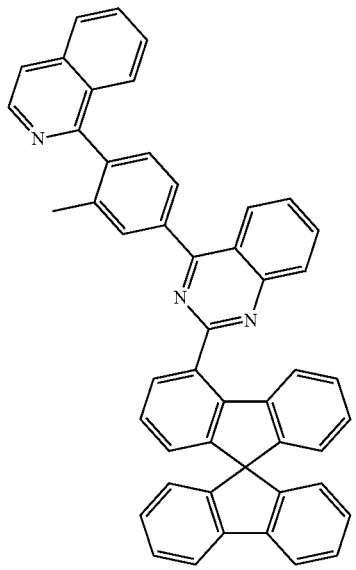
Formula 40
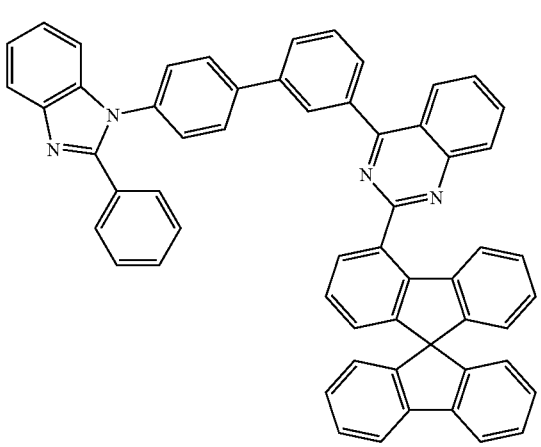
Formula 41
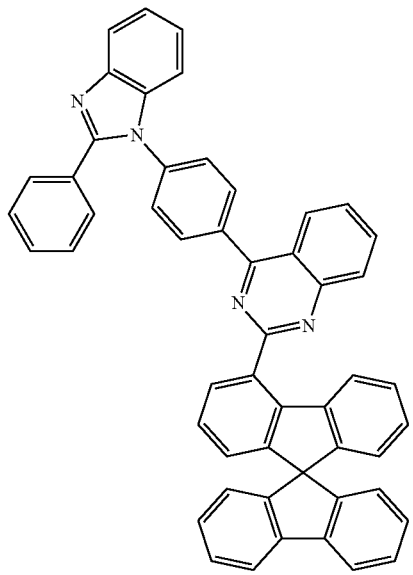
Formula 42
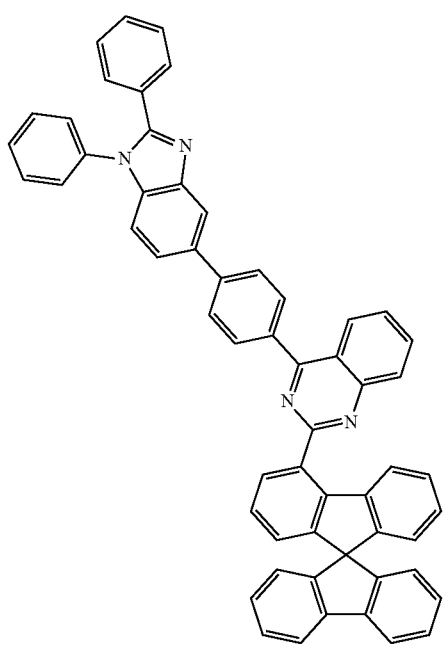

Formula 43
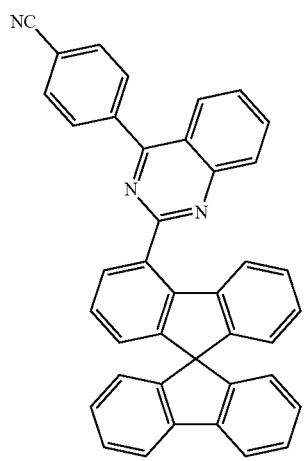
Formula 44
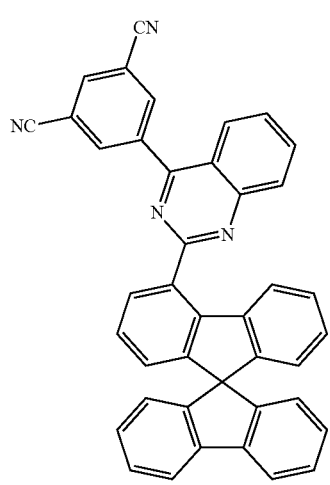
Formula 45
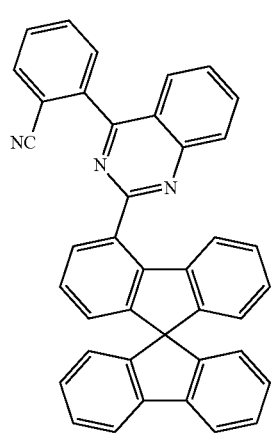
Formula 46
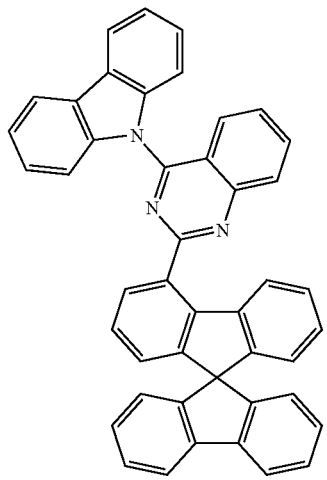
Formula 47
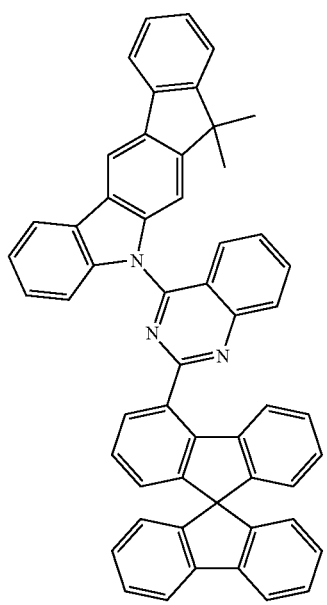

Formula 48
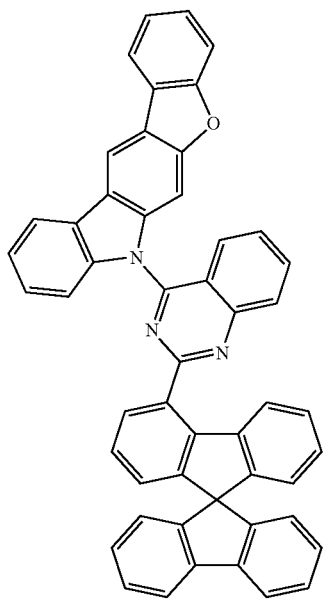
Formula 49
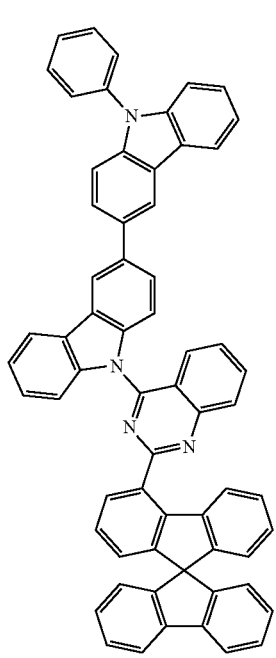
Formula 50
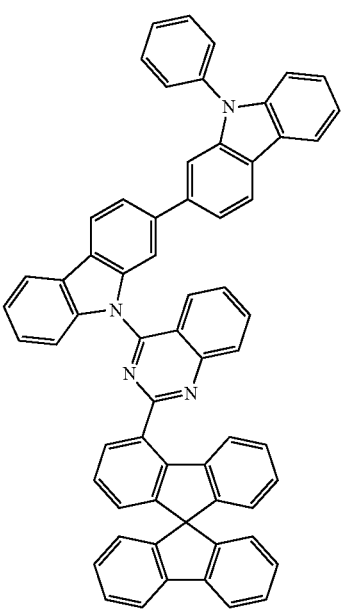
Formula 51
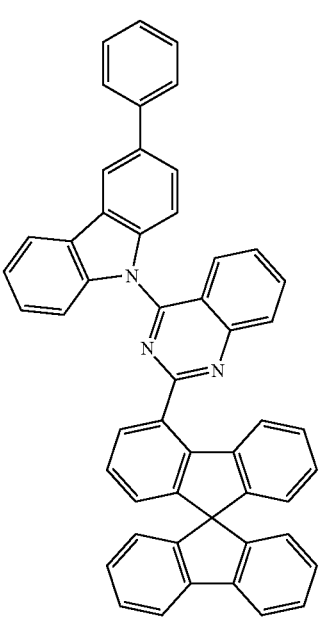

Formula 52
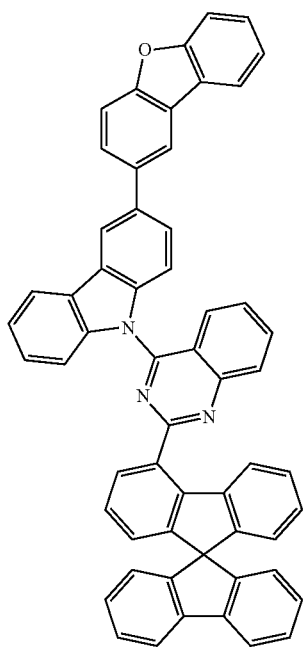
Formula 53
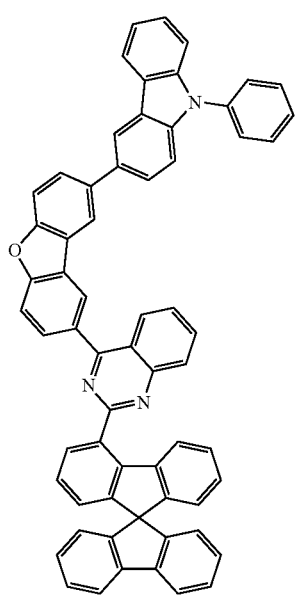
Formula 54
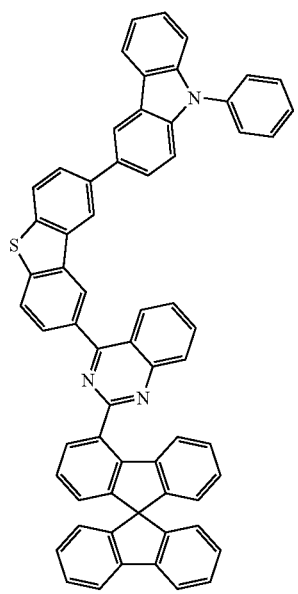
Formula 55
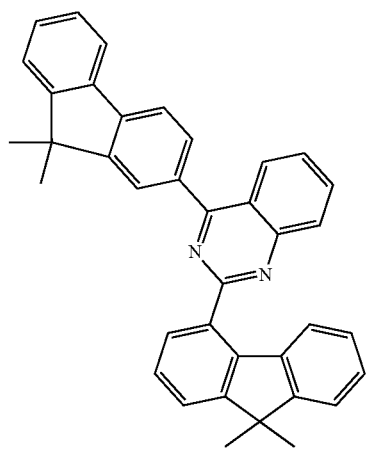
Formula 56
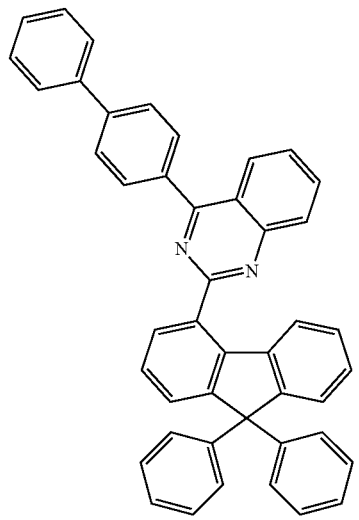

Formula 57
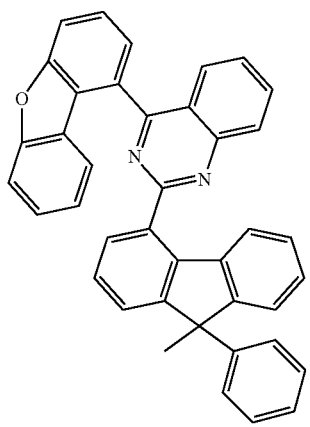
Formula 58
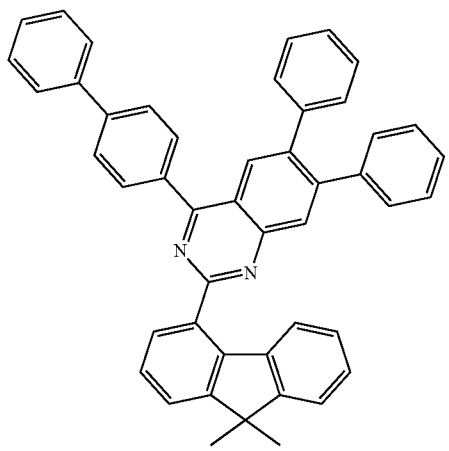
Formula 59
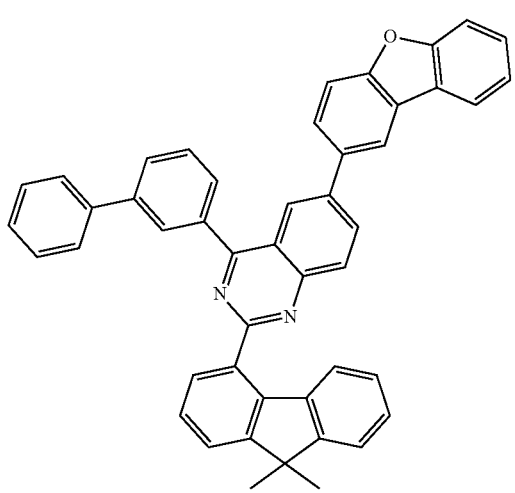
Formula 60
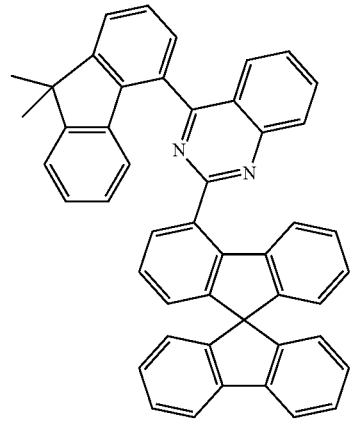
Formula 61
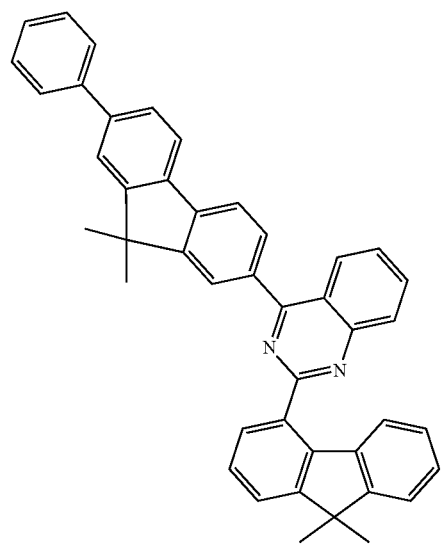
Formula 62
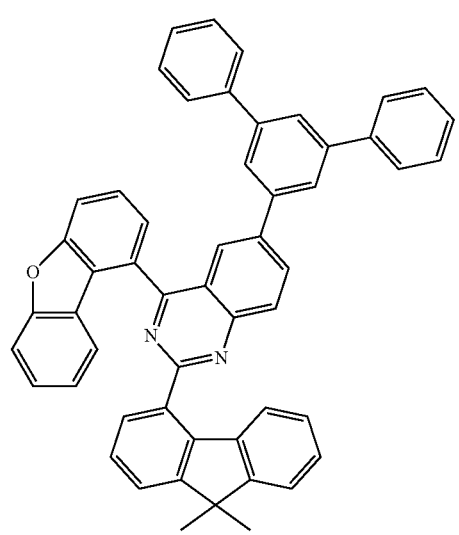

Formula 63
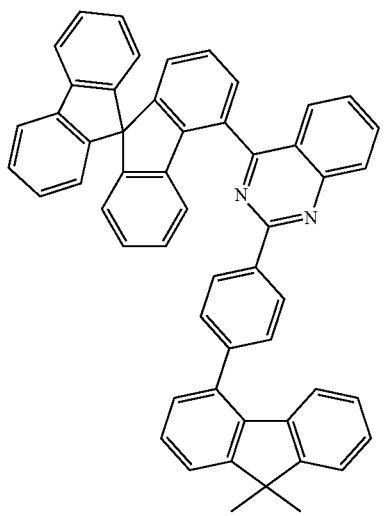
Formula 64
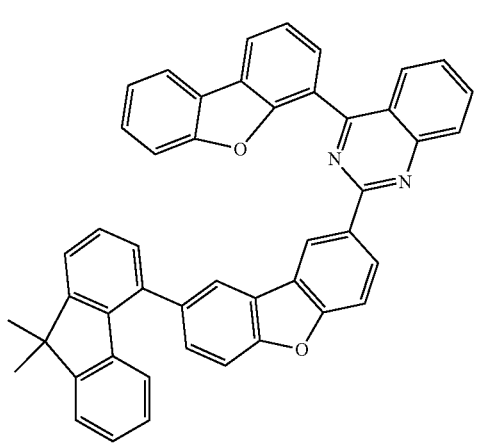
Formula 65
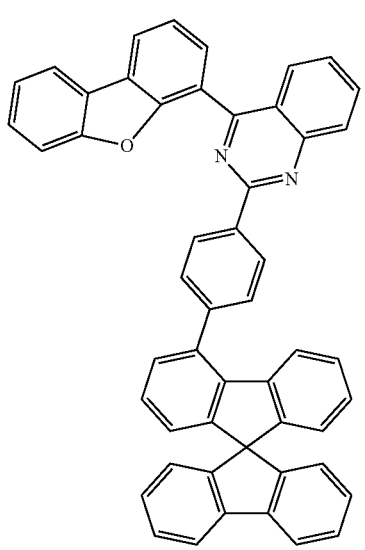
Formula 66
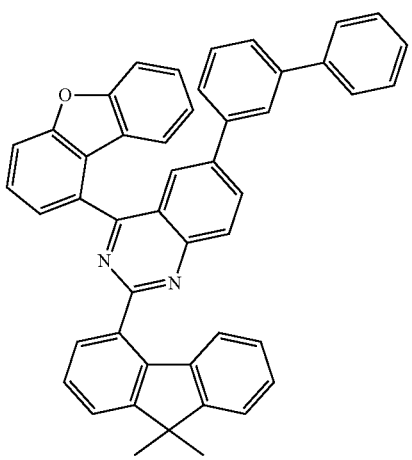
Formula 67
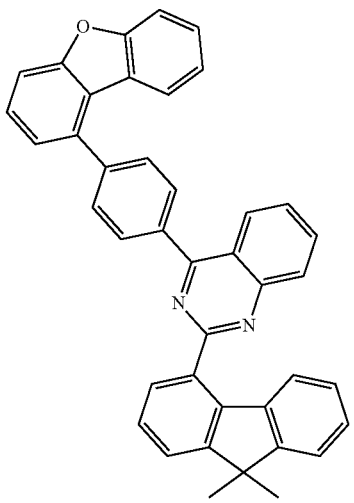
Formula 68
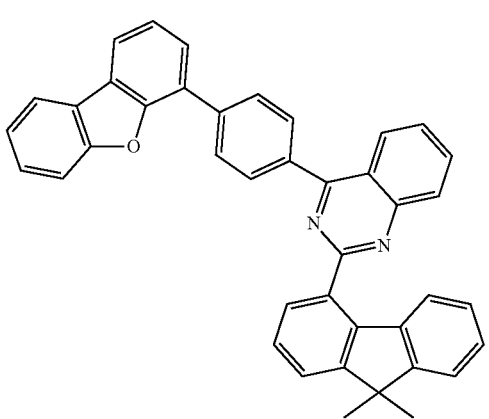

Formula 69
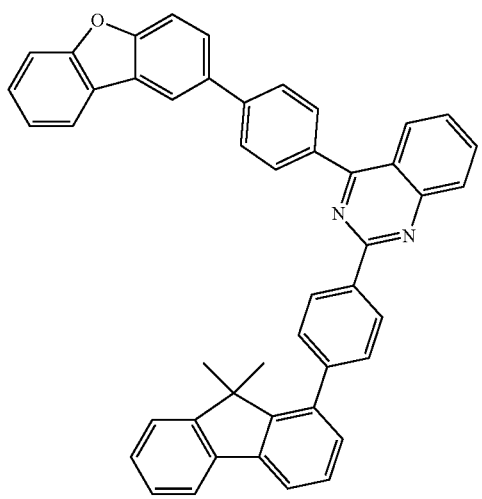
Formula 70
Formula 71
Formula 72
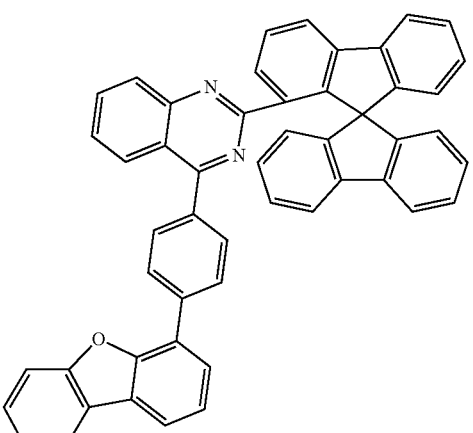
Formula 73
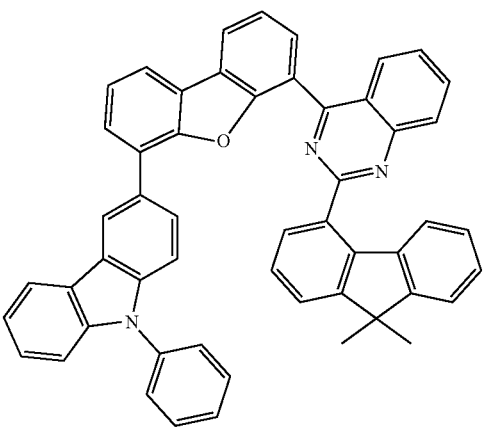
Formula 74
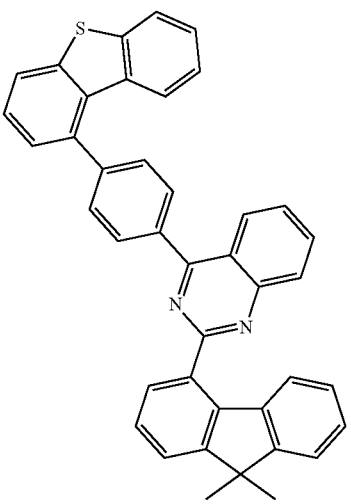

Formula 75
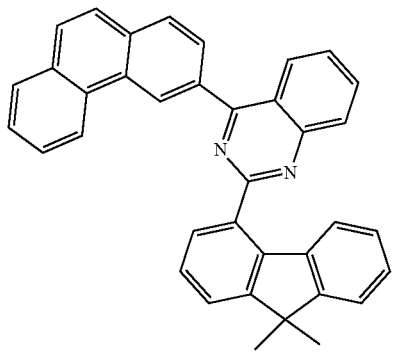
Formula 76
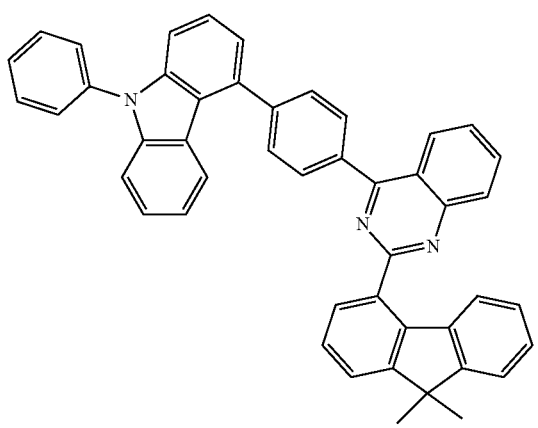
Formula 77
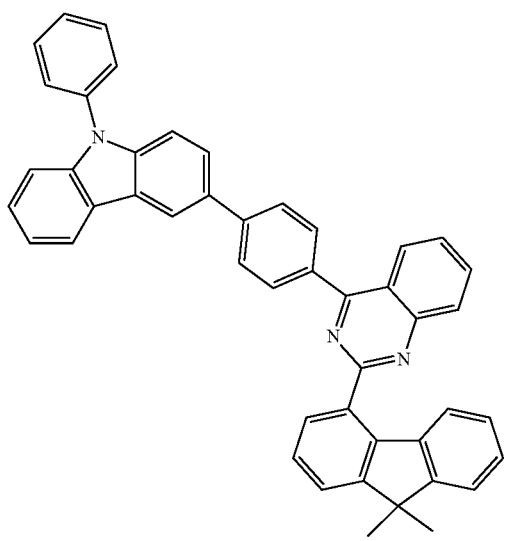
Formula 78
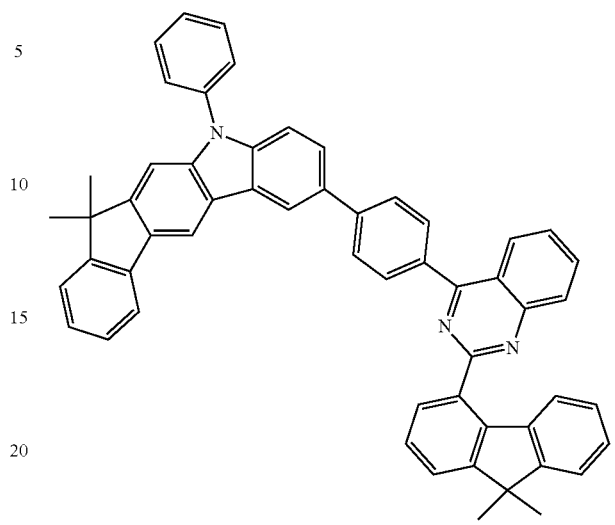
Formula 79
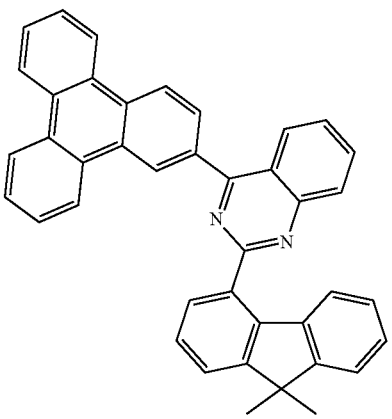
Formula 80
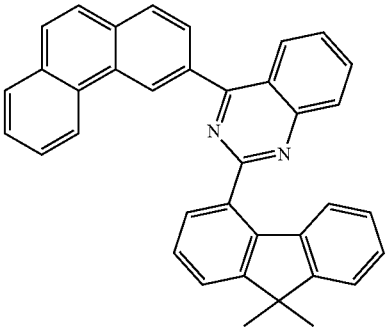

Formula 81
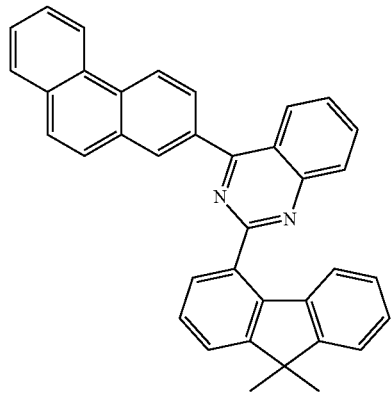
Formula 82
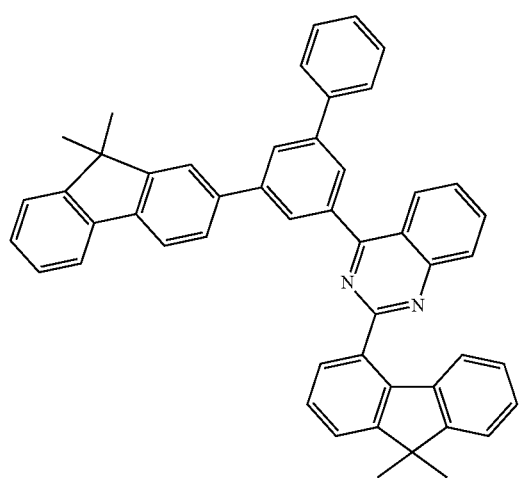
Formula 83
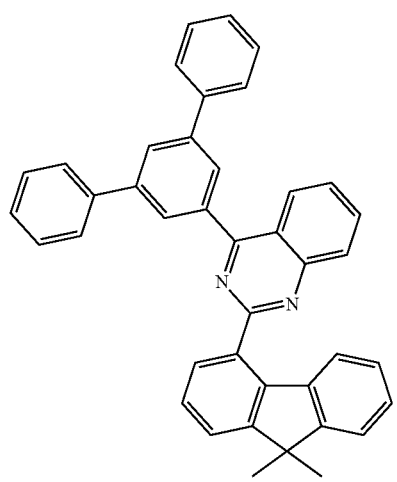
Formula 84
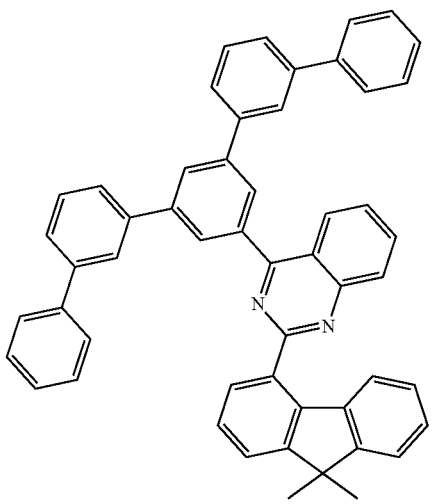
Formula 85
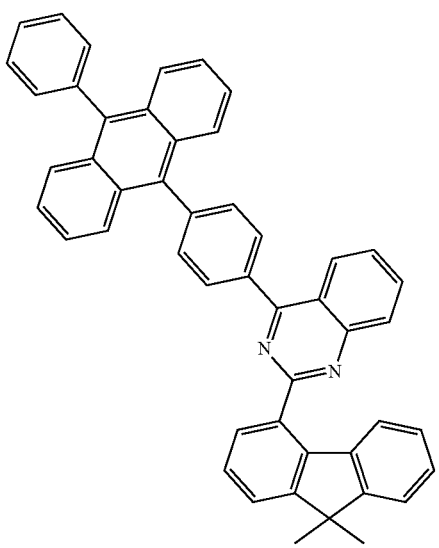
Formula 86
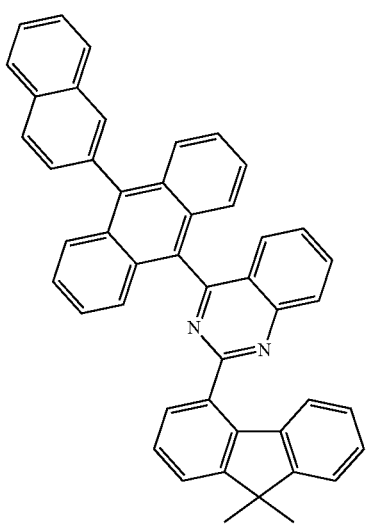

Formula 87
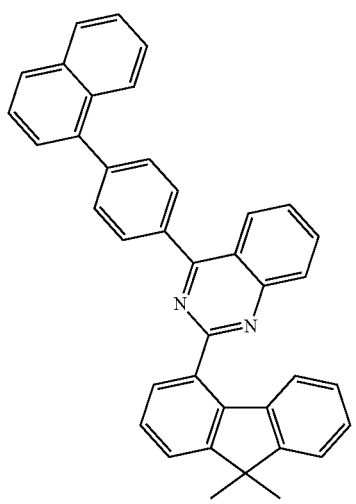
Formula 88
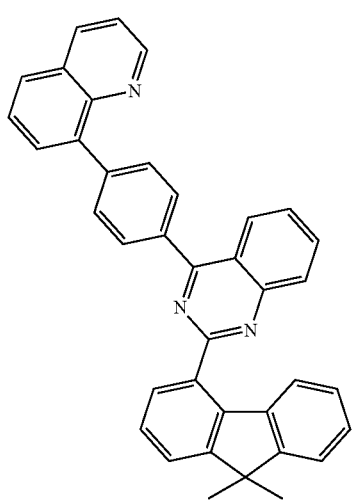
Formula 89
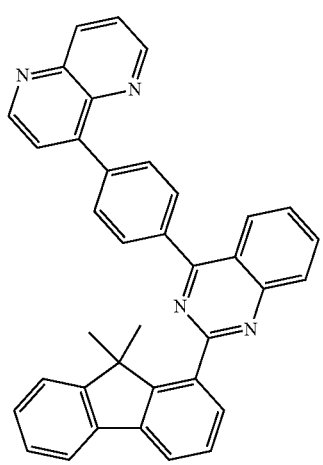
Formula 90
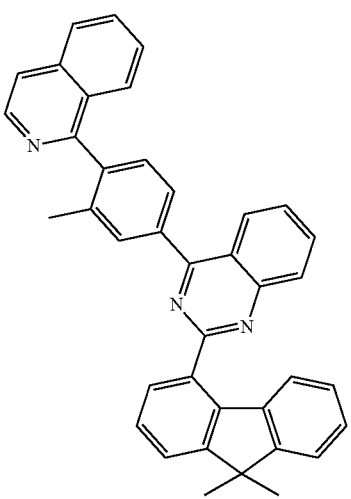
Formula 91
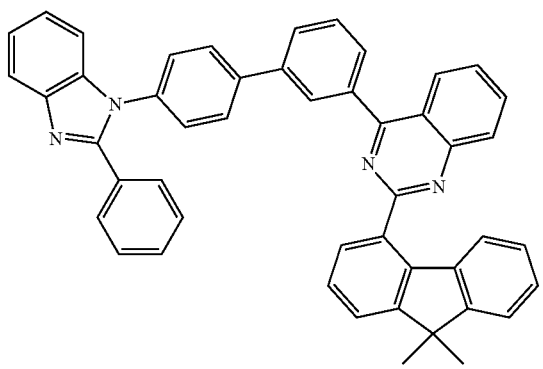
Formula 92
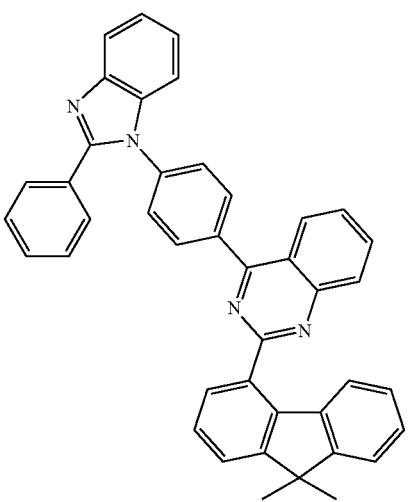

Formula 93

Formula 94

Formula 95

Formula 96

Formula 97

Formula 98

-continued
Formula 99
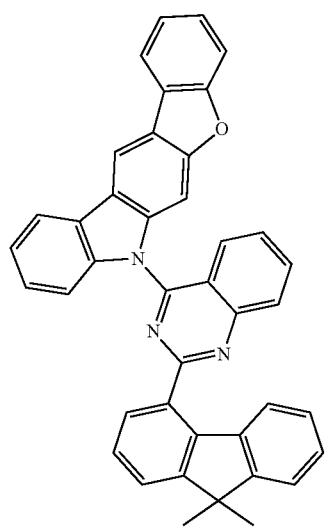
Formula 100
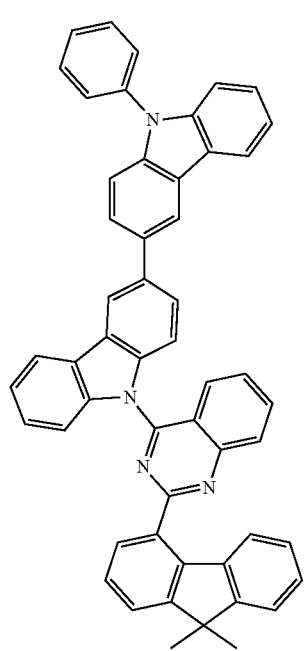
-continued
Formula 101
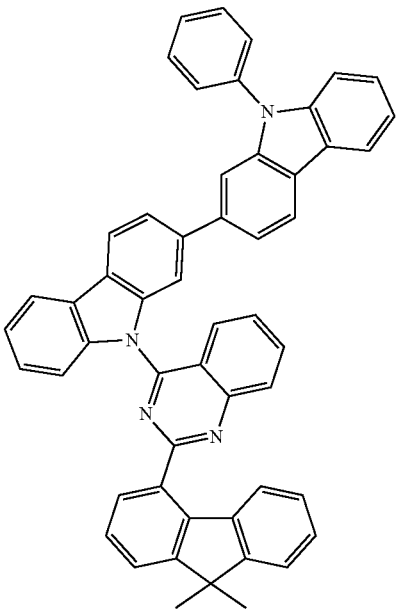
Formula 102

Formula 103
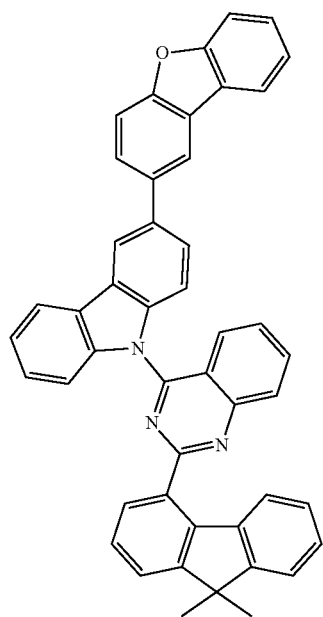
Formula 104
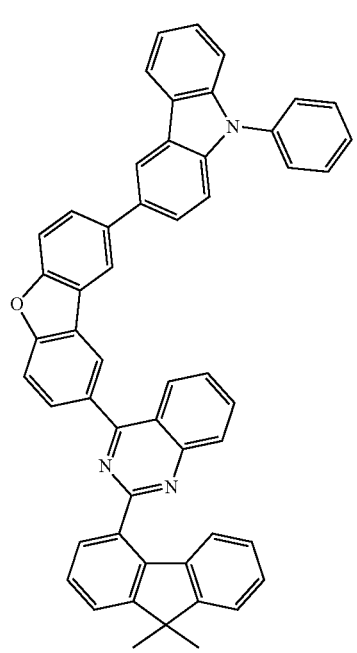
Formula 105
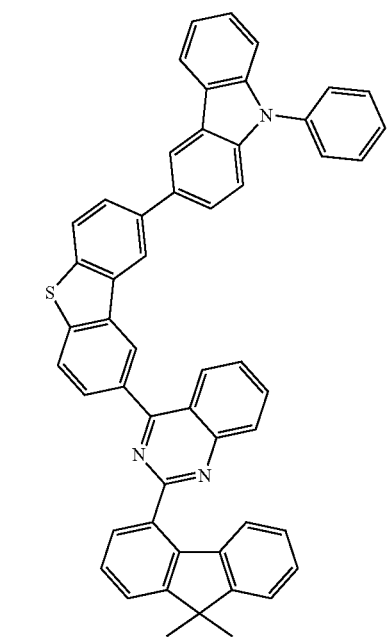
Formula 106
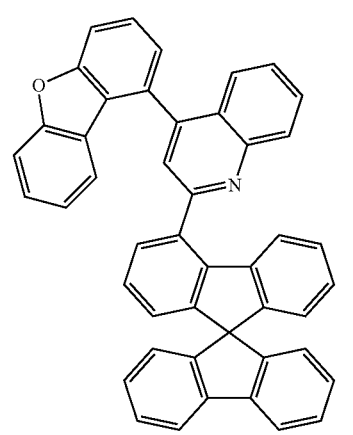
Formula 107

Formula 108
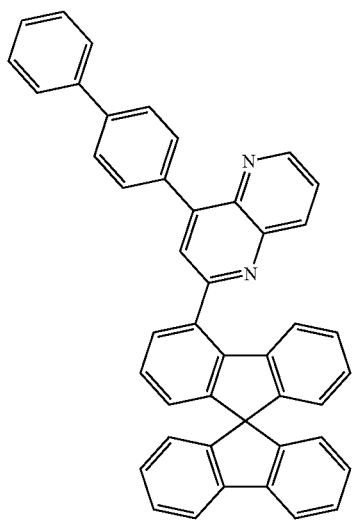
Formula 109
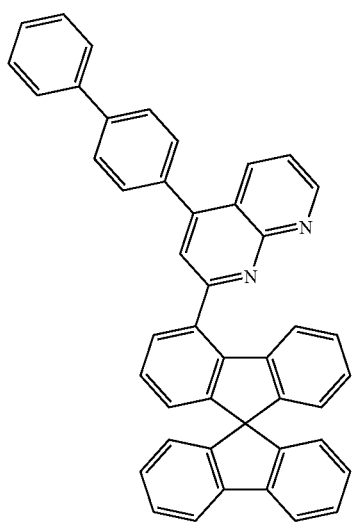
Formula 110
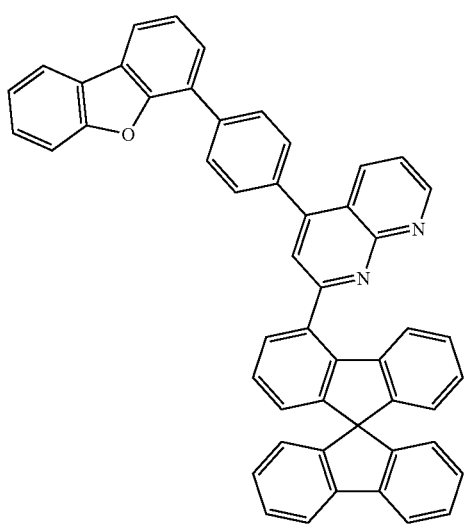
Formula 111
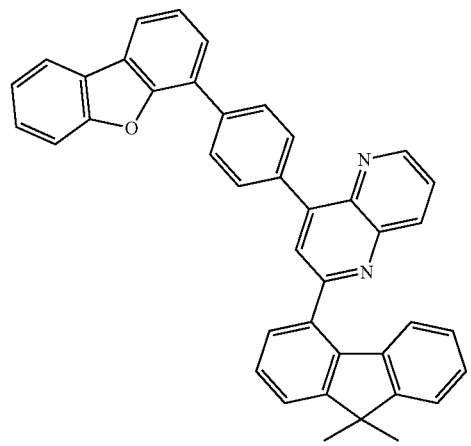
Formula 112
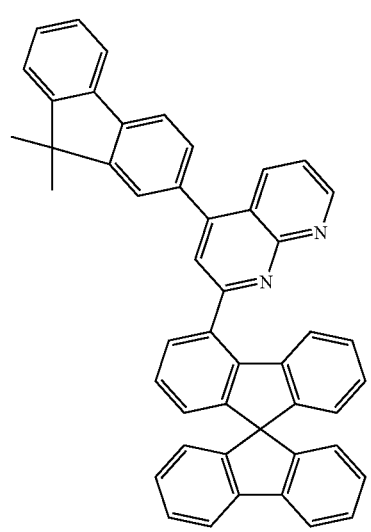
Formula 113
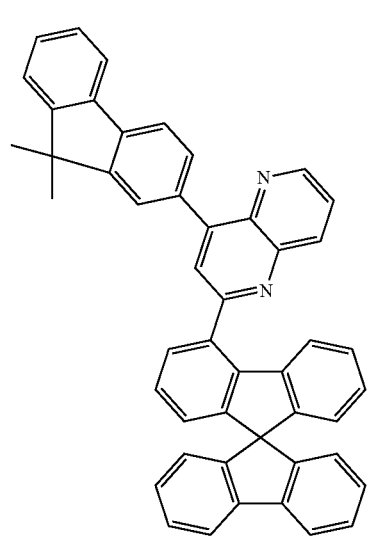

Formula 114
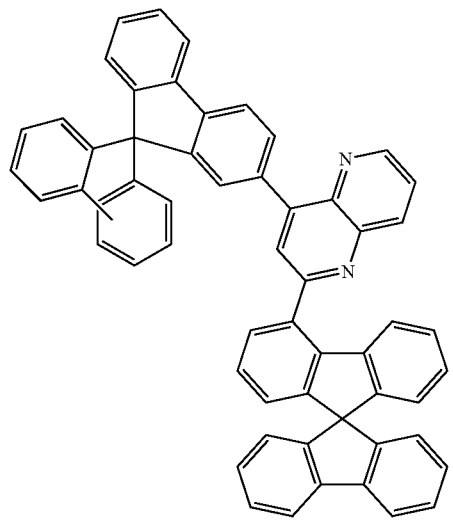
Formula 117
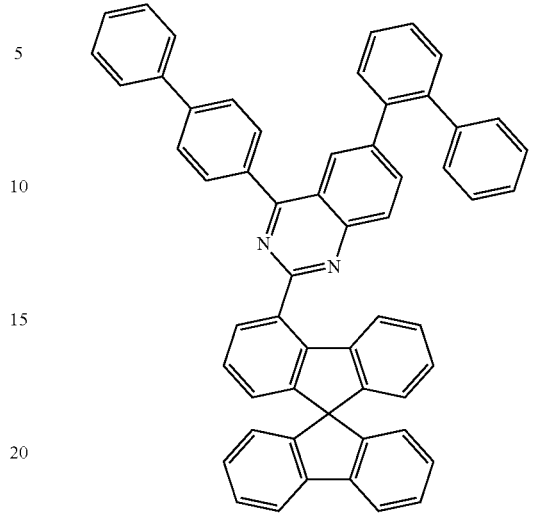
Formula 115
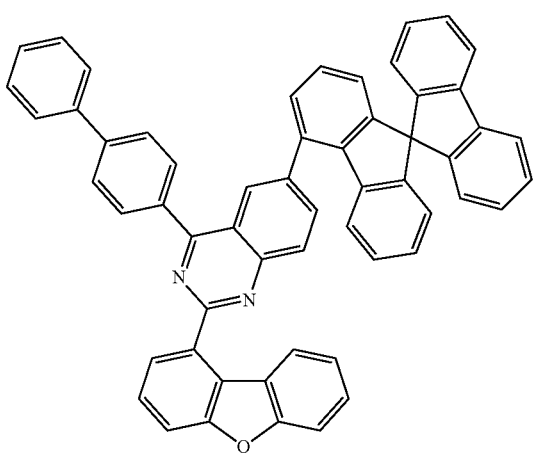
Formula 118
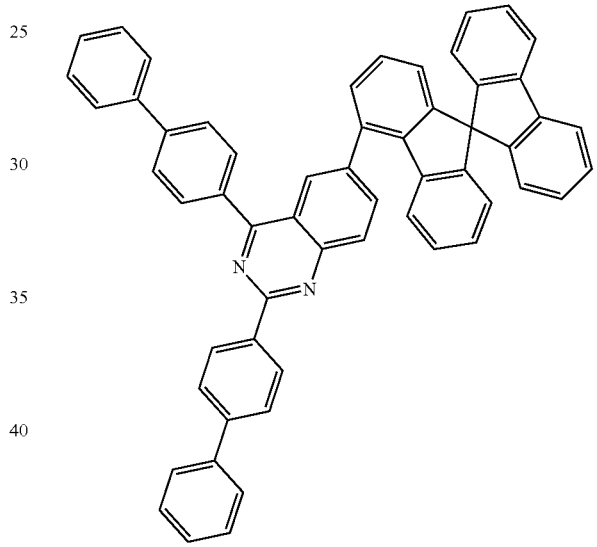
Formula 116
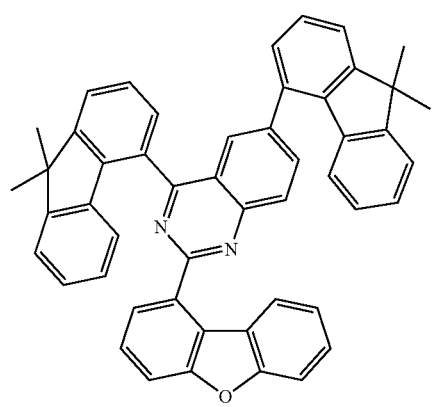
Formula 119
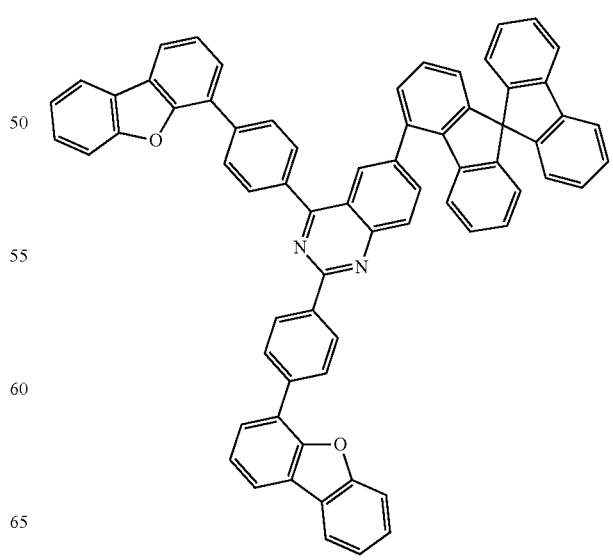

Formula 120
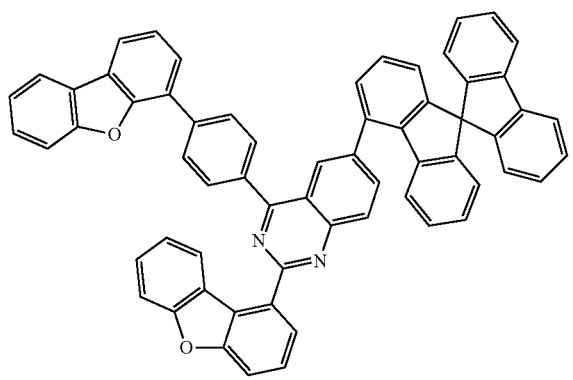
Formula 121
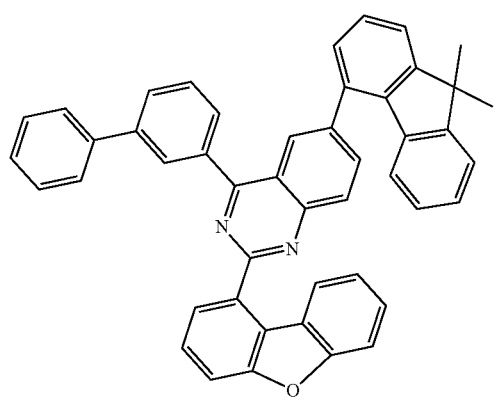
Formula 122
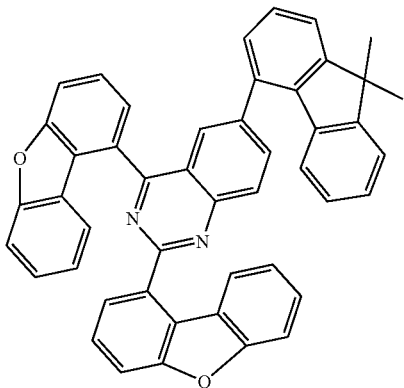
Formula 123
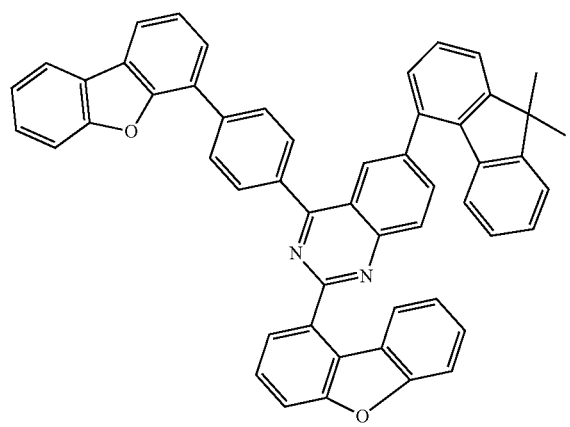
Formula 124
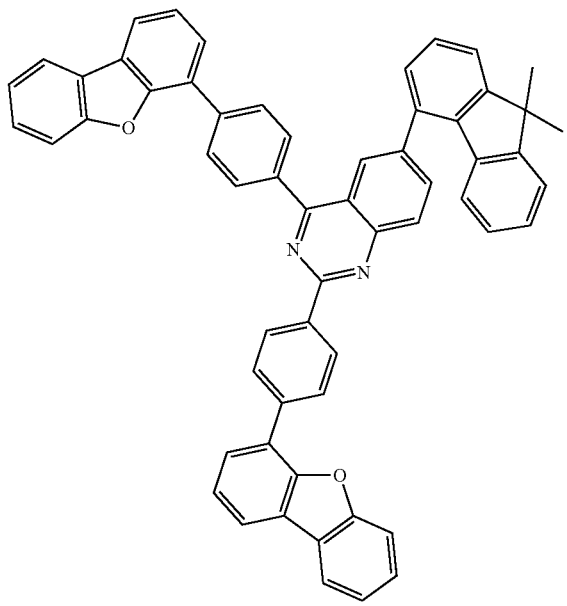
Formula 125
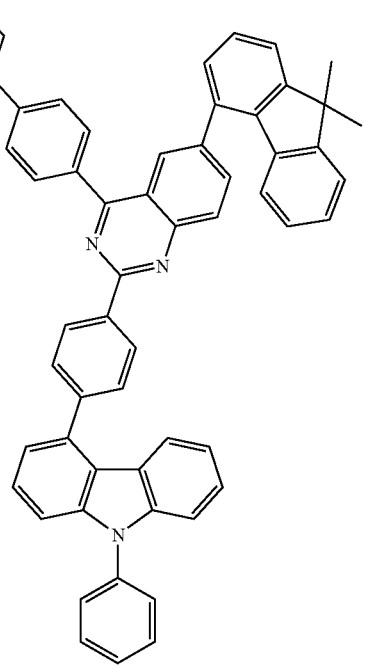

Formula 126
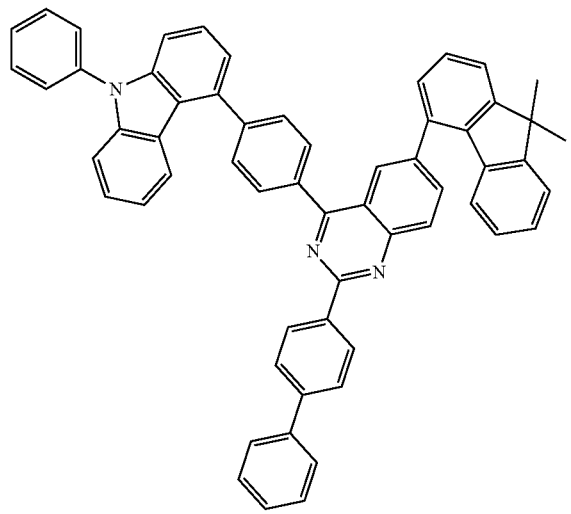
Formula 129
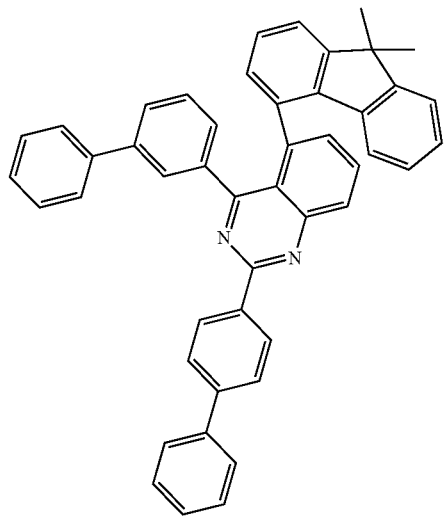
Formula 127
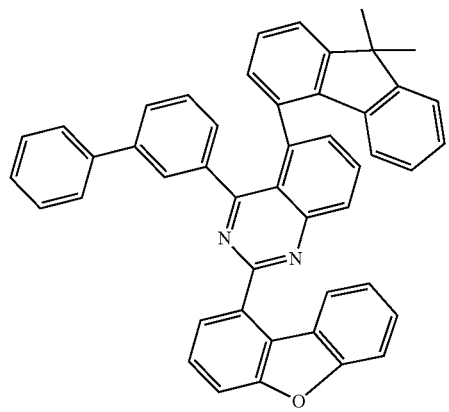
Formula 130
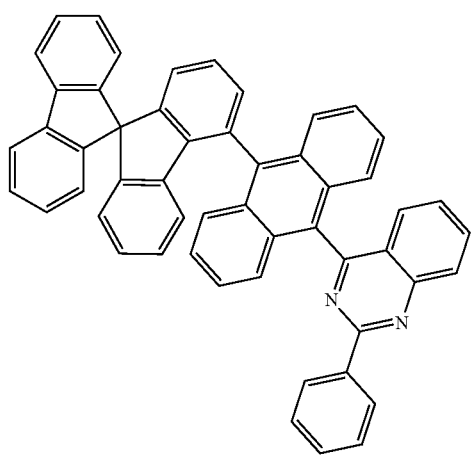
Formula 128
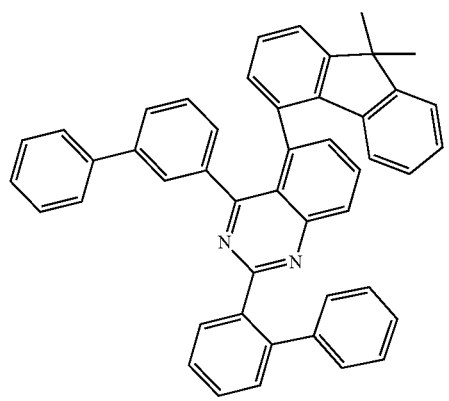
Formula 131

-continued
Formula 132
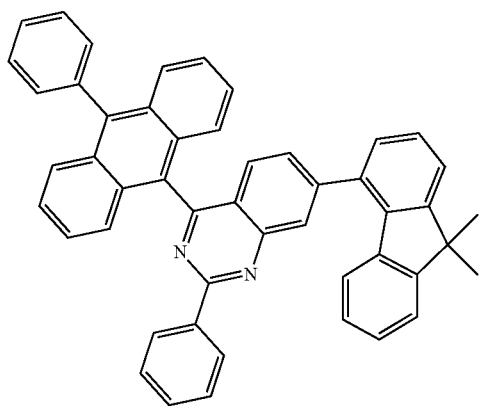
Formula 133
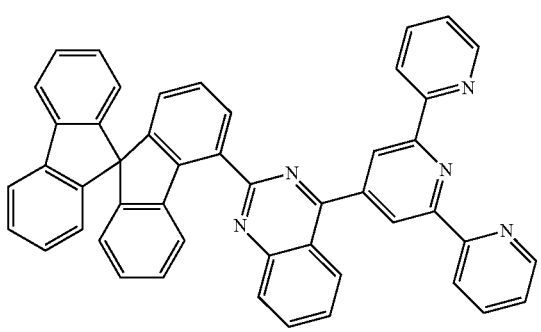
Formula 134
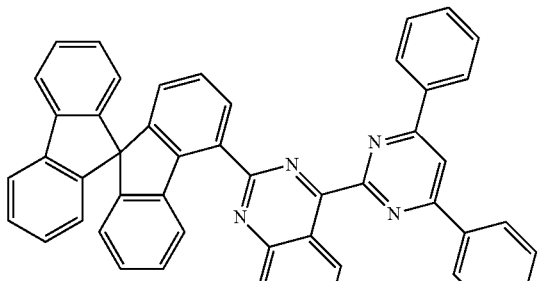
Formula 135
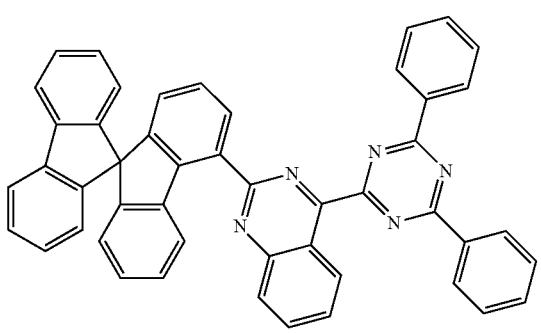
-continued
Formula 136
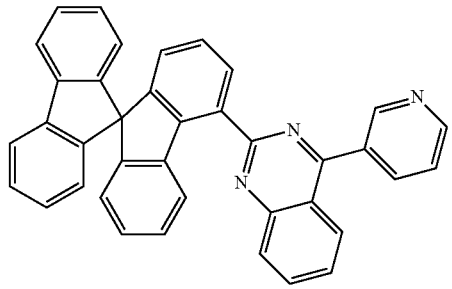
Formula 137
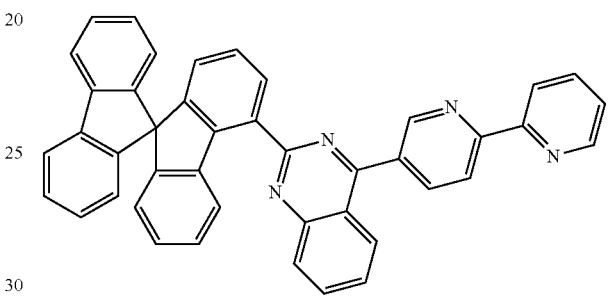
Formula 138
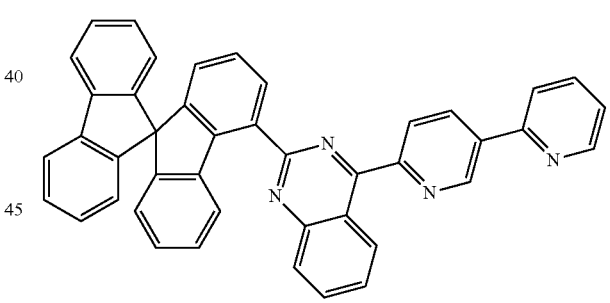
Formula 139
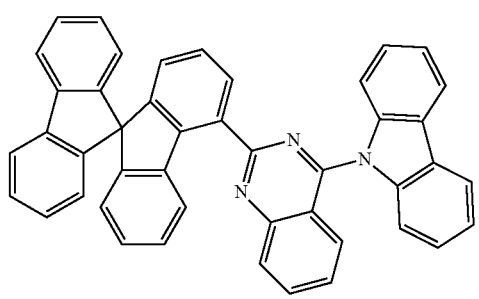

Formula 140
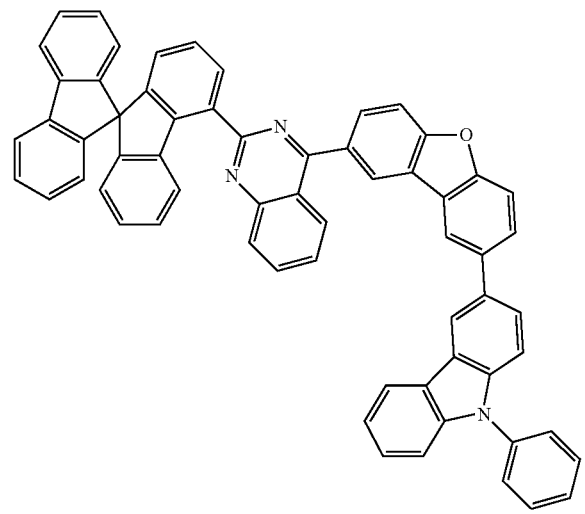
Formula 141
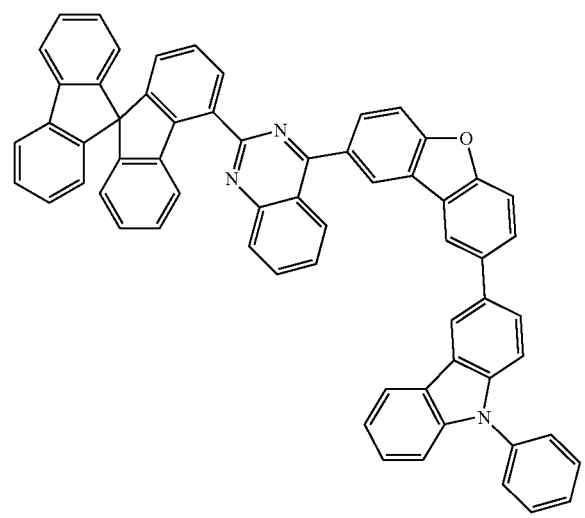
Formula 142
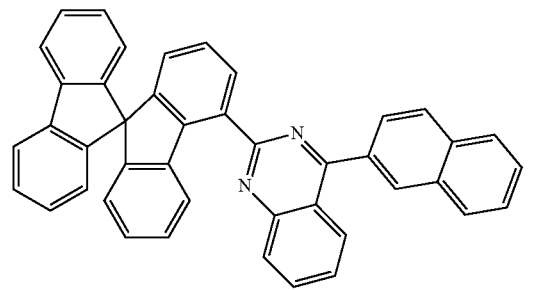
Formula 143
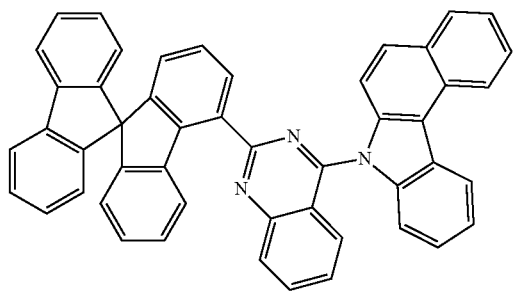
Formula 144
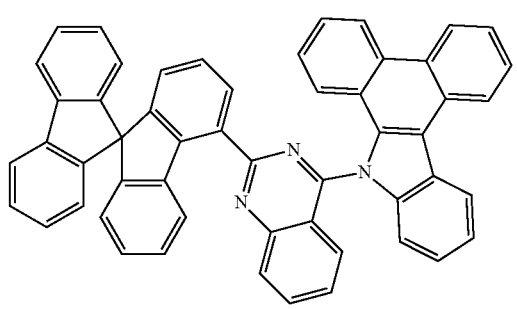
Formula 145
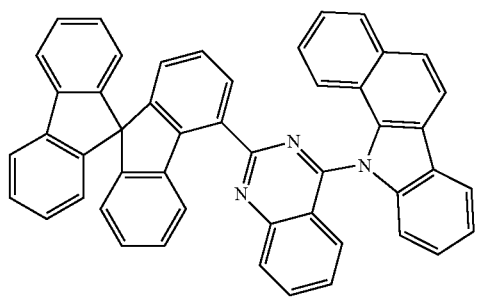
Formula 146
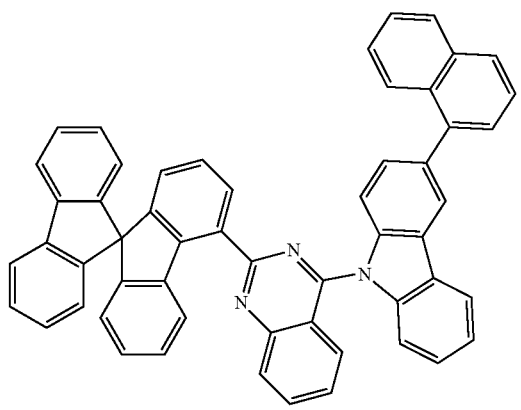

-continued
Formula 147
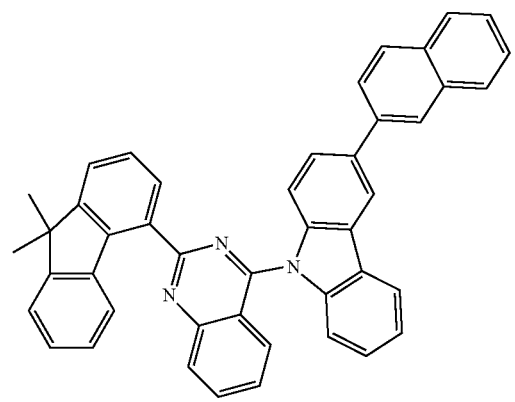
Formula 148
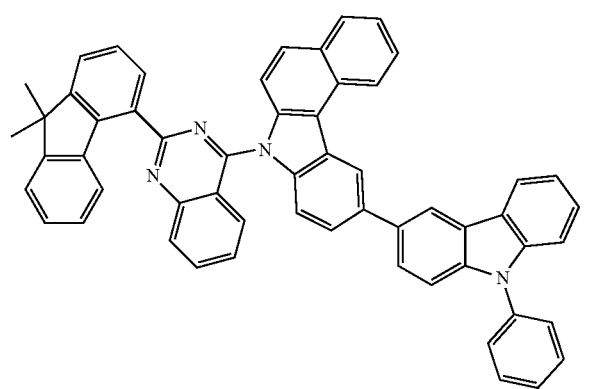
Formula 149
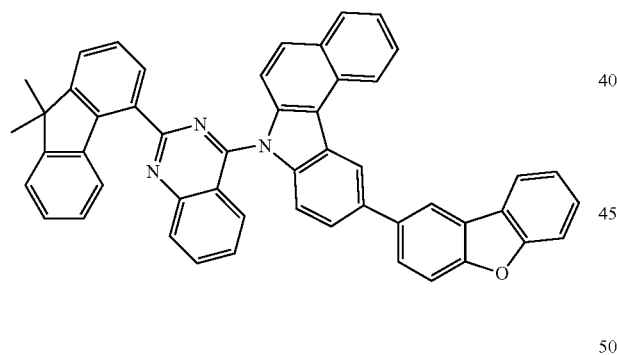
Formula 150
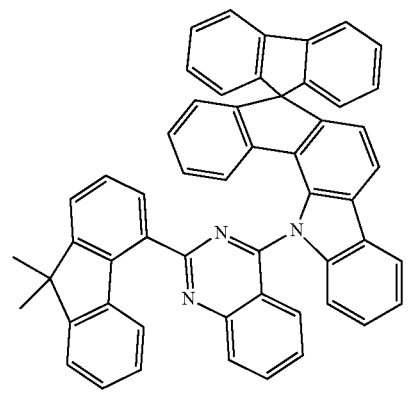
-continued
Formula 151
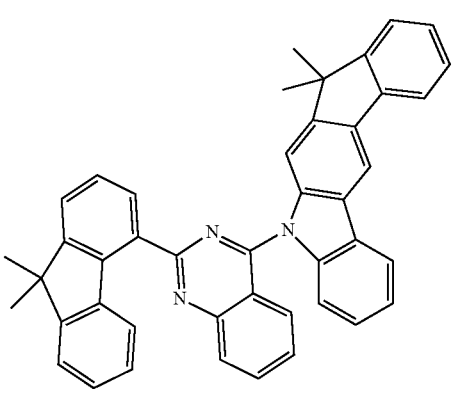
Formula 152
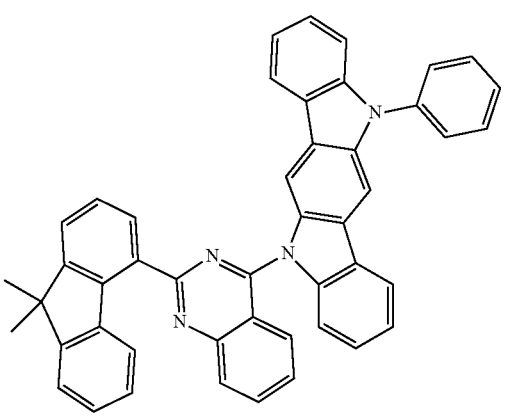
Formula 153
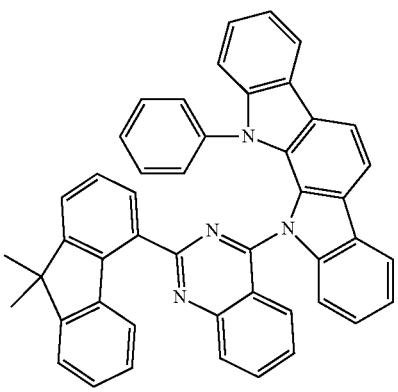
Formula 154
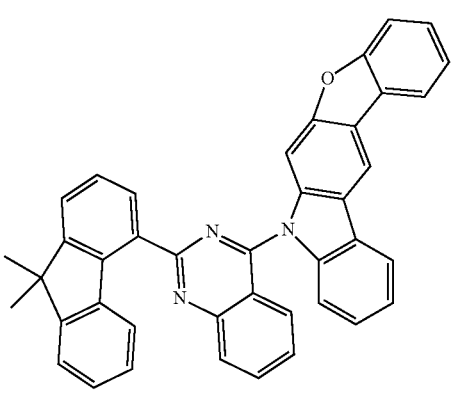

Formula 155
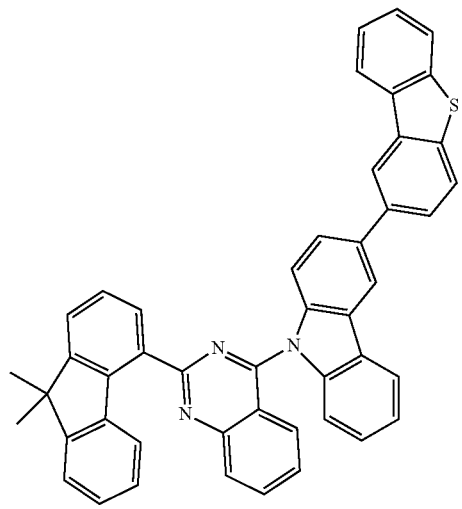
Formula 156
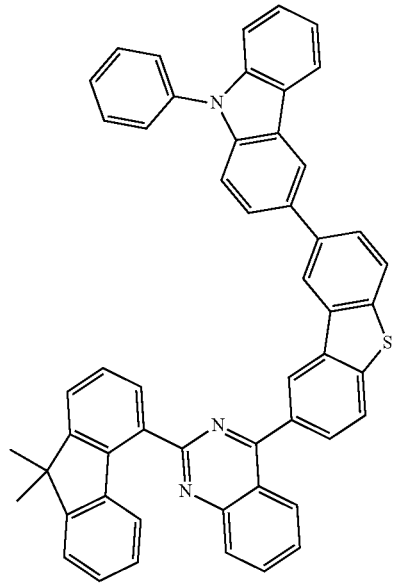
Formula 157
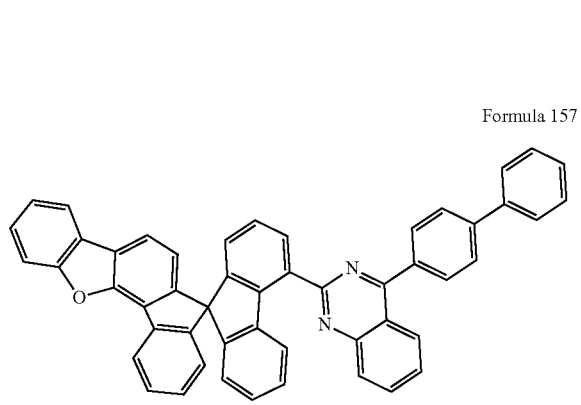
Formula 158
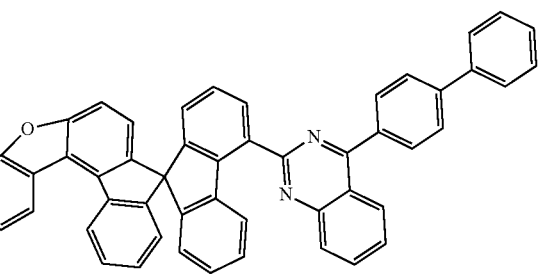
Formula 159
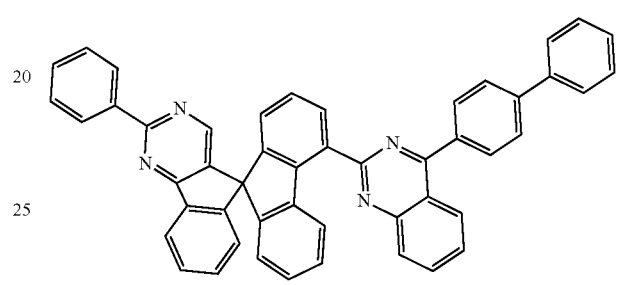
Formula 160
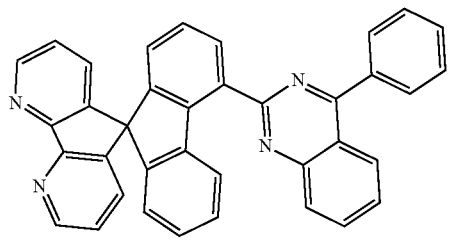
Formula 161
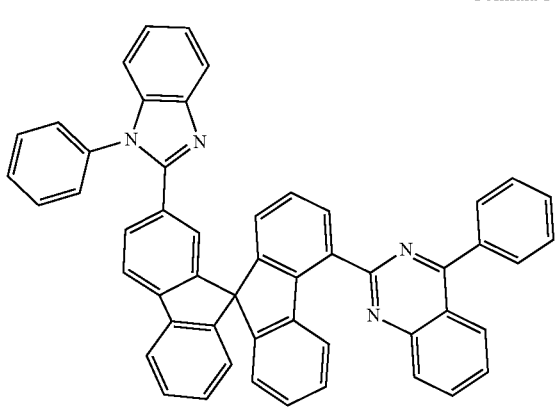

Formula 162
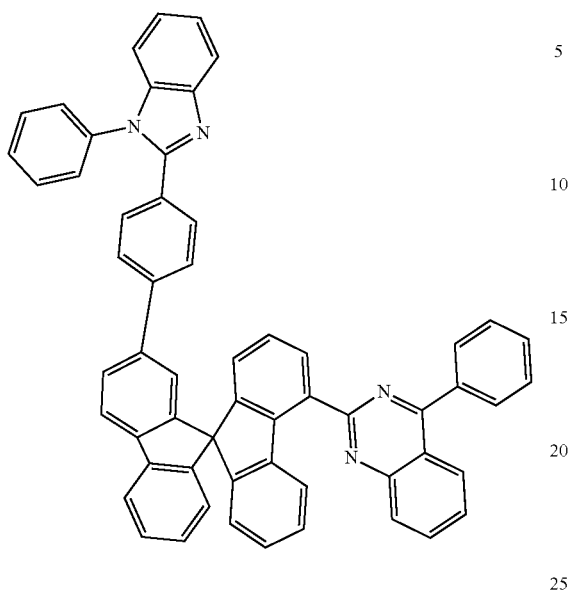
Formula 164
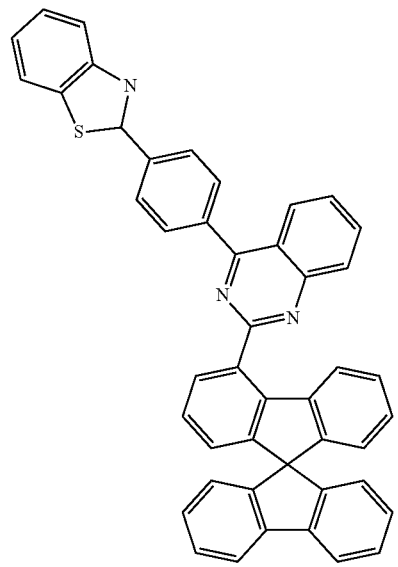
Formula 163
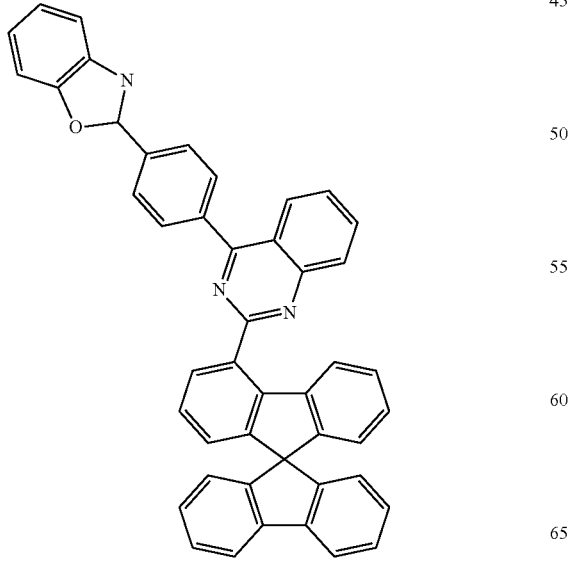
Formula 165
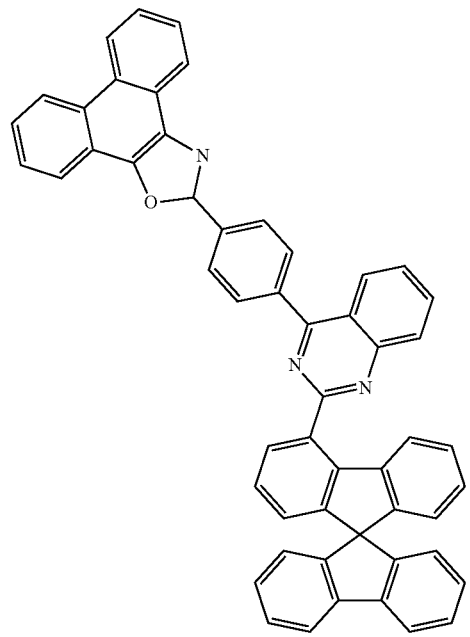

-continued
Formula 166
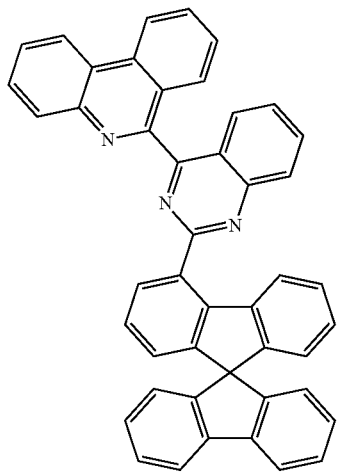
Formula 167
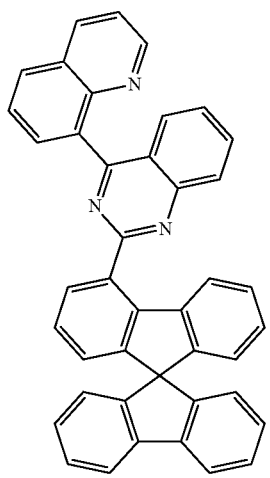
Formula 168
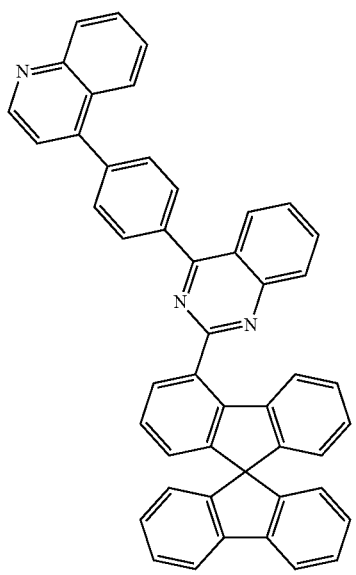
-continued
Formula 169
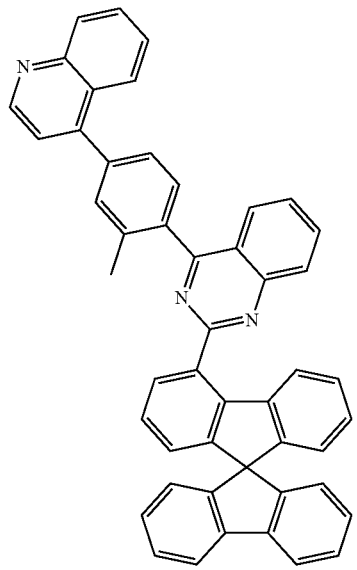
Formula 170
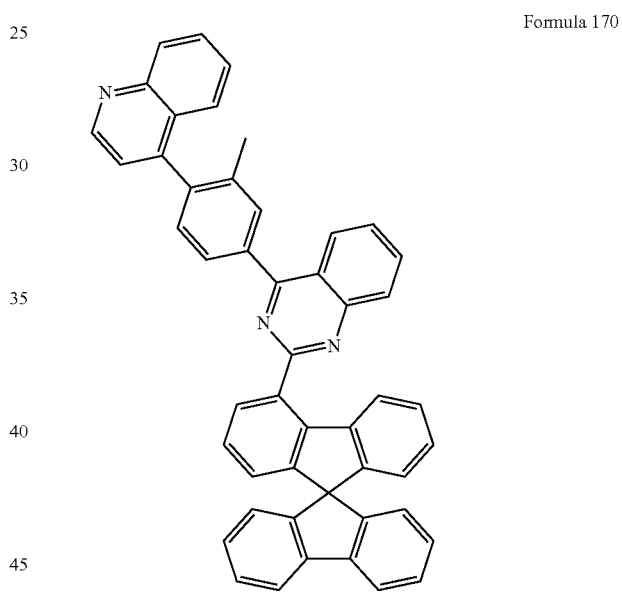
Formula 171
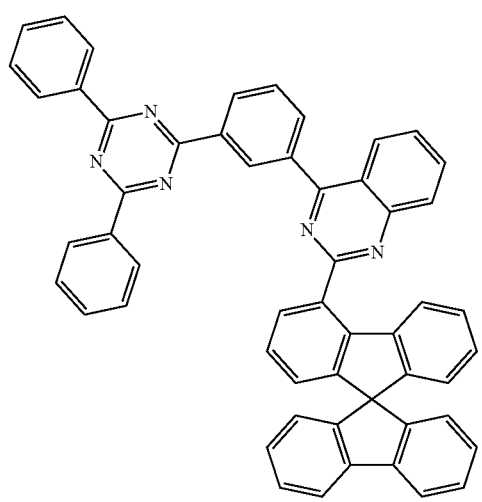

101
-continued
Formula 172
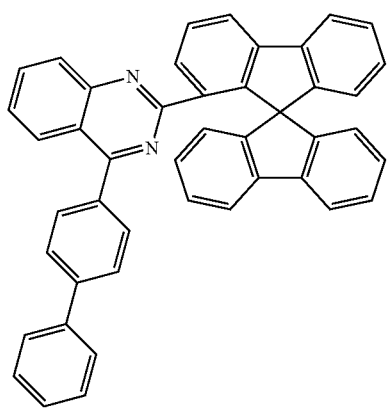
Formula 173
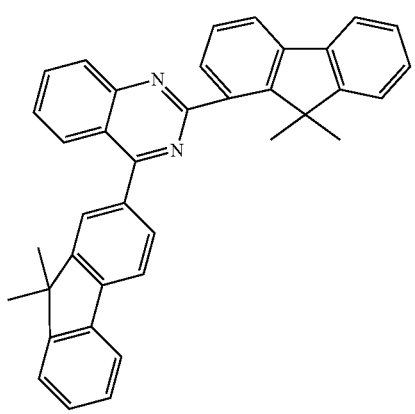
Formula 174
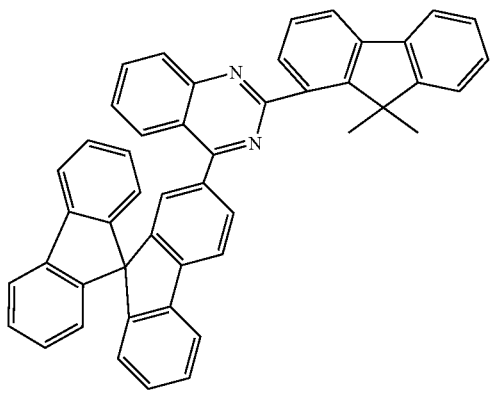
102
-continued
Formula 175
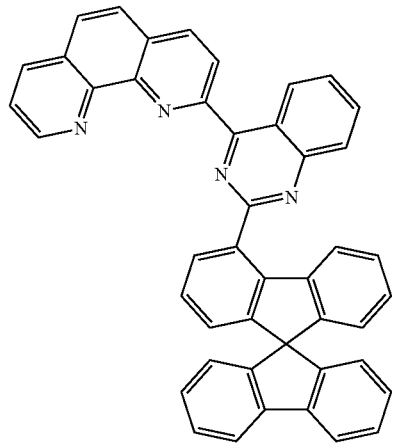
Formula 176
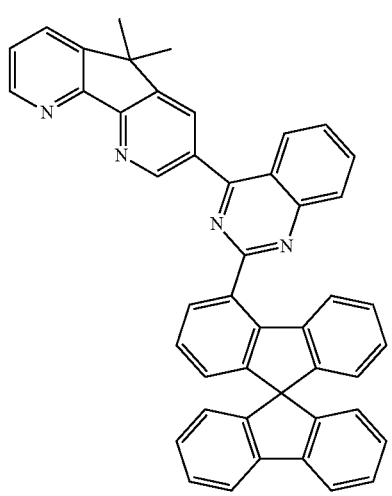
Formula 177
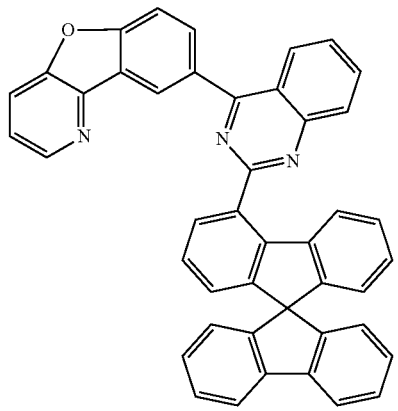

Formula 178
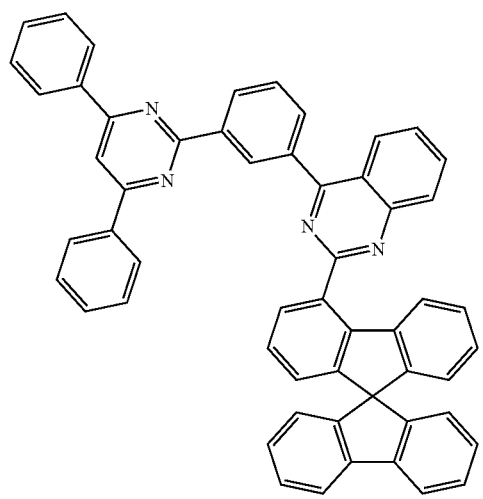
Formula 179
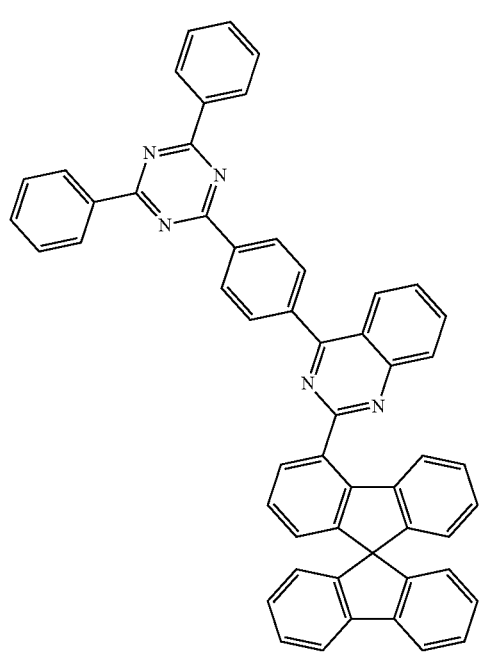
Formula 180
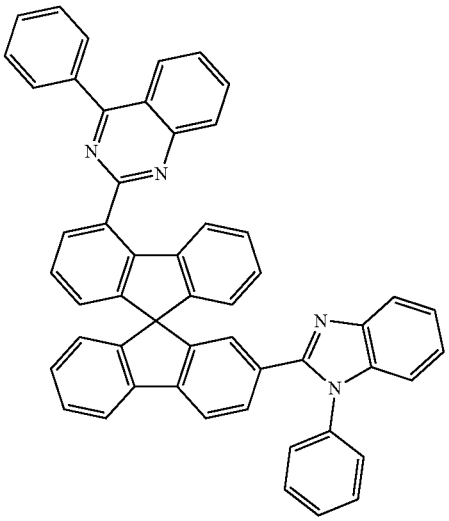
Formula 181
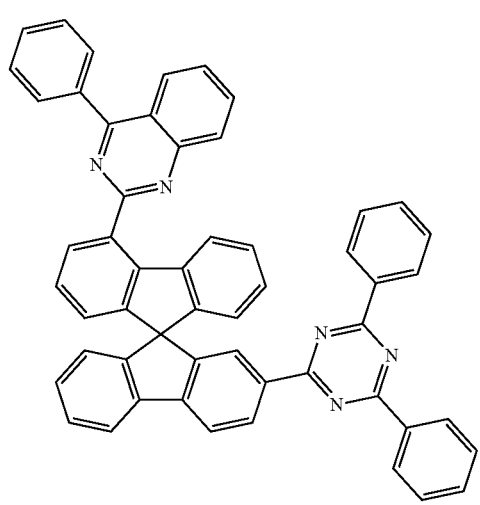

Formula 182
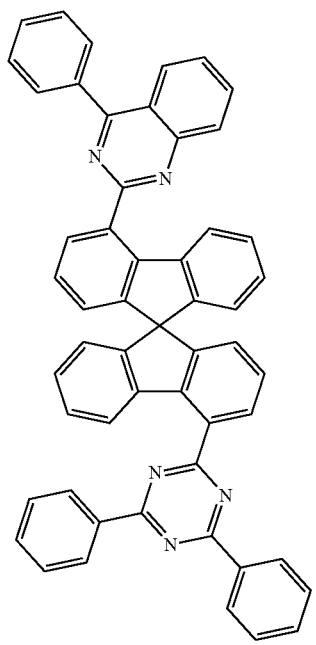
Formula 184
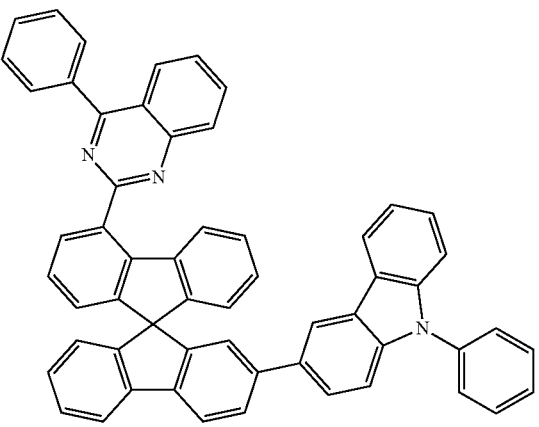
Formula 185
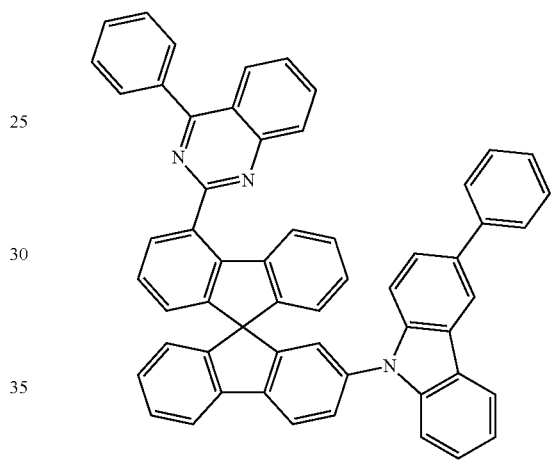
Formula 183
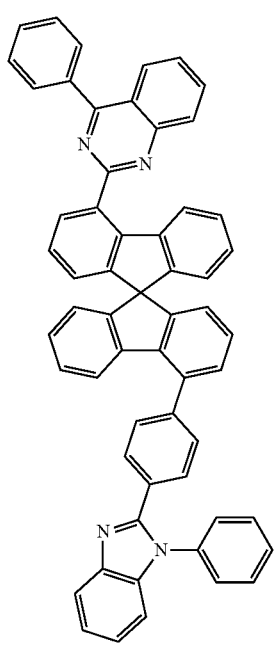
Formula 186
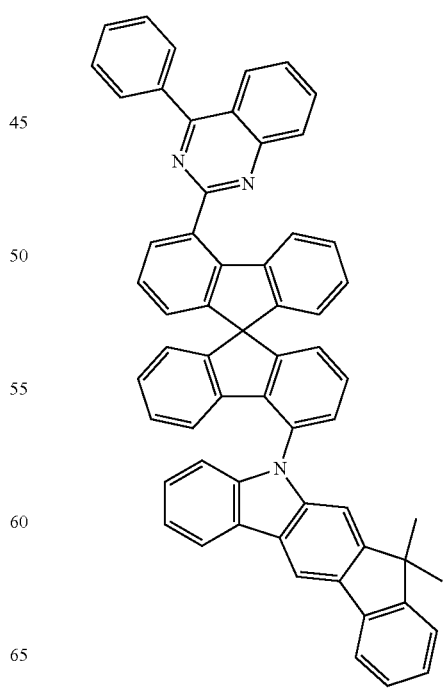

Formula 187
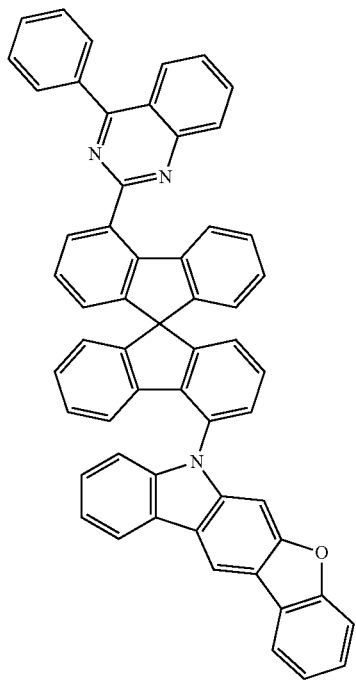
Formula 188
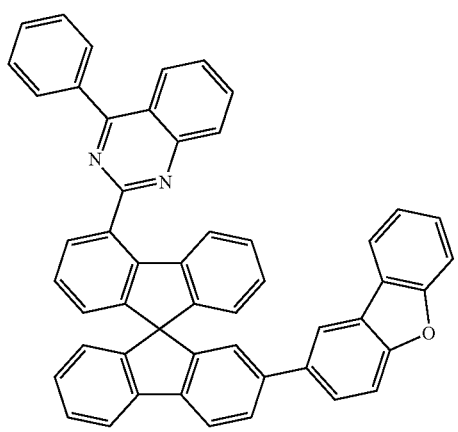
Formula 189
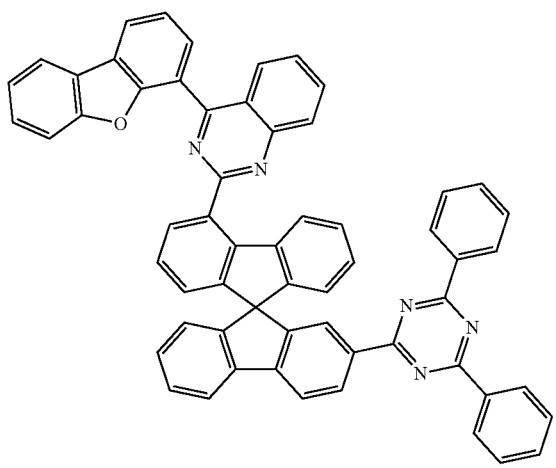
Formula 190
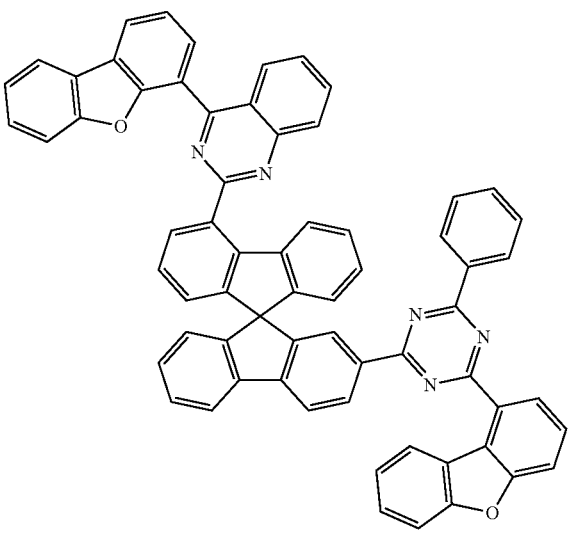
Formula 191
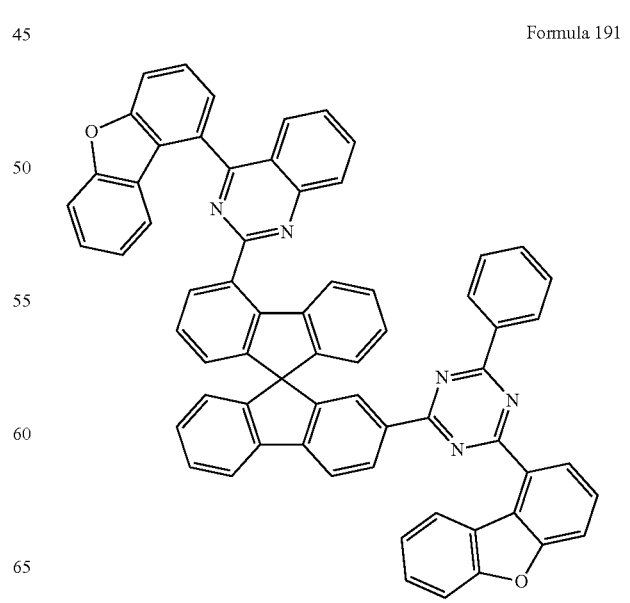

Formula 192
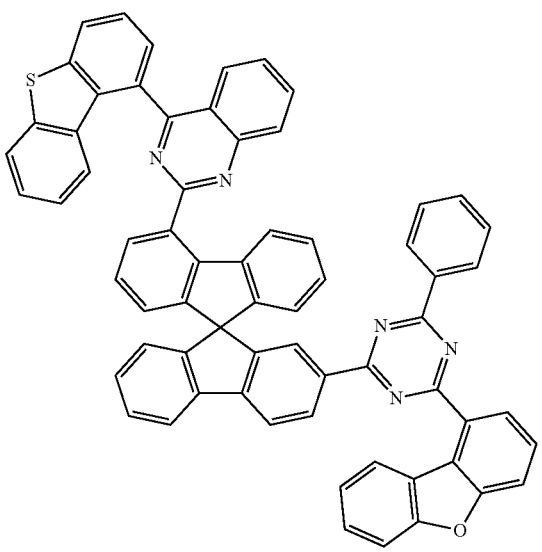
Formula 193
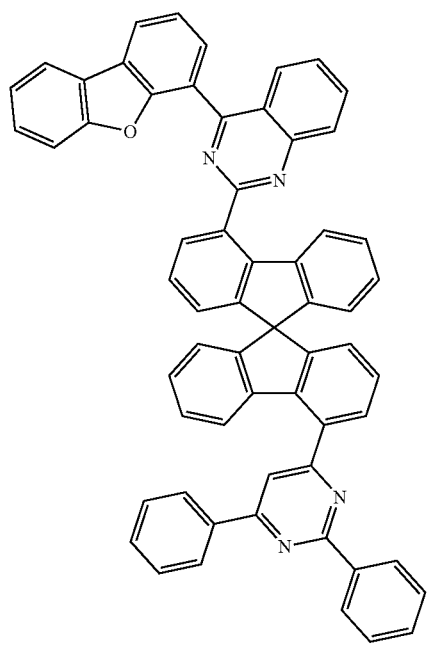
Formula 194
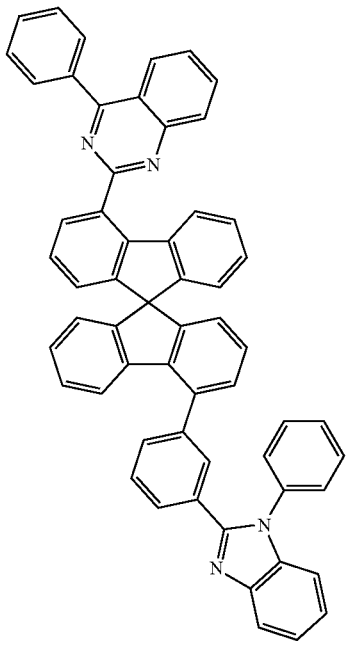
Formula 195
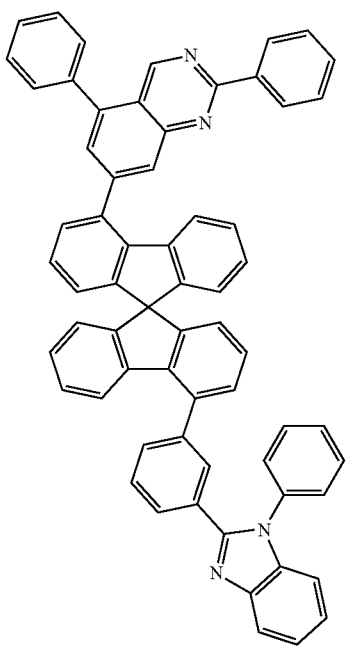

Formula 196
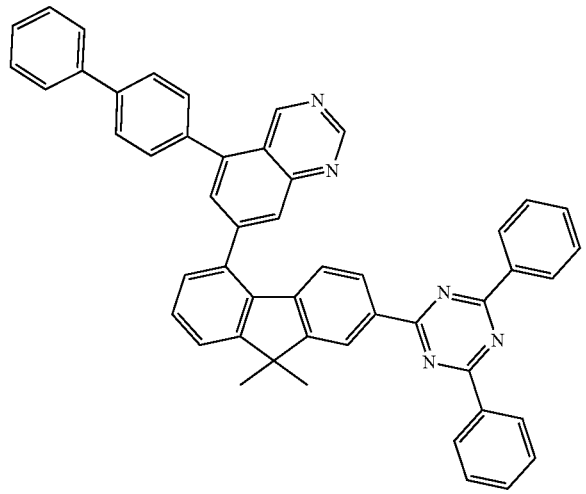
Formula 197
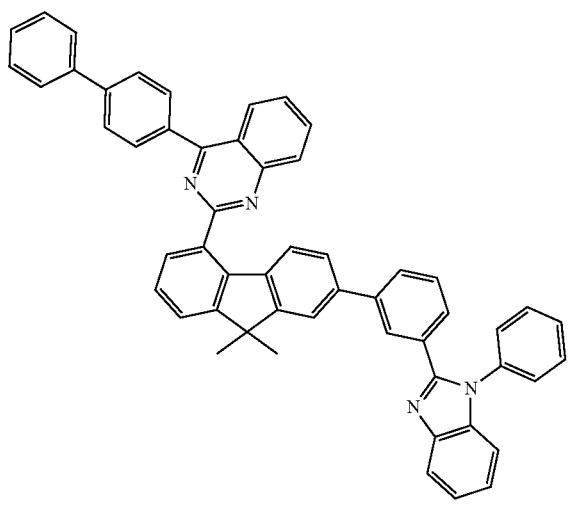
Formula 198
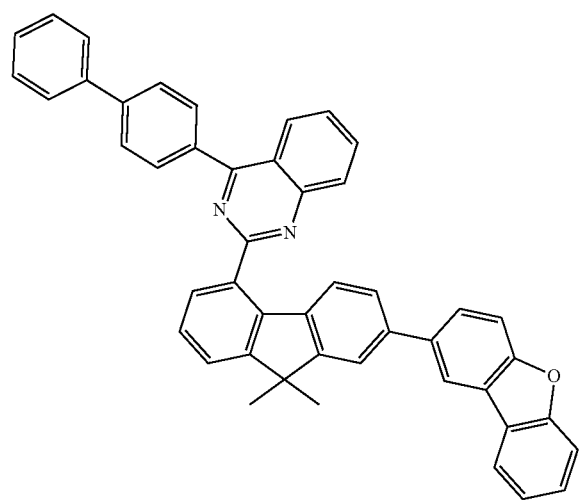
Formula 199
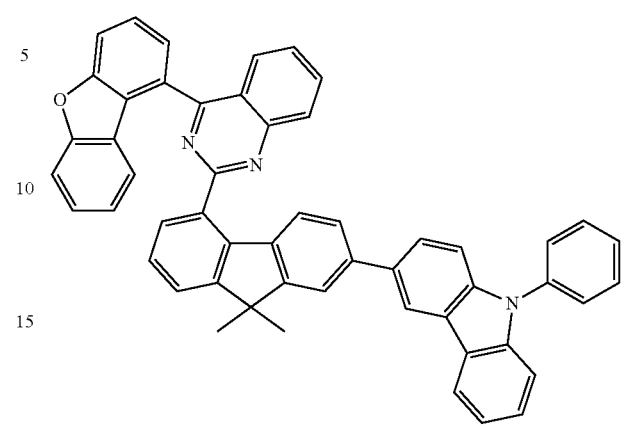
Formula 200
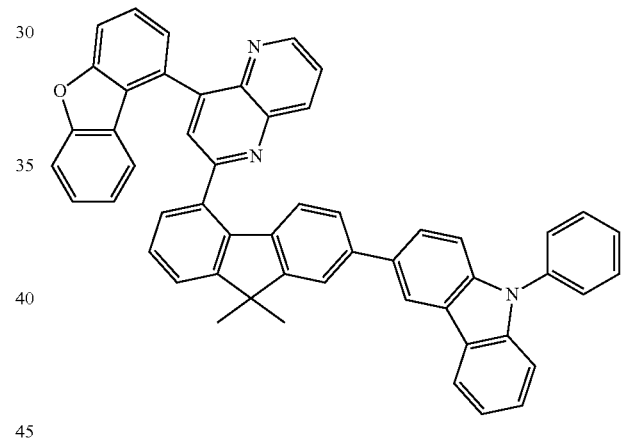
Formula 201
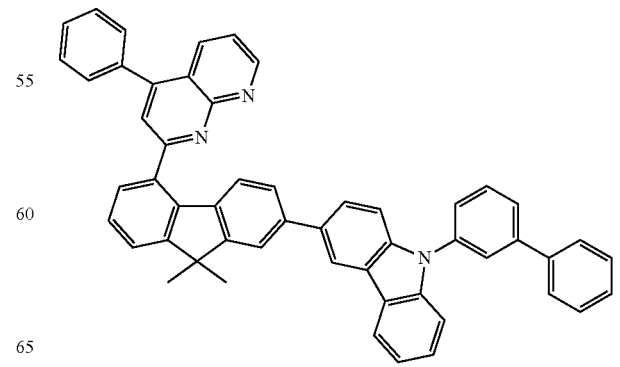

Formula 202
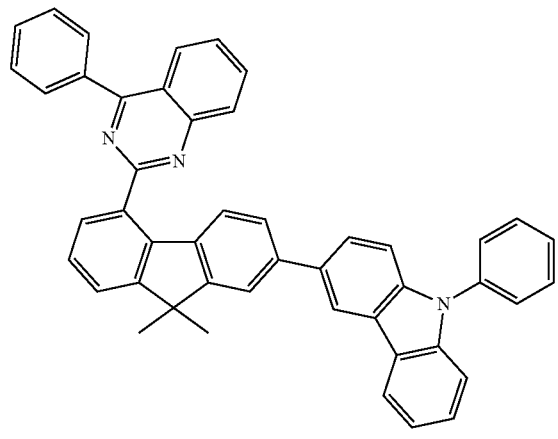
Formula 203
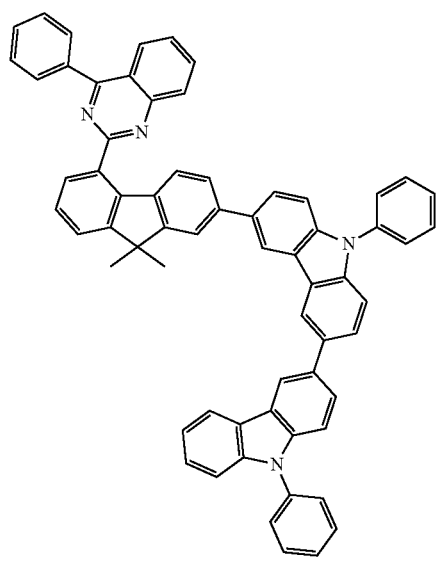
Formula 204
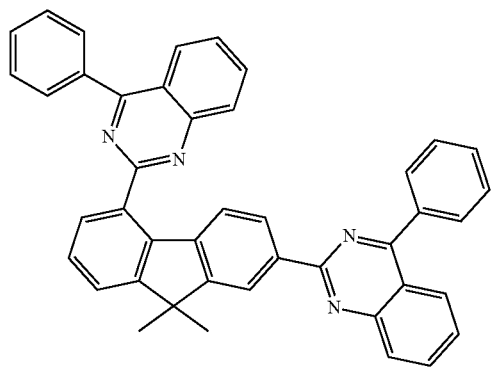
Formula 205
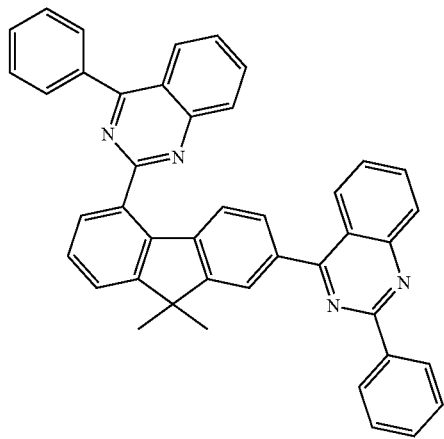
Formula 206
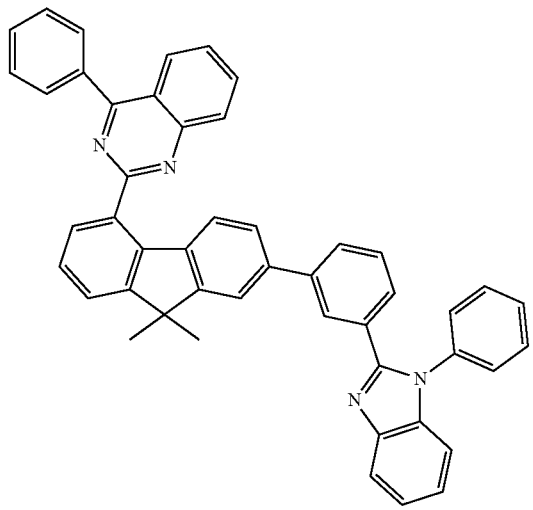
Formula 207
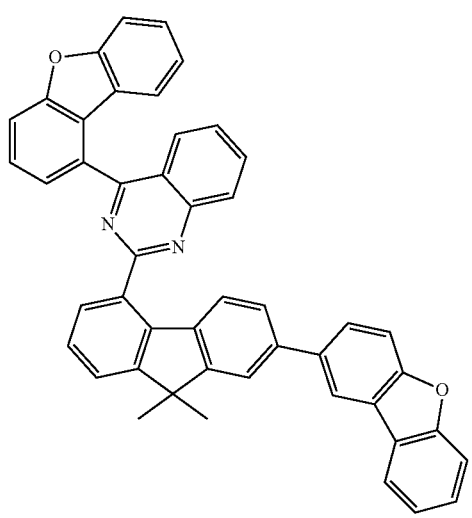

Formula 208
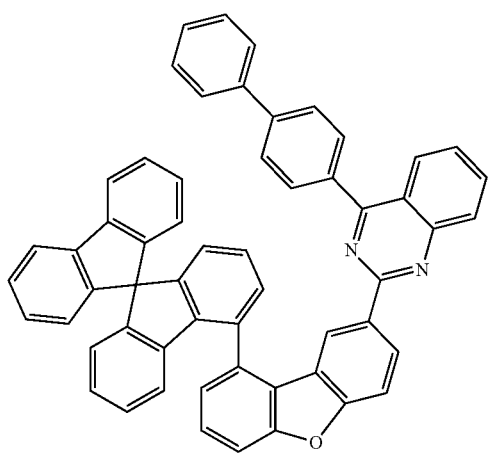
Formula 209
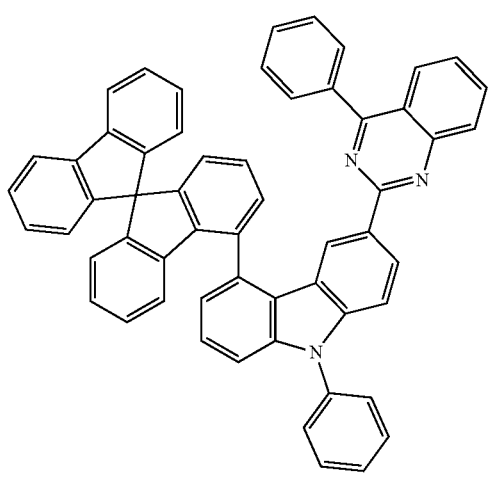
Formula 210
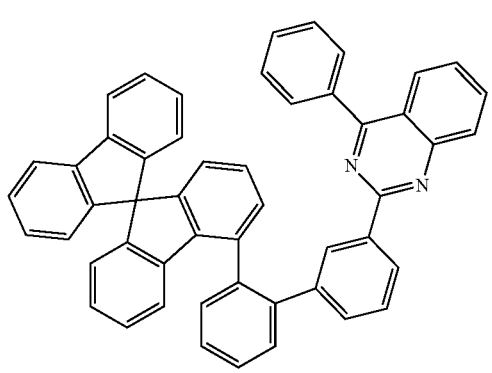
Formula 211
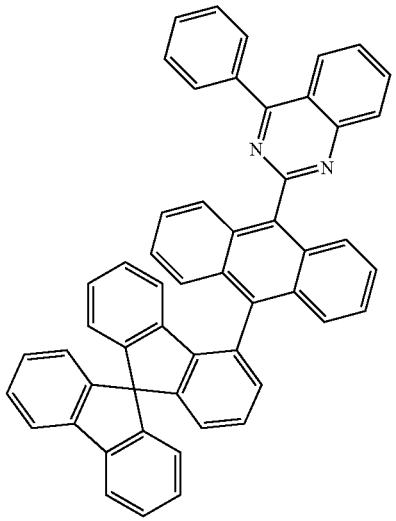
Formula 212
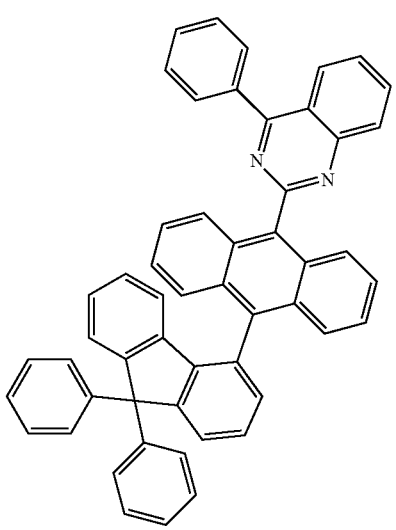
Formula 213
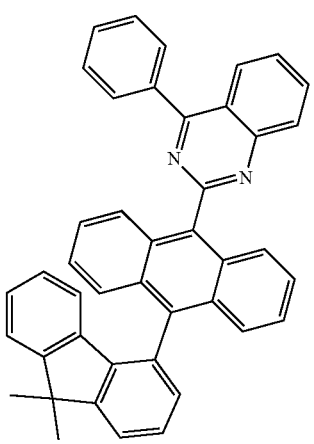

Formula 214
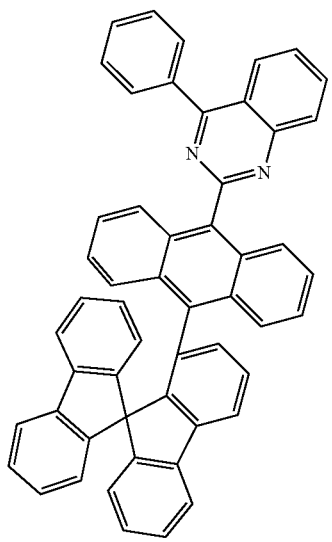
Formula 215
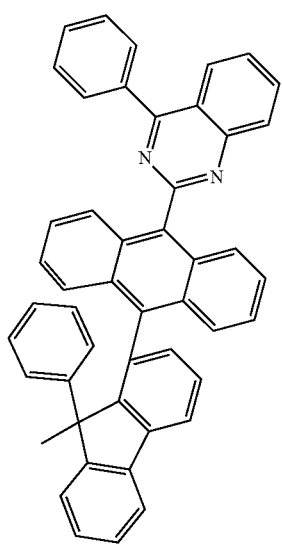
Formula 216
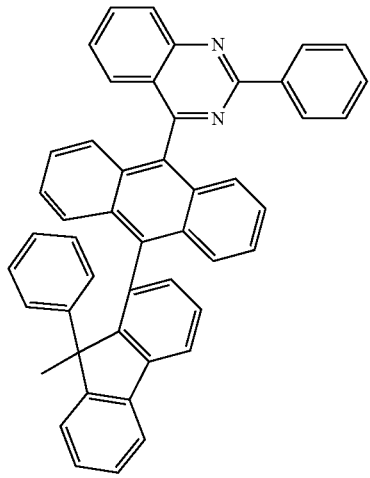
Formula 217
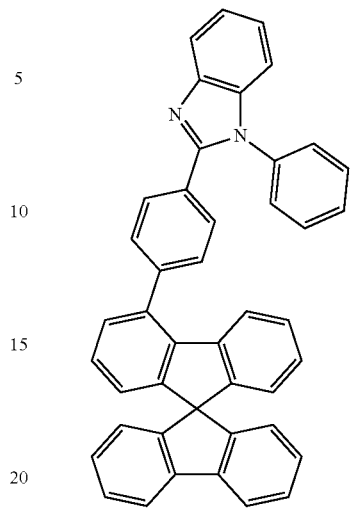
Formula 218
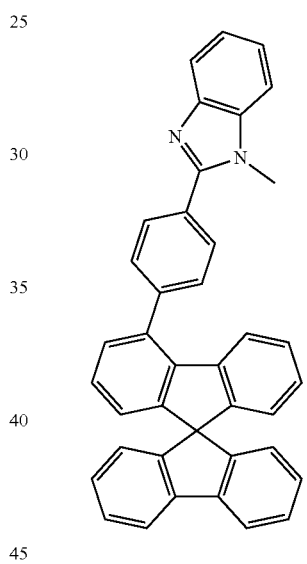
Formula 219
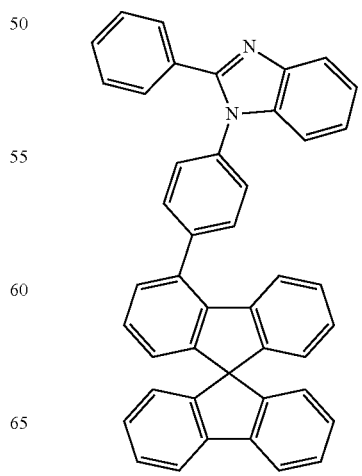

Formula 220
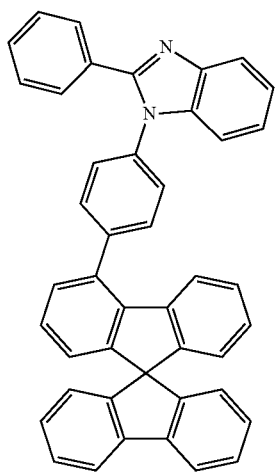
Formula 221
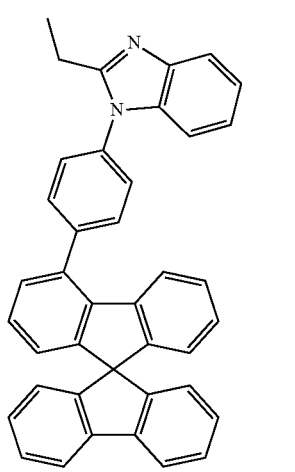
Formula 222
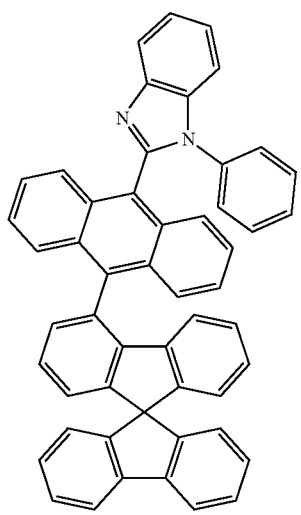
Formula 223
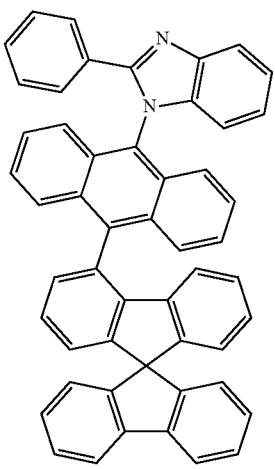
Formula 224
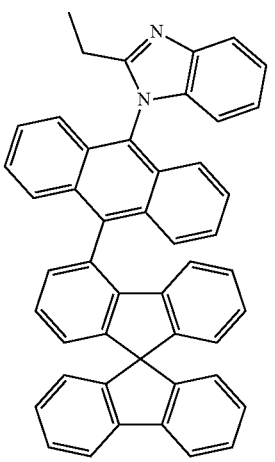
Formula 225
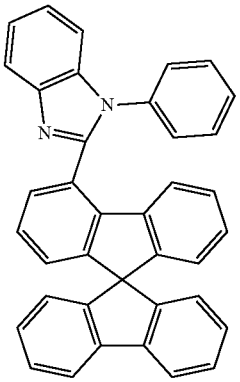
Formula 226
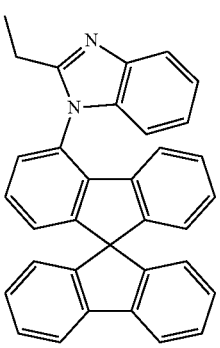

Formula 14
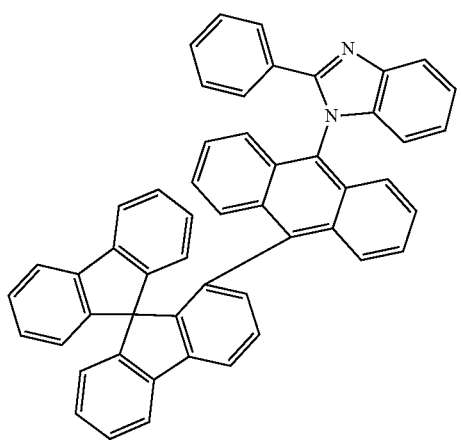
Formula 15
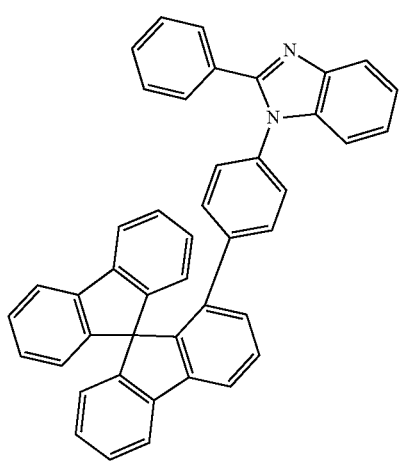
Formula 217
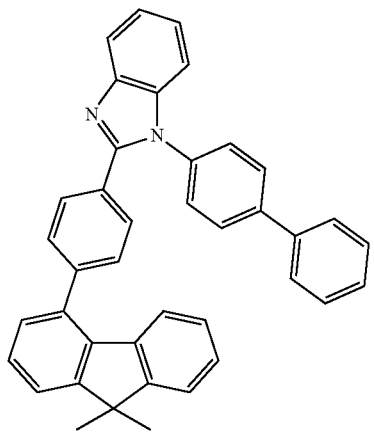
Formula 218
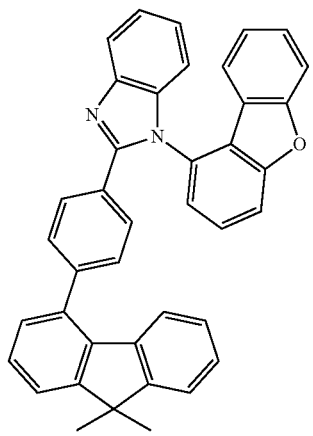
Formula 219
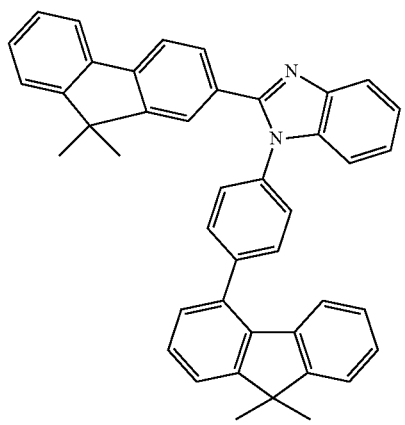
Formula 220
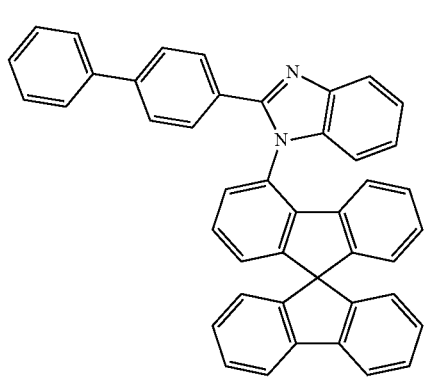

-continued

Formula 221

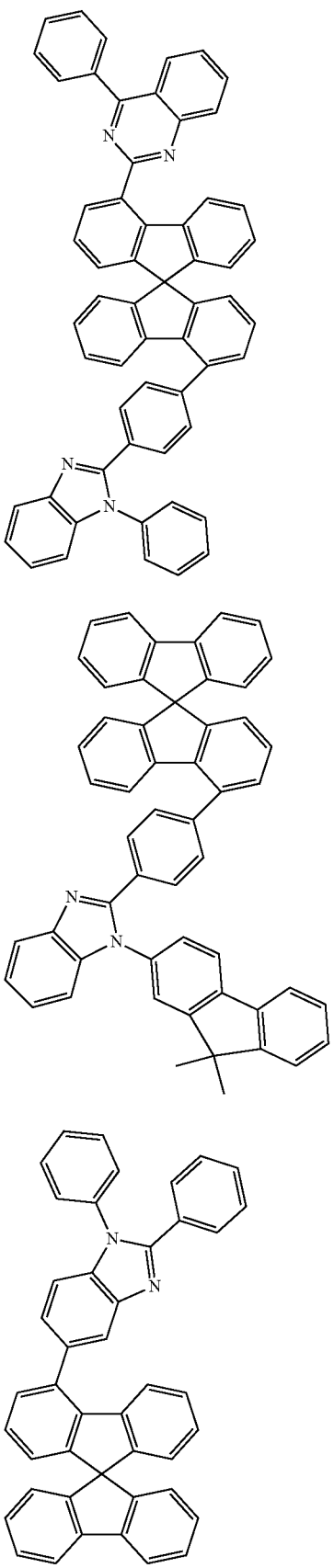

Formula 222

Formula 220

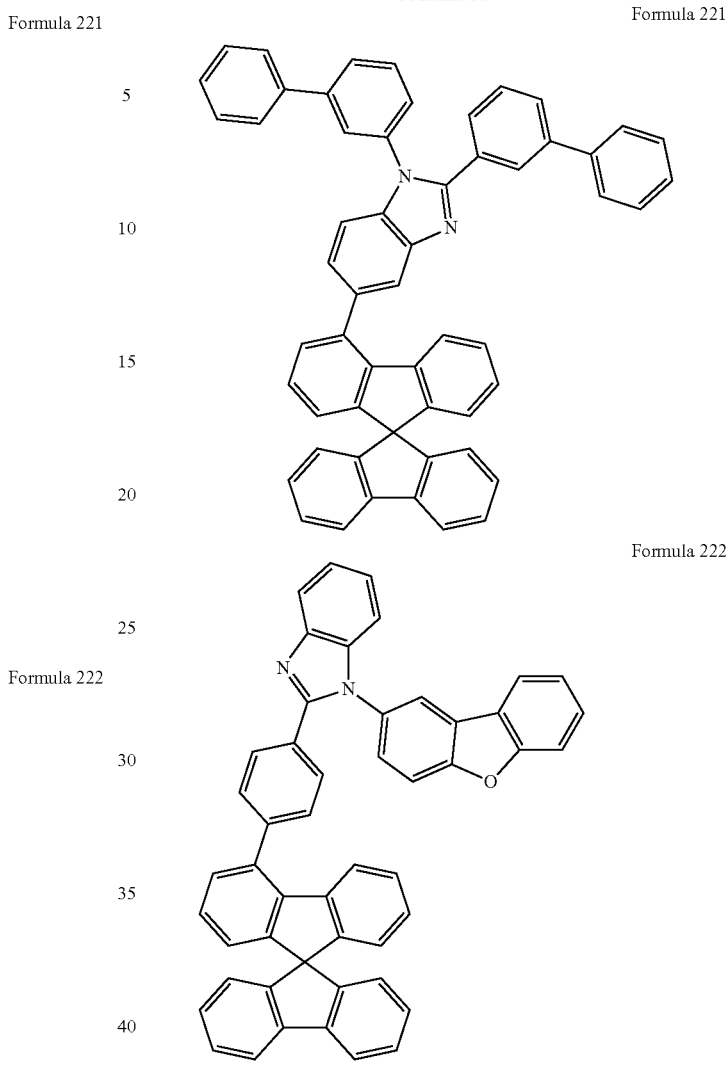

Formula 221

Formula 222

Preferred embodiments of compounds of the invention are detailed specifically in the examples, these compounds being usable alone or in combination with further compounds for all purposes of the invention.

Provided that the conditions specified in Claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds comprising structures of formula (I) and/or (II) in which, in a coupling reaction, a compound comprising at least one electron-transporting group is reacted with a compound comprising at least one fluorene radical.

Suitable compounds having an electron-transporting group are in many cases commercially available, and the starting compounds detailed in the examples are obtainable by known processes, and so reference is made thereto.

These compounds can be reacted with further aryl compounds by known coupling reactions, the necessary conditions for this purpose being known to the person skilled in the art, and detailed specifications in the examples give support to the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

In all the synthesis schemes which follow, the compounds are shown with a small number of substituents to simplify the structures. This does not rule out the presence of any desired further substituents in the processes.

An illustrative implementation is given by the schemes which follow, without any intention that these should impose a restriction. The component steps of the individual schemes may be combined with one another as desired.

The processes shown for synthesis of the compounds of the invention should be understood by way of example. The person skilled in the art will be able to develop alternative synthesis routes within the scope of his common knowledge in the art.

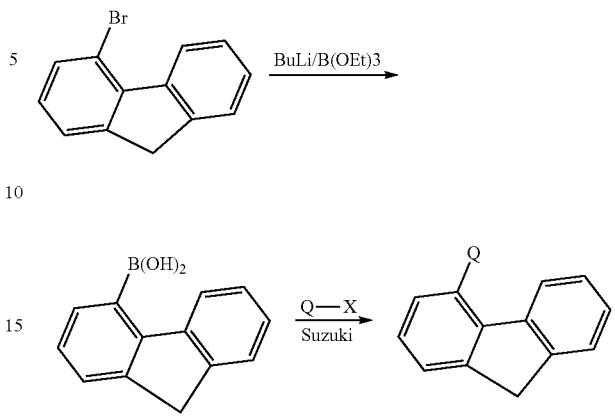

The Q group is an electron transport group, and X is a leaving group, for example halogen.

Scheme 2 below elucidates the reaction shown in Scheme 1 for a number of different electron transport groups.

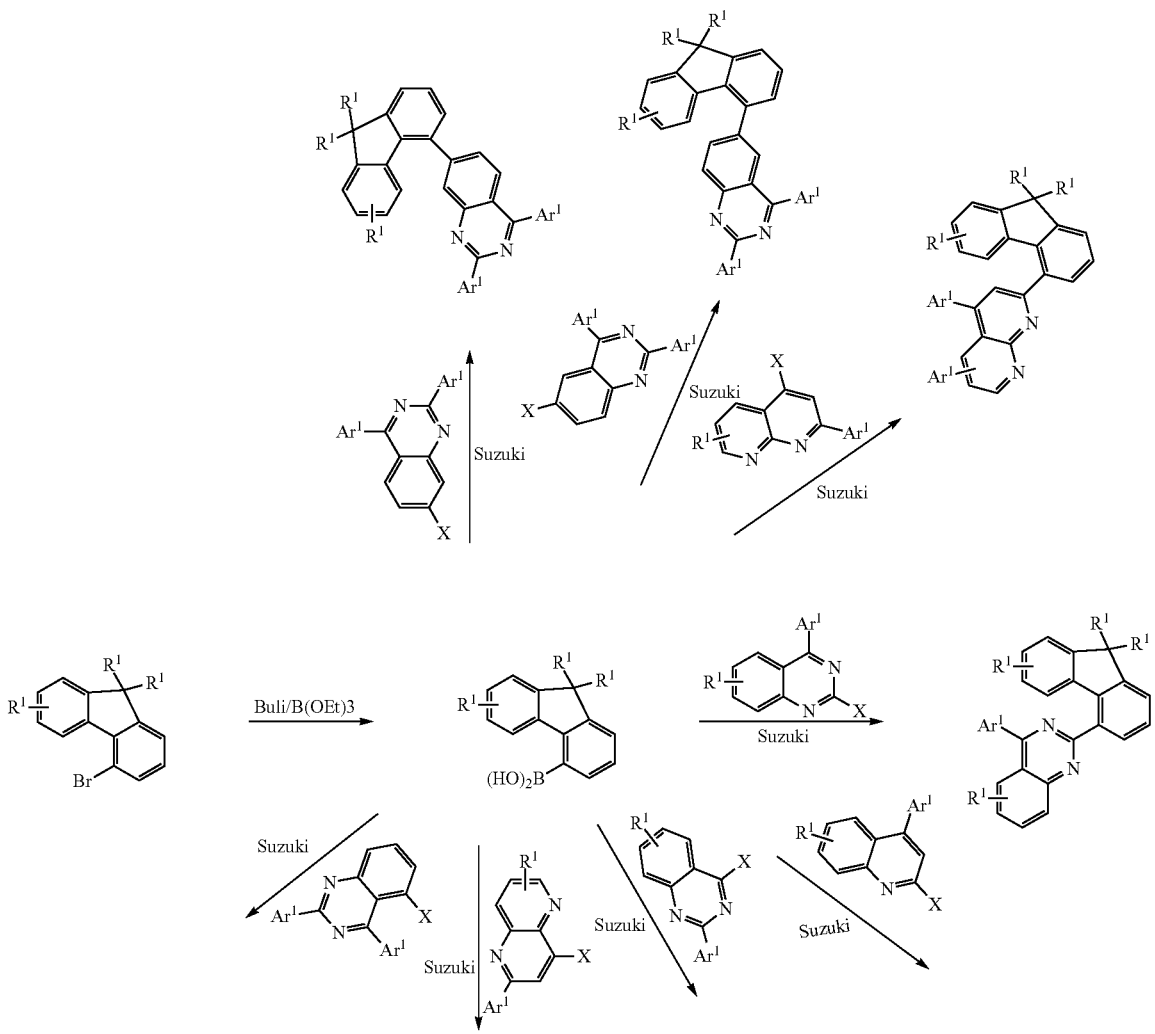

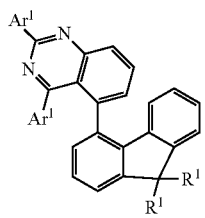 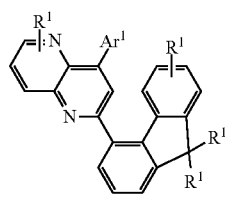 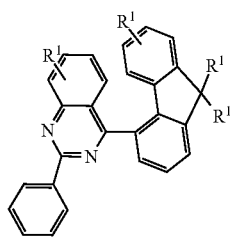 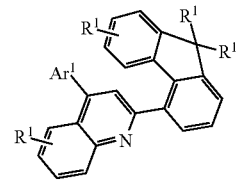

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of the formula (I) and/or formula (II) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in a sufficient concentration soluble, in order to be able to process the compounds from solution. These soluble compounds are of particularly good suitability for processing from solution, for example by printing methods. In addition, it should be emphasized that the compounds of the invention comprising at least one structure of the formula (I) and/or formula (II) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed structures of the formula (I) and/or (II) or compounds of the invention, wherein one or more bonds in the compounds of the invention or in the structures of the formula (I) and/or (II) to the polymer, oligomer or dendrimer are present. According to the linkage of the structures of the formula (I) and/or (II) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) and/or formula (II) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the general formula (I) and/or (II) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, especially a phosphorescent dopant, and/or a further matrix material. This further compound may also be polymeric.

The present invention therefore still further provides a composition comprising a compound of the invention and at least one further organically functional material. Functional materials are generally the organic or inorganic materials introduced between the anode and cathode. Preferably, the organic functional material is selected from the group consisting of fluorescent emitters, phosphorescent emitters, host materials, matrix materials, electron transport materials, electron injection materials, hole conductor materials, hole injection materials, n-dopants, wide band gap materials, electron blocker materials and hole blocker materials.

The present invention therefore also relates to a composition comprising at least one compound comprising structures of formula (I) and/or formula (II) or the preferred embodiments recited above and hereinafter and at least one further matrix material. According to a particular aspect of the present invention, the further matrix material has hole-transporting properties.

The present invention further provides a composition comprising at least one compound comprising at least one structure of formula (I) and/or formula (II) or the preferred embodiments recited above and hereinafter and at least one wide band gap material, a wide band gap material being understood to mean a material in the sense of the disclosure of U.S. Pat. No. 7,294,849. These systems exhibit particularly advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

$$HOMO\ (eV) = ((HEh*27.212) - 0.9899)/1.1206$$

$$LUMO\ (eV) = ((LEh*27.212) - 2.0041)/1.385$$

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

The present invention also relates to a composition comprising at least one compound comprising structures of formula (I) and/or formula (II) or the preferred embodiments recited above and hereinafter and at least one phosphorescent emitter, the term "phosphorescent emitter" also being understood to mean phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/

007086, WO 2014/008982, WO 2014/023377, WO 2014/094961, WO 2014/094960 and the as yet unpublished applications EP 13004411.8, EP 14000345.0, EP 14000417.7 and EP 14002623.8. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

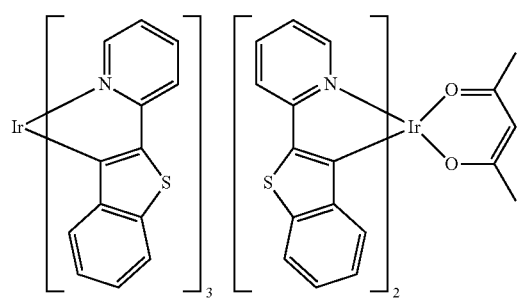

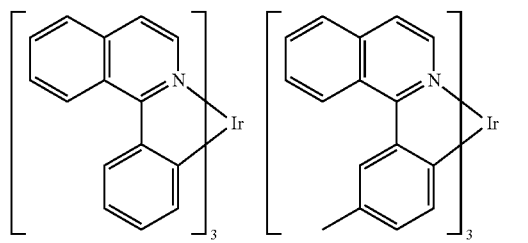

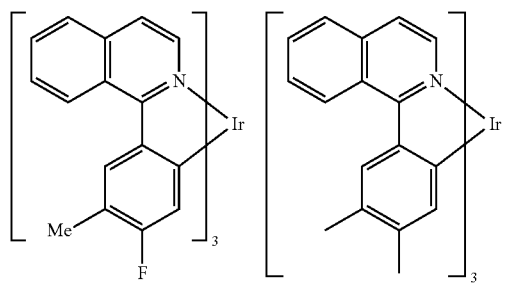

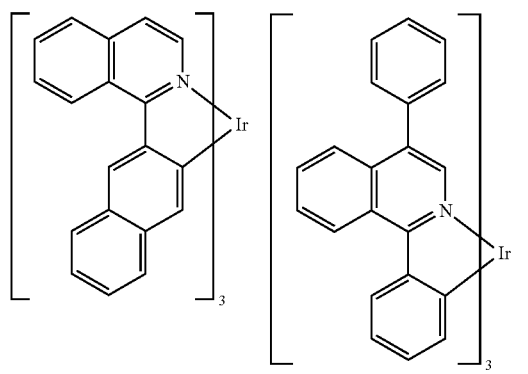

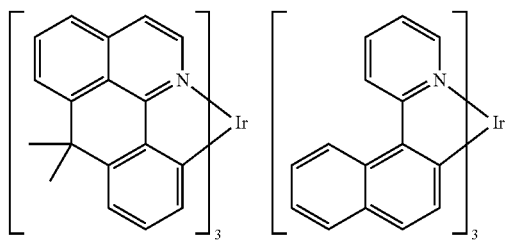

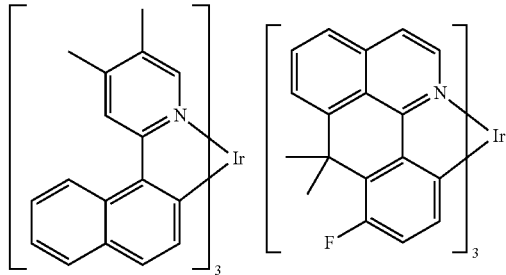

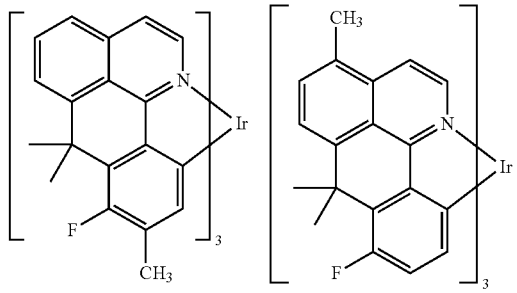

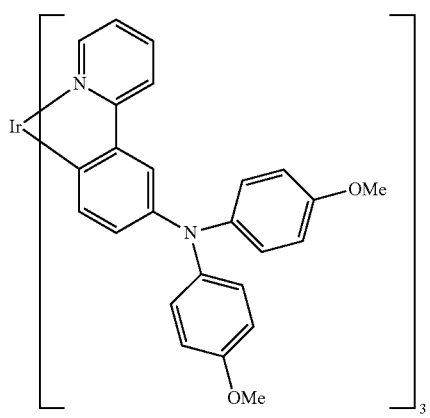

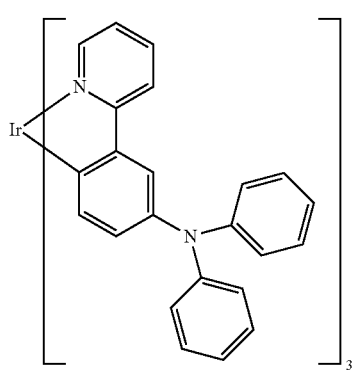

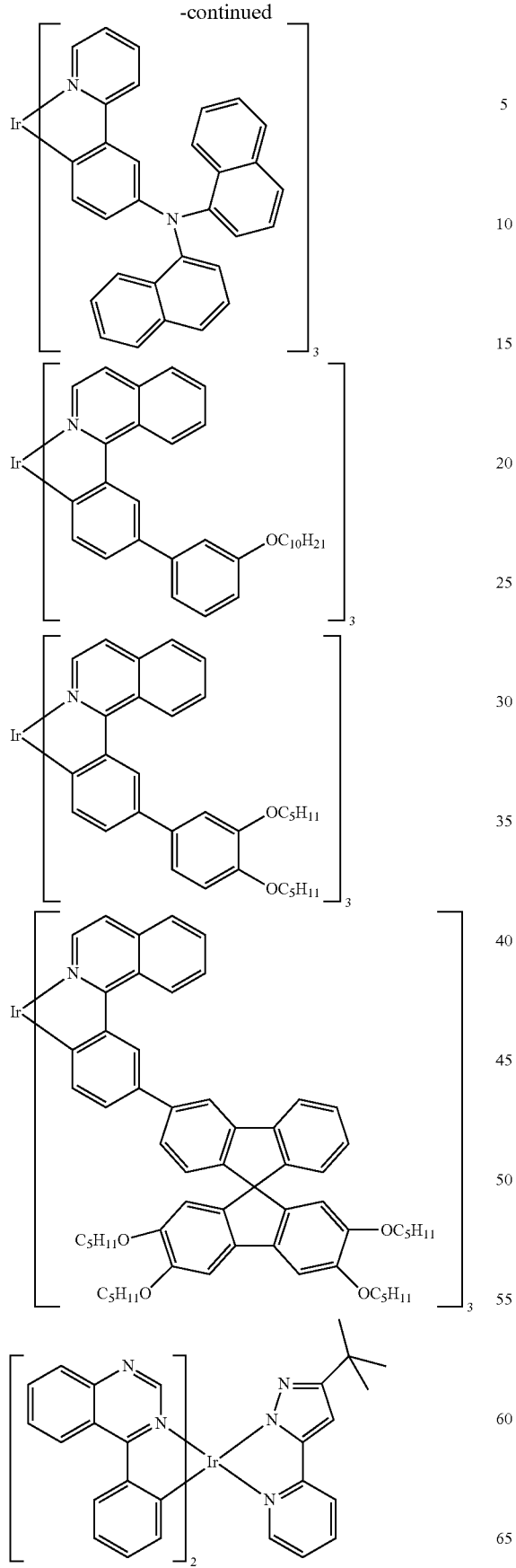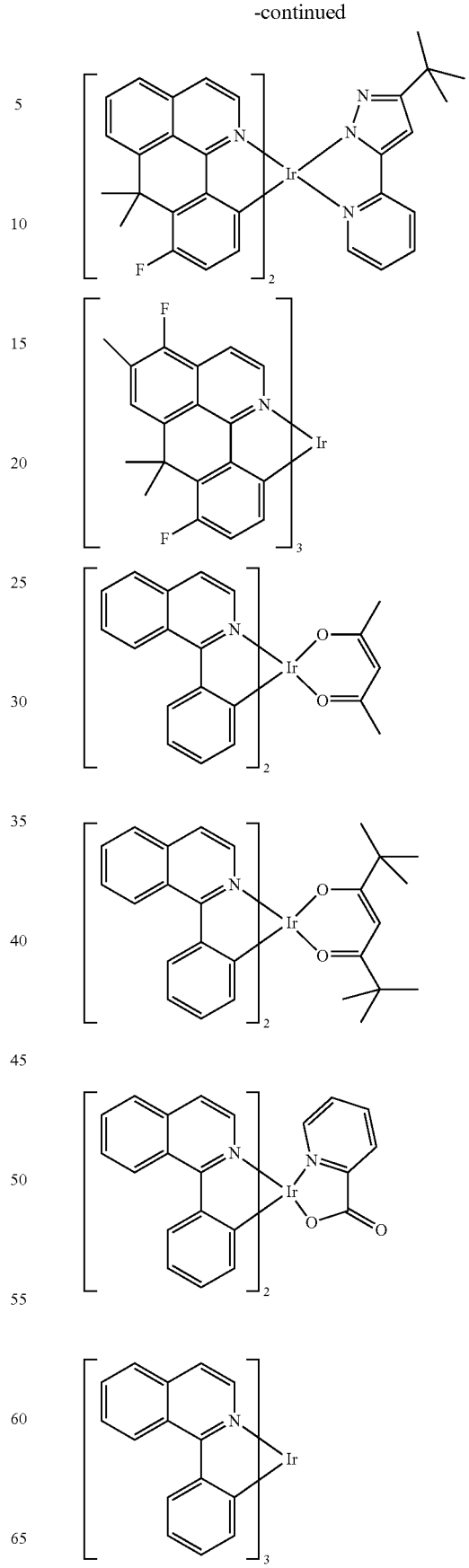

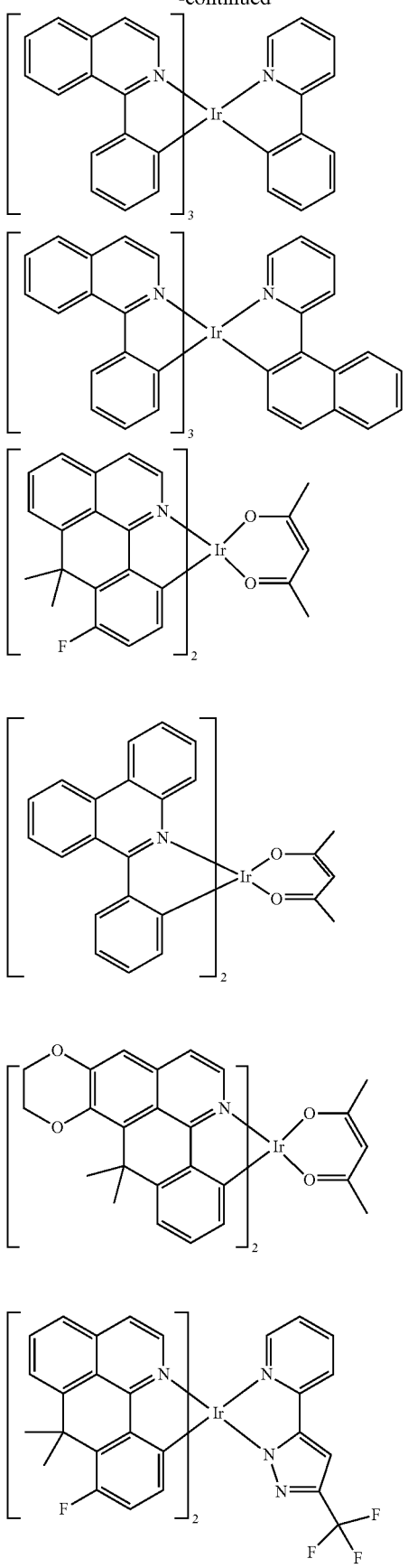
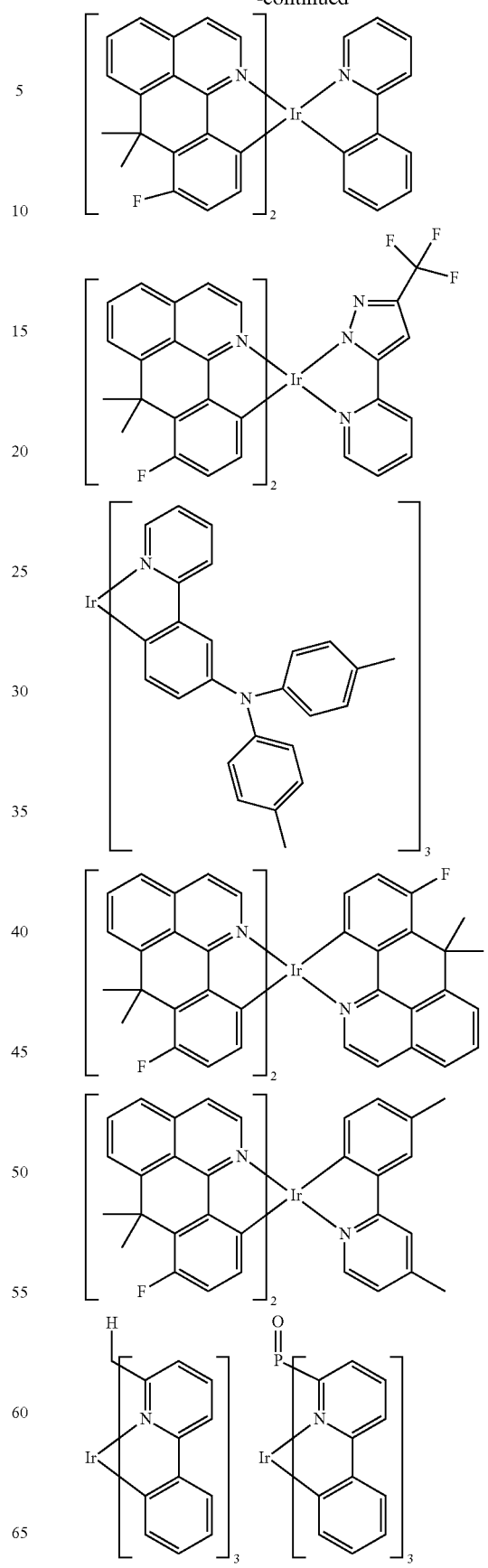

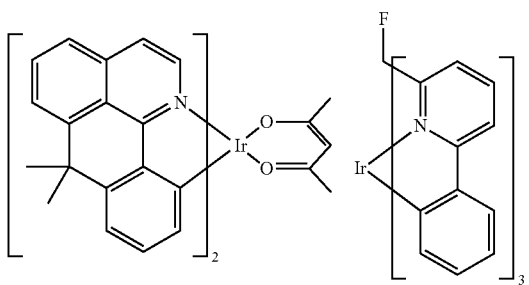
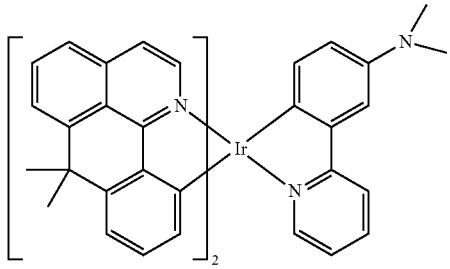
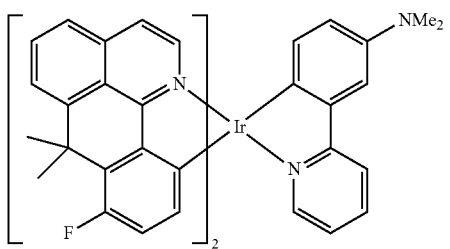
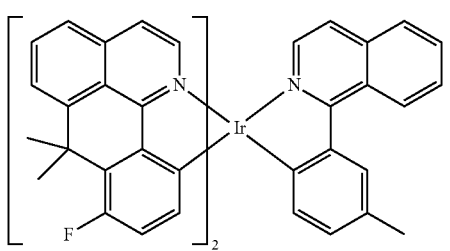
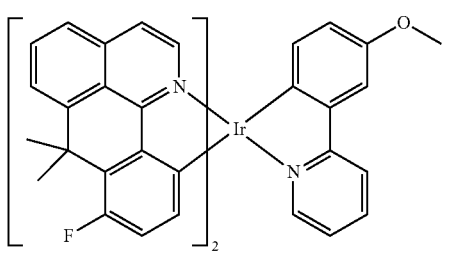
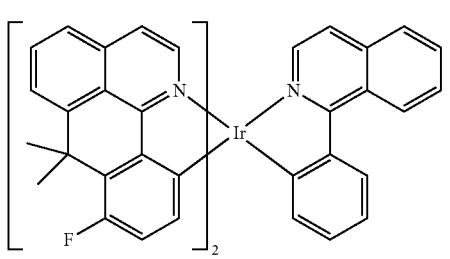
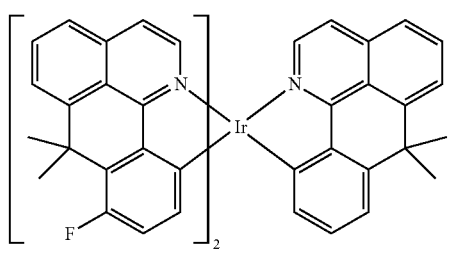
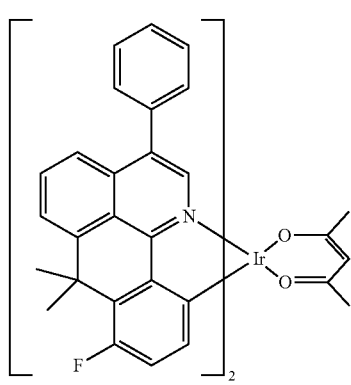
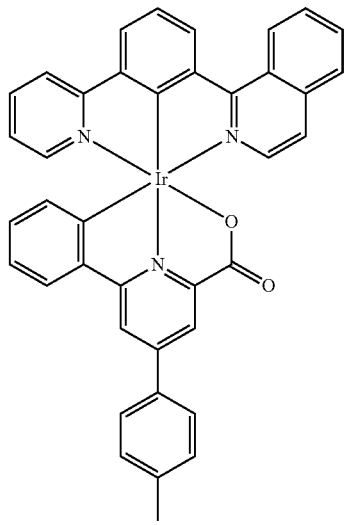
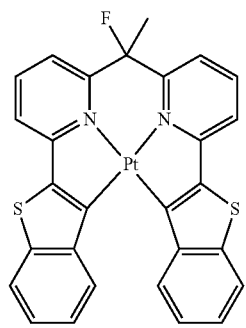

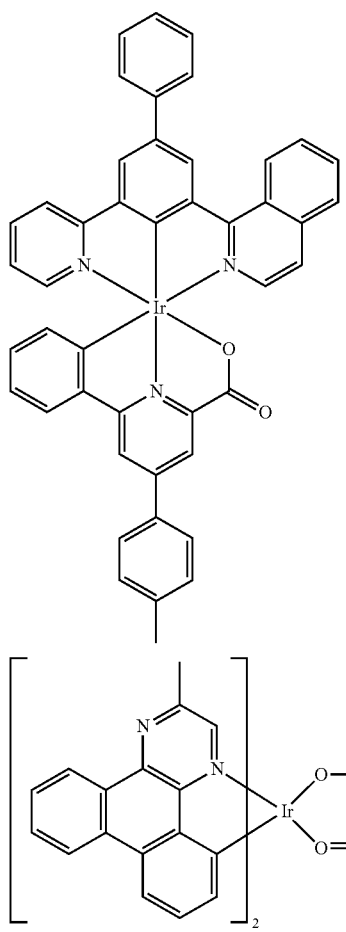
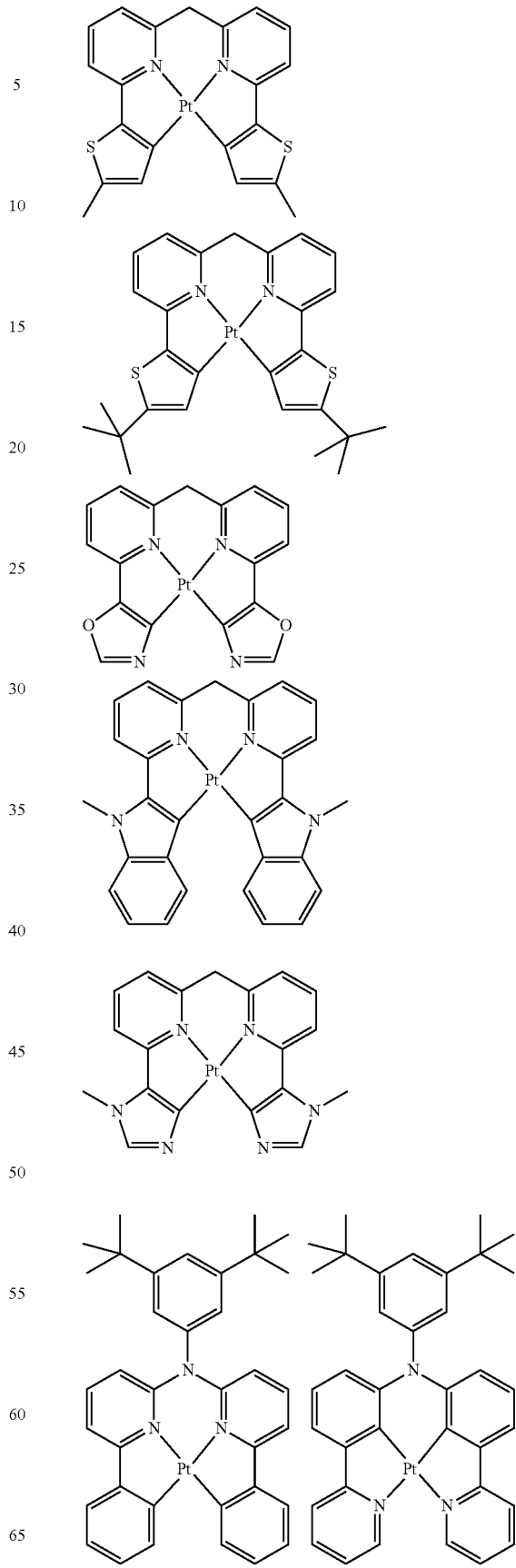

141
-continued
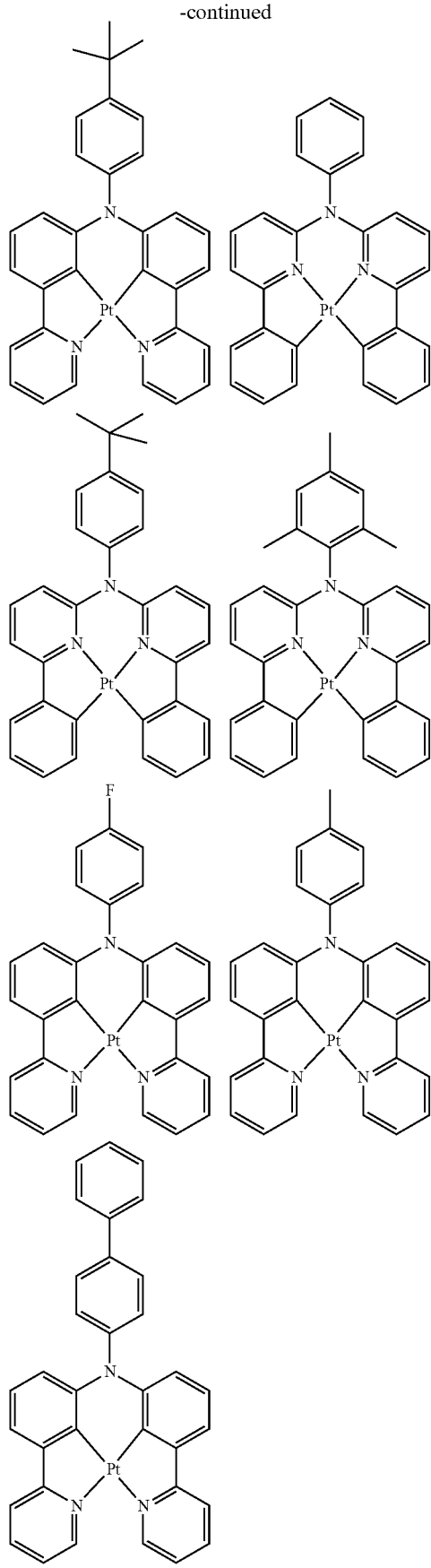
142
-continued
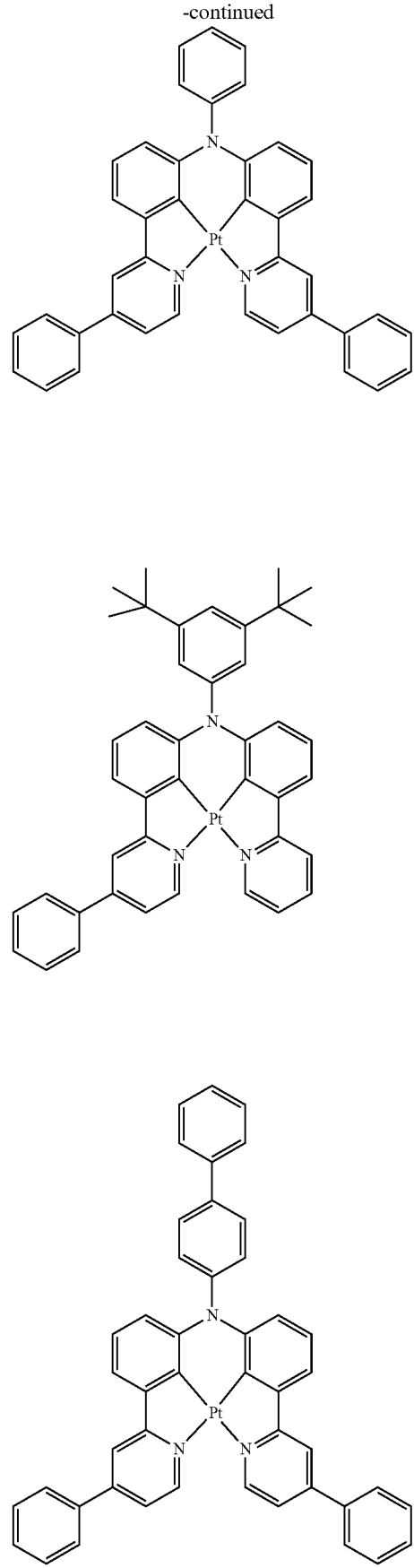

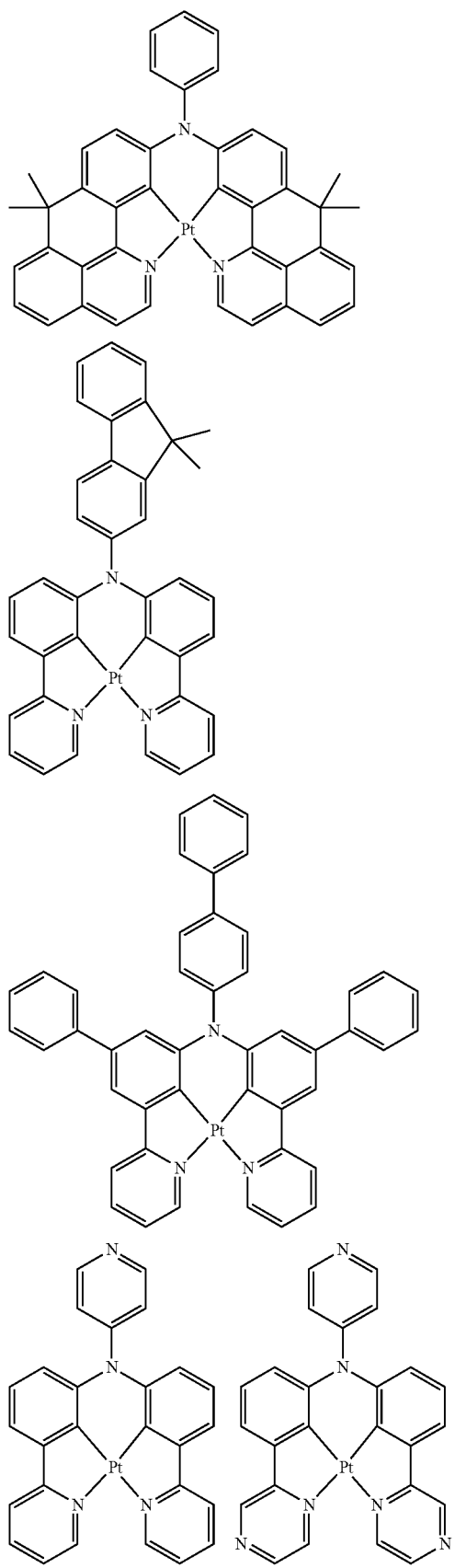
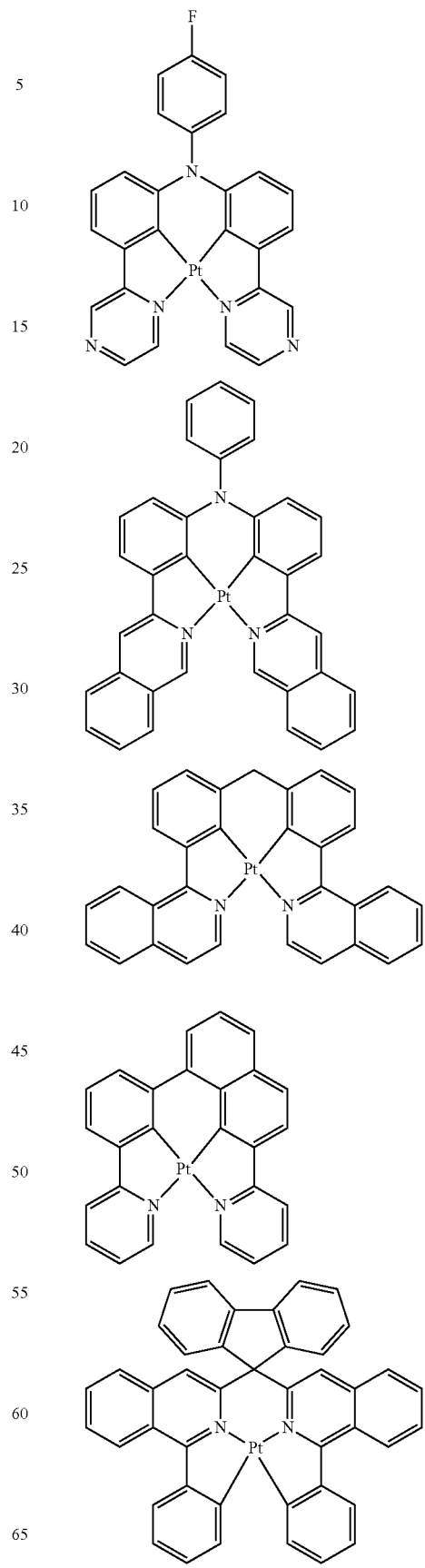

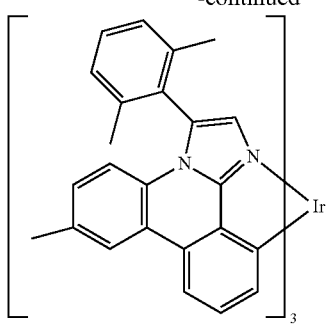
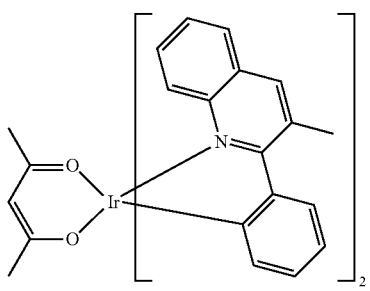
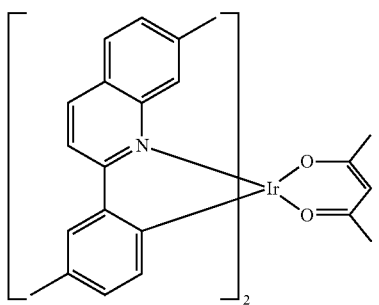
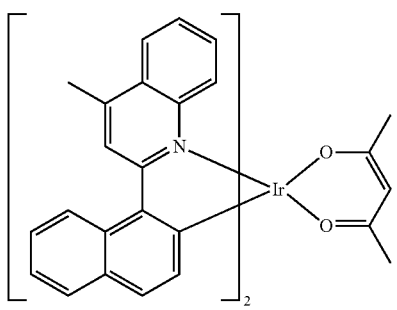
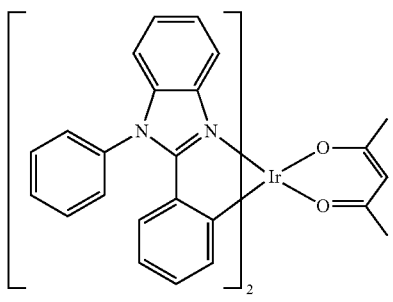
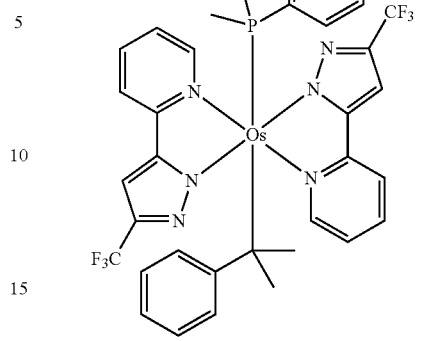
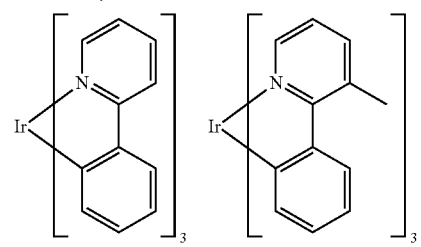
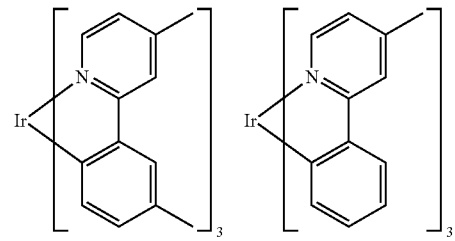
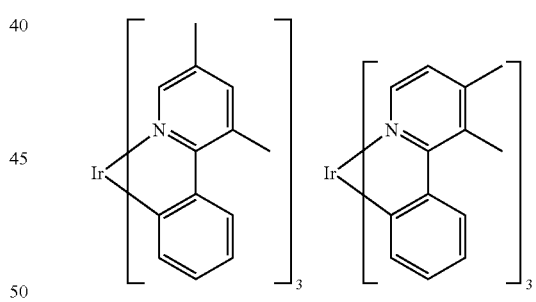
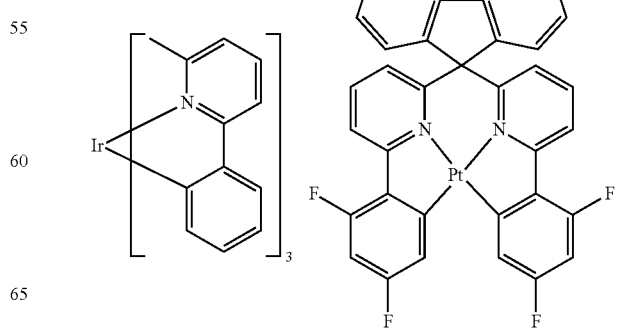

147
-continued
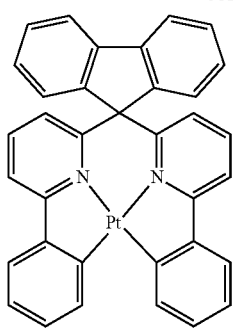
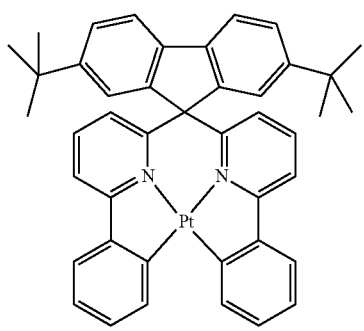
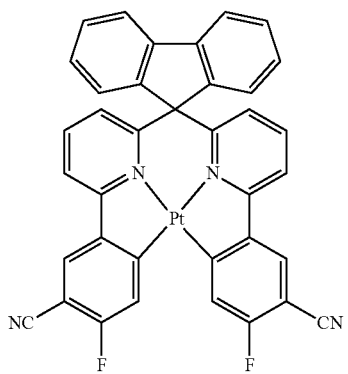
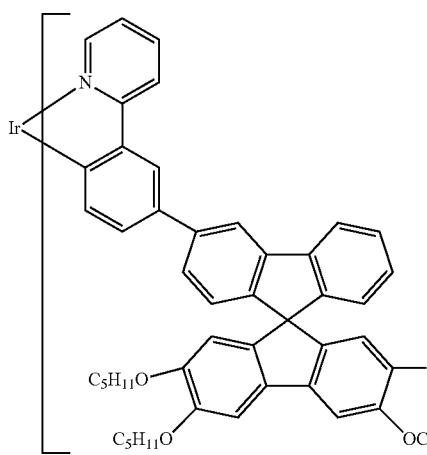
148
-continued
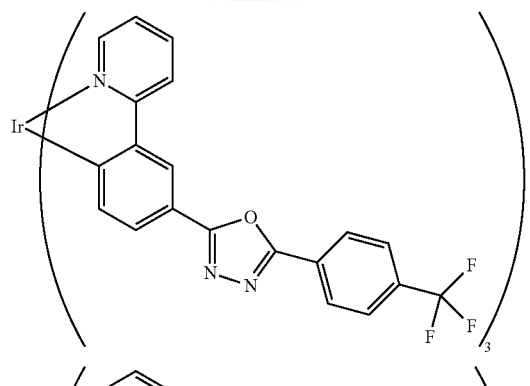
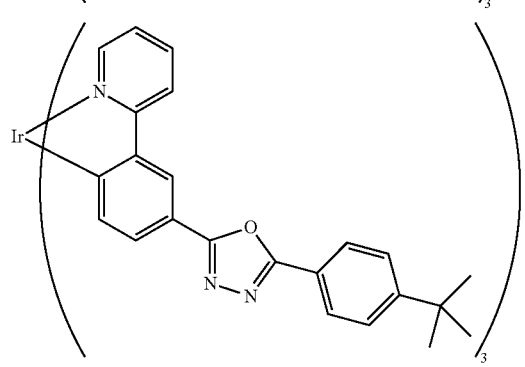
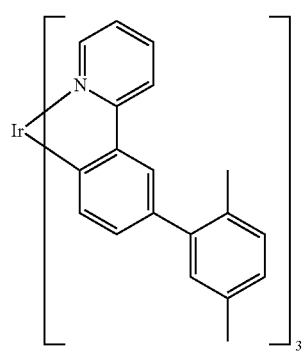
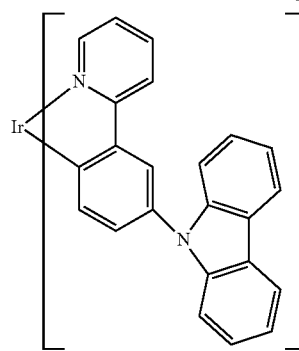
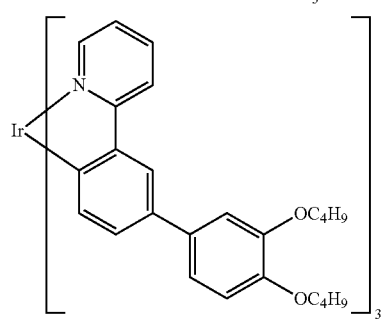

149
-continued
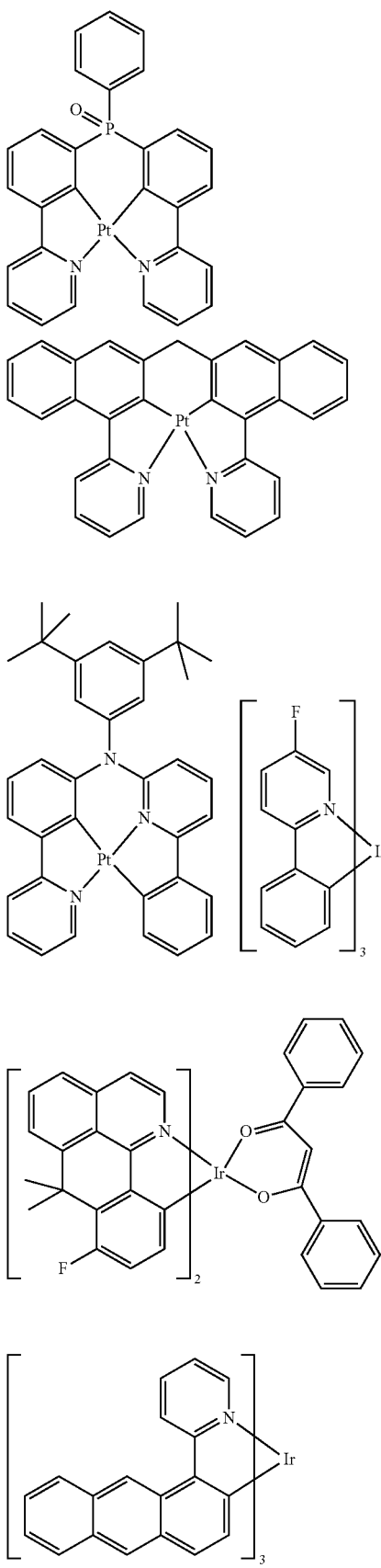
150
-continued
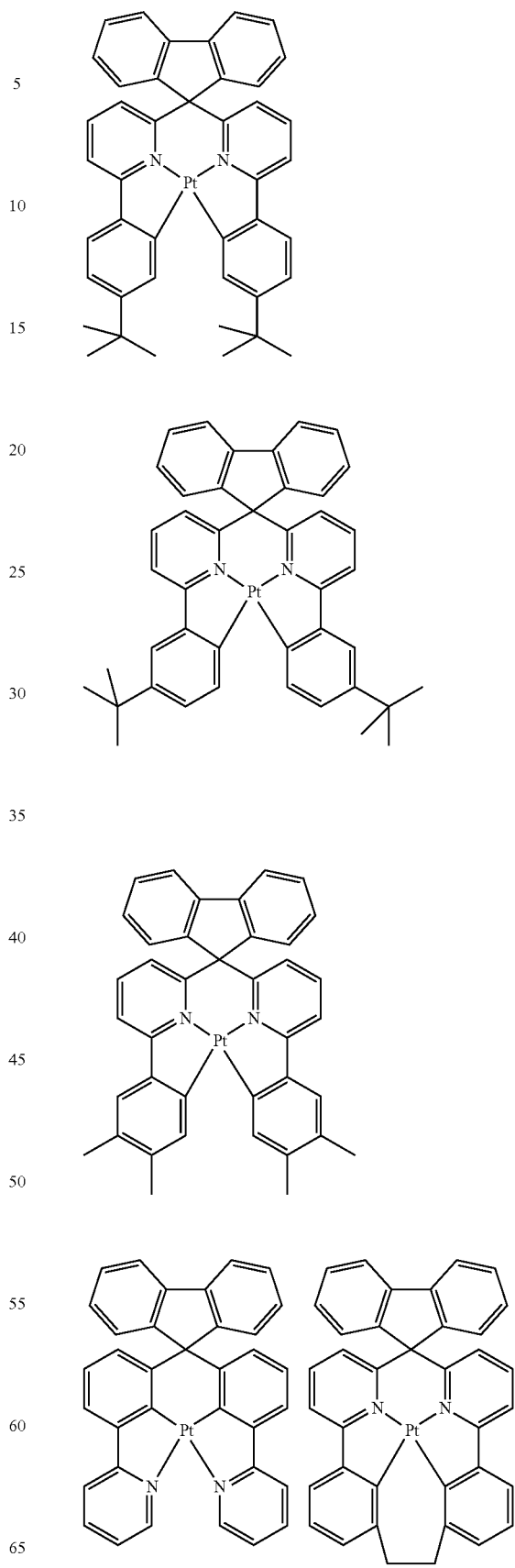

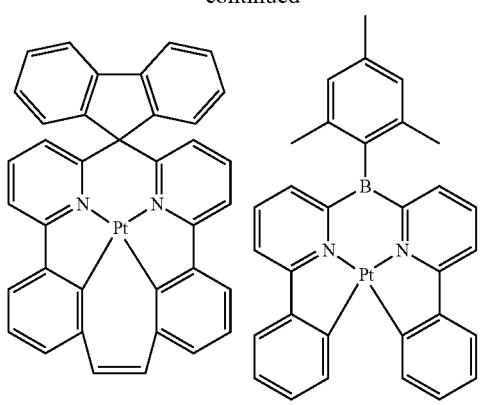
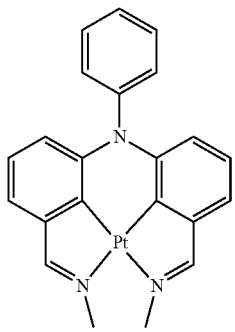
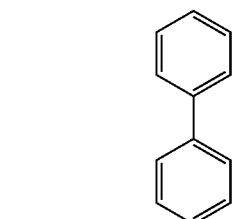
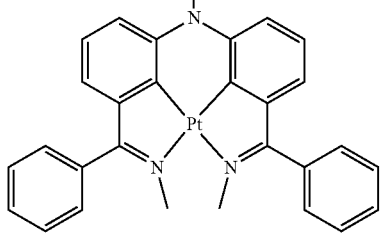
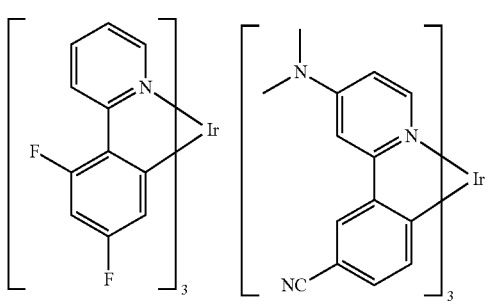
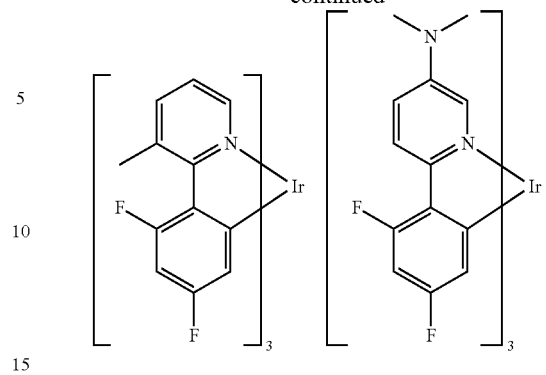
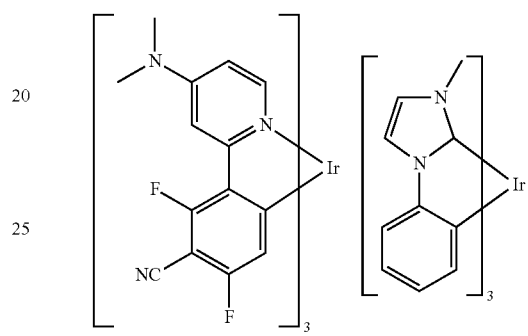
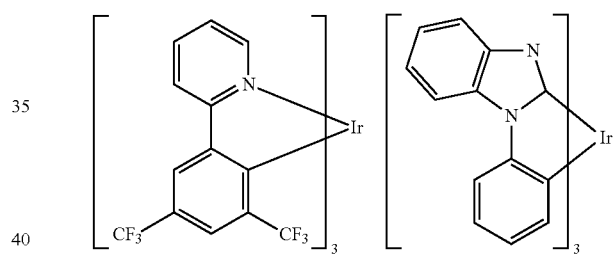
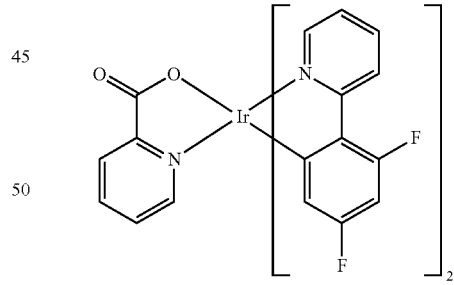
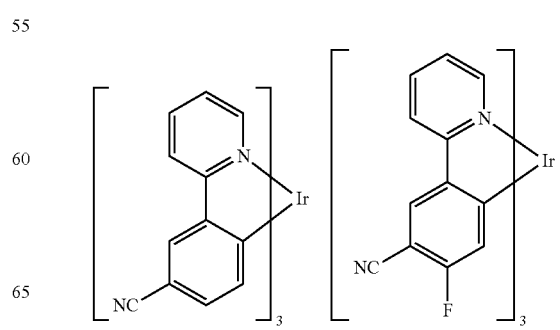

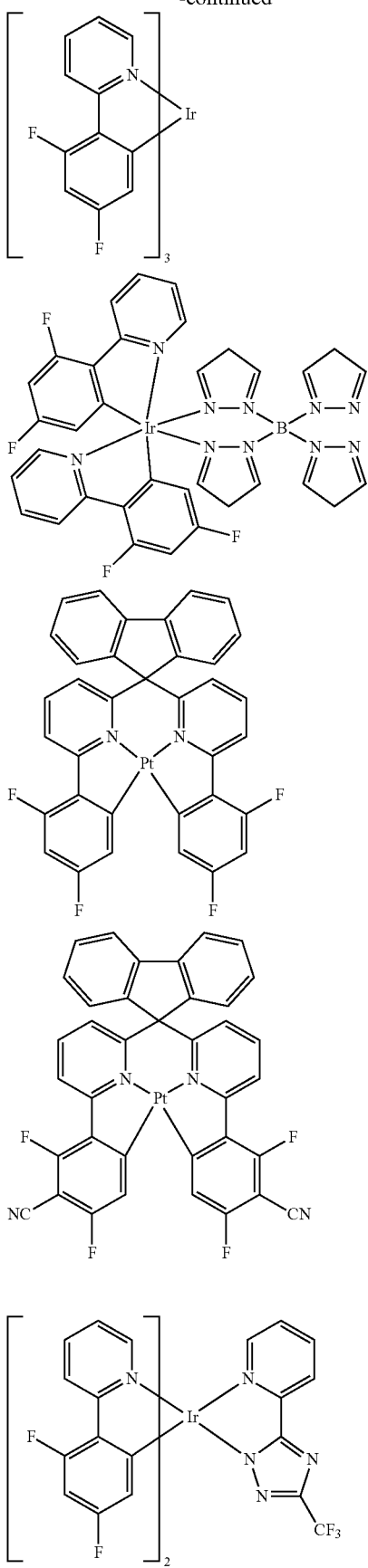
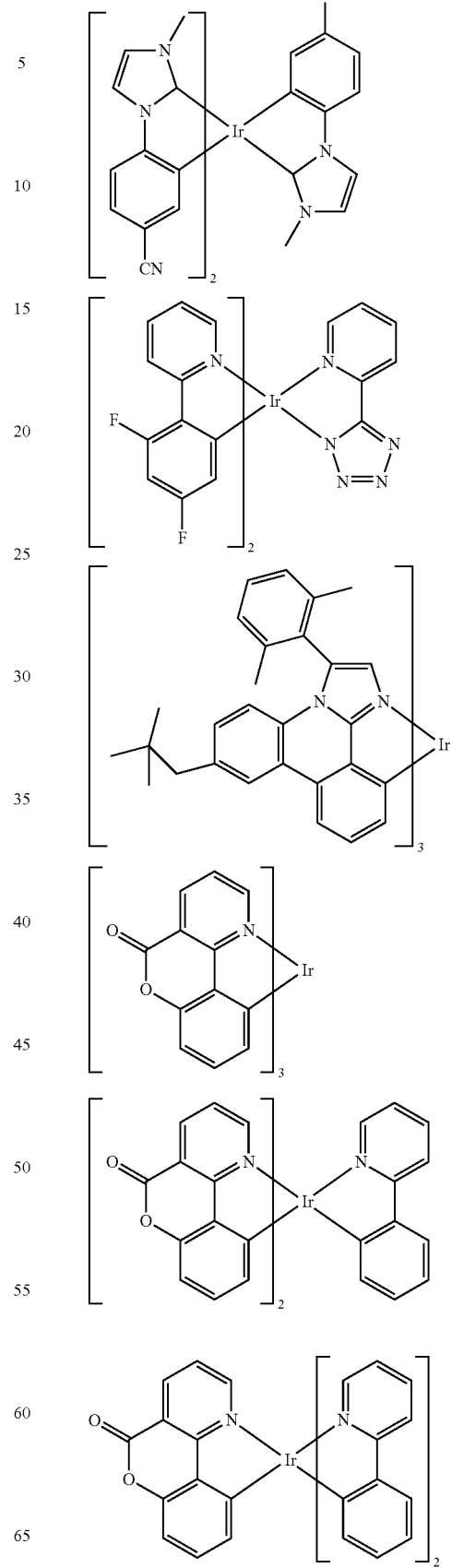

-continued

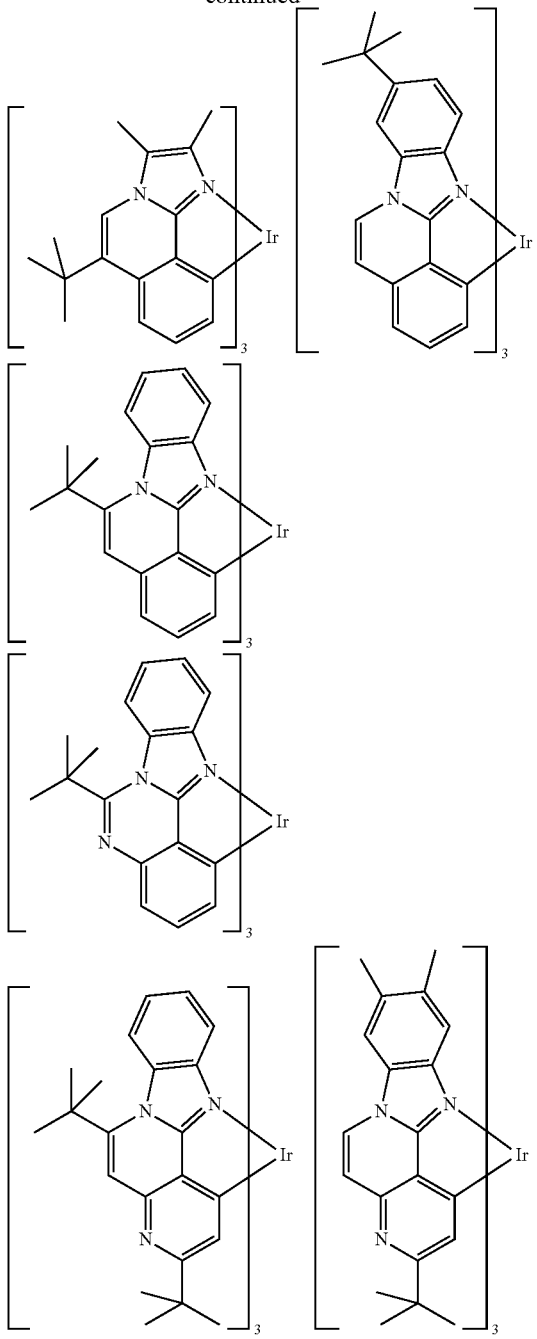

The above-described compound comprising structures of the formula (I) and/or formula (II) or the above-detailed preferred embodiments can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one layer in between containing at least one compound comprising structures of the formula (I) and/or formula (II). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., Nature Photonics 2008, 1-4), preferably organic electroluminescent devices (OLEDs, PLEDs), especially phosphorescent OLEDs, containing at least one compound comprising structures of the formula (I) and/or formula (II) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) and/or (II) or the above-detailed preferred embodiments as matrix material, preferably as electron-conducting matrix material, in one or more emitting layers, preferably in combination with a further matrix material, preferably a hole-conducting matrix material. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer. An emitting layer comprises at least one emitting compound.

Suitable matrix materials which can be used in combination with the compounds of formula (I) and/or (II) or according to the preferred embodiments are aromatic ketones, aromatic phosphine oxides or aromatic sulphoxides or sulphones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, or 4-spirocarbazole derivatives, for example according to WO 2014/094963 or the as yet unpublished application EP 14002104.9. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

Preferred triarylamine derivatives which are used as co-host materials together with the compounds of the invention are selected from the compounds of the following formula (TA-1):

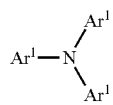

Formula (TA-1)

where $Ar^1$ is the same or different at each instance and is as defined above, especially for formula (Q-1). Preferably, the $Ar^1$ groups are the same or different at each instance and are selected from the abovementioned $R^1$-1 to $R^1$-79 groups, more preferably $R^1$-1 to $R^1$-51.

In a preferred embodiment of the compounds of the formula (TA-1), at least one $Ar^1$ group is selected from a biphenyl group, which may be an ortho-, meta- or para-biphenyl group. In a further preferred embodiment of the compounds of the formula (TA-1), at least one Ar group is selected from a fluorene group or spirobifluorene group, where these groups may each be bonded to the nitrogen atom in the 1, 2, 3 or 4 position. In yet a further preferred embodiment of the compounds of the formula (TA-1), at least one $Ar^1$ group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (TA-1), an $Ar^1$ group selected from a fluorene or spirobifluorene group, especially a 4-fluorene or 4-spirobifluorene group, and an $Ar^1$ group is selected from a biphenyl group, especially a para-biphenyl group, or a fluorene group, especially a 2-fluorene group, and the third $Ar^1$ group is selected from a para-phenylene group or a para-biphenyl group, substituted by a dibenzofuran group, especially a 4-dibenzofuran group, or a carbazole group, especially an N-carbazole group or a 3-carbazole group.

Preferred indenocarbazole derivatives which are used as co-host materials together with the compounds of the invention are selected from the compounds of the following formula (TA-2):

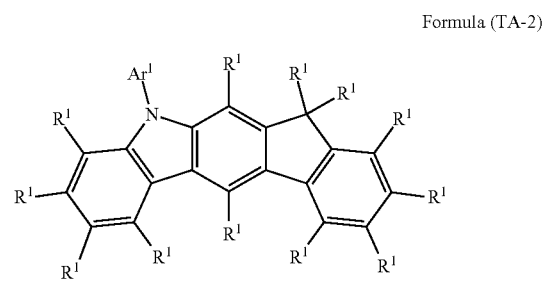

Formula (TA-2)

where $Ar^1$ and $R^1$ have the definitions listed above, especially for formulae (I), (II) and/or (Q-1). Preferred embodiments of the $Ar^1$ group are the above-listed structures $R^1$-1 to $R^1$-79, more preferably $R^1$-1 to $R^1$-51.

A preferred embodiment of the compounds of the formula (TA-2) is the compounds of the following formula (TA-2a):

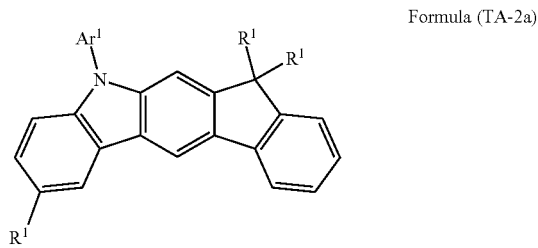

Formula (TA-2a)

where $Ar^1$ and $R^1$ have the definitions given above, especially for formulae (I), (II) and/or (Q-1). The two $R^1$ groups bonded to the indeno carbon atom here are preferably the same or different and are each an alkyl group having 1 to 4 carbon atoms, especially methyl groups, or an aromatic ring system having 6 to 12 carbon atoms, especially phenyl groups. More preferably, the two $R^1$ groups bonded to the indeno carbon atom are methyl groups. Further preferably, the $R^1$ substituent bonded to the indenocarbazole base skeleton in formula (TA-2a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (TA-3):

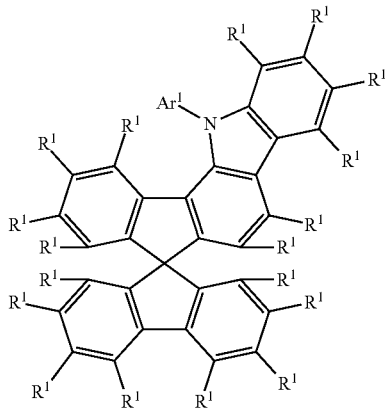

Formula (TA-3)

where $Ar^1$ and $R^1$ have the definitions listed above, especially for formulae (I), (II) and/or (Q-1). Preferred embodiments of the $Ar^1$ group are the above-listed structures $R^1$-1 to $R^1$-79, more preferably $R^1$-1 to $R^1$-51.

A preferred embodiment of the compounds of the formula (TA-3) is the compounds of the following formula (TA-3a):

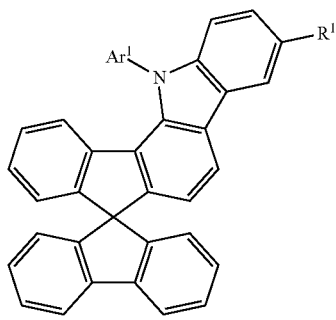

Formula (TA-3a)

where $Ar^1$ and $R^1$ have the definitions listed above, especially for formulae (I), (II) and/or (Q-1). Preferred embodiments of the $Ar^1$ group are the above-listed structures $R^1$-1 to $R^1$-79, more preferably $R^1$-1 to $R^1$-51.

Preferred lactams which are used as co-host materials together with the compounds of the invention are selected from the compounds of the following formula (LAC-1):

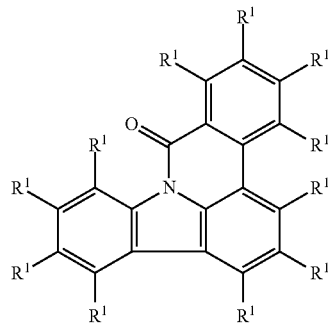

Formula (LAC-1)

where $R^1$ has the definition listed above, especially for formulae (I) and/or (II).

A preferred embodiment of the compounds of the formula (LAC-1) is the compounds of the following formula (LAC-1a):

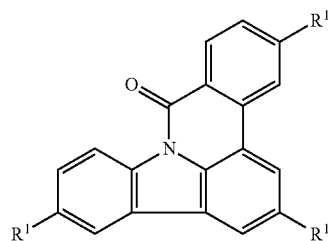

Formula (LAC-1a)

where $R^1$ has the definition given above, especially for formulae (I) and/or (II). $R^1$ is preferably the same or different at each instance and is H or an aromatic or heteroaromatic ring system which has 5 to 40 aromatic ring atoms and may be substituted by one or more $R^2$ radicals, where $R^2$ may have the definition given above, especially for formula (I) and/or formula (II). Most preferably, the $R^1$ substituents are selected from the group consisting of H and an aromatic or heteroaromatic ring system having 6 to 18 aromatic ring atoms, preferably having 6 to 13 aromatic ring atoms, each of which may be substituted by one or more nonaromatic $R^2$ radicals, but is preferably unsubstituted. Examples of suitable $R^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted. Suitable $R^1$ structures are the same structures as depicted above for R-1 to R-79, more preferably $R^1$-1 to $R^1$-51.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, a compound of the invention comprising structures of formula (I) and/or formula (II), in a preferred embodiment, can be used as matrix material in an emission layer of an organic electronic device, especially in an organic electroluminescent device, for example in an OLED or OLEC. In this case, the matrix material containing compound comprising structures of formula (I) and/or formula (II) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) and/or formula (II) or the preferred embodiments recited above and hereinafter is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, 0-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapour deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., Appl. Phys. Lett. 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device can also be produced as a hybrid system by applying one or more layers from solution and applying one or more other layers by vapour deposition. For example, it is thus possible to apply an emitting layer comprising a compound of the invention comprising structures of formula (I) and/or formula (II) and a matrix material from solution, and to apply a hole blocker layer and/or an electron transport layer thereto by vapour deposition under reduced pressure.

These methods are known in general terms to those skilled in the art and can be applied without difficulty to electronic devices, especially organic electroluminescent devices comprising compounds of the invention comprising structures of formula (I) and/or formula (II) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (I) and/or (II) or the preferred embodiments recited above and hereinafter, especially as electron-conducting materials, have a very good lifetime.
2. Electronic devices, especially organic electroluminescent devices, comprising compounds, oligomers, polymers or dendrimers having structures of formula (I) and/or (II) or the preferred embodiments recited above and hereinafter, as electron-conducting materials have excellent efficiency. More particularly, efficiency is much higher compared to analogous compounds containing no structural unit of formula (I) and/or (II).
3. The compounds, oligomers, polymers or dendrimers of the invention having structures of formula (I) and/or (II) or the preferred embodiments detailed above and hereinafter exhibit very high stability and lead to compounds having a very long lifetime.
4. With compounds, oligomers, polymers or dendrimers having structures of formula (I) and/or (II) or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
5. The use of compounds, oligomers, polymers or dendrimers having structures of formula (I) and/or (II) or the preferred embodiments recited above and hereinafter in layers of electronic devices, especially organic electroluminescent devices, leads to high mobility of the electron conductor structures.
6. Compounds, oligomers, polymers or dendrimers having structures of formula (I) and/or (II) or the preferred embodiments recited above and hereinafter feature excellent thermal stability, and compounds having a molar mass of less than about 1200 g/mol have good sublimability.
7. Compounds, oligomers, polymers or dendrimers having structures of formula (I) and/or (II) or the preferred embodiments recited above and hereinafter have excellent glass film formation.
8. Compounds, oligomers, polymers or dendrimers having structures of formula (I) and/or (II) or the preferred embodiments detailed above and hereinafter form very good films from solutions.
9. The compounds, oligomers, polymers or dendrimers comprising structures of formula (I) and/or (II) or the preferred embodiments recited above and hereinafter have a surprisingly high triplet level $T_1$, this being particularly true of compounds which are used as electron-conducting materials.

These abovementioned advantages are not accompanied by a deterioration in the further electronic properties.

The inventive compounds and mixtures are suitable for use in an electronic device. An electronic device is understood to mean a device containing at least one layer containing at least one organic compound. This component may also comprise inorganic materials or else layers formed entirely from inorganic materials.

The present invention therefore further provides for the use of the inventive compounds or mixtures in an electronic device, especially in an organic electroluminescent device.

The present invention still further provides for the use of a compound of the invention and/or an oligomer, polymer or dendrimer of the invention in an electronic device as hole blocker material, electron injection material and/or electron transport material.

The present invention still further provides an electronic device comprising at least one of the above-detailed inventive compounds or mixtures. In this case, the preferences detailed above for the compound also apply to the electronic devices.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In addition, it is possible to use the compounds of the invention in a hole blocker or electron transport layer. This is especially true of compounds of the invention which do not have a carbazole structure. These may preferably also be substituted by one or more further electron-transporting groups, for example benzimidazole groups.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (I) and/or (II) or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention.

Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The solvents and reagents can be purchased, for example, from Sigma-ALDRICH or ABCR. For the compounds known from the literature, the corresponding CAS numbers are also reported in each case.

Synthesis Examples a) 4-Bromo-9-methyl-9-phenyl-9H-fluorene

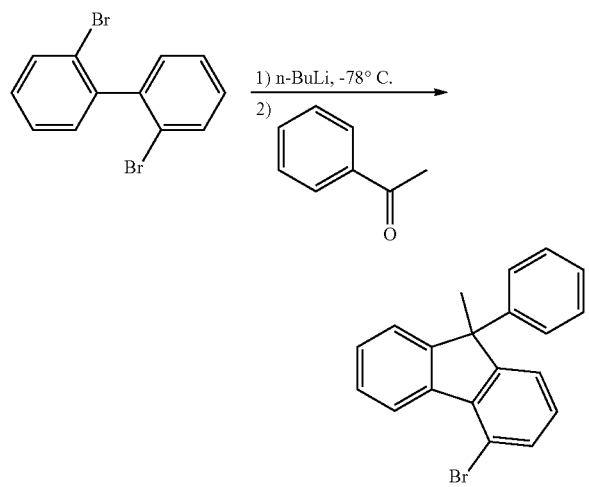

30 g (94 mmol) of 2,2'-dibromobiphenyl are dissolved in a baked-out flask in 200 ml of dried THF. The reaction mixture is cooled to −78° C. At this temperature, 37.7 ml of a 2.5 M solution of n-butyllithium in hexane (94 mmol) are slowly added dropwise (over about 1 h). The mixture is stirred at −70° C. for a further 1 h. Subsequently, 11.1 ml of acetophenone (94 mmol) are dissolved in 100 ml of THF and added dropwise at −70° C. After the addition has ended, the reaction mixture is warmed gradually to room temperature, quenched with $NH_4Cl$ and then concentrated on a rotary evaporator. 300 ml of acetic acid are added cautiously to the concentrated solution and then 50 ml of fuming HCl are added. The mixture is heated to 75° C. and kept there for 6 h. During this time, a white solid precipitates out.

The mixture is cooled to room temperature, and the precipitated solid is filtered off with suction and washed with methanol. The residue is dried at 40° C. under reduced pressure. Yield is 25.3 g (75 mmol) (80% of theory).

b) 4-Bromo-9,9-diphenyl-9H-fluorene

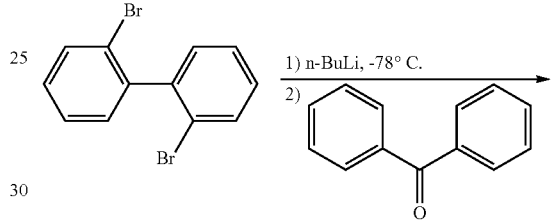

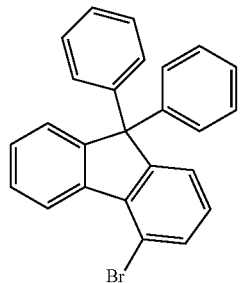

37 g (152 mmol) of 2,2'-dibromobiphenyl are dissolved in a baked-out flask in 300 ml of dried THF. The reaction mixture is cooled to −78° C. At this temperature, 75 ml of a 15% solution of n-butyllithium in hexane (119 mmol) are slowly added dropwise (over about 1 hour). The mixture is stirred at −70° C. for a further 1 h. Subsequently, 21.8 g of benzophenone (119 mmol) are dissolved in 100 ml of THF and added dropwise at −70° C. After the addition has ended, the reaction mixture is warmed gradually to room temperature, quenched with $NH_4Cl$ and then concentrated on a rotary evaporator. 510 ml of acetic acid are added cautiously to the concentrated solution and then 100 ml of fuming HCl are added. The mixture is heated to 75° C. and kept at this temperature for 4 h. During this time, a white solid precipitates out. The mixture is then cooled to room temperature, and the precipitated solid is filtered off with suction and washed with methanol. The residue is dried at 40° C. under reduced pressure. Yield is 33.2 g (83 mmol) (70% of theory).

In an analogous manner, the following brominated compounds are prepared:

| Reactant 1 | Reactant 2 | Product | Yield |
|---|---|---|---|
| b1 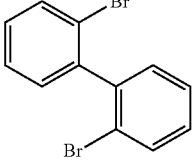 | 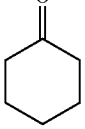 | 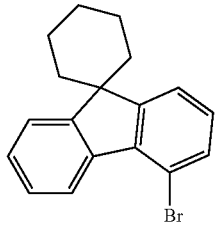 [SMILES: Brc1cccc2c1-c1ccccc1C21CCCCC1] | 78% |
| b2 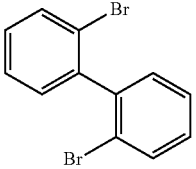 [SMILES: Brc1ccccc1-c1ccccc1Br] |  | 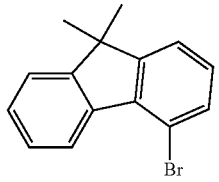 [SMILES: CC1(C)c2ccccc2-c2c(Br)cccc21] | 70% |
| b3 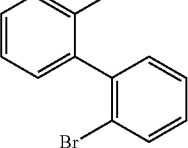 | 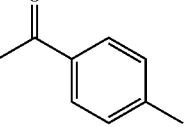 | 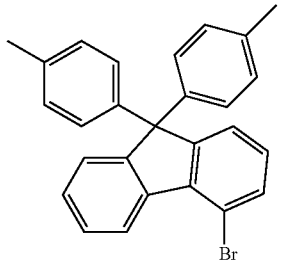 | 82% | c) 1-Bromospiro-9,9′-bifluorene

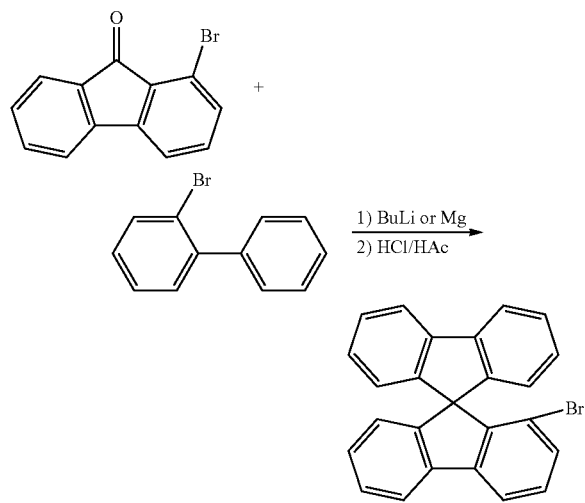

2.7 g (110 mmol) of iodine-activated magnesium turnings and a mixture of 25.6 g (110 mmol) of 2-bromobiphenyl, 0.8 ml of 1,2-dichloroethane, 50 ml of 1,2-dimethoxyethane, 400 ml of THF and 200 ml of toluene are used to prepare the corresponding Grignard reagent by trace heating with an oil bath at 70° C. Once the magnesium has reacted fully, the mixture is cooled to room temperature and then a solution of 25.9 g (100 mmol) of 1-bromofluorenone [36804-63-4] in 500 ml of THF is added dropwise, and the reaction mixture is heated to 50° C. for 4 h and then stirred at room temperature for a further 12 h. 100 ml of water are added, the mixture is stirred briefly, the organic phase is removed and the solvent is removed under reduced pressure. The residue is suspended in 500 ml of glacial acetic acid heated to 40° C., 0.5 ml of conc. sulphuric acid is added to the suspension and the mixture is then stirred at 100° C. for 2 h. After cooling, the precipitated solid is filtered off with suction and washed once with 100 ml of glacial acetic acid and three times with 100 ml each time of ethanol, and finally recrystallized from dioxane. Yield: 26.9 g (68 mmol), 68%; purity: about 98% by $^1$H NMR.

The following compound is obtained in an analogous manner:

| | Reactant 1 | Reactant 2 | Product | Yield |
|---|---|---|---|---|
| 1c | 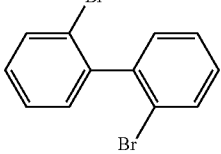 13029-09-9 | 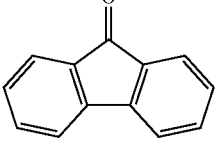 486-25-9 | 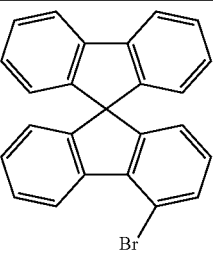 1161009-88-6 | 90% | d) 4-Biphenyl-4-yl-2-chloroquinazoline

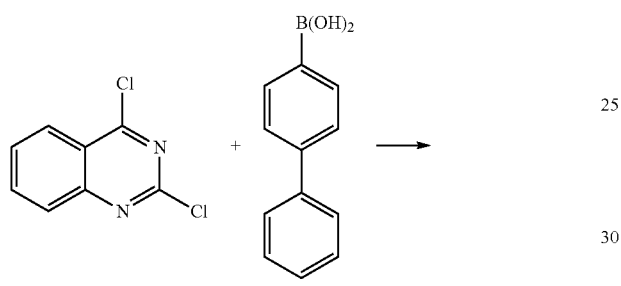

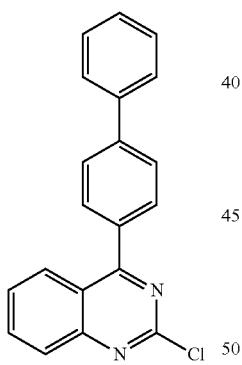

13 g (70 mmol) of biphenyl-4-boronic acid, 13.8 g (70 mmol) of 2,4-dichloroquinazoline and 14.7 g (139 mmol) of sodium carbonate are suspended in 200 ml of toluene, 52 ml of ethanol and 100 ml of water. 800 mg (0.69 mmol) of tetrakisphenylphosphinepalladium(0) are added to this suspension, and the reaction mixture is heated under reflux for 16 h. After cooling, the organic phase is removed, filtered through silica gel, washed three times with 200 ml of water and then concentrated to dryness. The residue is recrystallized from heptane/dichloromethane. The yield is 13 g (41 mmol), corresponding to 59% of theory.

In an analogous manner, the following compounds are obtained:
| | Reactant 1 | Reactant 2 | Product | Yield |
|---|---|---|---|---|
| 2d | 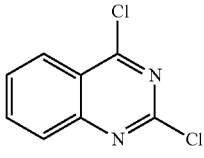 [607-68-1] | 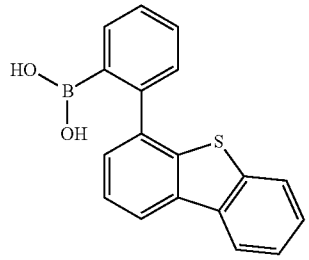 [1384699-53-9] | 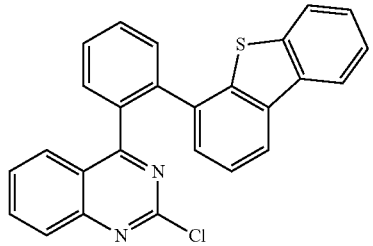 [SMILES: Clc1nc(-c2ccccc2-c2cccc3c2sc2ccccc23)c2ccccc2n1] | 76% |
| 3d | 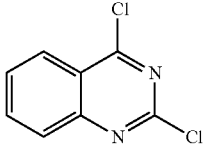 [607-68-1] | 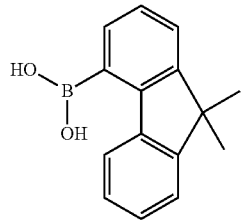 [1246022-50-3] | 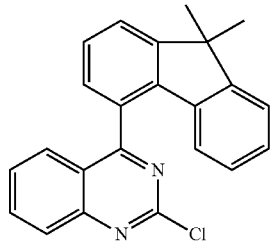 [SMILES: CC1(C)c2ccccc2-c2c(-c3nc(Cl)nc4ccccc34)cccc21] | 75% |
| 4d | 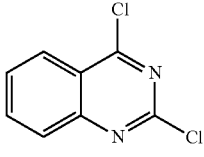 [607-68-1] | 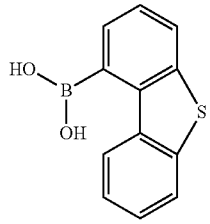 [1245943-60-5] | 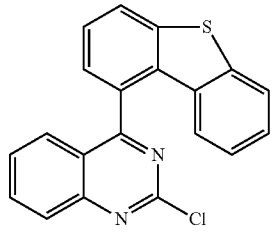 | 73% |
| 5d | 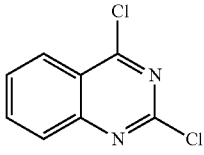 [607-68-1] | 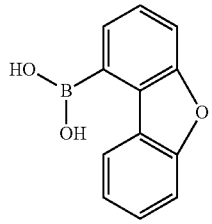 [162607-19-4] | 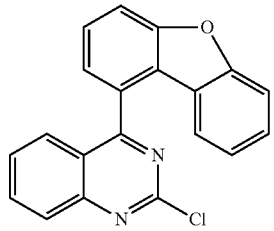 | 78% |
| 6d | 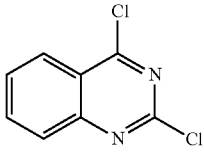 [607-68-1] | 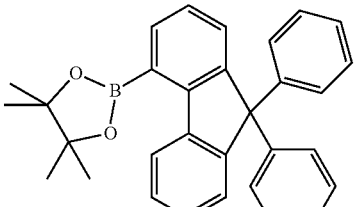 [1259280-37-9] | 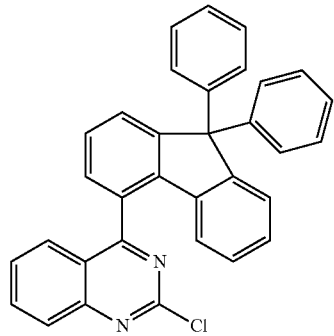 [SMILES: Clc1nc(-c2cccc3c2-c2ccccc2C3(c2ccccc2)c2ccccc2)c2ccccc2n1] | 76% |

-continued
| | Reactant 1 | Reactant 2 | Product | Yield |
|---|---|---|---|---|
| 7d | 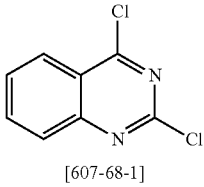 [SMILES: Clc1nc(Cl)c2ccccc2n1] [607-68-1] | 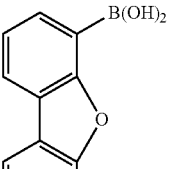 [100124-06-9] | 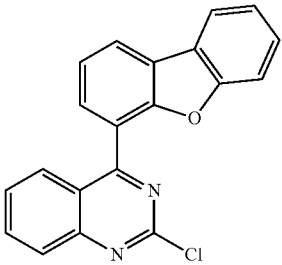 [SMILES: Clc1nc(-c2cccc3c2oc2ccccc23)c2ccccc2n1] | 77% |
| 8d | 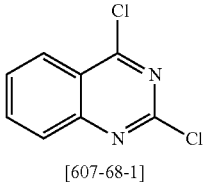 [SMILES: Clc1nc(Cl)c2ccccc2n1] [607-68-1] | 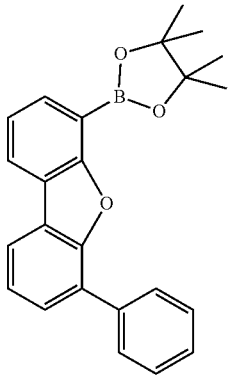 [1556069-49-8] | 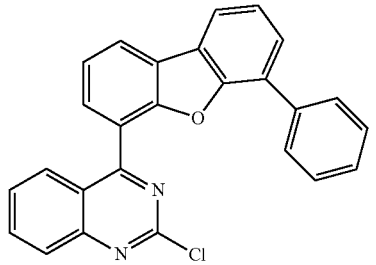 [SMILES: Clc1nc(-c2cccc3c2oc2c(-c4ccccc4)cccc23)c2ccccc2n1] | 72% |
| 9d | 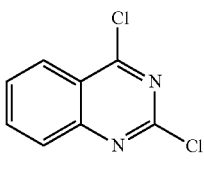 [607-68-1] | 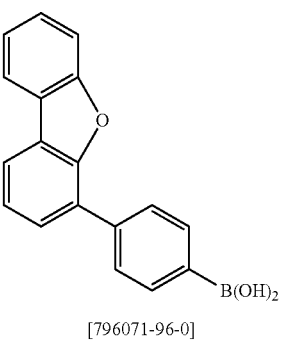 [SMILES: OB(O)c1ccc(-c2cccc3c2oc2ccccc23)cc1] [796071-96-0] | 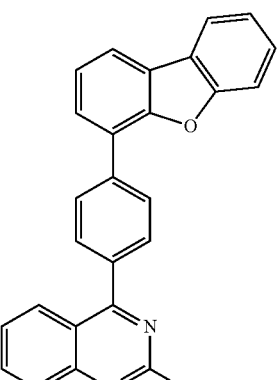 [607-68-1] | 73% |
| 10d | 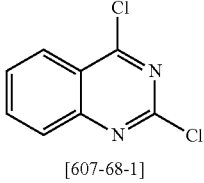 [SMILES: Clc1nc(Cl)c2ccccc2n1] [607-68-1] | 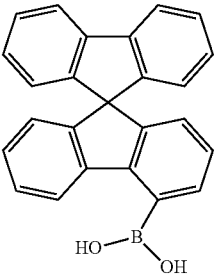 [SMILES: OB(O)c1cccc2c1-c1ccccc1C21c2ccccc2-c2ccccc21] | 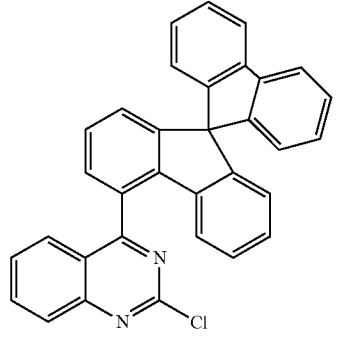 [SMILES: Clc1nc(-c2cccc3c2-c2ccccc2C32c3ccccc3-c3ccccc32)c2ccccc2n1] | 72% | e) Synthesis of 4-(9H,9'H-[9,9']bifluorenyl-1-yl)-2-phenylquinazoline

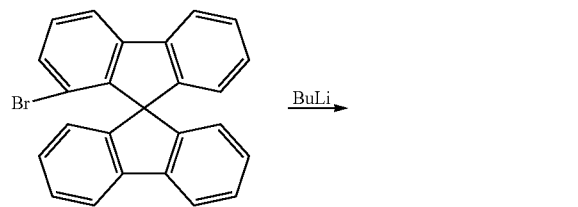

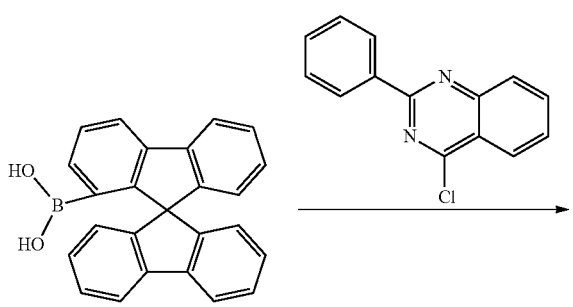

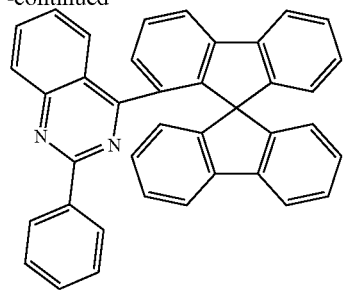

Step 1) Synthesis of spiro-9,9'-bifluorene-1-boronic acid

To a solution, cooled to −78° C., of 106 g (270 mmol) of 1-bromo-9-spirobifluorene in 1500 ml of diethyl ether are added dropwise 110 ml (276 mmol) of n-butyllithium (2.5 M in hexane). The reaction mixture is stirred at −78° C. for 30 min. The mixture is allowed to come to room temperature and cooled again to −78° C., and then a mixture of 40 ml (351 mmol) of trimethyl borate in 50 ml of diethyl ether is added rapidly. After warming to −10° C., hydrolysis is effected with 135 ml of 2 N hydrochloric acid. The organic phase is removed, washed with water, dried over sodium sulphate and concentrated to dryness. The residue is taken up in 300 ml of n-heptane, and the colourless solid is filtered off with suction, washed with n-heptane and dried under reduced pressure. Yield: 94.5 g (255 mmol), 99% of theory; purity: 99% by HPLC.

In an analogous manner, the following compounds are obtained:

| | Reactant 1 | Product | Yield |
|---|---|---|---|
| 1e | | | 83% |
| 2e | | | 80% |
| 3e | | | 83% |

-continued

| | Reactant 1 | Product | Yield |
|---|---|---|---|
| 4e | | | 75% |
| 5e | | | 70% |
| 6e | | | 72% |
| 7e | [1225053-54-2] | | 63% |
| 8e | [1613372-04-5] | | 74% |

| Reactant 1 | Product | Yield |
|---|---|---|
| 9e 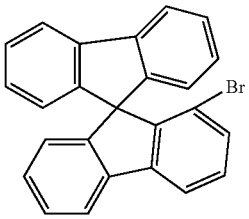 [1450933-18-2] | 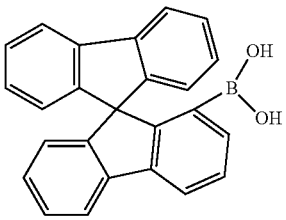 [1450933-18-2] | 70% |

Step 2) 4-(9H,9'H-[9,9']bifluorenyl-1-yl)-2-phenylquinazoline 56.8 g (110 mmol) of spiro-9,9'-bifluorene-1-boronic acid, 26 g (110.0 mmol) of 4-chloro-2-phenylquinazoline and 44.6 g (210.0 mmol) of tripotassium phosphate are suspended in 500 ml of toluene, 500 ml of dioxane and 500 ml of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 ml of water and then concentrated to dryness. The residue is recrystallized from toluene and from dichloromethane/iso-propanol and finally sublimed under high vacuum ($p=5\times10^{-5}$ mbar, T=350° C.). The yield is 64 g (43.5 mmol), corresponding to 80% of theory.

In an analogous manner, the following compounds are obtained:

| | Reactant 1 | Reactant 2 | Product | Yield |
|---|---|---|---|---|
| 9e | ![](spiro-fluorene boronic acid) | [29874-83-7] | ![](product 9e) | 81% |
| 10e | ![](spiro-fluorene boronic acid) | [6484-25-9] | ![](product 10e) | 80% |

-continued

| | Reactant 1 | Reactant 2 | Product | Yield |
|---|---|---|---|---|
| 11e | | [1627575-10-3] | | 72% |
| 12e | | | | 70% |

| | Reactant 1 | Reactant 2 | Product | Yield |
|---|---|---|---|---|
| 13e | | | | 82% |
| 14e | | | | 78% |

-continued

| | Reactant 1 | Reactant 2 | Product | Yield |
|---|---|---|---|---|
| 15e | 9,9-diphenylfluorene-4-boronic acid | 2-chloro-4-(4-(dibenzofuran-4-yl)phenyl)quinazoline [607-68-1] | | 79% |
| 16e | 9,9-dimethylfluorene-1-boronic acid | 2-chloro-4-(4-(dibenzofuran-4-yl)phenyl)quinazoline [607-68-1] | | 70% |

-continued

| | Reactant 1 | Reactant 2 | Product | Yield |
|---|---|---|---|---|
| 17e | | | | 65% |
| 18e | | | | 79% |

| | Reactant 1 | Reactant 2 | Product | Yield |
|---|---|---|---|---|
| 19e | | | | 63% |
| 20e | | | | 73% |

-continued
| | Reactant 1 | Reactant 2 | Product | Yield |
|---|---|---|---|---|
| 21e | 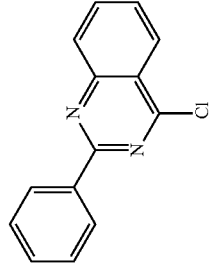 | 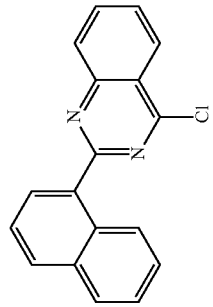 [6484-25-9] | 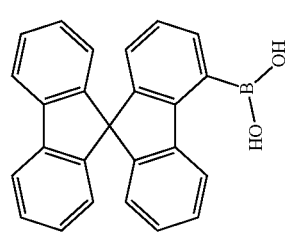 | 72% |
| 22e | | [133594-92-0] | 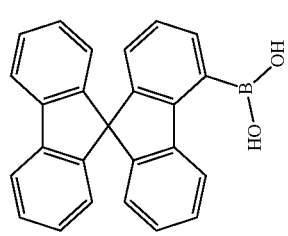 | 77% |

| | Reactant 1 | Reactant 2 | Product | Yield |
|---|---|---|---|---|
| 23e | | [1561960-15-3] | | 74% |
| 24e | | [1400697-34-8] | | 81% |

| | Reactant 1 | Reactant 2 | Product | Yield |
|---|---|---|---|---|
| 25e | 9,9'-spirobifluorene-boronic acid | 6-bromo-2,4-diphenylquinazoline [1229609-99-7] | | 80% |
| 26e | 9,9'-spirobifluorene-boronic acid | 6-bromo-4-chloro-2-phenylquinazoline [64484-25-9] | | 69% |
| 27e | 9,9-dimethylfluorene-4-boronic acid | | | 73% |

-continued
| | Reactant 1 | Reactant 2 | Product | Yield |
|---|---|---|---|---|
| 28f | 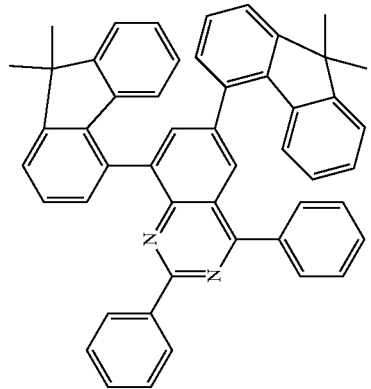 | 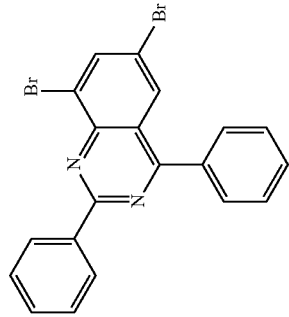 [107288-87-9] | 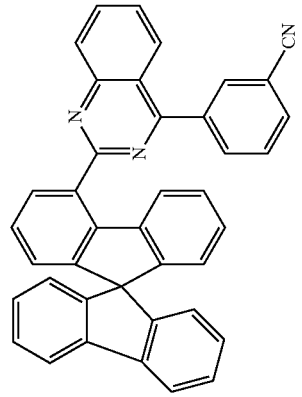 | 68% |
| 29e | 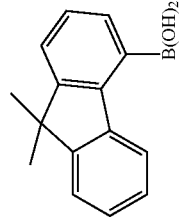 | 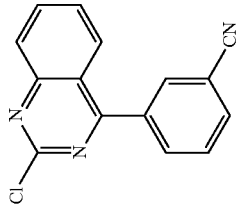 [1292317-90-8] | 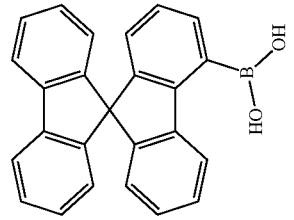 | 65% |

-continued

| | Reactant 1 | Reactant 2 | Product | Yield |
|---|---|---|---|---|
| 30e | (9,9-diphenylfluoren-4-yl)-phenyl-4-B(OH)₂ | 2-chloro-4-phenylquinazoline [29874-83-7] | 201 | 68% |
| 31e | (9,9-dimethylfluoren-4-yl)-B(OH)₂ | 2-(3-chlorophenyl)-4-phenylquinazoline [540466-41-9] | 202 | 63% |

-continued

| | Reactant 1 | Reactant 2 | Product | Yield |
|---|---|---|---|---|
| 32e | (9,9-dimethylfluoren-4-yl)boronic acid | 4-(4-bromophenyl)-2-phenylquinazoline [160254-04-6] | | 79% |
| 33e | (9,9-dimethylfluoren-4-yl)boronic acid | 2,4-bis(4-bromophenyl)quinazoline [144678 5-97-2] | | 81% |

-continued

| | Reactant 1 | Reactant 2 | Product | Yield |
|---|---|---|---|---|
| 34e | (9,9'-spirobifluorene-boronic acid) | 2-(4-bromonaphthalen-1-yl)-4-phenylquinazoline [1621469-45-1] | | 65% |
| 35e | (9,9'-spirobifluorene-boronic acid) | 4-(3-bromophenyl)-2-phenyl-1,7-naphthyridine [1632307-99-3] | | 66% |

-continued
| | Reactant 1 | Reactant 2 | Product | Yield |
|---|---|---|---|---|
| 36e | 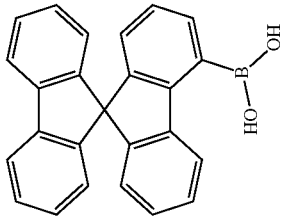 | 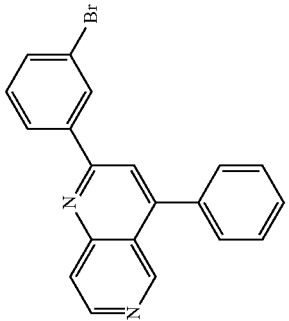 [1632307-97-1] | 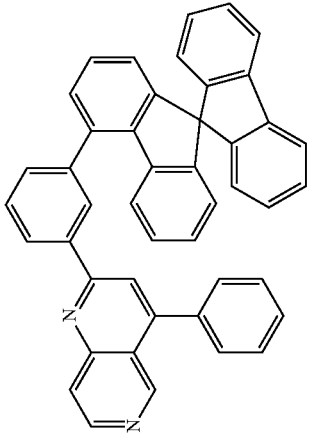 | 71% |
| 37e | 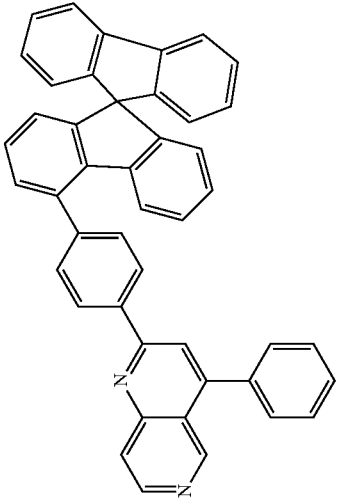 | 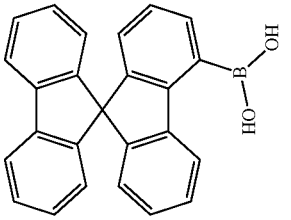 [1632307-96-0] | | 69% |

-continued
| | Reactant 1 | Reactant 2 | Product | Yield |
|---|---|---|---|---|
| 38e | 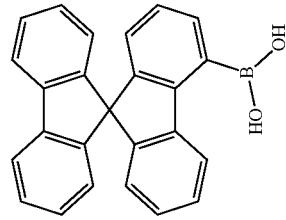 | 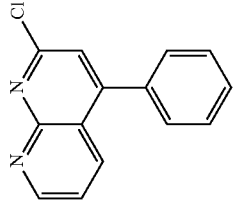 [33760-75-7] | 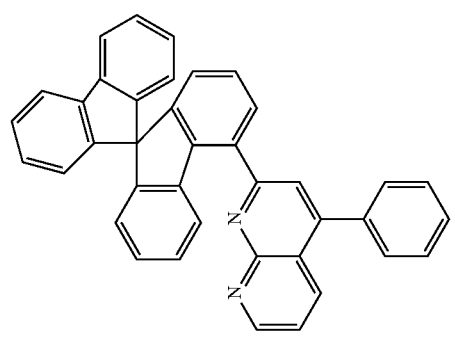 | 63% |
| 39e | 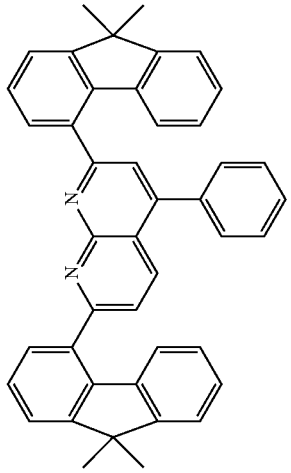 | [58035-57-7] | | 65% |

| | Reactant 1 | Reactant 2 | Product | Yield |
|---|---|---|---|---|
| 40e | | | | 60% |
| 41e | | | | 61% |

-continued

| | Reactant 1 | Reactant 2 | Product | Yield |
|---|---|---|---|---|
| 42e | 854952-60-6 | | 213 | 69% |
| 43e | 1426392-81-5 | | 214 | 64% |

| | Reactant 1 | Reactant 2 | Product | Yield |
|---|---|---|---|---|
| 44e | [334658-75-2] | | | 66% |
| 45e | [1553408-82-4] | | | 69% |
| 46e | [1236181-90-0] | | | 70% |

| | Reactant 1 | Reactant 2 | Product | Yield |
|---|---|---|---|---|
| 47e | [936901-91-6] | | | 61% |
| 48e | [952514-79-3] | | | 64% |

| | Reactant 1 | Reactant 2 | Product | Yield |
|---|---|---|---|---|
| 49e | 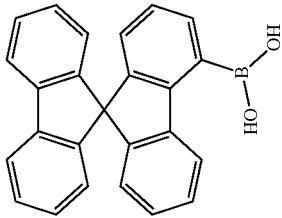 | 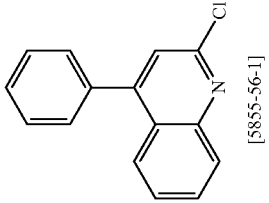 [5855-56-1] | 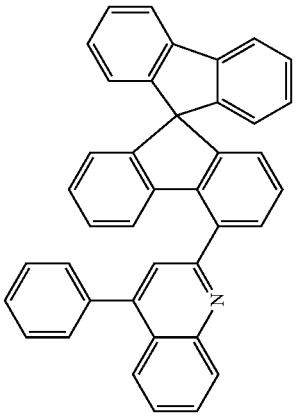 | 73% |
| 50e | 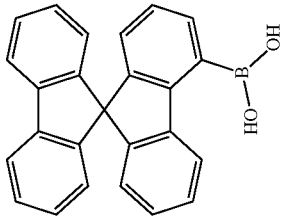 | 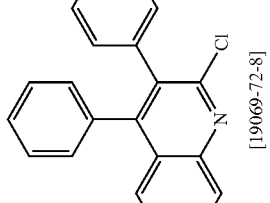 [19069-72-8] | 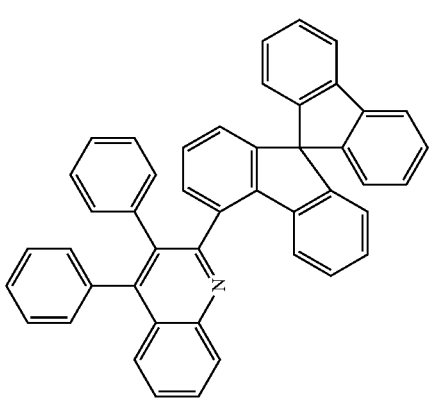 | 62% |
| 51e | 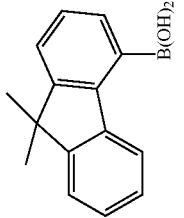 | 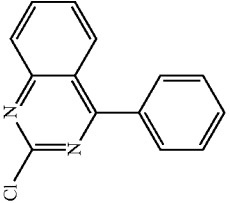 [29874-83-7] | 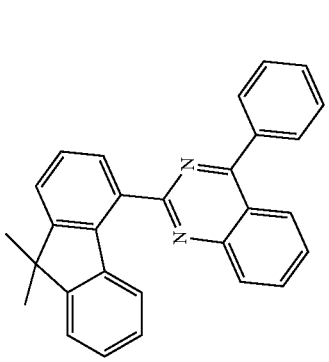 | 75% |

| | Reactant 1 | Reactant 2 | Product | Yield |
|---|---|---|---|---|
| 52e | 9,9-dimethylfluorenyl-4-boronic acid | 7-bromo-2,4-diphenylquinazoline [1400697-34-8] | product | 68% |
| 53e | 9,9-dimethylfluorenyl-4-boronic acid | 4-chloro-2-phenylquinazoline [6484-25-9] | product | 60% |
| 54e | 9,9-dimethylfluorenyl-4-boronic acid | 2-chloro-4-phenylquinazoline [29874-83-7] | product | 61% |

| | Reactant 1 | Reactant 2 | Product | Yield |
|---|---|---|---|---|
| 55e | 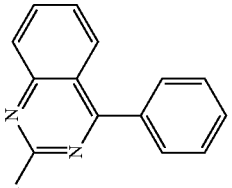 [1450933-18-2] | 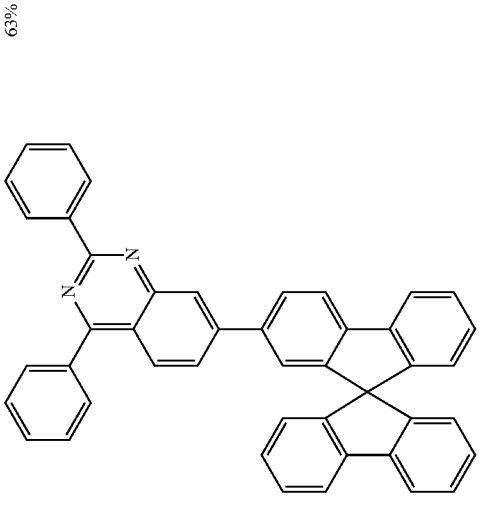 [29874-83-7] | 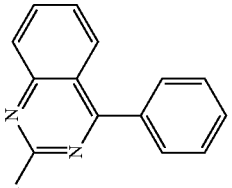 | 59% |
| 56e | 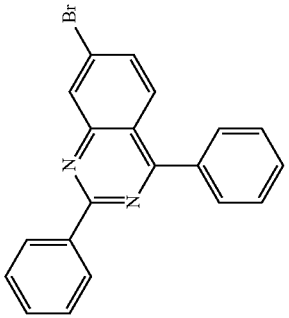 [236389-21-2] | 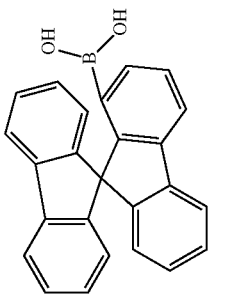 [1400697-34-8] | 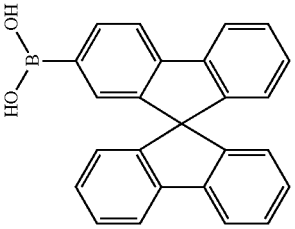 | 63% |

| | Reactant 1 | Reactant 2 | Product | Yield |
|---|---|---|---|---|
| 57e | 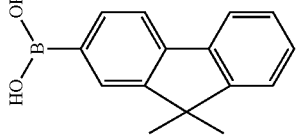<br>[333432-28-3] | 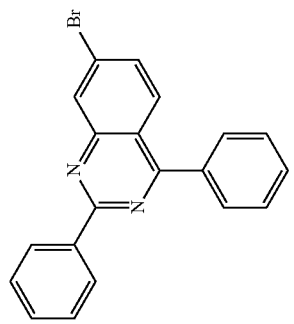<br>[1400697-34-8] | | 65% |
| 58e | 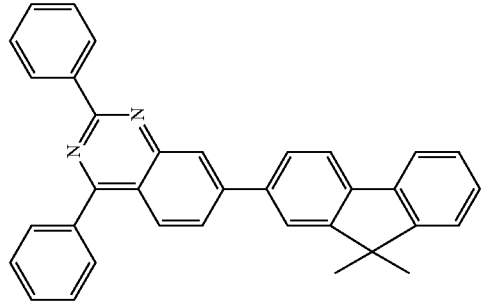 | 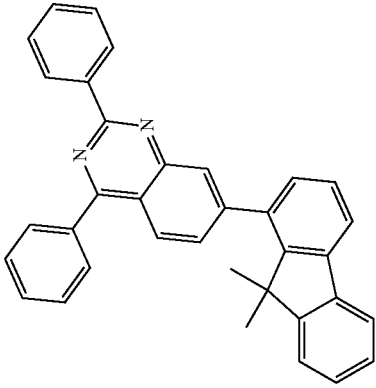<br>[1400697-34-8] | | 62% |

| | Reactant 1 | Reactant 2 | Product | Yield |
|---|---|---|---|---|
| 59e | [1251773-34-8] | [1400697-34-8] | | 60% |
| 60e | [1772611-33-2] | | | 64% |

-continued f) 2-(7-Bromo-9,9-dimethyl-9H-fluoren-4-yl)-4-phenylquinazoline

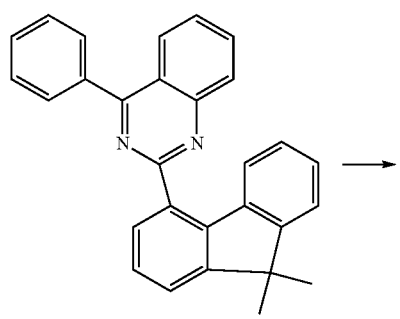

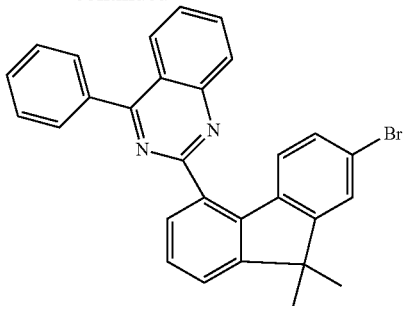

75.6 g (190.0 mmol) of 2-(9,9-dimethyl-9H-fluoren-4-yl)-4-phenylquinazoline are suspended in 2000 ml of acetic acid (100%) and 2000 ml of sulphuric acid (95-98%). 34 g (190 mmol) of NBS are added to this suspension and the mixture is stirred in the dark for 2 hours. Thereafter, water/ice is added and solids are removed and washed with ethanol. The residue is recrystallized in toluene. The yield is 68 g (142 mmol), corresponding to 76% of theory.

The following compounds are prepared in an analogous manner:

| | Reactant 1 | Product | Yield |
|---|---|---|---|
| 1f | | | 71% |
| 2f | | | 74% |

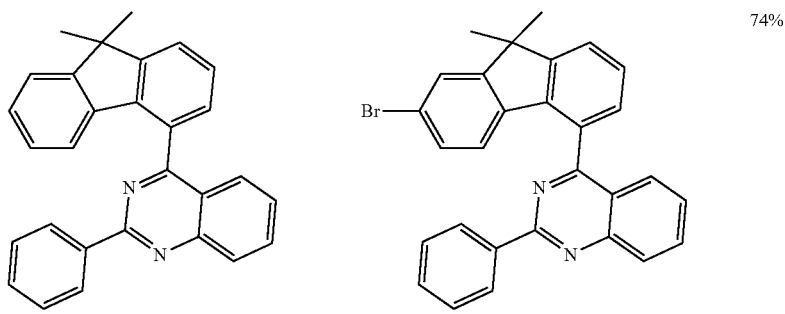

| Reactant 1 | Product | Yield |
|---|---|---|
| 36 | | 65% | g) 9,9-Dimethyl-5-(4-phenylquinazolin-2-yl)-9H-fluorene-2-boronic acid

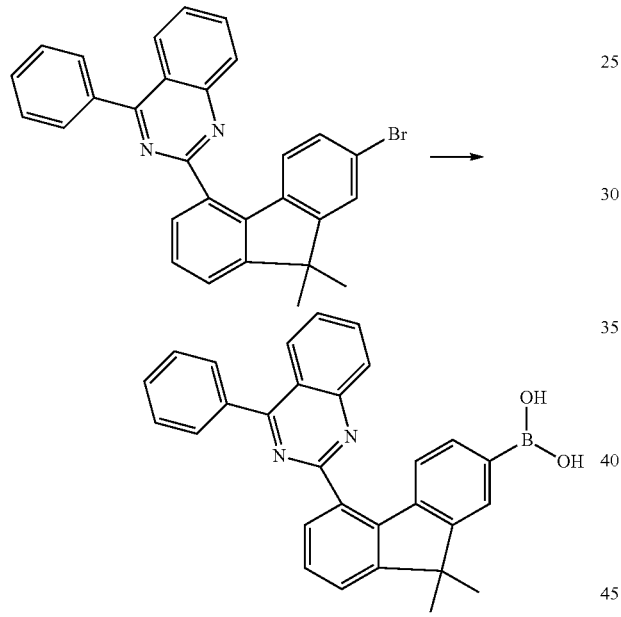

To a solution, cooled to −78° C., of 128 g (270 mmol) of 4-[3-(7'-bromo-9,9'-spirobi[fluoren]-4'-yl)phenyl]-1-phenylbenzimidazole in 1500 ml of diethyl ether are added dropwise 110 ml (276 mmol) of n-butyllithium (2.5 M in hexane). The reaction mixture is stirred at −78° C. for 30 min. The mixture is allowed to come to room temperature and cooled again to −78° C., and then a mixture of 40 ml (351 mmol) of trimethyl borate in 50 ml of diethyl ether is added rapidly. After warming to −10° C., hydrolysis is effected with 135 ml of 2 N hydrochloric acid. The organic phase is removed, washed with water, dried over sodium sulphate and concentrated to dryness. The residue is taken up in 300 ml of n-heptane, and the colourless solid is filtered off with suction, washed with n-heptane and dried under reduced pressure. Yield: 126 g (241 mmol), 99% of theory; purity: 90% by HPLC.

In an analogous manner, the following compounds are obtained:

| Reactant 1 | Product | Yield |
|---|---|---|
| 1g | | 83% |

-continued

| Reactant 1 | Product | Yield |
|---|---|---|
| 2g | | 87% |
| 3g | | 80% | h) 2-[7-(4,6-Diphenyl-[1,3,5]triazin-2-yl)-9,9-dimethyl-9H-fluoren-4-yl]-4-phenylquinazoline

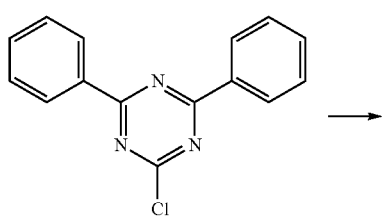

→

-continued

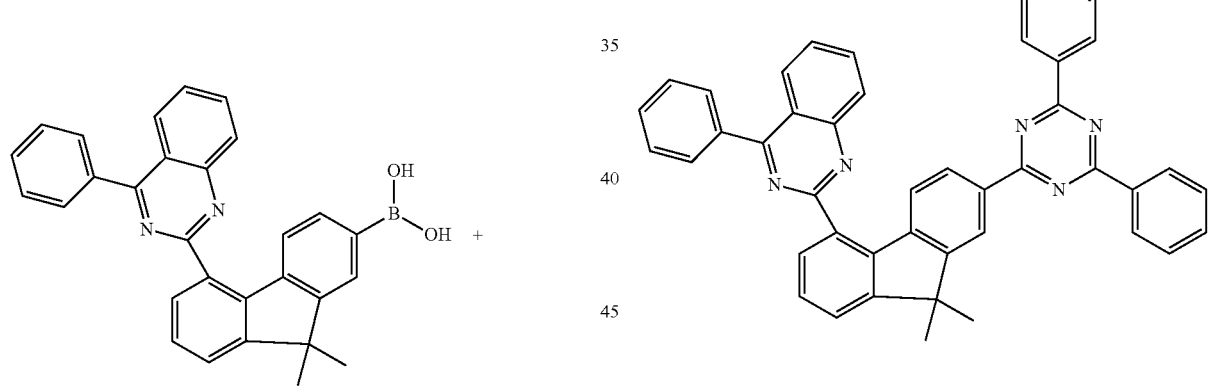

48 g (110.0 mmol) of 9,9-dimethyl-5-(4-phenylquinazolin-2-yl)-9H-fluorene-2-boronic acid, 29.5 g (110.0 mmol) of 2-chloro-4,6-diphenyl-1,3,5-triazine and 21 g (210.0 mmol) of sodium carbonate are suspended in 500 ml of ethylene glycol diamine ether and 500 ml of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 ml of water and then concentrated to dryness. The residue is recrystallized from toluene and from dichloromethane/iso-propanol and finally sublimed under high vacuum ($p=5\times10^{-5}$ mbar, T=350° C.). The yield is 58 g (93 mmol), corresponding to 86% of theory.

The following compounds are prepared in an analogous manner:

| | Reactant 1 | Reactant 2 | Product | Yield |
|---|---|---|---|---|
| 1h | | [40734-24-5] | | 73% |
| 2h | | 77989-15-2 | | 82% |

| Reactant 1 | Reactant 2 | Product | Yield |
|---|---|---|---|
| 3h (fluorene-isoquinoline boronic acid) | 2-chloro-4,6-diphenyl-1,3,5-triazine [3842-55-5] | | 73% |
| 4h (fluorene-quinazoline boronic acid) | 2-chloro-4,6-diphenyl-1,3,5-triazine [3842-55-5] | | 70% |

| Reactant 1 | Reactant 2 | Product | Yield |
|---|---|---|---|
| 5h | [864377-22-0] | | 72% |
| 6h | [1153-85-1] | | 70% |

| | Reactant 1 | Reactant 2 | Product | Yield |
|---|---|---|---|---|
| 7h | (boronic acid of dimethylfluorene linked to 4-phenylquinazoline) | (bromo-dimethyl-indenocarbazole with N-phenyl) [1257220-44-2] | | 69% |
| 8h | (boronic acid of dimethylfluorene linked to 4-phenylquinazoline) | 2-bromo-1-phenyl-benzimidazole [1418123-78-0] | | 68% |

-continued

| | Reactant 1 | Reactant 2 | Product | Yield |
|---|---|---|---|---|
| 9h | (structure) | (structure) [760212-40-6] | (structure) | 70% |
| 10h | (structure) | (structure) [29874-83-7] | (structure) | 71% | i) 4-[3-(7'-bromo-9,9'-spirobi[fluoren]-4'-yl)phenyl]-1-phenylbenzimidazole

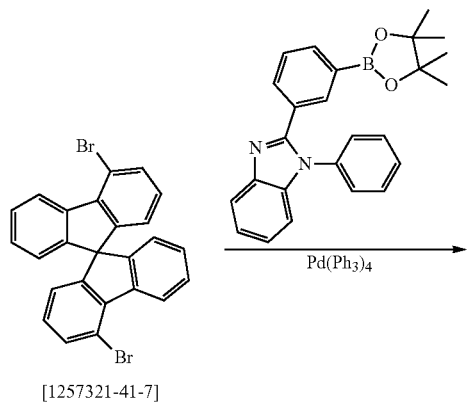

[1257321-41-7]

A 2 l four-neck flask under protective gas is initially charged with 50.0 g (105 mmol, 1.00 eq) of 4,4'-dibromo-9,9'-spirobifluorene, 41.7 g (105 mmol, 1.00 eq) of 1-phenyl-2-[e-(4,4,5,5-tetramethyl-[1,3,2]dioxaborolan-y-yl)phenyl]-1H-benzimidazole, and 36.4 g (263 mmol, 2.50 eq) of potassium carbonate in 400 ml of toluene, 400 ml 1,4-dioxane and 200 ml of demineralized water, and the mixture is degassed. Subsequently, 1.22 g (1.05 mmol, 0.01 eq) of tetrakis(triphenylphosphine)palladium(0) are added and the mixture is heated at reflux overnight. After the reaction has ended, the mixture is cooled down, filtered through Celite and diluted with 1 l of toluene. The solution is washed 3× with 300 ml each time of semi-saturated sodium chloride solution, dried over sodium sulphate and concentrated to about 200 ml on a rotary evaporator. The precipitated solids are filtered off and dried under reduced pressure. The disubstituted by-product is removed by means of sublimation. 21.0 g (32 mmol, 31%) of the desired product are obtained.

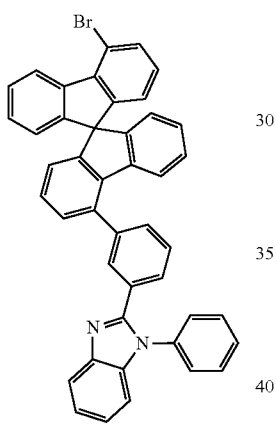

Variant B:

Procedure analogous to variant A; rather than tetrakis(triphenylphosphine)palladium(0), 0.01 eq of palladium(II) acetate and 0.01 eq of dicyclohexyl(2',6'-dimethoxybiphenyl-2-yl)phosphine (SPhos) are used.

In an analogous manner, the following compounds are obtained:

| No. | Reactant 1 | Reactant 2 | Product 3 | Variant | Yield |
|---|---|---|---|---|---|
| 1i | [1257321-41-7] | [1169709-19-6] | | B | 41% |

| No. | Reactant 1 | Reactant 2 | Product 3 | Variant | Yield |
|---|---|---|---|---|---|
| 2i | 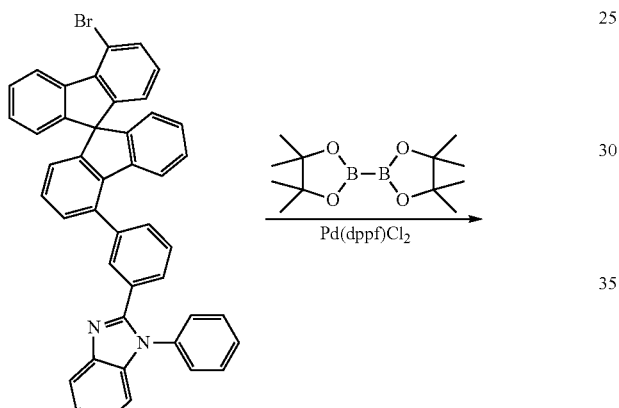 [1257321-41-7] | | | B | 62% |
j) 1-Phenyl-2-[3-[7'-(4,4,5,5-tetramethyl-1,3,2-dioxaborolan-4-yl)-9,9'-spirobi[fluoren]-4'-yl]phenyl]benzimidazole
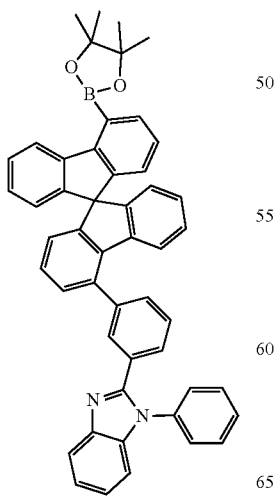

A 1 l four-neck flask is initially charged with 22.0 g (33.1 mmol, 1.00 eq) of 2-[3-(7'-bromo-9,9'-spirobi[fluoren]-2'-yl)phenyl]-1-phenylbenzimidazole, 8.84 g (30.1 mmol, 0.91 eq) of bis(pinacolato)diboron and 26.0 g (265 mmol, 8.00 eq) of potassium acetate in 500 ml of dried 1,4-dioxane and the mixture is degassed for 30 minutes. Subsequently, 812 mg (0.995 mmol, 0.0300 eq) of 1,1-bis(diphenylphosphino)ferrocenedichloropalladium(II) complex are added together with DCM and the mixture is heated to internal temperature 80° C. After stirring overnight, the mixture is cooled down and the precipitated solids are filtered off with suction. The filtrate is concentrated to about 50 ml on a rotary evaporator and the precipitated solids are likewise filtered off with suction. The solids are combined and dried. 21.0 g (29.5 mmol, 89%) of the boronic ester are obtained.

In an analogous manner, the following compounds are obtained:

| No. | Reactant 3 | Product 4 | Yield |
|---|---|---|---|
| 1j | 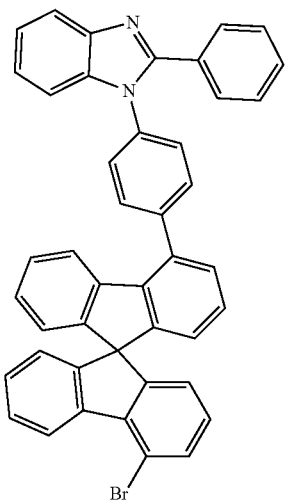 [SMILES: Brc1cccc2c1-c1ccccc1C21c2ccccc2-c2c(-c3ccc(-n4c(-c5ccccc5)nc5ccccc54)cc3)cccc21] | 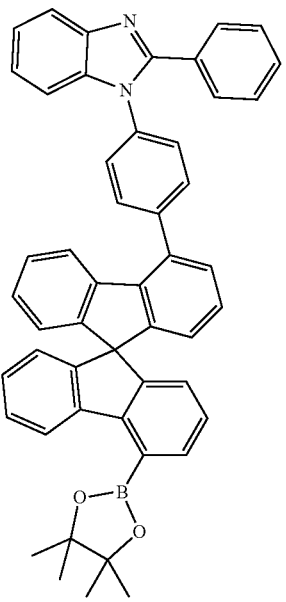 [SMILES: CC1(C)OB(c2cccc3c2-c2ccccc2C32c3ccccc3-c3c(-c4ccc(-n5c(-c6ccccc6)nc6ccccc65)cc4)cccc32)OC1(C)C] | 97% |
| 2j | 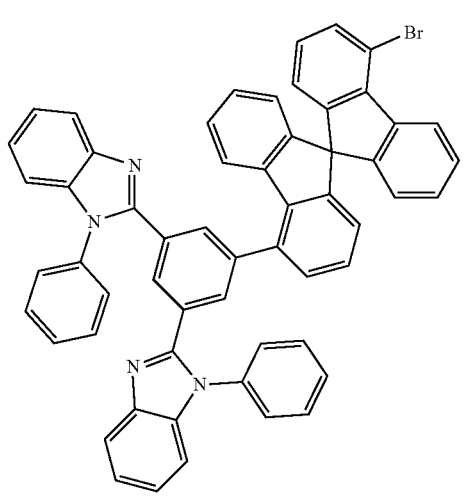 [SMILES: Brc1cccc2c1-c1ccccc1C21c2ccccc2-c2c(-c3cc(-c4nc5ccccc5n4-c4ccccc4)cc(-c4nc5ccccc5n4-c4ccccc4)c3)cccc21] | 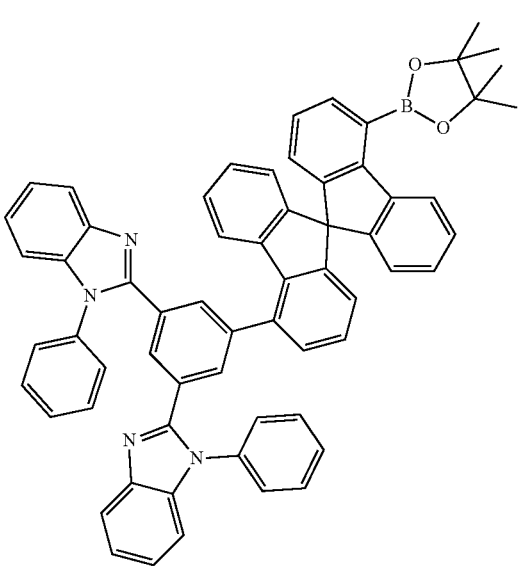 [SMILES: CC1(C)OB(c2cccc3c2-c2ccccc2C32c3ccccc3-c3c(-c4cc(-c5nc6ccccc6n5-c5ccccc5)cc(-c5nc6ccccc6n5-c5ccccc5)c4)cccc32)OC1(C)C] | 47% | k) 2-[3-[7'-(2-phenylquinazolin-4-yl)-9,9'-spirobi[fluoren]-4'-yl]phenyl]-1-phenylbenzimidazole

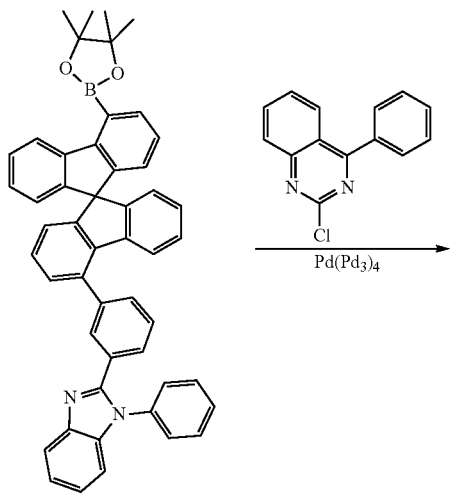

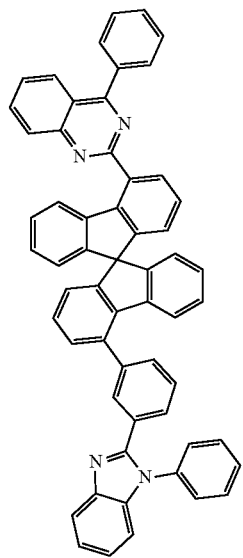

Variant A:

In a 1 l three-neck flask, 21.0 g (29.5 mmol, 1.00 eq) of 1-phenyl-2-[3-[7'-(4,4,5,5-tetramethyl-1,3,2-dioxaborolan-2-yl)-9,9'-spirobi[fluoren]-2'-yl]phenyl]benzimidazole and 7.2 g (29.5 mmol, 1.00 eq) of 4-chloro-2-phenylquinazoline are initially charged together with 3.75 g (35.4 mmol, 1.20 eq) of sodium carbonate in 200 ml of toluene, 200 ml of 1,4-dioxane and 100 ml of demineralized water, and the mixture is degassed for 20 minutes. After adding 1.02 g (0.885 mmol, 0.0300 eq) of tetrakis(triphenylphosphine) palladium(0), the mixture is heated under reflux for 2 days and, after the reaction has ended, cooled down. The precipitated solids are filtered off with suction, washed with water and a little toluene, and then recrystallized repeatedly from toluene/heptane until an HPLC purity of >99.9% is attained. After sublimation, 11.5 g (14.0 mmol, 46%) of a colourless solid are obtained.

Variant B:

Procedure analogous to variant A; rather than tetrakis(triphenylphosphine)palladium(0), 0.01 eq of palladium(II) acetate and 0.04 eq of tri(o-tolyl)phosphine (SPhos) are used.

Variant C:

Procedure analogous to variant A; rather than tetrakis(triphenylphosphine)palladium(0), 0.01 eq of palladium(II) acetate and 0.01 eq of dicyclohexyl(2',6'-dimethoxybiphenyl-2-yl)phosphine (SPhos) are used.

The following were prepared analogously:

| No. | Reactant 4 | Reactant 5 | Product 6 | Variant | Yield |
|---|---|---|---|---|---|
| 6k | | [29874-83-7] | | B | 62% |

| No. | Reactant 4 | Reactant 5 | Product 6 | Variant | Yield |
|---|---|---|---|---|---|
| 7k | | [6484-25-9] | | A | 41% |

| No. | Reactant 4 | Reactant 5 | Product 6 | Variant | Yield |
|---|---|---|---|---|---|
| 8k | | | | A | 40% |

| No. | Reactant 4 | Reactant 5 | Product 6 | Variant | Yield |
|---|---|---|---|---|---|
| 9k | 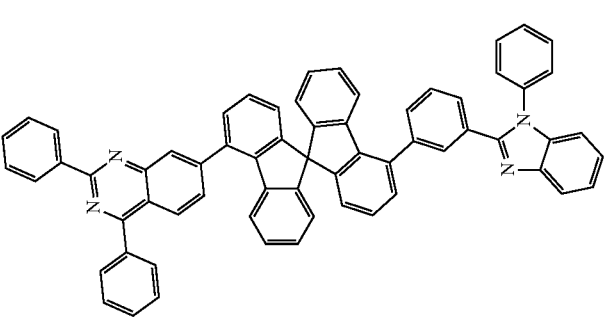 | 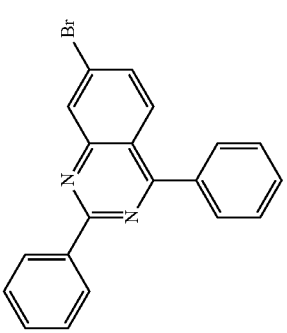 [1400697-34-8] | 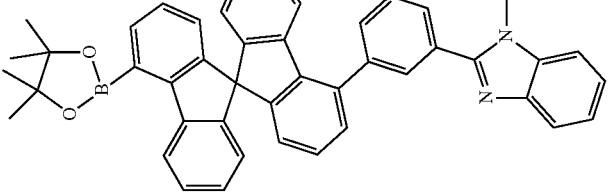 | B | 57% |

-continued
| No. | Reactant 4 | Reactant 5 | Product 6 | Variant | Yield |
|---|---|---|---|---|---|
| 10k | 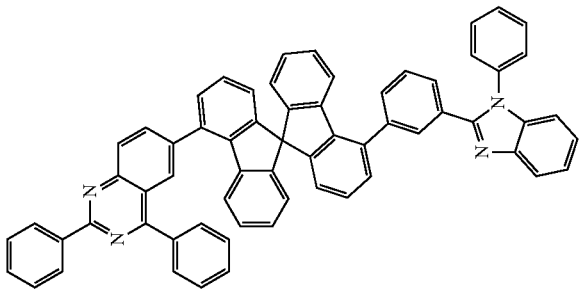 | 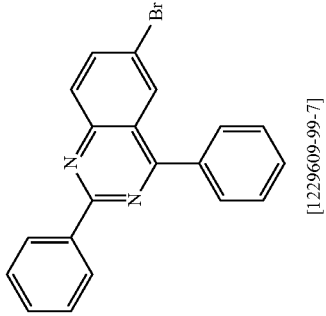 [1229609-99-7] | 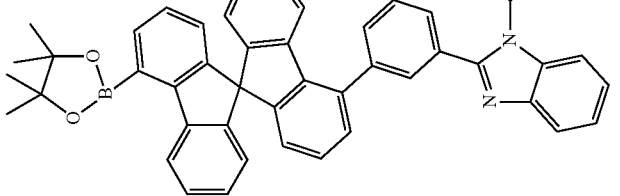 | A | 61% |

Production of the OLEDs

In examples C1 to I14 which follow (see tables 1 and 2), the data of various OLEDs are presented.

Pretreatment for Examples C1-I14:

Glass plaques which have been coated with structured ITO (indium tin oxide) in a thickness of 50 nm are the substrates to which the OLEDs are applied.

The OLEDs basically have the following layer structure: substrate/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in table 1. The materials required for production of the OLEDs are shown in table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:IC3:TEG1 (55%:35%:10%) mean here that the material 101 is present in the layer in a proportion by volume of 55%, 103 in a proportion of 35% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) are determined as a function of luminance, calculated from current-voltage-luminance characteristics (IUL characteristics) assuming Lambertian emission characteristics. The electroluminescence spectra are determined at a luminance of 1000 cd/m$^2$, and the CIE 1931 x and y colour coordinates are calculated therefrom. The parameter U1000 in table 2 refers to the voltage which is required for a luminance of 1000 cd/m$^2$. CE1000 and PE1000 respectively refer to the current and power efficiencies which are achieved at 1000 cd/m$^2$. Finally, EQE1000 refers to the external quantum efficiency at an operating luminance of 1000 cd/m$^2$.

The data for the various OLEDs are collated in table 2. Examples C1-C4 are comparative examples according to the prior art; examples I1-I14 show data of OLEDs of the invention.

Some of the examples are elucidated in detail hereinafter, in order to illustrate the advantages of the OLEDs of the invention.

Use of Materials of the Invention in Phosphorescent OLEDs

The materials of the invention, when used as hole blocker layer (HBL) in phosphorescent OLEDs, give a significant improvement in efficiency over the prior art. By use of the inventive compounds 24e, 52e and 58e, it is possible to observe an increase in external quantum efficiency by about 10% compared to the prior art PA1, PA2 and PA3. In the case of use of the materials of the invention in the electron transport layer (ETL) as well, it is possible to achieve an improvement in external quantum efficiency over the prior art (compare Example C4 to Example I4).

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| C1 | SpA1 70 nm | HATCN 5 nm | SpMA1 110 nm | IC1:TEG1 (85%:15%) 30 nm | PA1 10 nm | ST2:LiQ (50%:50%) 30 nm | — |
| C2 | SpA1 70 nm | HATCN 5 nm | SpMA1 110 nm | IC1:IC3:TEG1 (50%:45%:5%) 30 nm | PA2 10 nm | ST2:LiQ (50%:50%) 30 nm | — |
| C3 | SpA1 70 nm | HATCN 5 nm | SpMA1 110 nm | IC1:TEG1 (85%:15%) 30 nm | PA3 10 nm | ST2:LiQ (50%:50%) 30 nm | — |
| C4 | SpA1 70 nm | HATCN 5 nm | SpMA1 110 nm | IC1:IC3:TEG1 (50%:45%:5%) 30 nm | — | ST2:PA4 (40%:60%) 40 nm | LiQ 3 nm |
| I1 | SpA1 70 nm | HATCN 5 nm | SpMA1 110 nm | IC1:TEG1 (85%:15%) 30 nm | 24e 10 nm | ST2:LiQ (50%:50%) 30 nm | — |
| I2 | SpA1 70 nm | HATCN 5 nm | SpMA1 110 nm | IC1:IC3:TEG1 (50%:45%:5%) 30 nm | 52e 10 nm | ST2:LiQ (50%:50%) 30 nm | — |
| I3 | SpA1 70 nm | HATCN 5 nm | SpMA1 110 nm | IC1:TEG1 (85%:15%) 30 nm | 58e 10 nm | ST2:LiQ (50%:50%) 30 nm | — |
| I4 | SpA1 70 nm | HATCN 5 nm | SpMA1 110 nm | IC1:IC3:TEG1 (50%:45%:5%) 30 nm | — | ST2:60e (40%:60%) 40 nm | LiQ 3 nm |
| I5 | SpMA1 140 nm | — | — | 16e:TER4 (95%:5%) 40 nm | — | ST2:LiQ (50%:50%) 35 nm | — |
| I6 | SpMA1 140 nm | — | — | IC1:TER4 (95%:5%) 40 nm | 19e 10 nm | ST2:LiQ (50%:50%) 25 nm | — |

TABLE 1-continued

Structure of the OLEDs

| Ex. | HTL thickness | IL thickness | EBL thickness | EML thickness | HBL thickness | ETL thickness | EIL thickness |
|---|---|---|---|---|---|---|---|
| I7 | SpMA1 140 nm | — | — | 22e:TER4 (97%:3%) 40 nm | — | ST2:LiQ (50%:50%) 35 nm | — |
| I8 | SpA1 70 nm | HATCN 5 nm | SpMA1 110 nm | IC1:TEG1 (90%:10%) 30 nm | 10k 10 nm | ST2:LiQ (50%:50%) 30 nm | — |
| I9 | SpMA1 140 nm | — | — | 41e:SpMA1:TER4 (55%:22%:3%) 40 nm | — | ST2:LiQ (50%:50%) 35 nm | — |
| I10 | SpMA1 140 nm | — | — | 43e:TER4 (95%:5%) 40 nm | IC1 10 nm | ST2:LiQ (50%:50%) 25 nm | — |
| I11 | SpA1 70 nm | HATCN 5 nm | SpMA1 110 nm | IC1:TEG1 (90%:10%) 30 nm | IC1 10 nm | ST2:44e (40%:60%) 40 nm | LiQ 3 nm |
| I12 | SpMA1 140 nm | — | — | IC1:TER4 (95%:5%) 40 nm | 48e 10 nm | ST2:LiQ (50%:50%) 25 nm | — |
| I13 | SpA1 70 nm | HATCN 5 nm | SpMA1 110 nm | IC1:TEG1 (90%:10%) 30 nm | — | 1h:LiQ (50%:50%) 30 nm | — |
| I14 | SpMA1 140 nm | — | — | 7h:TEG1:TER4 (85%:10%:5%) 40 nm | — | ST2:LiQ (50%:50%) 35 nm | — |

TABLE 2

Measurement results for the various OLEDs

| Ex. | U1000 (V) | CE1000 (cd/A) | PE1000 (lm/W) | EQE 1000 | CIE x/y at 1000 cd/m$^2$ |
|---|---|---|---|---|---|
| C1 | 3.6 | 55 | 48 | 15.2% | 0.31/0.64 |
| C2 | 3.4 | 55 | 51 | 14.9% | 0.34/0.63 |
| C3 | 3.5 | 56 | 50 | 15.5% | 0.31/0.64 |
| C4 | 3.7 | 52 | 44 | 14.1% | 0.34/0.62 |
| I1 | 3.6 | 64 | 56 | 17.2% | 0.33/0.63 |
| I2 | 3.3 | 59 | 56 | 16.2% | 0.32/0.64 |
| I3 | 3.5 | 63 | 57 | 17.1% | 0.33/0.63 |
| I4 | 3.7 | 56 | 48 | 15.3% | 0.33/0.63 |
| I5 | 4.6 | 17 | 12 | 14.6% | 0.66/0.34 |
| I6 | 4.9 | 16 | 10 | 14.4% | 0.67/0.33 |
| I7 | 4.7 | 16 | 11 | 14.9% | 0.67/0.33 |
| I8 | 3.5 | 64 | 57 | 17.4% | 0.32/0.64 |
| I9 | 4.5 | 16 | 11 | 15.3% | 0.67/0.33 |
| I10 | 4.6 | 17 | 12 | 15.1% | 0.66/0.34 |
| I11 | 3.6 | 58 | 51 | 15.8% | 0.31/0.64 |
| I12 | 5.0 | 15 | 9 | 14.8% | 0.67/0.33 |
| I13 | 3.7 | 63 | 53 | 17.2% | 0.31/0.64 |
| I14 | 4.4 | 18 | 13 | 16.5% | 0.67/0.33 |

TABLE 3

Structural formulae of the materials for the OLEDs

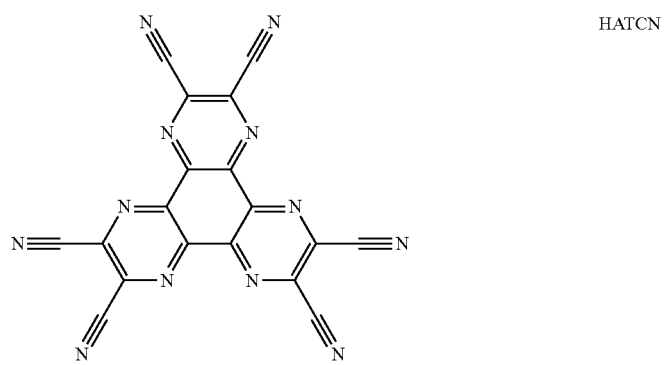

HATCN

TABLE 3-continued
Structural formulae of the materials for the OLEDs
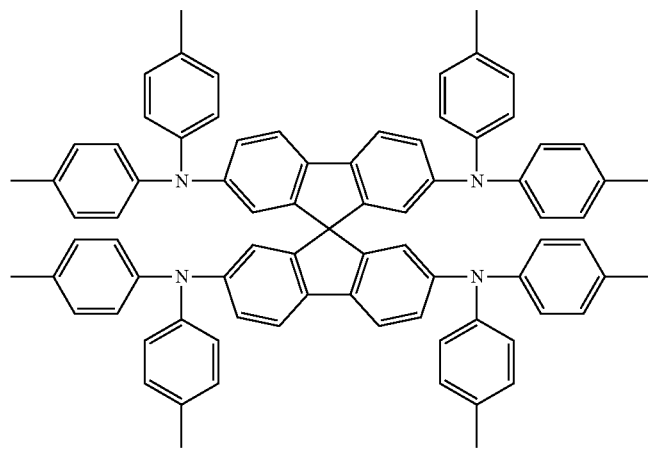
SpA1
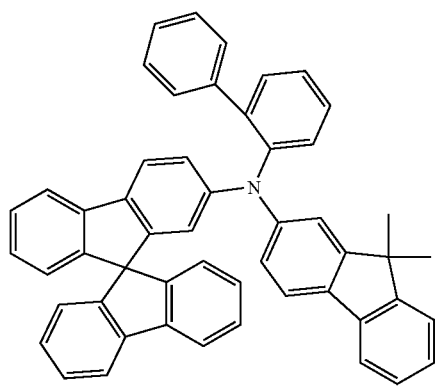 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
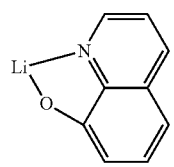
LiQ
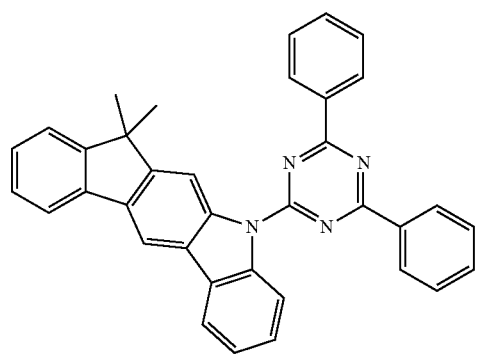 [SMILES: CC1(C)c2ccccc2-c2cc3c4ccccc4n(-c4nc(-c5ccccc5)nc(-c5ccccc5)n4)c3cc21]
IC1
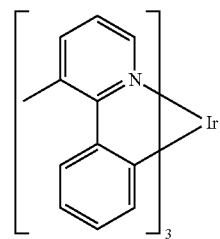
TEG1

TABLE 3-continued
Structural formulae of the materials for the OLEDs
ST2
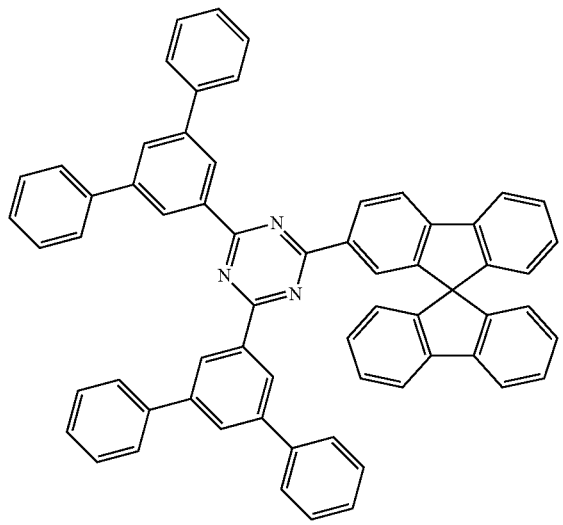 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
TER4
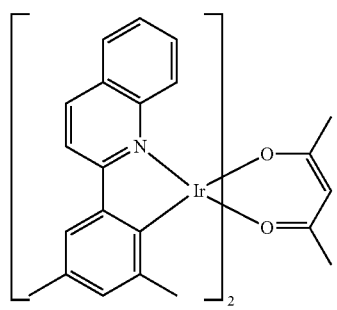
IC3
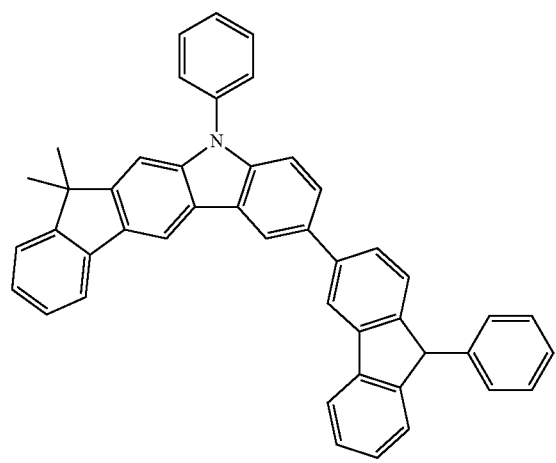 [SMILES: CC1(C)c2ccccc2-c2cc3c4cc(-c5ccc6c(c5)-c5ccccc5C6c5ccccc5)ccc4n(-c4ccccc4)c3cc21]
PA1
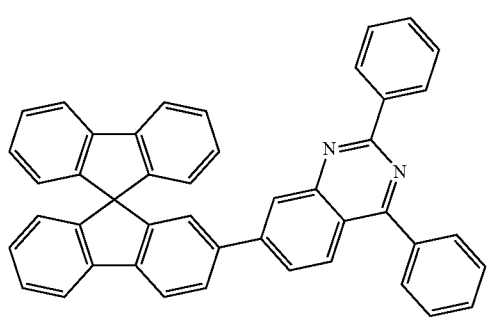 [SMILES: c1ccc(-c2nc(-c3ccccc3)c3ccc(-c4ccc5c(c4)C4(c6ccccc6-c6ccccc64)c4ccccc4-5)cc3n2)cc1]

TABLE 3-continued
Structural formulae of the materials for the OLEDs
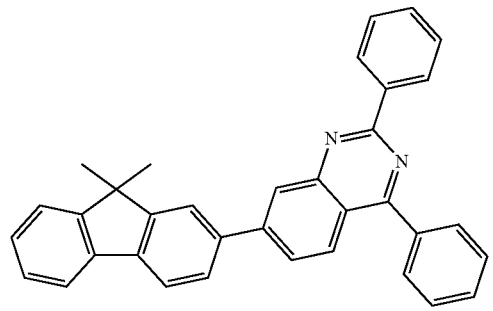 [SMILES: CC1(C)c2ccccc2-c2ccc(-c3ccc4c(-c5ccccc5)nc(-c5ccccc5)nc4c3)cc21]
PA2
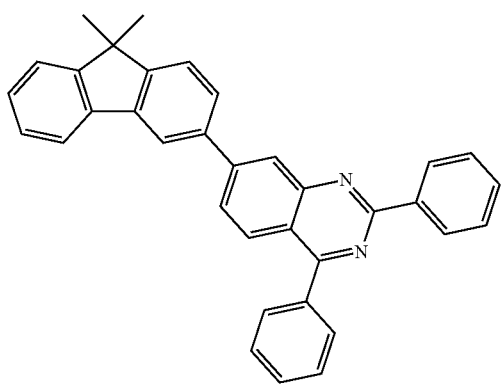 [SMILES: CC1(C)c2ccccc2-c2cc(-c3ccc4c(-c5ccccc5)nc(-c5ccccc5)nc4c3)ccc21]
PA3
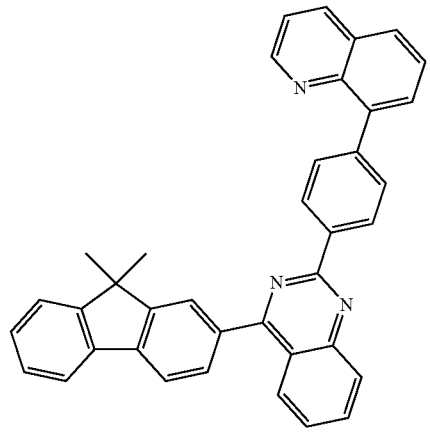 [SMILES: CC1(C)c2ccccc2-c2ccc(-c3nc(-c4ccc(-c5cccc6cccnc56)cc4)nc4ccccc34)cc21]
PA4
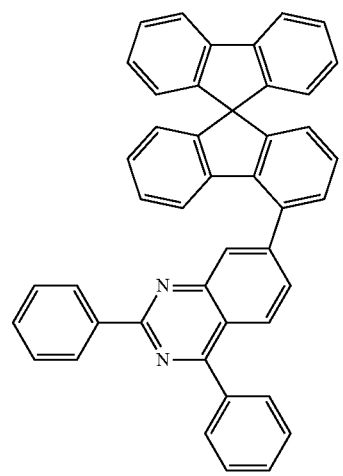 [SMILES: c1ccc(-c2nc(-c3ccccc3)c3ccc(-c4cccc5c4-c4ccccc4C54c5ccccc5-c5ccccc54)cc3n2)cc1]
24e TABLE 3-continued
Structural formulae of the materials for the OLEDs
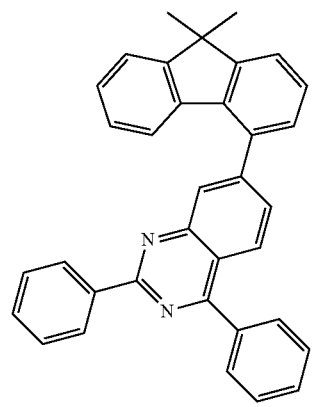 [SMILES: CC1(C)c2ccccc2-c2c(-c3ccc4c(-c5ccccc5)nc(-c5ccccc5)nc4c3)cccc21]
52e
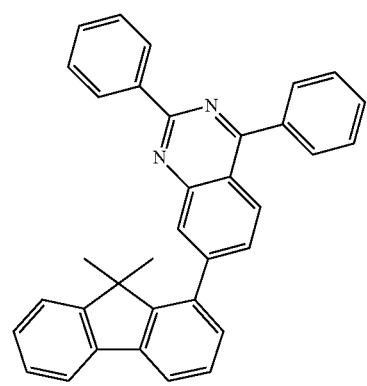 [SMILES: CC1(C)c2ccccc2-c2cccc(-c3ccc4c(-c5ccccc5)nc(-c5ccccc5)nc4c3)c21]
58e
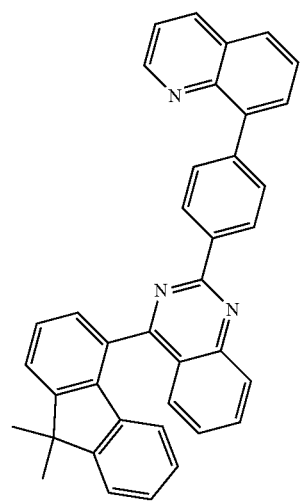 [SMILES: CC1(C)c2ccccc2-c2c(-c3nc(-c4ccc(-c5cccc6cccnc56)cc4)nc4ccccc34)cccc21]
60e TABLE 3-continued
Structural formulae of the materials for the OLEDs
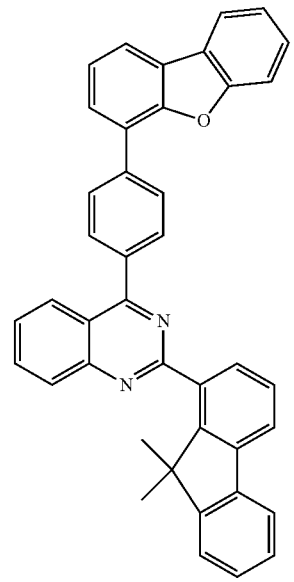 [SMILES: CC1(C)c2ccccc2-c2cccc(-c3nc(-c4ccc(-c5cccc6c5oc5ccccc56)cc4)c4ccccc4n3)c21]
16e
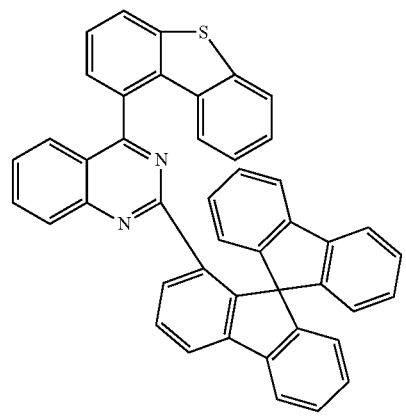 [SMILES: c1ccc2c(c1)-c1ccccc1C21c2ccccc2-c2cccc(-c3nc(-c4cccc5sc6ccccc6c45)c4ccccc4n3)c21]
19e
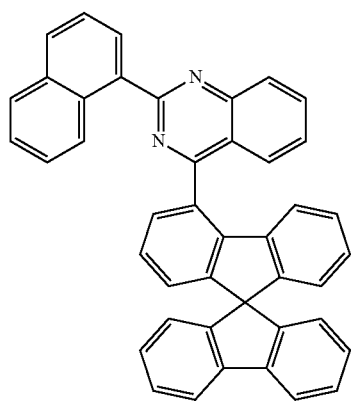 [SMILES: c1ccc2c(c1)-c1ccccc1C21c2ccccc2-c2c(-c3nc(-c4cccc5ccccc45)nc4ccccc34)cccc21]
22e TABLE 3-continued
Structural formulae of the materials for the OLEDs
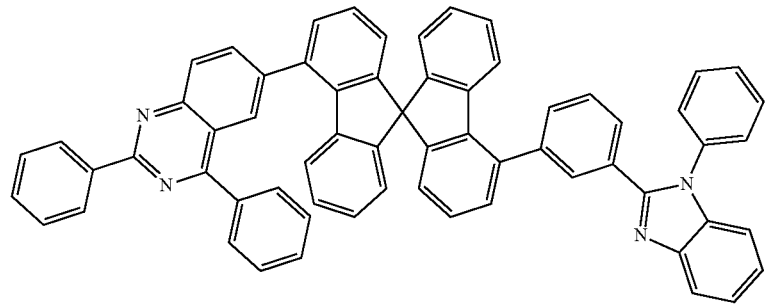 [SMILES: c1ccc(-c2nc(-c3ccccc3)c3cc(-c4cccc5c4-c4ccccc4C54c5ccccc5-c5c(-c6cccc(-c7nc8ccccc8n7-c7ccccc7)c6)cccc54)ccc3n2)cc1]
10k
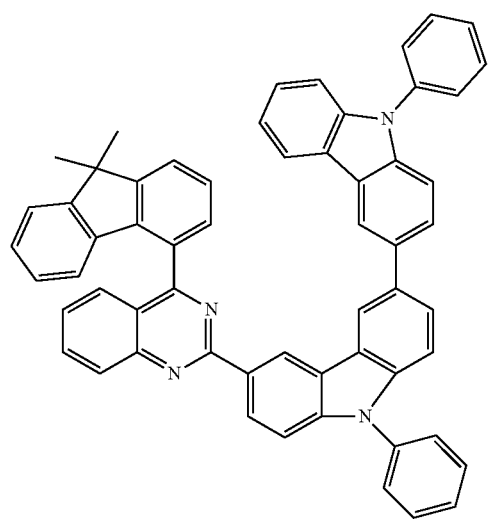 [SMILES: CC1(C)c2ccccc2-c2c(-c3nc(-c4ccc5c(c4)c4cc(-c6ccc7c(c6)c6ccccc6n7-c6ccccc6)ccc4n5-c4ccccc4)nc4ccccc34)cccc21]
41e
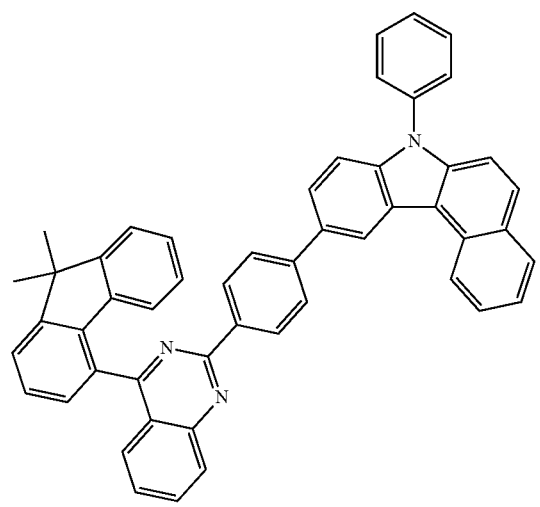 [SMILES: CC1(C)c2ccccc2-c2c(-c3nc(-c4ccc(-c5ccc6c(c5)c5c7ccccc7ccc5n6-c5ccccc5)cc4)nc4ccccc34)cccc21]
43e TABLE 3-continued
Structural formulae of the materials for the OLEDs
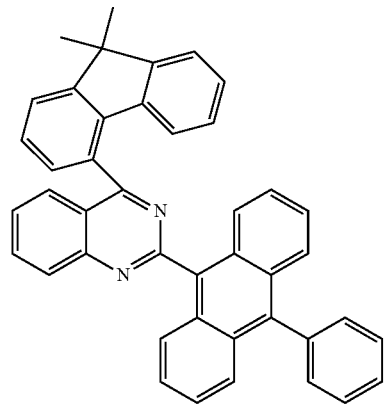 [SMILES: CC1(C)c2ccccc2-c2c(-c3nc(-c4c5ccccc5c(-c5ccccc5)c5ccccc45)nc4ccccc34)cccc21]
44e
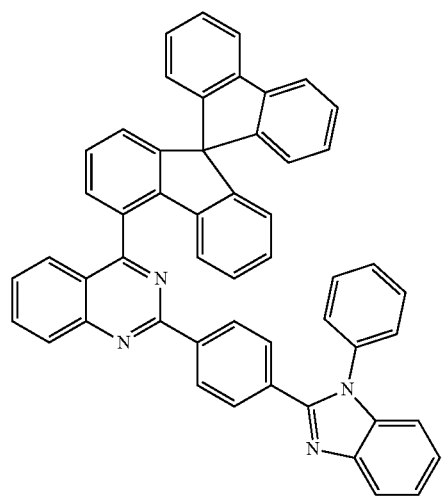 [SMILES: c1ccc(-n2c(-c3ccc(-c4nc(-c5cccc6c5-c5ccccc5C65c6ccccc6-c6ccccc65)c5ccccc5n4)cc3)nc3ccccc32)cc1]
48e
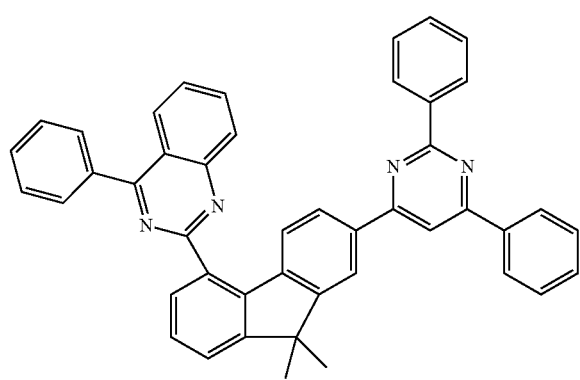 [SMILES: CC1(C)c2cc(-c3cc(-c4ccccc4)nc(-c4ccccc4)n3)ccc2-c2c(-c3nc(-c4ccccc4)c4ccccc4n3)cccc21]
1h TABLE 3-continued Structural formulae of the materials for the OLEDs

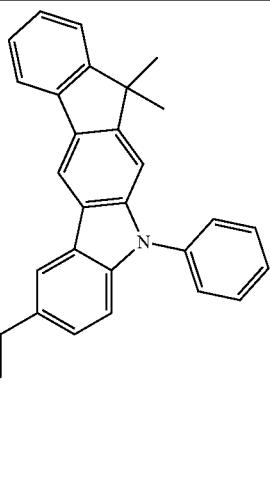

7h

The invention claimed is:

1. A compound of formulae (I) or (II) or a mixture of a compound of formula (I) and a compound of formula (II):

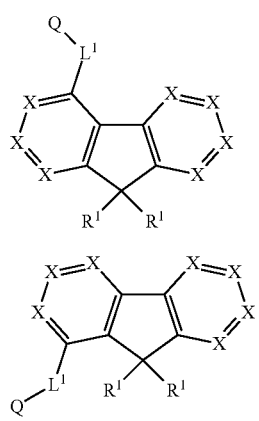

(I)

(II)

wherein

X is, the same or differently in each instance, N or $CR^1$, with the proviso that not more than two groups X in one cycle are N;

Q is selected from the group consisting of structures of formulae (Q-1) and (Q-3):

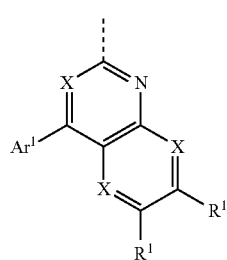

(Q-1)

(Q-3)

wherein the dotted bond denotes the attachment position; and $Ar^1$ is an aromatic or heteroaromatic ring system having 6 to 40 carbon atoms and is optionally substituted in each case by one or more radicals $R^2$, an aryloxy group having 5 to 60 aromatic ring atoms and is optionally substituted by one or more $R^2$ radicals, or an aralkyl group having 5 to 60 aromatic ring atoms and is optionally substituted in each case by one or more radicals $R^2$, and wherein two or more adjacent radicals $R^1$ or $R^2$ together optionally define a mono- or polycyclic aliphatic ring system with each other and which is optionally substituted by one or more radicals $R^3$;

$L^1$ is a bond, C(=O), pyrimidine which is optionally substituted by one or more $R^1$, triazine which is optionally substituted by one or more $R^1$ radicals or a group of the Formula (L-1) to (L-70)

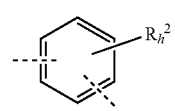

Formula (L-1)

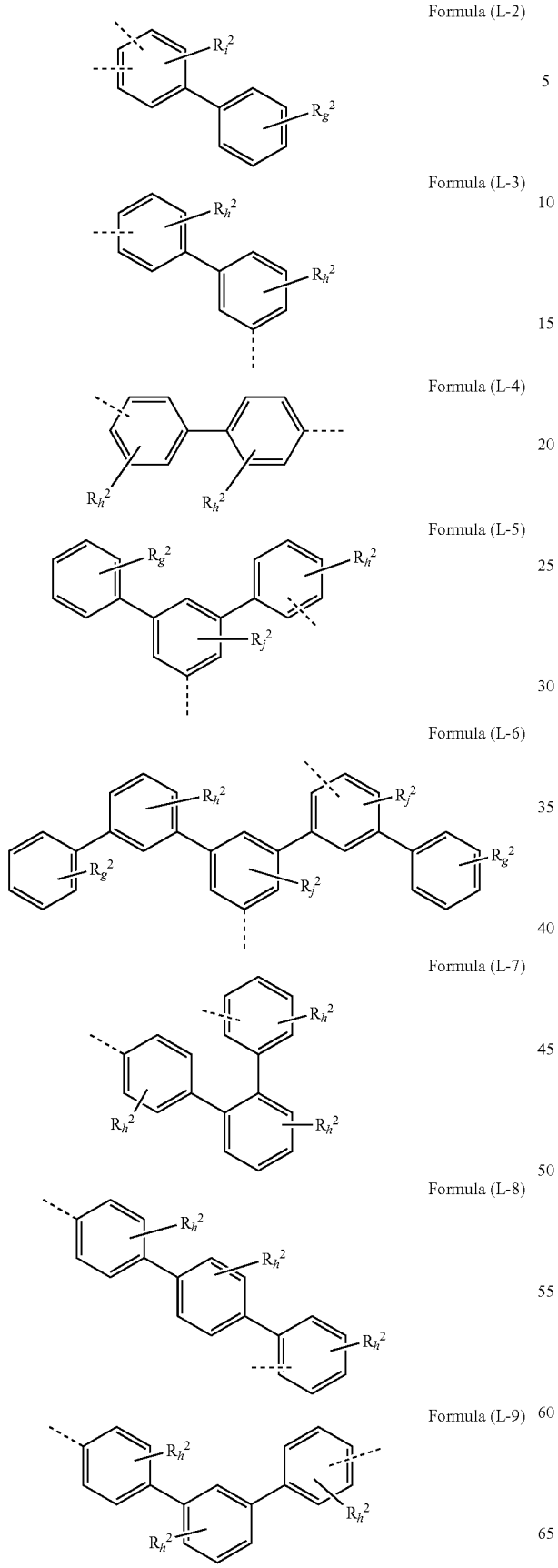
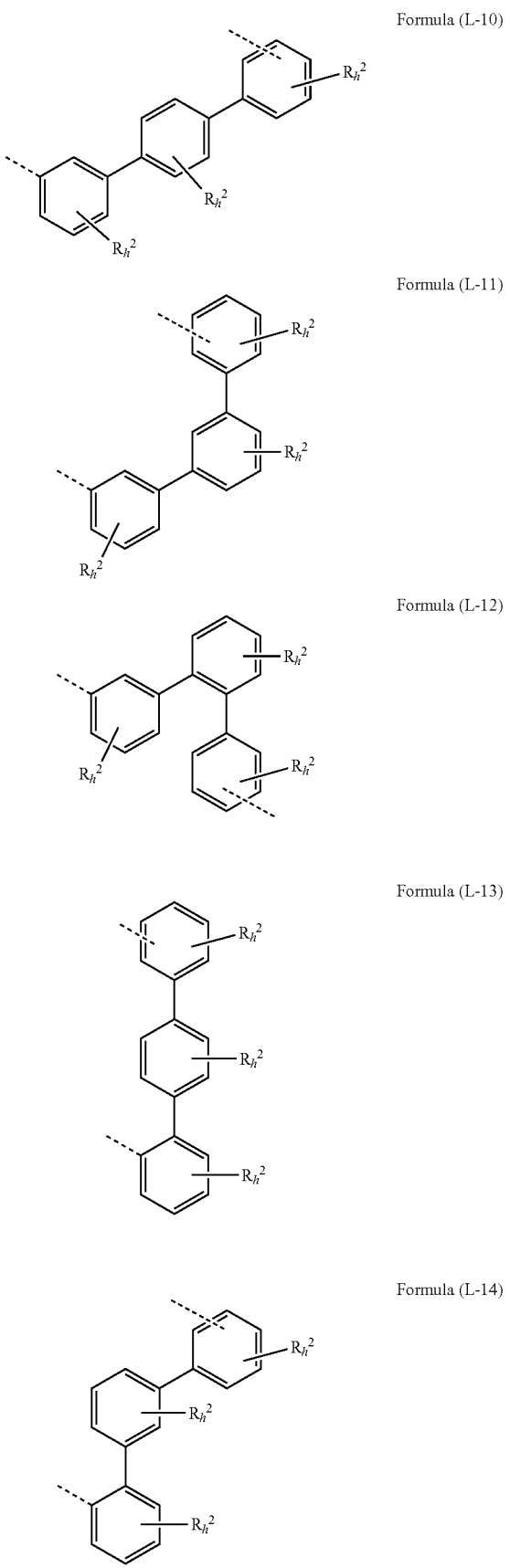

Formula (L-15)
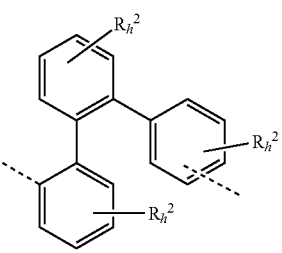
Formula (L-16)
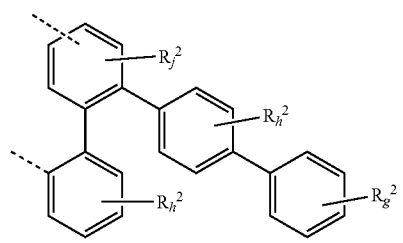
Formula (L-17)
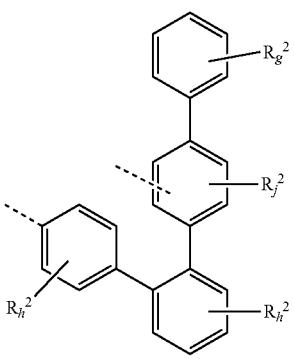
Formula (L-18)
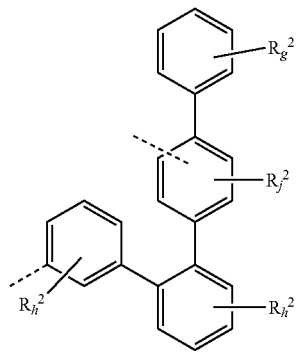
Formula (L-19)
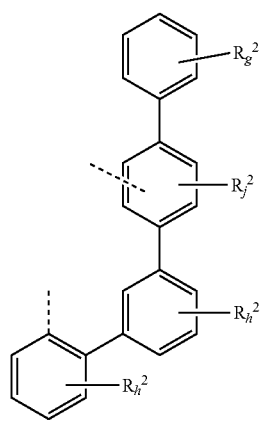
Formula (L-20)
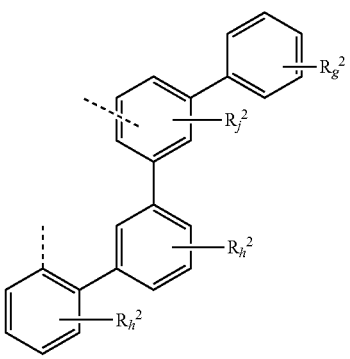
Formula (L-21)
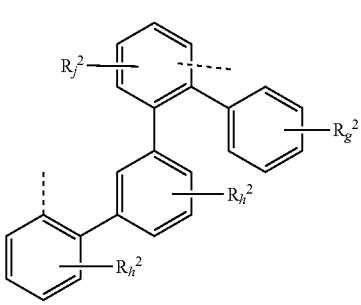
Formula (L-22)
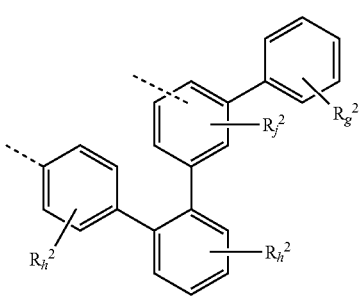
Formula (L-23)
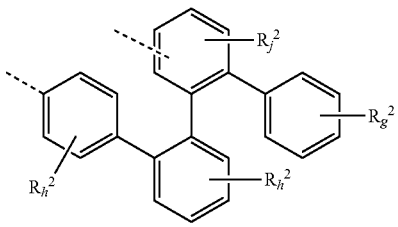
Formula (L-24)
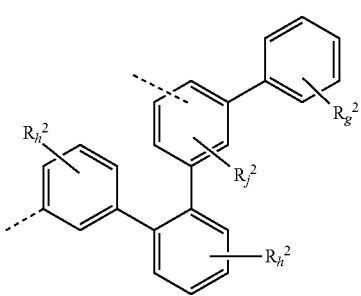

Formula (L-25)
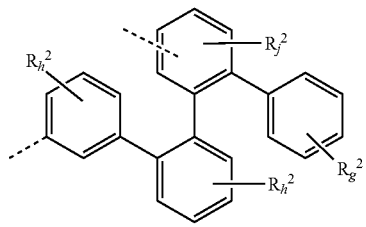
Formula (L-26)
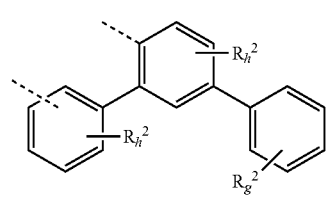
Formula (L-27)
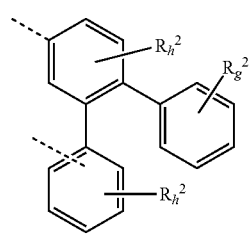
Formula (L-28)
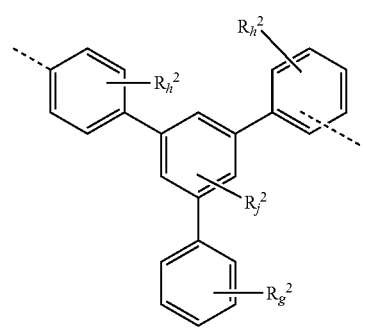
Formula (L-29)
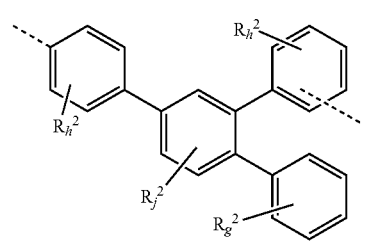
Formula (L-30)
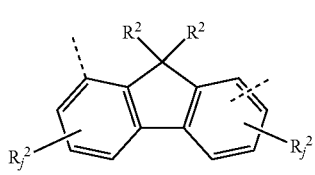
Formula (L-31)
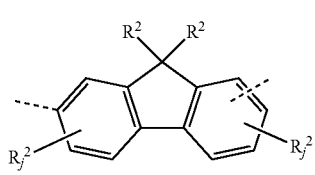
Formula (L-32)
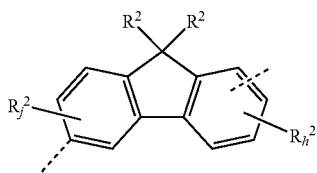
Formula (L-33)
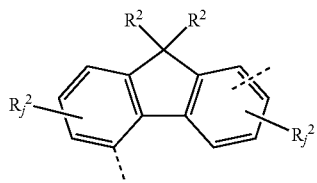
Formula (L-34)
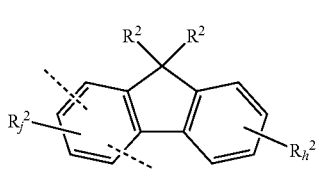
Formula (L-35)
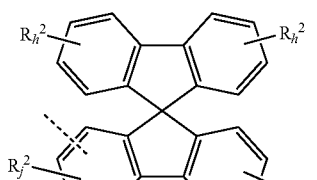
Formula (L-36)
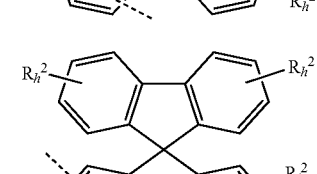
Formula (L-37)
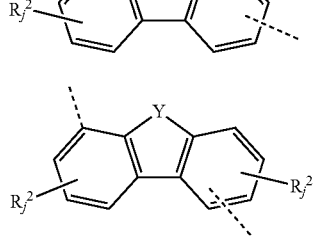
Formula (L-38)
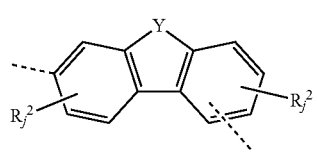
Formula (L-39)
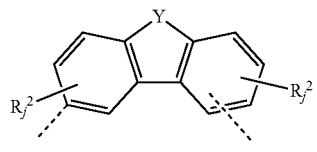
Formula (L-40)
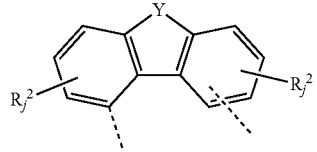

-continued
Formula (L-41)
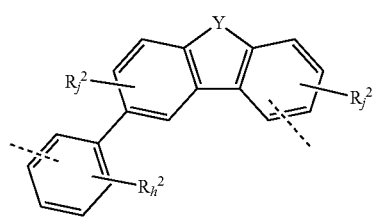
Formula (L-42)
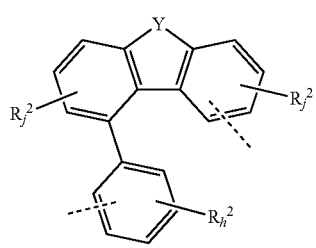
Formula (L-43)
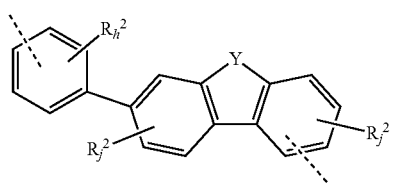
Formula (L-44)
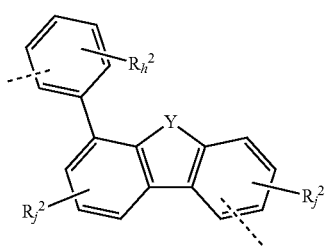
Formula (L-45)
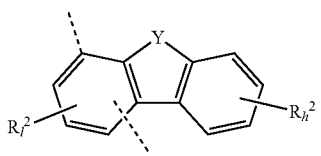
Formula (L-46)
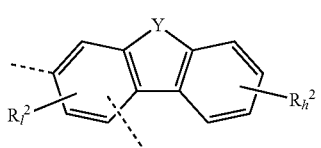
Formula (L-47)
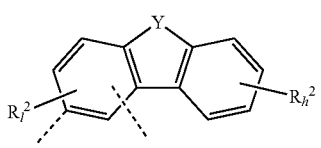
Formula (L-48)
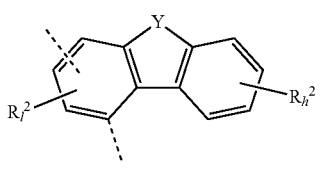
-continued
Formula (L-49)
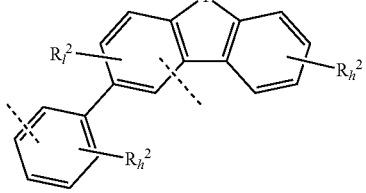
Formula (L-50)
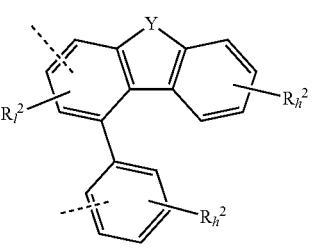
Formula (L-51)
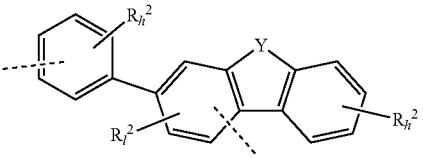
Formula (L-52)
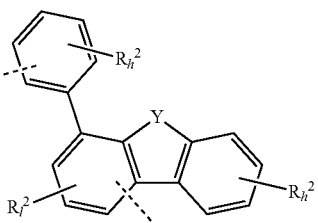
Formula (L-53)
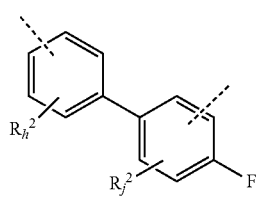
Formula (L-54)
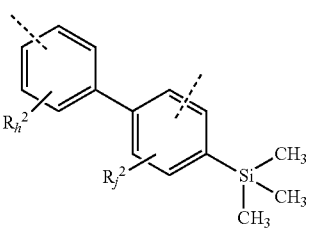
Formula (L-55)
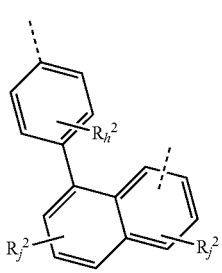

Formula (L-56)
Formula (L-57)
Formula (L-58)
Formula (L-59)
Formula (L-60)
Formula (L-61)

Formula (L-62)
Formula (L-63)
Formula (L-64)
Formula (L-65)
Formula (L-66)
Formula (L-67)
Formula (L-68)
Formula (L-69)

-continued

Formula (L-70)

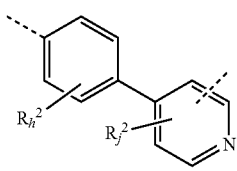

wherein the dotted bonds in each case mark the attachment positions,
the index 1 is 0, 1 or 2,
the index g is 0, 1, 2, 3, 4 or 5,
j independently at each instance is 0, 1, 2 or 3;
h independently at each instance is 0, 1, 2, 3 or 4;
Y is O, S or $NR^2$;
$R^1$ is, the same or differently in each instance, H, D, a straight-chain alkyl, alkoxy, or thioalkoxy group having 1 to 40 carbon atoms, or a branched or cyclic alkyl, alkoxy, or thioalkoxy group having 3 to 40 carbon atoms, each of which is optionally substituted by one or more radicals $R^2$, wherein one or more nonadjacent $CH_2$ groups is optionally replaced by —$R^2C$=$CR^2$—, —C≡C—, $Si(R^2)_2$, C=O, C=S, C=$NR^2$, —C(=O)O—, —C(=O)$NR^2$—, $NR^2$, P(=O)($R^2$), —O—, —S—, SO, or $SO_2$, and wherein one or more hydrogen atoms are optionally replaced by D, F, Cl, Br, I, CN, or $NO_2$, an aromatic or heteroaromatic ring system having 5 to 40 aromatic ring atoms, each of which is optionally substituted by one or more radicals $R^2$, or an aryloxy or heteroaryloxy group having 5 to 40 aromatic ring atoms and is optionally substituted by one or more radicals $R^2$, or a combination of these systems; and wherein two or more adjacent radicals $R^1$ together optionally define a mono- or polycyclic aliphatic or aromatic ring system with one another;
$R^2$ is, the same or differently in each instance, H, D, a straight-chain alkyl, alkoxy, or thioalkoxy group having 1 to 40 carbon atoms, or a branched or cyclic alkyl, alkoxy, or thioalkoxy group having 3 to 40 carbon atoms, each of which is optionally substituted by one or more radicals $R^3$, wherein one or more nonadjacent $CH_2$ groups is optionally replaced by —$R^3C$=$CR^3$—, —C≡C—, $Si(R^3)_2$, C=O, C=S, C=$NR^3$, —C(=O)O—, —C(=O)$NR^3$—, $NR^3$, P(=O)($R^3$), —O—, —S—, SO, or $SO_2$, and wherein one or more hydrogen atoms is optionally replaced by D, F, Cl, Br, I, CN, or $NO_2$, an aromatic or heteroaromatic ring system having 5 to 40 aromatic ring atoms, each of which is optionally substituted by one or more $R^3$ radicals, or an aryloxy or heteroaryloxy group having 5 to 40 aromatic ring atoms and is optionally substituted by one or more $R^3$ radicals, or a combination of these systems; and wherein two or more adjacent radicals $R^2$ together optionally define a mono- or polycyclic aliphatic or aromatic ring system with one another;
$R^3$ is, the same or differently in each instance, H, D, F, or an aliphatic hydrocarbyl radical having 1 to 20 carbon atoms, wherein one or more hydrogen atoms is optionally replaced by D or F, an aromatic and/or heteroaromatic ring system having 5 to 30 carbon atoms, wherein one or more hydrogen atoms are optionally replaced by D or F; and wherein two or more adjacent radicals $R^3$ together optionally define a mono- or polycyclic, aliphatic or aromatic ring system with one another.

2. The compound or mixture of compounds of claim 1, wherein the compound is a compound of formulae (III) or (IV) and the mixture is a mixture of a compound of formula (III) and a compound of formula (IV):

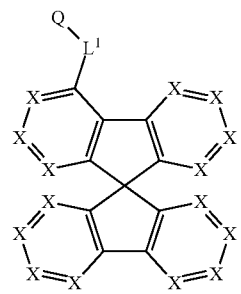

(III)

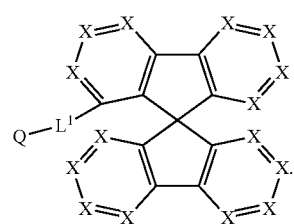

(IV)

3. The compound or mixture of compounds of claim 1, wherein the compound is a compound of formulae (Ia), (IIa), (IIIa), or (IVa) and the mixture is a mixture of at least one compound of formulae (Ia), (IIa), (IIIa), and (IVa):

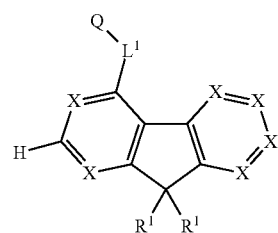

(Ia)

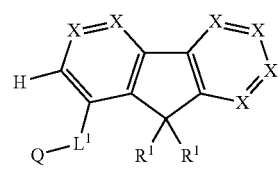

(IIa)

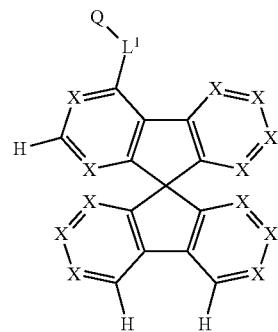

(IIIa)

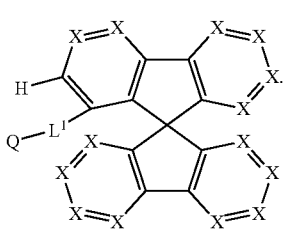
(IVa)

4. The compound or mixture of compounds of claim 3, wherein not more than two groups X in the compounds of formulae (Ia), (IIa), (IIIa), and (IVa) are N.

5. The compound or mixture of compounds of claim 1, wherein the compound is a compound of formulae (Ib), (IIb), (IIIb), or (IVb) and the mixture is a mixture of at least one compound of formulae (Ib), (IIb), (IIIb), and (IVb):

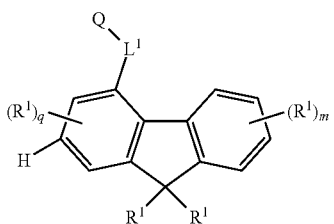
(Ib)

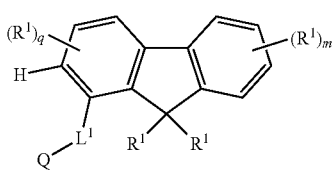
(IIb)

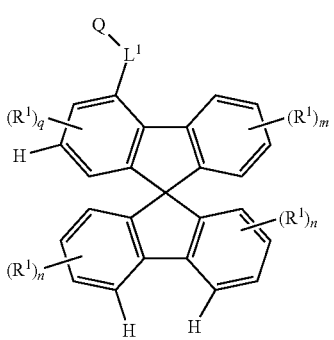
(IIIb)

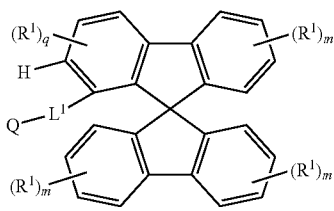
(IVb)

wherein
m is 0, 1, 2, 3, or 4.

6. The compound or mixture of compounds of claim 1, wherein Q is selected from the group consisting of structures of formulae (Q-4), (Q-6), (Q-8), (Q-9), (Q-10), (Q-12), (Q-13), and (Q-15):

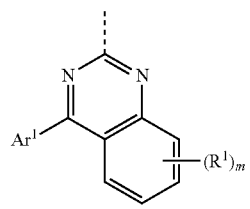
(Q-4)

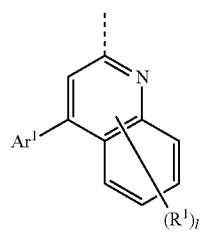
(Q-6)

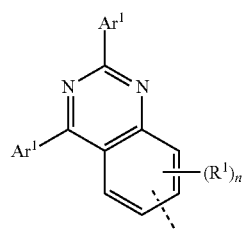
(Q-8)

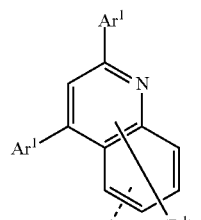
(Q-9)

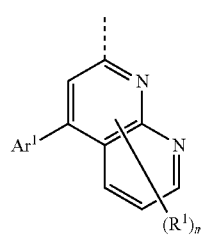
(Q-10)

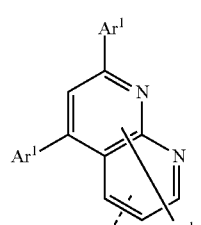
(Q-12)

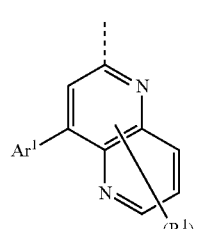
(Q-13)

-continued
(Q-15)
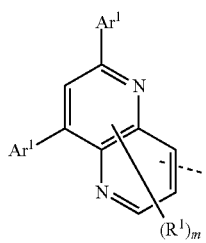
wherein
m is 0, 1, 2, 3 or 4.
7. The compound or mixture of compounds of claim 1, wherein Ar¹ and/or a radical R² bonded to Ar¹ of formulae (Q-1) or (Q-3) comprises a structural element selected from the group consisting of structures of formulae (Q-4), (Q-5), (Q-6), (Q-7), (Q-8), (Q-9), (Q-10), (Q-11), (Q-12), (Q-13), (Q-14), (Q-15), (Q-16), and (Q-17):
(Q-4)
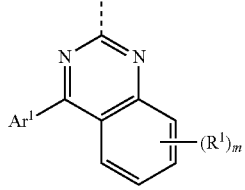
(Q-5)
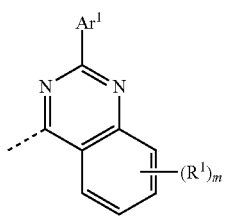
(Q-6)
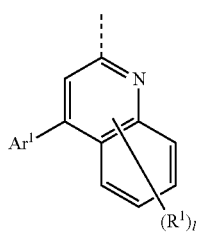
(Q-7)
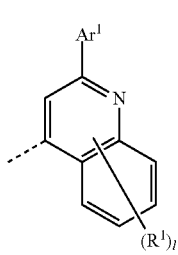
-continued
(Q-8)
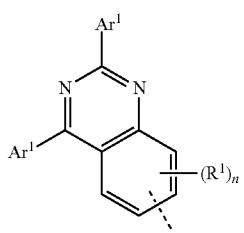
(Q-9)
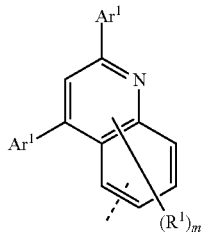
(Q-10)
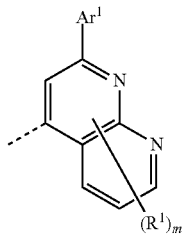
(Q-11)
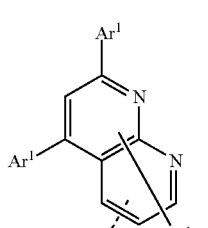
(Q-12)
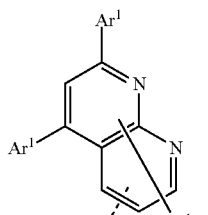
(Q-13)
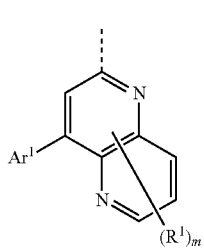

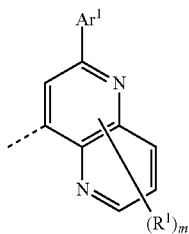

(Q-14)

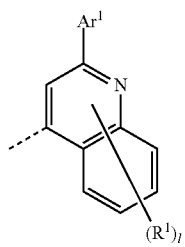

(Q-7)

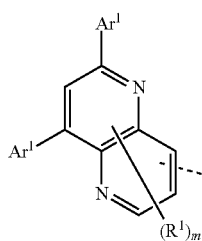

(Q-15)

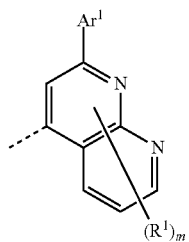

(Q-11)

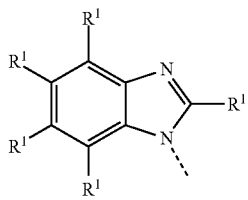

(Q-16)

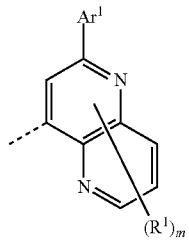

(Q-14)

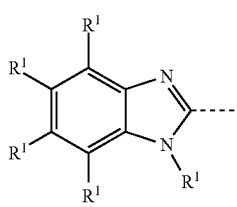

(Q-17)

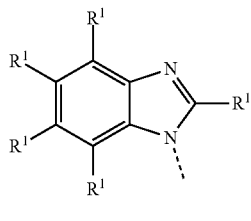

(Q-16)

wherein
m is 0, 1, 2, 3 or 4; and
the dotted bond denotes the attachment position or, with regard to formulae (Q-16) and (Q-17), the attachment positions at which the structural element of formula (Q-16) or (Q-17) binds to other structural elements of the radical $Ar^1$ or to the radical $R^2$ or to a structure of formulae (Q-4), (Q-5), (Q-6), (Q-7), (Q-8), (Q-9), (Q-10), (Q-11), (Q-12), (Q-13), (Q-14), or (Q-15).

8. The compound or mixture of compounds of claim 6, wherein $Ar^1$ and/or a radical $R^2$ bonded to $Ar^1$ of formulae (Q-4), (Q-6), (Q-8), (Q-9), (Q-10), (Q-12), (Q-13), and (Q-15) comprises a structural element selected from the group consisting of structures of formulae (Q-4), (Q-5), (Q-6), (Q-7), (Q-8), (Q-9), (Q-10), (Q-11), (Q-12), (Q-13), (Q-14), (Q-15), (Q-16), and (Q-17):

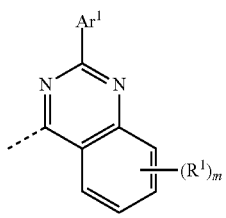

(Q-5)

(Q-17)

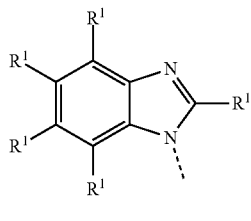

wherein
the dotted bond denotes the attachment position or, with regard to formulae (Q-16) and (Q-17), the attachment positions at which the structural element of formula (Q-16) or (Q-17) binds to other structural elements of the radical $Ar^1$ or to the radical $R^2$ or to a structure of formulae (Q-1), (Q-2), (Q-3), (Q-4), (Q-5), (Q-6), (Q-7), (Q-8), (Q-9), (Q-10), (Q-11), (Q-12), (Q-13), (Q-14), or (Q-15).

9. The compound or mixture of compounds of claim 1, wherein the compound does not or the compounds of the mixture do not comprise a carbazole and/or triarylamine group.

10. The compound or mixture of compounds of claim 1, wherein the compound does not or the compounds of the mixture do not comprise a hole-transporting group.

11. An oligomer, polymer, or dendrimer comprising the compound or mixture of compounds of claim 1, wherein one or more bonds of the compound or mixture of compounds to the polymer, oligomer, or dendrimer are present.

12. A composition comprising the compound or mixture of compounds of claim 1 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

13. A composition comprising the oligomer, polymer, or dendrimer of claim 11 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

14. A formulation comprising the compound or mixture of compounds of claim 1 and at least one solvent.

15. A formulation comprising the oligomer, polymer, or dendrimer of claim 11 and at least one solvent.

16. A formulation comprising the composition of claim 12 and at least one solvent.

17. A formulation comprising the composition of claim 13 and at least one solvent.

18. A process for preparing a compound or a compound of the mixture of compounds of claim 1 comprising reacting a compound comprising at least one electron-transporting group with a compound comprising at least one fluorene radical in a coupling reaction.

19. An electronic device comprising a compound or mixture of compounds of claim 1.

20. The electronic device of claim 19, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

21. An electronic device comprising the oligomer, polymer, or dendrimer of claim 11.

22. The electronic device of claim 21, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

23. An electronic device comprising the composition of claim 12.

24. The electronic device of claim 23, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

25. An electronic device comprising the composition of claim 13.

26. The electronic device of claim 25, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

27. A compound of formulae (I) or (II) or a mixture of a compound of formula (I) and a compound of formula (II):

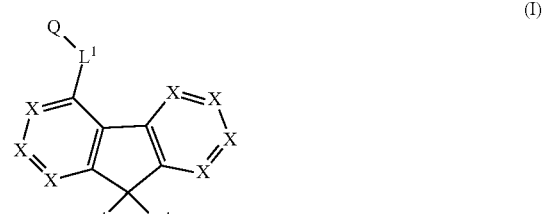

(I)

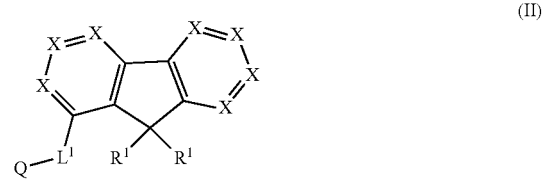

(II)

wherein

X is, the same or differently in each instance, N or CR', with the proviso that not more than two groups X in one cycle are N;

Q is selected from the group consisting of structures of formulae (Q-4), (Q-6), (Q-7), (Q-8), (Q-9), (Q-10), (Q-11), (Q-12), (Q-13), (Q-14), (Q-15), (Q-16), and (Q-17):

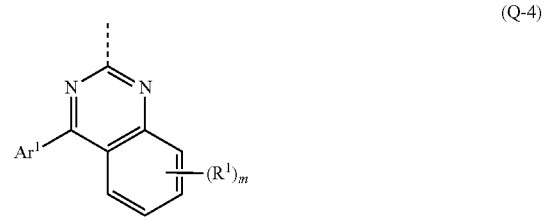

(Q-4)

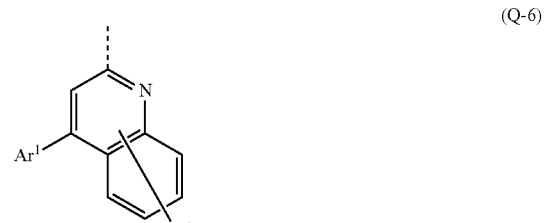

(Q-6)

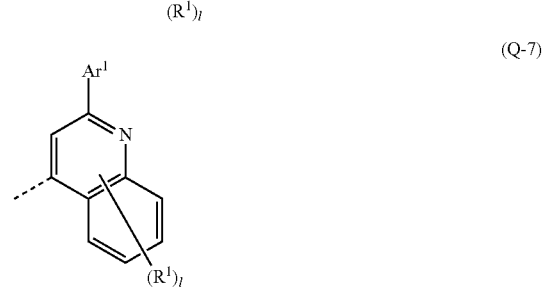

(Q-7)

(Q-8) 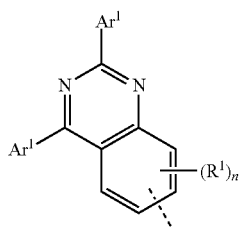

(Q-9) 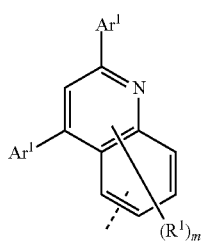

(Q-10) 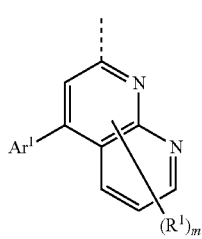

(Q-11) 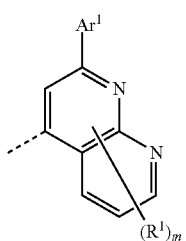

(Q-12) 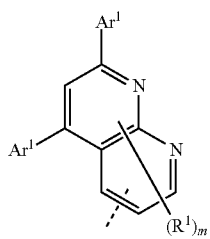

(Q-13) 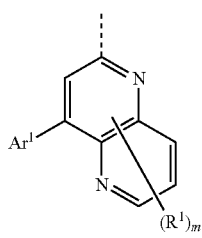

(Q-14) 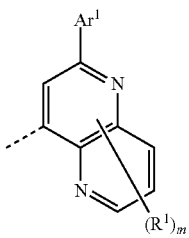

(Q-15) 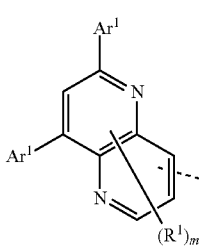

(Q-16) 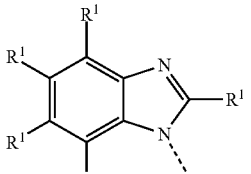

(Q-17) 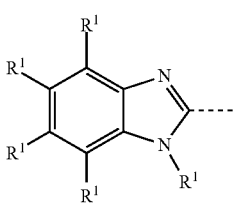

wherein the dotted bond denotes the attachment position or, with regard to formulae (Q-16) and (Q-17), the attachment positions at which the structural element of formula (Q-16) or (Q-17) binds to other structural elements of the radical $Ar^1$ or to the radical $R^2$ or to a structure of formulae (Q-4), (Q-5), (Q-6), (Q-7), (Q-8), (Q-9), (Q-10), (Q-11), (Q-12), (Q-13), (Q-14), or (Q-15);

$Ar^1$ is an aromatic or heteroaromatic ring system having 6 to 40 carbon atoms and is optionally substituted in each case by one or more radicals $R^2$, an aryloxy group having 5 to 60 aromatic ring atoms and is optionally substituted by one or more $R^2$ radicals, or an aralkyl group having 5 to 60 aromatic ring atoms and is optionally substituted in each case by one or more radicals $R^2$, and wherein two or more adjacent radicals $R^1$ or $R^2$ together optionally define a mono- or polycyclic aliphatic ring system with each other and which is optionally substituted by one or more radicals $R^3$;

$L^1$ is a bond, C(=O), pyrimidine which is optionally substituted by one or more $R^1$, triazine which is optionally substituted by one or more $R^1$ radicals or a group of the Formula (L-1) to (L-70):

Formula (L-1)
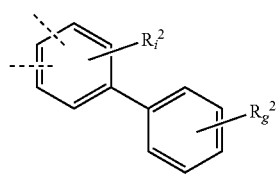
Formula (L-2)
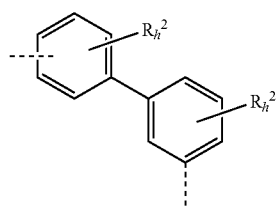
Formula (L-3)
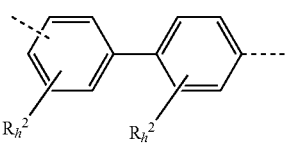
Formula (L-4)
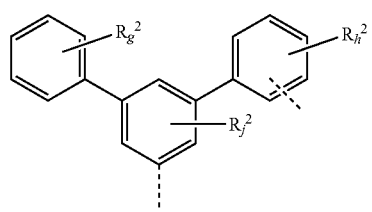
Formula (L-5)
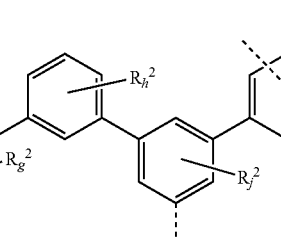
Formula (L-6)
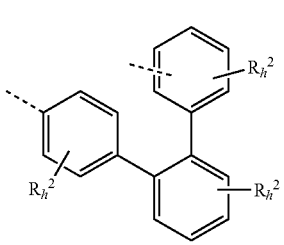
Formula (L-7)
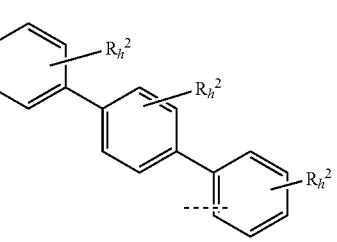
Formula (L-8)
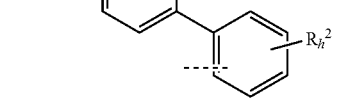
Formula (L-9)
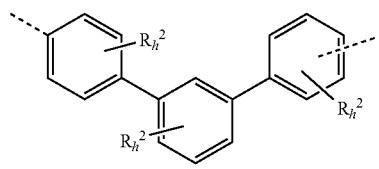
Formula (L-10)
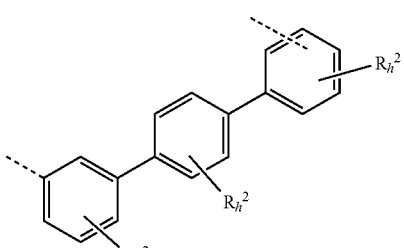
Formula (L-11)
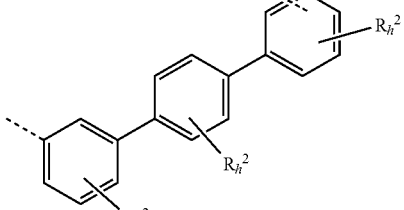
Formula (L-12)
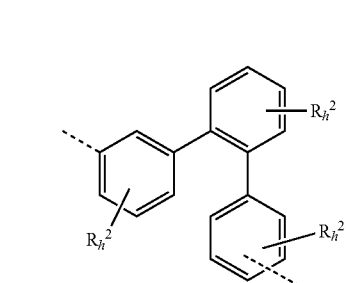
Formula (L-13)
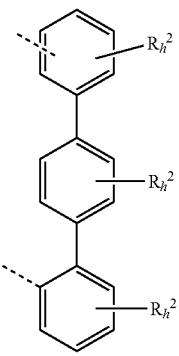

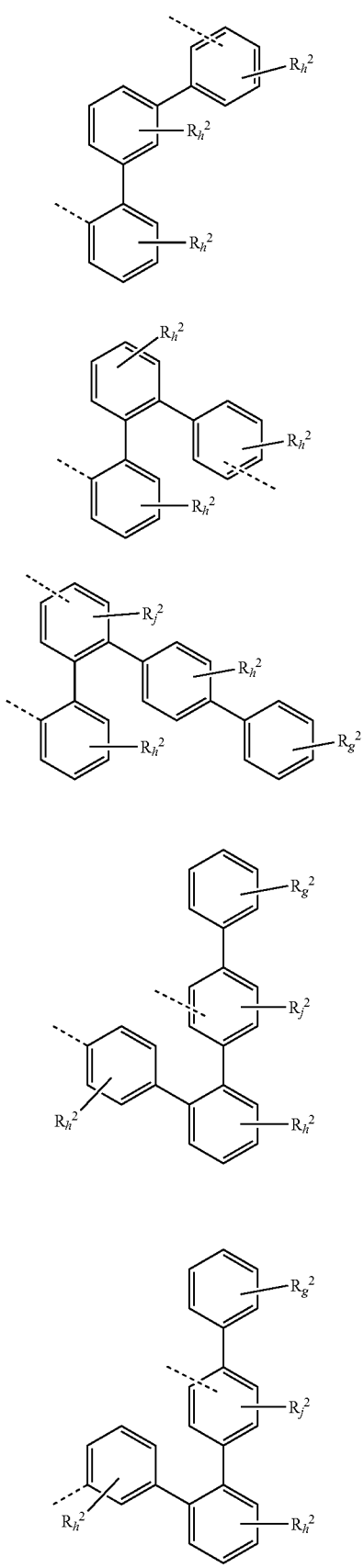
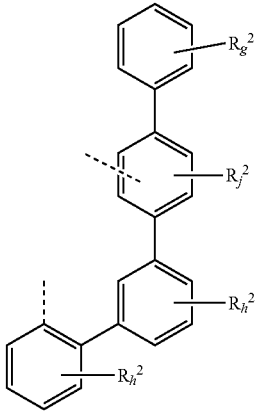

309
-continued
Formula (L-24)
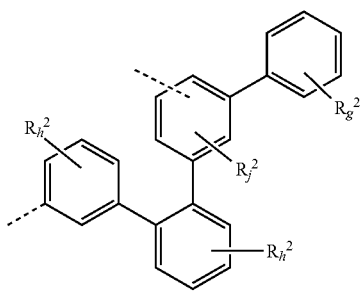
Formula (L-25)
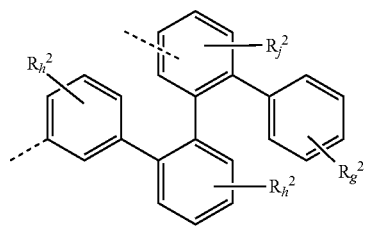
Formula (L-26)
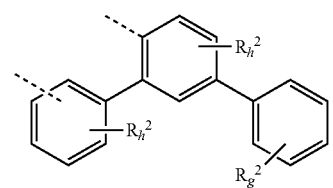
Formula (L-27)
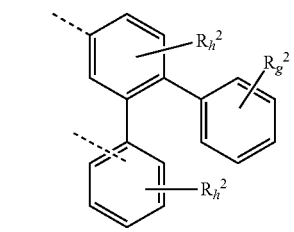
Formula (L-28)
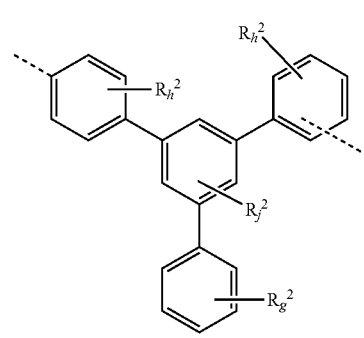
Formula (L-29)
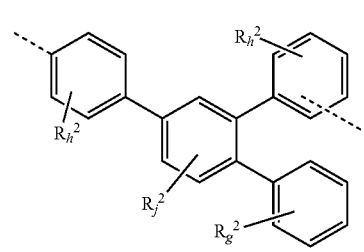
310
-continued
Formula (L-30)
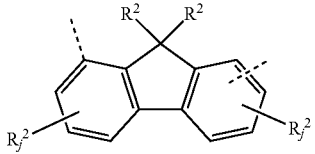
Formula (L-31)
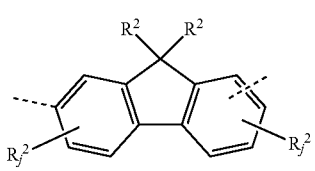
Formula (L-32)
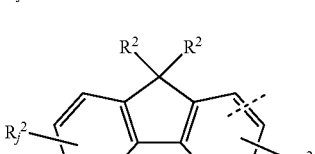
Formula (L-33)
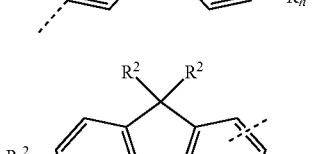
Formula (L-34)
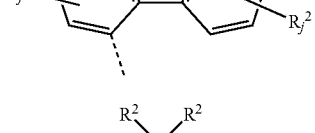
Formula (L-35)
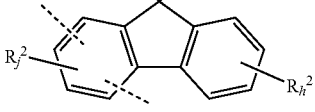
Formula (L-36)
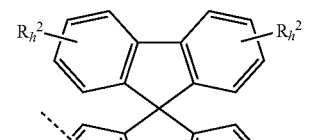
Formula (L-37)
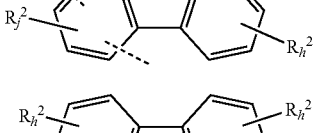
Formula (L-38)
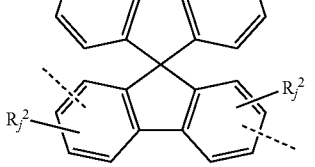

-continued
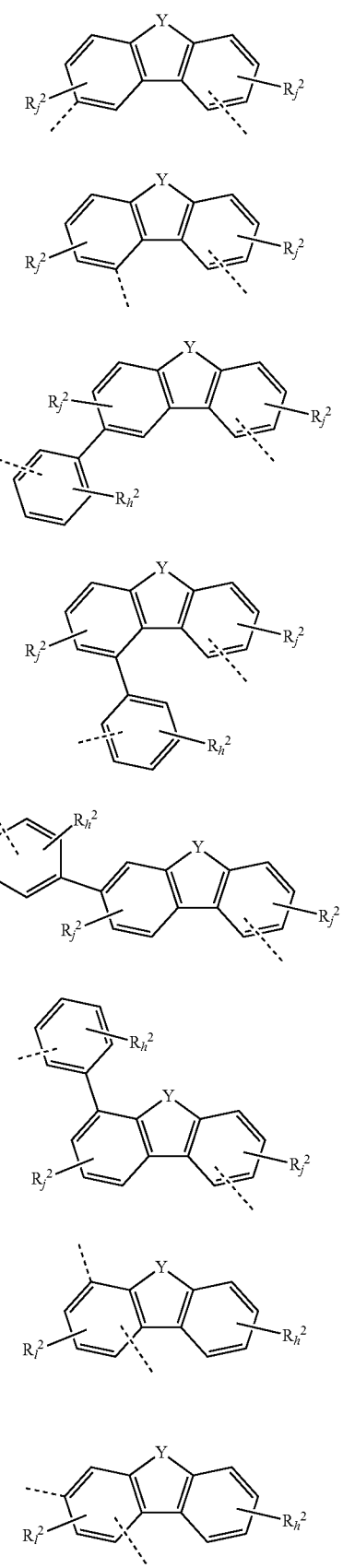
Formula (L-39)
Formula (L-40)
Formula (L-41)
Formula (L-42)
Formula (L-43)
Formula (L-44)
Formula (L-45)
Formula (L-46)
-continued
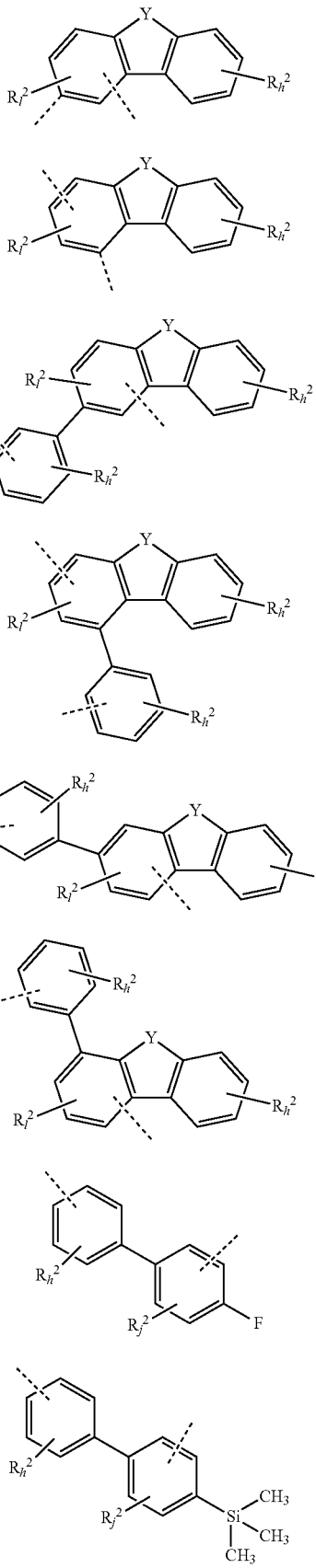
Formula (L-47)
Formula (L-48)
Formula (L-49)
Formula (L-50)
Formula (L-51)
Formula (L-52)
Formula (L-53)
Formula (L-54)

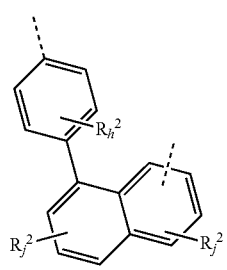 Formula (L-55)
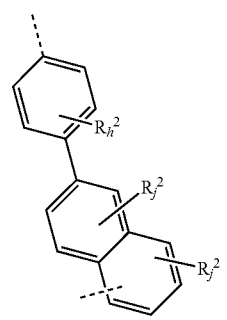 Formula (L-56)
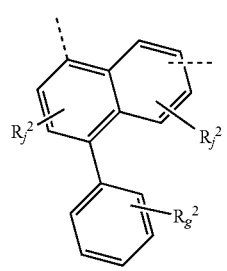 Formula (L-57)
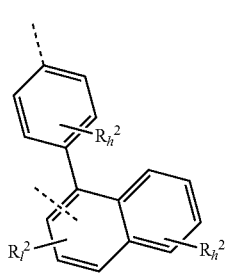 Formula (L-58)
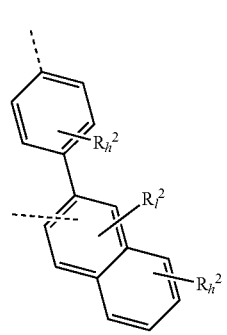 Formula (L-59)
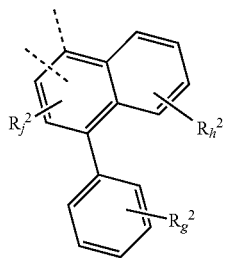 Formula (L-60)
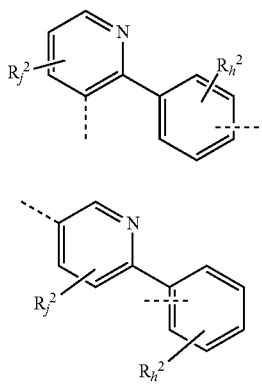 Formula (L-61)
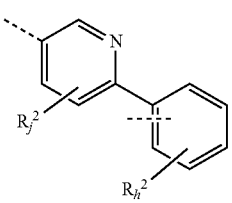 Formula (L-62)
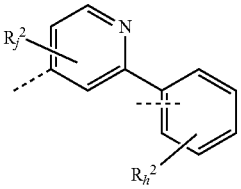 Formula (L-63)
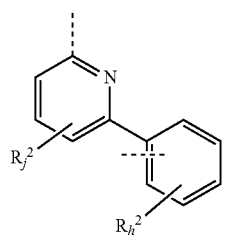 Formula (L-64)
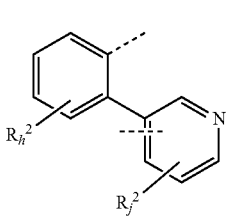 Formula (L-65)
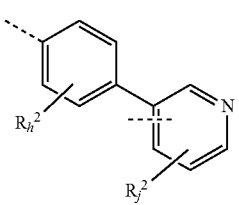 Formula (L-66)

-continued

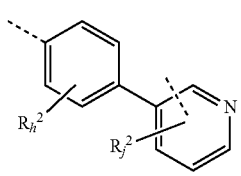

Formula (L-67)

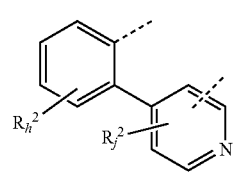

Formula (L-68)

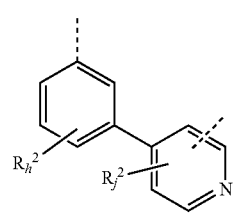

Formula (L-69)

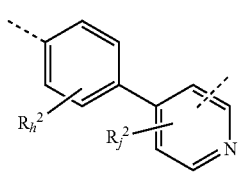

Formula (L-70)

wherein the dotted bonds in each case mark the attachment positions, the index 1 is 0, 1 or 2, the index g is 0, 1, 2, 3, 4 or 5, j independently at each instance is 0, 1, 2 or 3;

h independently at each instance is 0, 1, 2, 3 or 4;

Y is O, S or $NR^2$;

$R^1$ is, the same or differently in each instance, H, D, a straight-chain alkyl, alkoxy, or thioalkoxy group having 1 to 40 carbon atoms, or a branched or cyclic alkyl, alkoxy, or thioalkoxy group having 3 to 40 carbon atoms, each of which is optionally substituted by one or more radicals $R^2$, wherein one or more nonadjacent $CH_2$ groups is optionally replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, SO, or $SO_2$, and wherein one or more hydrogen atoms are optionally replaced by D, F, Cl, Br, I, CN, or $NO_2$, an aromatic or heteroaromatic ring system having 5 to 40 aromatic ring atoms, each of which is optionally substituted by one or more radicals $R^2$, or an aryloxy or heteroaryloxy group having 5 to 40 aromatic ring atoms and is optionally substituted by one or more radicals $R^2$, or a combination of these systems; and wherein two or more adjacent radicals $R^1$ together optionally define a mono- or polycyclic aliphatic or aromatic ring system with one another;

$R^2$ is, the same or differently in each instance, H, D, a straight-chain alkyl, alkoxy, or thioalkoxy group having 1 to 40 carbon atoms, or a branched or cyclic alkyl, alkoxy, or thioalkoxy group having 3 to 40 carbon atoms, each of which is optionally substituted by one or more radicals $R^3$, wherein one or more nonadjacent $CH_2$ groups is optionally replaced by $-R^3C=CR^3-$, $-C\equiv C-$, $Si(R^3)_2$, $C=O$, $C=S$, $C=NR^3$, $-C(=O)O-$, $-C(=O)NR^3-$, $NR^3$, $P(=O)(R^3)$, $-O-$, $-S-$, SO, or $SO_2$, and wherein one or more hydrogen atoms is optionally replaced by D, F, Cl, Br, I, CN, or $NO_2$, an aromatic or heteroaromatic ring system having 5 to 40 aromatic ring atoms, each of which is optionally substituted by one or more $R^3$ radicals, or an aryloxy or heteroaryloxy group having 5 to 40 aromatic ring atoms and is optionally substituted by one or more $R^3$ radicals, or a combination of these systems; and wherein two or more adjacent radicals $R^2$ together optionally define a mono- or polycyclic aliphatic or aromatic ring system with one another;

$R^3$ is, the same or differently in each instance, H, D, F, or an aliphatic hydrocarbyl radical having 1 to 20 carbon atoms, wherein one or more hydrogen atoms is optionally replaced by D or F, an aromatic and/or heteroaromatic ring system having 5 to 30 carbon atoms, wherein one or more hydrogen atoms are optionally replaced by D or F; and wherein two or more adjacent radicals $R^3$ together optionally define a mono- or polycyclic, aliphatic or aromatic ring system with one another.

28. The compound or mixture of compounds of claim 3, wherein $L^1$ is selected from the formulae (L-1) to (L-54).

29. The compound or mixture of compounds of claim 3, wherein $L^1$ is selected from the group consisting of ortho-phenylene, meta-phenylene, para-phenylene, biphenyl, fluorene, pyridine, pyrimidine, triazine, dibenzofuran and dibenzothiophene, each of which may be substituted by one or more $R^2$ radicals.

30. A compound of formulae (I) or (II) or a mixture of a compound of formula (I) and a compound of formula (II):

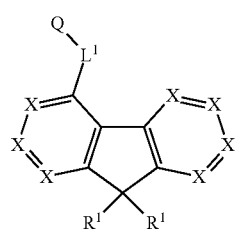

(I)

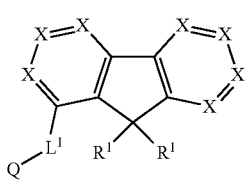

(II)

wherein

X is, the same or differently in each instance, N or CR', with the proviso that not more than two groups X in one cycle are N;

Q is selected from the group consisting of structures of formulae (Q-1), and (Q-3):

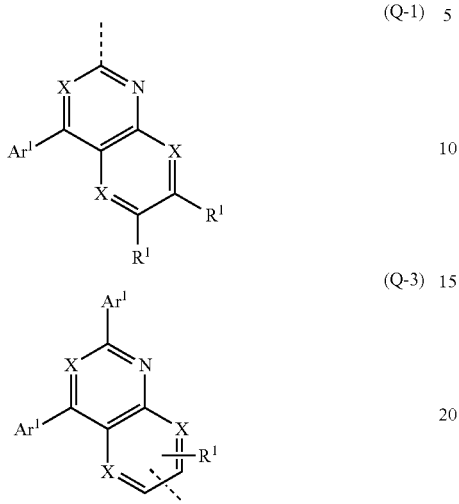

wherein
the dotted bond denotes the attachment position; and
Ar¹
is an aromatic or heteroaromatic ring system having 6 to 40 carbon atoms and is optionally substituted in each case by one or more radicals R², an aryloxy group having 5 to 60 aromatic ring atoms and is optionally substituted by one or more R² radicals, or an aralkyl group having 5 to 60 aromatic ring atoms and is optionally substituted in each case by one or more radicals R², and wherein two or more adjacent radicals R¹ or R² together optionally define a mono- or polycyclic aliphatic ring system with each other and which is optionally substituted by one or more radicals R³;
L¹ is a bond, C(=O), or an aromatic ring system having 5 to 24 aromatic ring atoms and is optionally substituted by one or more R¹ radicals with the proviso that L¹ does not comprise an anthracene;
R¹ is, the same or differently in each instance, H, D, a straight-chain alkyl, alkoxy, or thioalkoxy group having 1 to 40 carbon atoms, or a branched or cyclic alkyl, alkoxy, or thioalkoxy group having 3 to 40 carbon atoms, each of which is optionally substituted by one or more radicals R², wherein one or more nonadjacent CH₂ groups is optionally replaced by —R²C=CR²—, —C≡C—, Si(R²)₂, C=O, C=S, C=NR², —C(=O) O—, —C(=O)NR²—, NR², P(=O)(R²), —O—, —S—, SO, or SO₂, and wherein one or more hydrogen atoms are optionally replaced by D, F, Cl, Br, I, CN, or NO₂, an aromatic or heteroaromatic ring system having 5 to 40 aromatic ring atoms, each of which is optionally substituted by one or more radicals R², or an aryloxy or heteroaryloxy group having 5 to 40 aromatic ring atoms and is optionally substituted by one or more radicals R², or a combination of these systems; and wherein two or more adjacent radicals R¹ together optionally define a mono- or polycyclic aliphatic ring system with one another;

R² is, the same or differently in each instance, H, D, a straight-chain alkyl, alkoxy, or thioalkoxy group having 1 to 40 carbon atoms, or a branched or cyclic alkyl, alkoxy, or thioalkoxy group having 3 to 40 carbon atoms, each of which is optionally substituted by one or more radicals R³, wherein one or more nonadjacent CH₂ groups is optionally replaced by —R³C=CR³—, —C≡C—, Si(R³)₂, C=O, C=S, C=NR³, —C(=O) O—, —C(=O)NR³—, NR³, P(=O)(R³), —O—, —S—, SO, or SO₂, and wherein one or more hydrogen atoms is optionally replaced by D, F, Cl, Br, I, CN, or NO₂, an aromatic or heteroaromatic ring system having 5 to 40 aromatic ring atoms, each of which is optionally substituted by one or more R³ radicals, or an aryloxy or heteroaryloxy group having 5 to 40 aromatic ring atoms and is optionally substituted by one or more R³ radicals, or a combination of these systems; and wherein two or more adjacent radicals R² together optionally define a mono- or polycyclic aliphatic or aromatic ring system with one another;

R³ is, the same or differently in each instance, H, D, F, or an aliphatic hydrocarbyl radical having 1 to 20 carbon atoms, wherein one or more hydrogen atoms is optionally replaced by D or F, an aromatic and/or heteroaromatic ring system having 5 to 30 carbon atoms, wherein one or more hydrogen atoms are optionally replaced by D or F; and wherein two or more adjacent radicals R³ together optionally define a mono- or polycyclic, aliphatic or aromatic ring system with one another.

31. The compound or mixture of compounds of claim 3, wherein indices l, g, h and j in the structures of the formula (L-1) to (L-70) is at most 3 in each case.

32. The compound or mixture of compounds of claim 3, wherein indices l, g, h and j in the structures of the formula (L-1) to (L-70) is at most 1 in each case.

33. A compound of formulae (I) or (II) or a mixture of a compound of formula (I) and a compound of formula (II):

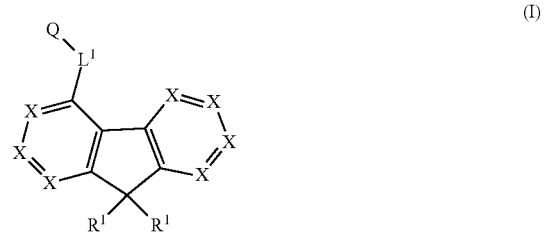

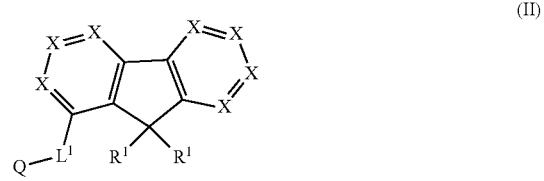

wherein
X is, the same or differently in each instance, N or CR', with the proviso that not more than two groups X in one cycle are N;

Q is selected from the group consisting of structures of formulae (Q-1), (Q-2), and (Q-3):

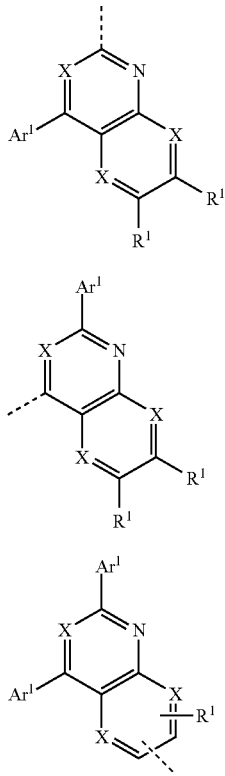

(Q-1)

(Q-2)

(Q-3)

wherein
the dotted bond denotes the attachment position; and
Ar¹
is an aromatic ring system having 6 to 40 carbon atoms and is optionally substituted in each case by one or more radicals R², an aryloxy group having 5 to 60 aromatic ring atoms and is optionally substituted by one or more R² radicals, or an aralkyl group having 5 to 60 aromatic ring atoms and is optionally substituted in each case by one or more radicals R², and wherein two or more adjacent radicals R¹ or R² together optionally define a mono- or polycyclic aliphatic ring system with each other and which is optionally substituted by one or more radicals R³;
L¹ is a bond, C(═O), or an aromatic ring system having 5 to 24 aromatic ring atoms and is optionally substituted by one or more R¹ radicals with the proviso that L¹ does not comprise an anthracene;
R¹ is, the same or differently in each instance, H, D, a straight-chain alkyl, alkoxy, or thioalkoxy group having 1 to 40 carbon atoms, or a branched or cyclic alkyl, alkoxy, or thioalkoxy group having 3 to 40 carbon atoms, each of which is optionally substituted by one or more radicals R², wherein one or more nonadjacent CH₂ groups is optionally replaced by —R²C═CR²—, —C≡C—, Si(R²)₂, C═O, C═S, C═NR², —C(═O)O—, —C(═O)NR²—, NR², P(═O)(R²), —O—, —S—, SO, or SO₂, and wherein one or more hydrogen atoms are optionally replaced by D, F, Cl, Br, I, CN, or NO₂, an aromatic or heteroaromatic ring system having 5 to 40 aromatic ring atoms, each of which is optionally substituted by one or more radicals R², or an aryloxy or heteroaryloxy group having 5 to 40 aromatic ring atoms and is optionally substituted by one or more radicals R², or a combination of these systems; and wherein two or more adjacent radicals R¹ together optionally define a mono- or polycyclic aliphatic or aromatic ring system with one another;

R² is, the same or differently in each instance, H, D, a straight-chain alkyl, alkoxy, or thioalkoxy group having 1 to 40 carbon atoms, or a branched or cyclic alkyl, alkoxy, or thioalkoxy group having 3 to 40 carbon atoms, each of which is optionally substituted by one or more radicals R³, wherein one or more nonadjacent CH₂ groups is optionally replaced by —R³C═CR³—, —C≡C—, Si(R³)₂, C═O, C═S, C═NR³, —C(═O)O—, —C(═O)NR³—, NR³, P(═O)(R³), —O—, —S—, SO, or SO₂, and wherein one or more hydrogen atoms is optionally replaced by D, F, Cl, Br, I, CN, or NO₂, an aromatic or heteroaromatic ring system having 5 to 40 aromatic ring atoms, each of which is optionally substituted by one or more R³ radicals, or an aryloxy or heteroaryloxy group having 5 to 40 aromatic ring atoms and is optionally substituted by one or more R³ radicals, or a combination of these systems; and wherein two or more adjacent radicals R² together optionally define a mono- or polycyclic aliphatic or aromatic ring system with one another;

R³ is, the same or differently in each instance, H, D, F, or an aliphatic hydrocarbyl radical having 1 to 20 carbon atoms, wherein one or more hydrogen atoms is optionally replaced by D or F, an aromatic and/or heteroaromatic ring system having 5 to 30 carbon atoms, wherein one or more hydrogen atoms are optionally replaced by D or F; and wherein two or more adjacent radicals R³ together optionally define a mono- or polycyclic, aliphatic or aromatic ring system with one another.

34. The compound or mixture of compounds of claim 27, wherein the compound is a compound of formulae (III) or (IV) and the mixture is a mixture of a compound of formula (III) and a compound of formula (IV):

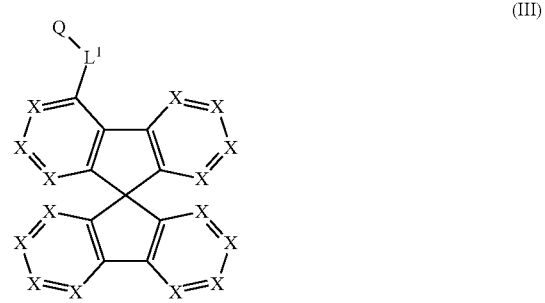

(III)

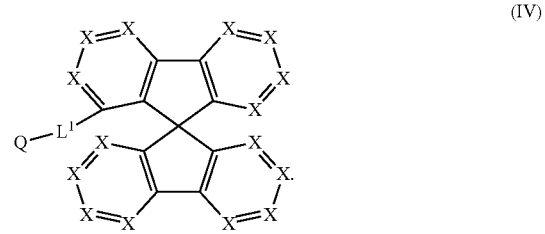

(IV)

35. The compound or mixture of compounds of claim 27, wherein the compound is a compound of formula (Ia), (IIa), (IIIa), or (IVa) and the mixture is a mixture of at least one compound of formulae (Ia), (IIa), and (IVa):

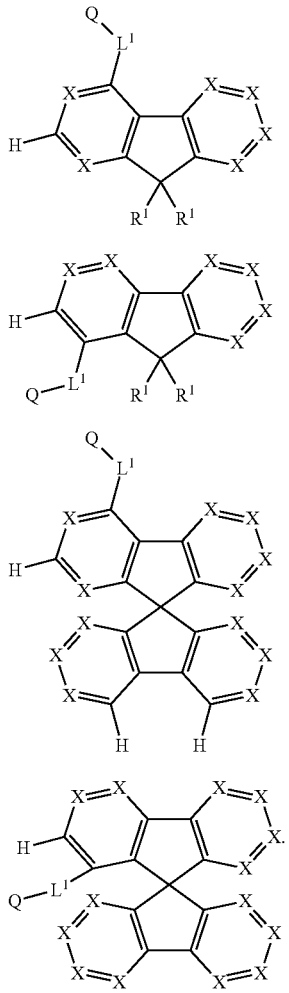

36. The compound or mixture of compounds of claim 35, wherein not more than two groups X in the compounds of formulae (Ia), (IIa), (IIIa) and (IVa) are N.

37. The compound or mixture of compounds of claim 27, wherein the compound does not or the compounds of the mixture do not comprise a carbazole and/or triarylamine group.

38. The compound or mixture of compounds of claim 27, wherein the compound does not or the compounds of the mixture do not a hole-transporting group.

39. An oligomer, polymer, or dendrimer comprising the compound or mixture of compounds of claim 27, wherein one or more bonds of the compound or mixture of compounds to the polymer, oligomer, or dendrimer are present.

40. A composition comprising the oligomer, polymer, or dendrimer of claim 39 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

41. A formulation comprising the oligomer, polymer, or dendrimer of claim 39 and at least one solvent.

42. A formulation comprising the composition of claim 40 and at least one solvent.

43. An electronic device comprising the oligomer, polymer, or dendrimer of claim 39.

44. The electronic device of claim 43, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

45. An electronic device comprising the composition of claim 40.

46. The electronic device of claim 45, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

47. The compound or mixture of compounds of claim 30, wherein the compound is a compound of formulae (III) or (IV) and the mixture is a mixture of a compound of formula (III) and a compound of formula (IV):

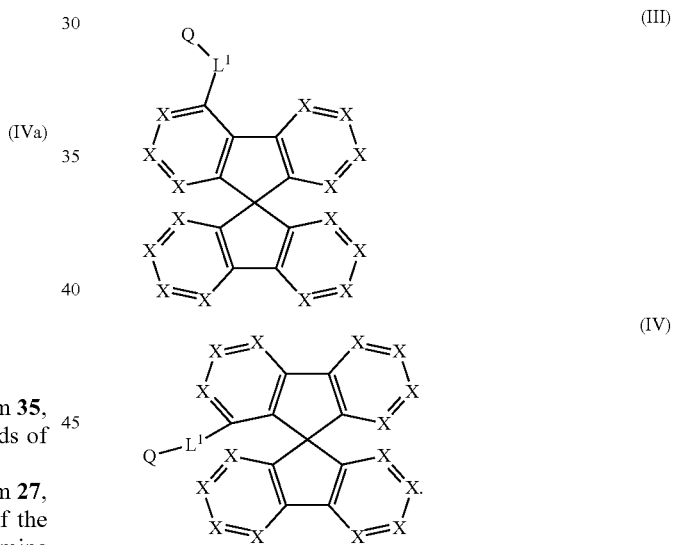

48. The compound or mixture of compounds of claim 30, wherein the compound is a compound of formulae (Ia), (IIa), (IIIa), or (IVa) and the mixture is a mixture of at least one compound of formulae (Ia), (IIa), (IIIa), and (IVa):

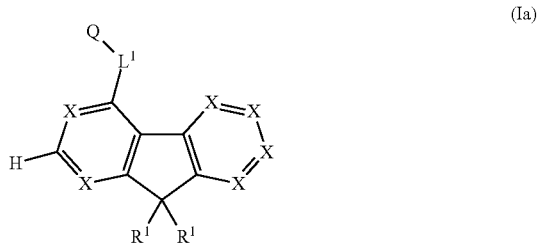

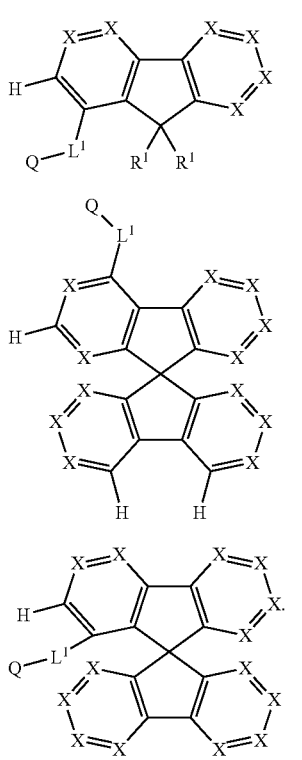

(IIa)

(IIIa)

(IVa)

49. The compound or mixture of compounds of claim 48, wherein not more than two groups X in the compounds of formulae (Ia), (IIa), (IIIa) and (IVa) are N.

50. The compound or mixture of compounds of claim 30, wherein the compound does not or the compounds of the mixture do not comprise a carbazole and/or triarylamine group.

51. The compound or mixture of compounds of claim 30, wherein the compound does not or the compounds of the mixture do not a hole-transporting group.

52. An oligomer, polymer, or dendrimer comprising the compound or mixture of compounds of claim 30, wherein one or more bonds of the compound or mixture of compounds to the polymer, oligomer, or dendrimer are present.

53. A composition comprising the oligomer, polymer, or dendrimer of claim 52 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

54. A formulation comprising the oligomer, polymer, or dendrimer of claim 52 and at least one solvent.

55. A formulation comprising the composition of claim 53 and at least one solvent.

56. An electronic device comprising the oligomer, polymer, or dendrimer of claim 52.

57. The electronic device of claim 56, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

58. An electronic device comprising the composition of claim 53.

59. The electronic device of claim 58, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

60. The compound or mixture of compounds of claim 33, wherein the compound is a compound of formulae (III) or (IV) and the mixture is a mixture of a compound of formula (III) and a compound of formula (IV):

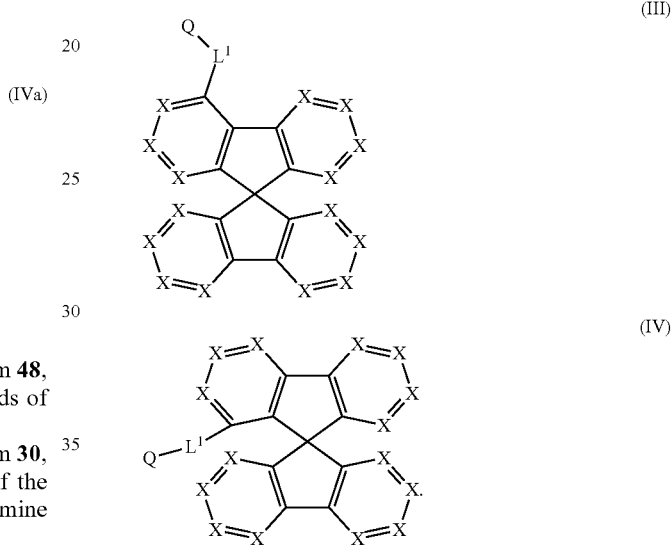

(III)

(IV)

61. The compound or mixture of compounds of claim 33, wherein the compound is a compound of formulae (Ia), (IIa), (IIIa), or (IVa) and the mixture is a mixture of at least one compound of formulae (Ia), (IIa), (IIIa), and (IVa):

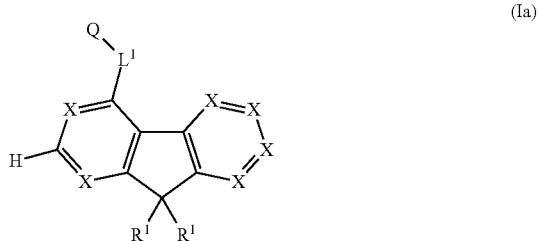

(Ia)

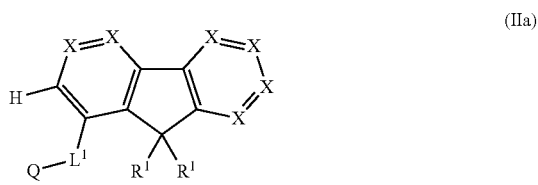

(IIa)

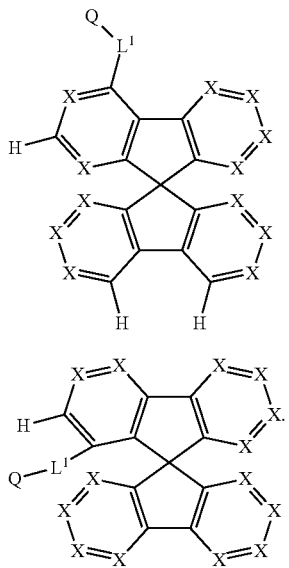

(IIIa)

(IVa)

62. The compound or mixture of compounds of claim 61, wherein not more than two groups X in the compounds of formulae (Ia), (IIa), (IIIa), and (IVa) are N.

63. The compound or mixture of compounds of claim 33, wherein the compound does not or the compounds of the mixture do not comprise a carazole and/or triarylamine group.

64. The compound or mixture of compounds of claim 33, wherein the compound does not or the compounds of the mixture do not a hole-transporting group.

65. An oligomer, polymer, or dendrimer comprising the compound or mixture of compounds of claim 33, wherein one or more bonds of the compound or mixture of compounds to the polymer, oligomer, or dendrimer are present.

66. A composition comprising the oligomer, polymer, or dendrimer of claim 65 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

67. A formulation comprising the oligomer, polymer, or dendrimer of claim 65 and at least one solvent.

68. A formulation comprising the composition of claim 66 and at least one solvent.

69. An electronic device comprising the oligomer, polymer, or dendrimer of claim 65.

70. The electronic device of claim 69, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

71. An electronic device comprising the composition of claim 66.

72. The electronic device of claim 71, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

73. The compound of mixture of compounds of claim 27, wherein $Ar^1$ and/or a radical $R^2$ bonded to $Ar^1$ of formulae (Q-1) (Q-2), or (Q-3) comprises a structural element selected from the group consisting of structures of formulae (Q-4), (Q-5), (Q-6), (Q-7), (Q-8), (Q-9), (Q-10), (Q-11), (Q-12), (Q-13), (Q-14), (Q-15), (Q-16), and (Q-17):

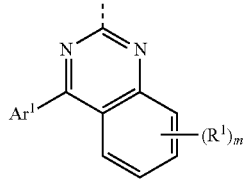

(Q-4)

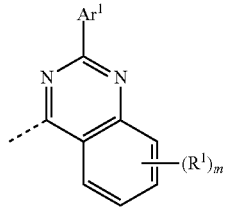

(Q-5)

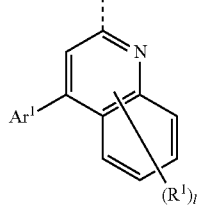

(Q-6)

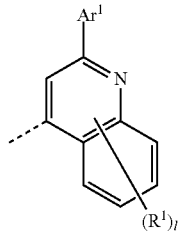

(Q-7)

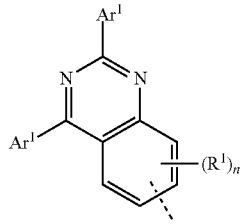

(Q-8)

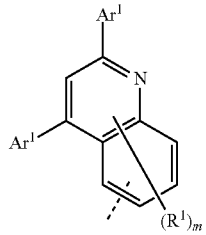

(Q-9)

(Q-10) 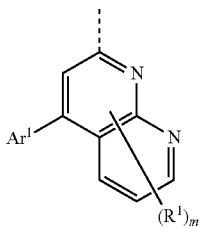

(Q-11) 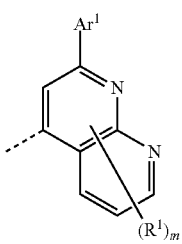

(Q-12) 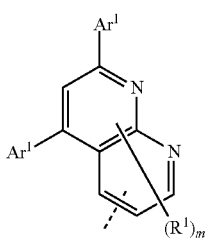

(Q-13) 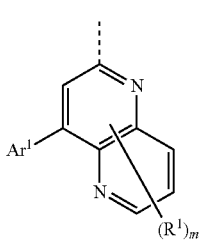

(Q-14) 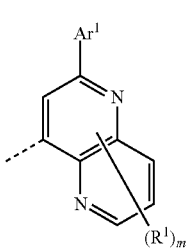

(Q-15) 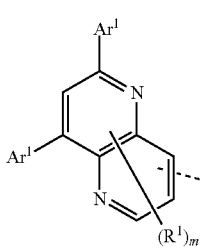

(Q-16) 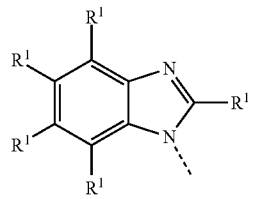

(Q-17) 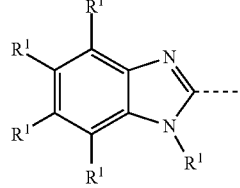

wherein m is 0, 1, 2, 3 or 4; and the dotted bond denotes the attachment position or, with regard to formulae (Q-16) and (Q-17), the attachment positions at which the structural element of formula (Q-16) or (Q-17) binds to other structural elements of the radical Ar$^1$ or to the radical R$^2$ or to a structure of formulae (Q-4), (Q-5), (Q-6), (Q-7), (Q-8), (Q-9), (Q-10), (Q-11), (Q-12), (Q-13), (Q-14), or (Q-15).

74. The compound or mixture of compounds of claim 30, wherein Ar$^1$ and/or a radical R$^2$ bonded to Ar$^1$ of formulae (Q-1) or (Q-3) comprises a structural element selected from the group consisting of structures of formulae (Q-4), (Q-5), (Q-6), (Q-7), (Q-8), (Q-9), (Q-10), (Q-11), (Q-12), (Q-13), (Q-14), (Q-15), (Q-16), and (Q-17):

(Q-4) 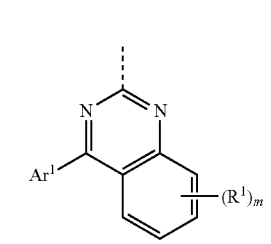

(Q-5) 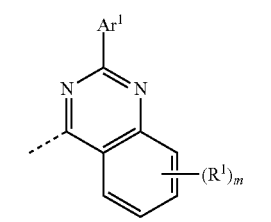

(Q-6) 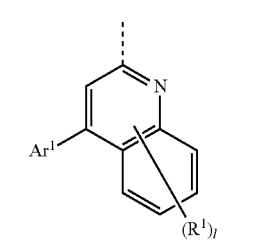

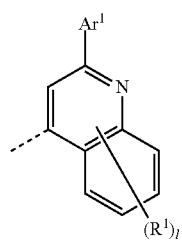
(Q-7)
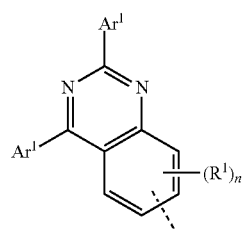
(Q-8)
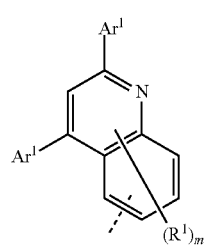
(Q-9)
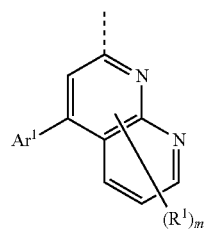
(Q-10)
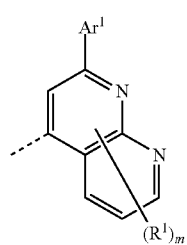
(Q-11)
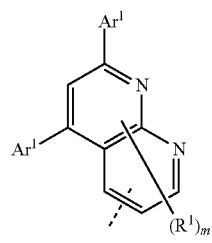
(Q-12)
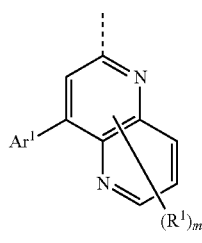
(Q-13)
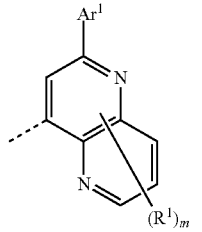
(Q-14)
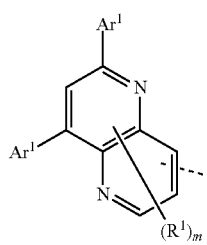
(Q-15)
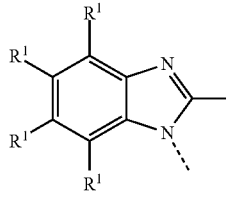
(Q-16)
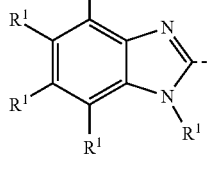
(Q-17)
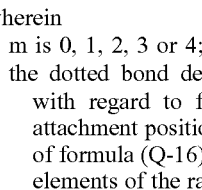
wherein
m is 0, 1, 2, 3 or 4; and
the dotted bond denotes the attachment position or, with regard to formulae (Q-16) and (Q-17), the attachment positions at which the structural element of formula (Q-16) or (Q-17) binds to other structural elements of the radical $Ar^1$ or to the radical $R^2$ or to a structure of formulae (Q-4), (Q-5), (Q-6), (Q-7), (Q-8), (Q-9), (Q-10), (Q-11), (Q-12), (Q-13), (Q-14), or (Q-15).
\* \* \* \* \*